United States Patent
Libertine et al.

(10) Patent No.: US 10,662,430 B2
(45) Date of Patent: May 26, 2020

(54) RNA INTERFERENCE IN OCULAR INDICATIONS

(71) Applicant: Phio Pharmaceuticals Corp., Marlborough, MA (US)

(72) Inventors: Lyn Libertine, Framingham, MA (US); Anastasia Khvorova, Westborough, MA (US); William Salomon, Worcester, MA (US); Joanne Kamens, Newton, MA (US); Dmitry Samarsky, Westborough, MA (US); Tod M. Woolf, Sudbury, MA (US); James Cardia, Franklin, MA (US); Pamela A. Pavco, Longmont, CO (US)

(73) Assignee: Phio Pharmaceuticals Corp., Marlborough, MA (US)

( * ) Notice: Subject to any disclaimer, the term of this patent is extended or adjusted under 35 U.S.C. 154(b) by 0 days.

(21) Appl. No.: 16/206,064

(22) Filed: Nov. 30, 2018

(65) Prior Publication Data

US 2019/0233826 A1    Aug. 1, 2019

Related U.S. Application Data

(63) Continuation of application No. 14/728,653, filed on Jun. 2, 2015, now Pat. No. 10,184,124, which is a continuation of application No. 13/636,748, filed as application No. PCT/US2011/029849 on Mar. 24, 2011, now Pat. No. 9,095,504.

(60) Provisional application No. 61/317,621, filed on Mar. 25, 2010, provisional application No. 61/317,254, filed on Mar. 24, 2010.

(51) Int. Cl.
| | | |
|---|---|---|
| *C12N 15/113* | (2010.01) | |
| *A61K 9/00* | (2006.01) | |
| *A61K 31/713* | (2006.01) | |
| *A61K 45/06* | (2006.01) | |
| *A61K 47/54* | (2017.01) | |

(52) U.S. Cl.
CPC ........ *C12N 15/1136* (2013.01); *A61K 9/0048* (2013.01); *A61K 9/0051* (2013.01); *A61K 31/713* (2013.01); *A61K 45/06* (2013.01); *A61K 47/554* (2017.08); *C12N 2310/14* (2013.01); *C12N 2310/313* (2013.01); *C12N 2310/321* (2013.01); *C12N 2310/322* (2013.01); *C12N 2310/3515* (2013.01); *C12N 2320/31* (2013.01); *C12N 2320/32* (2013.01)

(58) Field of Classification Search
CPC ............ C12N 15/1136; C12N 2310/14; C12N 2310/315; C12N 2310/32; A01K 2207/05
See application file for complete search history.

(56) References Cited

U.S. PATENT DOCUMENTS

| | | |
|---|---|---|
| 3,687,808 A | 8/1972 | Merigan et al. |
| 4,201,860 A | 5/1980 | Naito et al. |
| 4,415,732 A | 11/1983 | Caruthers et al. |
| 4,426,330 A | 1/1984 | Sears |
| 4,897,355 A | 1/1990 | Eppstein et al. |
| 4,904,582 A | 2/1990 | Tullis |
| 4,958,013 A | 9/1990 | Letsinger |
| 5,023,243 A | 6/1991 | Tullis |
| 5,112,963 A | 5/1992 | Pieles et al. |
| 5,151,510 A | 9/1992 | Stec et al. |
| 5,188,897 A | 2/1993 | Suhadolnik et al. |
| 5,264,423 A | 11/1993 | Cohen et al. |
| 5,264,562 A | 11/1993 | Matteucci |
| 5,405,939 A | 4/1995 | Suhadolnik |
| 5,416,203 A | 5/1995 | Letsinger |
| 5,417,978 A | 5/1995 | Tani et al. |
| 5,432,272 A | 7/1995 | Benner |
| 5,453,496 A | 9/1995 | Caruthers et al. |
| 5,459,255 A | 10/1995 | Cook et al. |
| 5,466,786 A | 11/1995 | Buhr et al. |
| 5,470,967 A | 11/1995 | Huie et al. |
| 5,486,603 A | 1/1996 | Buhr |
| 5,489,677 A | 2/1996 | Sanghvi et al. |
| 5,495,009 A | 2/1996 | Matteucci et al. |
| 5,514,786 A | 5/1996 | Cook et al. |
| 5,532,130 A | 7/1996 | Alul |
| 5,534,259 A | 7/1996 | Zalipsky et al. |
| 5,556,948 A | 9/1996 | Tagawa et al. |
| 5,561,225 A | 10/1996 | Maddry et al. |
| 5,578,718 A | 11/1996 | Cook et al. |
| 5,580,731 A | 12/1996 | Chang et al. |
| 5,580,972 A | 12/1996 | Tu et al. |
| 5,587,469 A | 12/1996 | Cook et al. |
| 5,591,721 A | 1/1997 | Agrawal et al. |
| 5,591,722 A | 1/1997 | Montgomery et al. |
| 5,591,843 A | 1/1997 | Eaton |
| 5,594,121 A | 1/1997 | Froehler et al. |

(Continued)

FOREIGN PATENT DOCUMENTS

| | | |
|---|---|---|
| AU | 2004206255 B2 | 8/2004 |
| CN | 1 568 373 A | 1/2005 |

(Continued)

OTHER PUBLICATIONS

Blalock et al., Hammerhead ribozyme targeting connective tissue growth factor mRNA blocks transforming growth factor-beta mediated cell proliferation. Exp Eye Res. Jun. 2004;78(6):1127-36.

(Continued)

*Primary Examiner* — Brian Whiteman

(74) *Attorney, Agent, or Firm* — Wolf, Greenfield & Sacks, P.C.

(57) ABSTRACT

The present invention relates to ocular administration of sd-rxRNA and rxRNAori molecules.

19 Claims, 19 Drawing Sheets

Specification includes a Sequence Listing.

(56) References Cited

U.S. PATENT DOCUMENTS

| | | |
|---|---|---|
| 5,596,086 A | 1/1997 | Matteucci et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,614,617 A | 3/1997 | Cook et al. |
| 5,614,621 A | 3/1997 | Ravikumar et al. |
| 5,623,070 A | 4/1997 | Cook et al. |
| 5,625,050 A | 4/1997 | Beaton et al. |
| 5,633,360 A | 5/1997 | Bischofberger et al. |
| 5,643,889 A | 7/1997 | Suhadolnik et al. |
| 5,646,126 A | 7/1997 | Cheng et al. |
| 5,646,265 A | 7/1997 | McGee |
| 5,658,731 A | 8/1997 | Sproat et al. |
| 5,661,134 A | 8/1997 | Cook et al. |
| 5,663,312 A | 9/1997 | Chaturvedula |
| 5,670,633 A | 9/1997 | Cook et al. |
| 5,681,940 A | 10/1997 | Wang et al. |
| 5,681,941 A | 10/1997 | Cook et al. |
| 5,684,143 A | 11/1997 | Gryaznov et al. |
| 5,700,920 A | 12/1997 | Altmann et al. |
| RE546,678 | 4/1998 | Buhr et al. |
| 5,750,666 A | 5/1998 | Caruthers et al. |
| 5,770,209 A | 6/1998 | Grotendorst et al. |
| 5,770,713 A | 6/1998 | Imbach et al. |
| 5,777,153 A | 7/1998 | Lin et al. |
| 5,789,416 A | 8/1998 | Lum et al. |
| 5,792,847 A | 8/1998 | Buhr et al. |
| 5,808,023 A | 9/1998 | Sanghvi et al. |
| 5,817,781 A | 10/1998 | Swaminathan et al. |
| 5,830,430 A | 11/1998 | Unger et al. |
| 5,830,653 A | 11/1998 | Froehler et al. |
| 5,856,455 A | 1/1999 | Cook |
| 5,914,396 A | 6/1999 | Cook et al. |
| 5,945,521 A | 8/1999 | Just et al. |
| 5,948,767 A | 9/1999 | Scheule et al. |
| 5,969,116 A | 10/1999 | Martin |
| 5,976,567 A | 11/1999 | Wheeler et al. |
| 5,981,501 A | 11/1999 | Wheeler et al. |
| 5,986,083 A | 11/1999 | Dwyer et al. |
| 6,001,841 A | 12/1999 | Cook et al. |
| 6,005,096 A | 12/1999 | Matteucci et al. |
| 6,015,886 A | 1/2000 | Dale et al. |
| 6,020,475 A | 2/2000 | Capaldi et al. |
| 6,020,483 A | 2/2000 | Beckvermit et al. |
| 6,028,183 A | 2/2000 | Lin et al. |
| 6,033,910 A | 3/2000 | Monia et al. |
| 6,043,352 A | 3/2000 | Manoharan et al. |
| 6,051,699 A | 4/2000 | Ravikumar |
| 6,107,094 A | 8/2000 | Crooke |
| 6,111,085 A | 8/2000 | Cook et al. |
| 6,121,437 A | 9/2000 | Guzaev |
| 6,153,737 A | 11/2000 | Manoharan et al. |
| 6,207,819 B1 | 3/2001 | Manoharan et al. |
| 6,232,064 B1 | 5/2001 | Grotendorst et al. |
| 6,248,878 B1 | 6/2001 | Matulic-Adamic et al. |
| 6,271,358 B1 | 8/2001 | Manoharan et al. |
| 6,299,895 B1 | 10/2001 | Hammang et al. |
| 6,326,358 B1 | 12/2001 | Manoharan |
| 6,328,765 B1 | 12/2001 | Hardwick et al. |
| 6,331,313 B1 | 12/2001 | Wong et al. |
| 6,331,617 B1 | 12/2001 | Weeks et al. |
| 6,333,152 B1 | 12/2001 | Vogelstein et al. |
| 6,335,434 B1 | 1/2002 | Guzaev et al. |
| 6,355,787 B1 | 3/2002 | Beckvermit et al. |
| 6,358,931 B1 | 3/2002 | Cook et al. |
| 6,378,526 B1 | 4/2002 | Bowman et al. |
| 6,395,492 B1 | 5/2002 | Manoharan et al. |
| 6,397,849 B1 | 6/2002 | Bowman et al. |
| 6,399,754 B1 | 6/2002 | Cook |
| 6,410,702 B1 | 6/2002 | Swaminathan et al. |
| 6,420,549 B1 | 7/2002 | Cook et al. |
| 6,432,963 B1 | 8/2002 | Hisamichi et al. |
| 6,436,427 B1 | 8/2002 | Hammang et al. |
| 6,440,943 B1 | 8/2002 | Cook et al. |
| 6,444,806 B1 | 9/2002 | Veerapanani et al. |
| 6,455,586 B1 | 9/2002 | Kaplan et al. |
| 6,465,628 B1 | 10/2002 | Ravikumar et al. |
| 6,475,490 B1 | 11/2002 | Srivastava et al. |
| 6,476,205 B1 | 11/2002 | Buhr et al. |
| 6,492,129 B1 | 12/2002 | Grotendorst |
| 6,506,559 B1 | 1/2003 | Fire et al. |
| 6,528,631 B1 | 3/2003 | Cook et al. |
| 6,531,584 B1 | 3/2003 | Cook et al. |
| 6,562,618 B1 | 5/2003 | Tamatani et al. |
| 6,673,611 B2 | 1/2004 | Thompson et al. |
| 6,683,167 B2 | 1/2004 | Meteley et al. |
| 6,706,491 B1 | 3/2004 | Chang et al. |
| 6,753,321 B2 | 6/2004 | Kovesdi |
| 6,815,432 B2 | 11/2004 | Wheeler et al. |
| 6,849,726 B2 | 2/2005 | Usman et al. |
| 6,858,225 B2 | 2/2005 | Semple et al. |
| 6,923,833 B2 | 8/2005 | Wasielewski |
| 6,965,025 B2 | 11/2005 | Gaarde et al. |
| 7,041,824 B2 | 5/2006 | Bordon-Pallier et al. |
| 7,044,945 B2 | 5/2006 | Sand |
| 7,056,704 B2 | 6/2006 | Tuschl et al. |
| 7,078,196 B2 | 7/2006 | Tuschl et al. |
| 7,108,721 B2 | 9/2006 | Huckle et al. |
| 7,115,390 B1 | 10/2006 | Grotendorst et al. |
| 7,148,342 B2 | 12/2006 | Tolentino et al. |
| 7,205,297 B2 | 4/2007 | Beauchamp et al. |
| 7,309,361 B2 | 12/2007 | Wasielewski |
| 7,348,155 B2 | 3/2008 | Kostenis et al. |
| 7,358,351 B2 | 4/2008 | St. Croix et al. |
| 7,384,634 B2 | 6/2008 | Grotendorst et al. |
| 7,393,932 B2 | 7/2008 | Carson-Walter et al. |
| 7,402,660 B2 | 7/2008 | St. Croix et al. |
| 7,405,274 B2 | 7/2008 | Lin et al. |
| 7,432,250 B2 | 10/2008 | Crooke |
| 7,462,602 B2 | 12/2008 | Schultz et al. |
| 7,504,493 B2 | 3/2009 | Velculescu et al. |
| 7,521,431 B2 | 4/2009 | Reich et al. |
| 7,534,774 B2 | 5/2009 | Sosnowski et al. |
| 7,538,095 B2 | 5/2009 | Fire et al. |
| 7,560,438 B2 | 7/2009 | Fire et al. |
| 7,579,186 B1 | 8/2009 | Sakamoto et al. |
| 7,595,387 B2 | 9/2009 | Leake et al. |
| 7,615,083 B2 | 11/2009 | Wasielewski et al. |
| 7,622,633 B2 | 11/2009 | Fire et al. |
| 7,629,321 B2 | 12/2009 | Crooke |
| 7,655,785 B1 | 2/2010 | Bentwich |
| 7,687,616 B1 | 3/2010 | Bentwich et al. |
| 7,695,902 B2 | 4/2010 | Crooke |
| 7,709,630 B2 | 5/2010 | Gaarde et al. |
| 7,745,608 B2 | 6/2010 | Manoharan et al. |
| 7,750,144 B2 | 7/2010 | Zamore et al. |
| 7,777,022 B2 | 8/2010 | Bentwich et al. |
| 7,786,290 B2 | 8/2010 | Woppmann et al. |
| 7,789,841 B2 | 9/2010 | Huckle et al. |
| 7,829,693 B2 | 11/2010 | Kreutzer et al. |
| 7,833,989 B2 | 11/2010 | Khvorova et al. |
| 7,838,507 B2 | 11/2010 | Shepard et al. |
| 8,110,674 B2 | 2/2012 | Manoharan et al. |
| 8,202,845 B2 | 6/2012 | Drumm et al. |
| 8,227,444 B2 | 7/2012 | Dejneka |
| 8,258,105 B2 | 9/2012 | Siwkowski et al. |
| 8,263,569 B2 | 9/2012 | Baulcombe et al. |
| 8,268,794 B2 | 9/2012 | Nakajima et al. |
| 8,293,719 B2 | 10/2012 | De Fougerolles et al. |
| 8,383,600 B2 | 2/2013 | Czech et al. |
| 8,470,792 B2 | 6/2013 | Frost et al. |
| 8,664,189 B2 | 3/2014 | Khvorova et al. |
| 8,796,443 B2 | 8/2014 | Khvorova et al. |
| 8,815,818 B2 | 8/2014 | Samarsky et al. |
| 9,074,211 B2 | 7/2015 | Woolf et al. |
| 9,080,171 B2 | 7/2015 | Khvorova et al. |
| 9,095,504 B2 | 8/2015 | Libertine et al. |
| 9,175,289 B2 | 11/2015 | Khvorova et al. |
| 9,222,092 B2 | 12/2015 | Giese et al. |
| 9,303,259 B2 | 4/2016 | Khvorova et al. |
| 9,340,786 B2 | 5/2016 | Khvorova et al. |
| 9,493,774 B2 | 11/2016 | Kamens |
| 9,745,574 B2 | 8/2017 | Woolf et al. |

(56) References Cited

U.S. PATENT DOCUMENTS

| | | |
|---|---|---|
| 9,938,530 B2 | 4/2018 | Khvorova et al. |
| 9,963,702 B2 | 5/2018 | Khvorova et al. |
| 10,041,073 B2 | 8/2018 | Khvorova et al. |
| 10,131,904 B2 | 11/2018 | Pavco et al. |
| 10,138,485 B2 | 11/2018 | Khvorova et al. |
| 10,167,471 B2 | 1/2019 | Kamens et al. |
| 10,184,124 B2 | 1/2019 | Libertine et al. |
| 10,240,149 B2 | 3/2019 | Khvorova et al. |
| 10,300,027 B2 | 5/2019 | Levis et al. |
| 2002/0086013 A1 | 7/2002 | King |
| 2002/0132788 A1 | 9/2002 | Lewis et al. |
| 2002/0147332 A1 | 10/2002 | Kaneko et al. |
| 2002/0160393 A1 | 10/2002 | Symonds et al. |
| 2002/0162126 A1 | 10/2002 | Beach et al. |
| 2003/0004325 A1 | 1/2003 | Cook et al. |
| 2003/0077829 A1 | 4/2003 | MacLachlan |
| 2003/0108923 A1 | 6/2003 | Tuschl et al. |
| 2003/0113816 A1 | 6/2003 | Weitz et al. |
| 2003/0139585 A1 | 7/2003 | Uhlmann et al. |
| 2003/0144223 A1 | 7/2003 | Gaarde et al. |
| 2003/0153524 A1 | 8/2003 | Hinton et al. |
| 2003/0157030 A1 | 8/2003 | Davis et al. |
| 2003/0158403 A1 | 8/2003 | Manoharan et al. |
| 2003/0166282 A1 | 9/2003 | Brown et al. |
| 2003/0175276 A1 | 9/2003 | Thorpe et al. |
| 2003/0180300 A1 | 9/2003 | Grotendorst et al. |
| 2004/0005319 A1 | 1/2004 | Grotendorst et al. |
| 2004/0009938 A1 | 1/2004 | Manoharan et al. |
| 2004/0014956 A1 | 1/2004 | Woolf et al. |
| 2004/0014957 A1 | 1/2004 | Eldrup et al. |
| 2004/0018999 A1 | 1/2004 | Beach et al. |
| 2004/0054155 A1 | 3/2004 | Woolf et al. |
| 2004/0092450 A1 | 5/2004 | Grotendorst et al. |
| 2004/0137471 A1 | 7/2004 | Vickers et al. |
| 2004/0167090 A1 | 8/2004 | Monahan et al. |
| 2004/0171033 A1 | 9/2004 | Baker et al. |
| 2004/0180351 A1 | 9/2004 | Giese et al. |
| 2004/0192629 A1 | 9/2004 | Xu et al. |
| 2004/0204377 A1 | 10/2004 | Rana |
| 2004/0229233 A1 | 11/2004 | Aburatani et al. |
| 2004/0229266 A1 | 11/2004 | Tuschl et al. |
| 2004/0235031 A1 | 11/2004 | Schultz et al. |
| 2004/0241845 A1 | 12/2004 | Desgroseillers et al. |
| 2004/0248839 A1 | 12/2004 | Kowalik |
| 2004/0259247 A1 | 12/2004 | Tuschl et al. |
| 2005/0020521 A1 | 1/2005 | Rana |
| 2005/0032733 A1 | 2/2005 | McSwiggen et al. |
| 2005/0059629 A1 | 3/2005 | Gaarde et al. |
| 2005/0080246 A1 | 4/2005 | Allerson et al. |
| 2005/0107325 A1 | 5/2005 | Manoharan et al. |
| 2005/0118625 A1 | 6/2005 | Mounts |
| 2005/0119202 A1 | 6/2005 | Kreutzer et al. |
| 2005/0142535 A1 | 6/2005 | Damha et al. |
| 2005/0181382 A1 | 8/2005 | Zamore et al. |
| 2005/0222066 A1 | 10/2005 | Richards et al. |
| 2005/0239731 A1 | 10/2005 | McSwiggen et al. |
| 2005/0245474 A1 | 11/2005 | Baker et al. |
| 2005/0246794 A1 | 11/2005 | Khvorova et al. |
| 2005/0255487 A1 | 11/2005 | Khvorova et al. |
| 2006/0009409 A1 | 1/2006 | Woolf |
| 2006/0035344 A1 | 2/2006 | Pachuk et al. |
| 2006/0069050 A1 | 3/2006 | Rana |
| 2006/0142228 A1 | 6/2006 | Ford et al. |
| 2006/0160133 A1 | 7/2006 | Czech et al. |
| 2006/0178324 A1 | 8/2006 | Hadwiger et al. |
| 2006/0178327 A1 | 8/2006 | Yeung |
| 2006/0211642 A1 | 9/2006 | McSwiggen et al. |
| 2006/0234970 A1 | 10/2006 | Jimenez |
| 2007/0020623 A1 | 1/2007 | Petersohn et al. |
| 2007/0032441 A1 | 2/2007 | McSwiggen et al. |
| 2007/0054271 A1 | 3/2007 | Polyak et al. |
| 2007/0066549 A1 | 3/2007 | Freier et al. |
| 2007/0087989 A1 | 4/2007 | Huang et al. |
| 2007/0166734 A1 | 7/2007 | Bhat et al. |
| 2007/0173476 A1 | 7/2007 | Leake et al. |
| 2007/0231392 A1 | 10/2007 | Wagner et al. |
| 2007/0269889 A1 | 11/2007 | Leake et al. |
| 2008/0070856 A1 | 3/2008 | Kreutzer et al. |
| 2008/0071068 A1 | 3/2008 | Oba et al. |
| 2008/0085869 A1 | 4/2008 | Yamada et al. |
| 2008/0107694 A1 | 5/2008 | Trogden et al. |
| 2008/0108583 A1 | 5/2008 | Feinstein et al. |
| 2008/0152654 A1 | 6/2008 | Reich |
| 2008/0193443 A1 | 8/2008 | Beskrovnaya et al. |
| 2008/0254487 A1 | 10/2008 | Klaus et al. |
| 2008/0286866 A1 | 11/2008 | Quay et al. |
| 2008/0300147 A1 | 12/2008 | Chegini et al. |
| 2008/0311040 A1 | 12/2008 | Berry et al. |
| 2009/0023216 A1 | 1/2009 | Woolf |
| 2009/0069623 A1 | 3/2009 | Oh |
| 2009/0131360 A1 | 5/2009 | Woolf et al. |
| 2009/0156524 A1 | 6/2009 | Feinstein et al. |
| 2009/0162365 A1 | 6/2009 | Feinstein et al. |
| 2009/0202520 A1 | 8/2009 | Lupher et al. |
| 2009/0208564 A1 | 8/2009 | Li et al. |
| 2009/0298916 A1 | 12/2009 | Kauppinen et al. |
| 2010/0010082 A1 | 1/2010 | Chong et al. |
| 2010/0035964 A1 | 2/2010 | Gaarde et al. |
| 2010/0069620 A1 | 3/2010 | Zon |
| 2010/0130595 A1 | 5/2010 | Dean et al. |
| 2010/0136695 A1 | 6/2010 | Woolf |
| 2010/0158907 A1 | 6/2010 | Grotendorst et al. |
| 2010/0190838 A1 | 7/2010 | Grotendorst |
| 2010/0286234 A1 | 11/2010 | Elmen et al. |
| 2010/0286236 A1 | 11/2010 | Schlingensiepen et al. |
| 2011/0021605 A1 | 1/2011 | Schulte et al. |
| 2011/0039914 A1 | 2/2011 | Pavco et al. |
| 2011/0054004 A1 | 3/2011 | Mustoe et al. |
| 2011/0117053 A1 | 5/2011 | Comeau et al. |
| 2011/0237522 A1 | 9/2011 | Khvorova et al. |
| 2011/0237648 A1 | 9/2011 | Khvorova et al. |
| 2011/0251258 A1 | 10/2011 | Samarsky et al. |
| 2011/0263680 A1 | 10/2011 | Khvorova et al. |
| 2011/0268761 A1 | 11/2011 | Levis et al. |
| 2011/0294869 A1 | 12/2011 | Petersen |
| 2012/0016005 A1 | 1/2012 | Samarsky et al. |
| 2012/0040459 A1 | 2/2012 | Khvorova et al. |
| 2012/0059046 A1 | 3/2012 | Woolf et al. |
| 2012/0065243 A1 | 3/2012 | Woolf et al. |
| 2013/0131141 A1 | 5/2013 | Khvorova et al. |
| 2013/0197055 A1 | 8/2013 | Kamens et al. |
| 2014/0018527 A1 | 1/2014 | Jiménez et al. |
| 2014/0072613 A1 | 3/2014 | Lander et al. |
| 2014/0113950 A1 | 4/2014 | Khvorova et al. |
| 2014/0187610 A1 | 7/2014 | Seeley |
| 2014/0315974 A1 | 10/2014 | Khvorova et al. |
| 2014/0364482 A1 | 12/2014 | Khvorova et al. |
| 2015/0057362 A1 | 2/2015 | Levis et al. |
| 2016/0115484 A1 | 4/2016 | Woolf et al. |
| 2016/0130578 A1 | 5/2016 | Khvorova et al. |
| 2016/0244765 A1 | 8/2016 | Khvorova et al. |
| 2016/0304873 A1 | 10/2016 | Wolfson et al. |
| 2016/0304875 A1 | 10/2016 | Cauwenbergh et al. |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0009239 A1 | 1/2017 | Khvorova et al. |
| 2017/0022501 A1 | 1/2017 | Dean et al. |
| 2017/0051288 A1 | 2/2017 | Byrne et al. |
| 2017/0051290 A1 | 2/2017 | Byrne et al. |
| 2017/0067056 A1 | 3/2017 | Khvorova et al. |
| 2017/0137823 A1 | 5/2017 | Kamens et al. |
| 2018/0030451 A1 | 2/2018 | Cauwenbergh |
| 2018/0155718 A1 | 6/2018 | Woolf et al. |
| 2018/0195066 A1 | 7/2018 | Byrne et al. |
| 2018/0195072 A1 | 7/2018 | Cardia et al. |
| 2018/0263925 A1 | 9/2018 | Cauwenbergh et al. |
| 2018/0327748 A1 | 11/2018 | Khvorova et al. |
| 2018/0371464 A1 | 12/2018 | Khvorova et al. |
| 2019/0029974 A1 | 1/2019 | Cauwenbergh et al. |
| 2019/0048341 A1 | 2/2019 | Cardia et al. |
| 2019/0161757 A1 | 5/2019 | Khvorova et al. |

(56) References Cited

U.S. PATENT DOCUMENTS

| | | |
|---|---|---|
| 2019/0169608 A1 | 6/2019 | Pavco et al. |
| 2019/0211337 A1 | 7/2019 | Khvorova et al. |
| 2019/0218557 A1 | 7/2019 | Kamens et al. |

FOREIGN PATENT DOCUMENTS

| | | |
|---|---|---|
| CN | 101160138 A | 4/2008 |
| EP | 0 552 766 A2 | 7/1993 |
| EP | 1 214 945 A2 | 6/2002 |
| EP | 1 144 623 B9 | 3/2003 |
| EP | 1 352 061 B1 | 10/2003 |
| EP | 0 928 290 B9 | 3/2005 |
| EP | 1 407 044 B1 | 9/2007 |
| EP | 1 605 978 B1 | 9/2010 |
| JP | H09-505057 A | 5/1997 |
| JP | 2003-501348 A | 1/2003 |
| JP | 2003-516716 | 5/2003 |
| JP | 2004-500846 | 1/2004 |
| JP | 4 095 895 B2 | 9/2004 |
| JP | 2004-527210 | 9/2004 |
| JP | 2004-533825 | 11/2004 |
| JP | 2005-512976 | 5/2005 |
| JP | 2005-519881 A | 7/2005 |
| JP | 2006-516288 A | 6/2006 |
| JP | 2007-525169 A | 9/2007 |
| JP | 2007-531520 A | 11/2007 |
| JP | 2009-519033 | 5/2009 |
| JP | 2009-540011 | 11/2009 |
| JP | 2010-501188 A | 1/2010 |
| JP | 2013-523650 A | 6/2013 |
| WO | WO 92/03464 A1 | 3/1992 |
| WO | WO 94/23028 A2 | 10/1994 |
| WO | WO 95/11910 A1 | 5/1995 |
| WO | WO 95/13827 A1 | 5/1995 |
| WO | WO 95/22553 A1 | 8/1995 |
| WO | WO 95/23162 A1 | 8/1995 |
| WO | WO 96/40964 A2 | 12/1996 |
| WO | WO 00/66631 A1 | 11/2000 |
| WO | WO 01/85941 A2 | 11/2001 |
| WO | WO 02/10217 A2 | 2/2002 |
| WO | WO 02/053773 A2 | 7/2002 |
| WO | WO 02/053774 A2 | 7/2002 |
| WO | WO 03/012052 A2 | 2/2003 |
| WO | WO 03/049773 A1 | 6/2003 |
| WO | WO 03/053340 A2 | 7/2003 |
| WO | WO 2003/064626 A2 | 8/2003 |
| WO | WO 2003/087367 A2 | 10/2003 |
| WO | WO 2003/087368 A2 | 10/2003 |
| WO | WO 2004/064760 A2 | 8/2004 |
| WO | WO 2004/065600 A2 | 8/2004 |
| WO | WO 2004/065601 A2 | 8/2004 |
| WO | WO 2004/090105 A2 | 10/2004 |
| WO | WO 2005/019430 A2 | 3/2005 |
| WO | WO 2005/019453 A2 | 3/2005 |
| WO | WO 2005/079533 A2 | 9/2005 |
| WO | WO 2005/097992 A2 | 10/2005 |
| WO | WO 2006/019430 A2 | 2/2006 |
| WO | WO 2006/039656 A2 | 4/2006 |
| WO | WO 2006/065601 A2 | 6/2006 |
| WO | WO 2006/069037 A1 | 6/2006 |
| WO | WO 2006/128141 A2 | 11/2006 |
| WO | WO 2007/030167 A1 | 3/2007 |
| WO | WO 2007/069068 A2 | 6/2007 |
| WO | WO 2007/089607 A2 | 8/2007 |
| WO | WO 2007/146953 A2 | 12/2007 |
| WO | WO 2008/024983 A2 | 2/2008 |
| WO | WO 2008/036825 A2 | 3/2008 |
| WO | WO 2008/109353 A1 | 9/2008 |
| WO | WO 2008/125908 A2 | 10/2008 |
| WO | WO 2009/020344 A2 | 2/2009 |
| WO | WO 2009/029688 A3 | 3/2009 |
| WO | WO 2009/029690 A1 | 3/2009 |
| WO | WO 2009/044392 A2 | 4/2009 |
| WO | WO 2009/078685 A2 | 6/2009 |
| WO | WO 2009/090639 A2 | 7/2009 |
| WO | WO 2009/102427 A2 | 8/2009 |
| WO | WO 2010/006237 A2 | 1/2010 |
| WO | WO 2010/006973 A2 | 1/2010 |
| WO | WO 2010/011346 A2 | 1/2010 |
| WO | WO 2010/027830 A2 | 3/2010 |
| WO | WO 2010/027831 A1 | 3/2010 |
| WO | WO 2010/027832 A1 | 3/2010 |
| WO | WO 2010/033246 A1 | 3/2010 |
| WO | WO 2010/033247 A2 | 3/2010 |
| WO | WO 2010/033248 A2 | 3/2010 |
| WO | WO 2010/042281 A2 | 4/2010 |
| WO | WO 2010/059226 A2 | 5/2010 |
| WO | WO 2011/109698 A1 | 9/2011 |
| WO | WO 2012/106508 A1 | 8/2012 |
| WO | WO 2017/048824 A1 | 3/2017 |

OTHER PUBLICATIONS

Cardia et al., Self-Delivering RNAi Compounds. Drug Delivery Technology. Sep. 2010;10(7):1-4.

Chiu et al., siRNA function in RNAi: a chemical modification analysis. RNA. Sep. 2003;9(9):1034-48.

Crooke et al., Silencing of P2Y2 receptor delays Ap4A-corneal re-epithelialization process. Mol Vis. Jun. 11, 2009;15:1169-78.

Gaudana et al., Ocular drug delivery. AAPS J. Sep. 2010;12(3):348-60. doi: 10.1208/s12248-010-9183-3. Epub May 1, 2010.

Hartong et al., Retinitis pigmentosa. Lancet. Nov. 18, 2006;368(9549):1795-809.

Hudziak et al., Resistance of morpholino phosphorodiamidate oligomers to enzymatic degradation. Antisense Nucleic Acid Drug Dev. 1996 Winter;6(4):267-72.

Patel et al., Ocular drug delivery systems: An overview. World J Pharmacol. 2013;2(2):47-64. Author manuscript.

Ramamurthi et al., Pathogenesis, clinical features and management of recurrent corneal erosions. Eye (Lond). Jun. 2006;20(6):635-44. Epub Jul. 15, 2005.

Rose et al., Functional polarity is introduced by Dicer processing of short substrate RNAs. Nucleic Acids Res. Jul. 26, 2005;33(13):4140-56. Print 2005.

Wasmuth et al., Topical antisense-oligonucleotides targeting IFN-gamma mRNA improve incidence and severity of herpetic stromal keratitis by cytokine specific and sequence unspecific effects. Graefes Arch Clin Exp Ophthalmol. Mar. 2008;246(3):443-51. Epub Nov. 21, 2007.

International Search Report and Written Opinion dated May 31, 2011 in connection with PCT/US2011/029849.

International Preliminary Report on Patentability dated Oct. 4, 2012 in connection with PCT/US2011/029849.

Extended European Search Report dated May 6, 2015 in connection with EP11760245.8.

[No Author Listed] RedChip Small-Cap Investor Conference. RXI Pharmaceuticals (Nasdaq RXII). Jun. 16, 2009 Presentation. 22 Pages.

[No Author Listed] Rxi Pharmaceucticals Completes Apthera Acquisition. Press Release. BusinessWire. Apr. 14, 2011. 2 pages.

[No Author Listed] Rxi Pharmaceutical Corporation. Ex 99.1. OTC: RXII. Mar. 2013. 38 pages.

[No Author Listed], RXi Pharmaceuticals Presents Self-Delivering RNAi Data at Scar Club Meeting in France. Drugs.com. Mar. 26, 2010. http://www.drugs.com/clinical_trials/rxi-pharmaceuticals-presents-self-delivering-rnai-data-scar-club-meeting-france-9093.html [last accessed Aug. 19, 2014].

Alahari et al., Inhibition of expression of the multidrug resistance-associated P-glycoprotein of by phosphorothioate and 5′ cholesterol-conjugated phosphorothioate antisense oligonucleotides. Mol Pharmacol. Oct. 1996;50(4):808-19.

Aleckovic et al., RNAi at Oxford. J RNAi Gene Silencing. May 27, 2008;4(1):266-8.

Aouadi et al., Orally delivered siRNA targeting macrophage Map4k4 suppresses systemic inflammation. Nature. Apr. 30, 2009;458(7242):1180-4. doi: 10.1038/nature07774.

(56) References Cited

OTHER PUBLICATIONS

Augustyns et al., Incorporation of hexose nucleoside analogues into oligonucleotides: synthesis, base-pairing properties and enzymatic stability. Nucleic Acids Res. Sep. 25, 1992;20(18):4711-6.
Baigude et al., Design and creation of new nanomaterials for therapeutic RNAi. ACS Chem Biol. Apr. 24, 2007;2(4):237-41.
Bergan et al., Electroporation enhances c-myc antisense oligodeoxynucleotide efficacy. Nucleic Acids Res. Jul. 25, 1993;21(15):3567-73.
Bjerke et al., Histone H3.3. mutations drive pediatric glioblastoma through upregulation of MYCN. Cancer Discov. May 2013;3(5):512-9.
Blalock et al., Connective tissue growth factor expression and action in human corneal fibroblast cultures and rat corneas after photorefractive keratectomy. Invest Ophthalmol Vis Sci. May 2003;44(5):1879-87.
Boutorin et al., Synthesis of alkylating oligonucleotide derivatives containing cholesterol or phenazinium residues at their 3'-terminus and their interaction with DNA within mammalian cells. FEBS Lett. Aug. 28, 1989;254(1-2):129-32.
Braasch et al., RNA interference in mammalian cells by chemically-modified RNA. Biochemistry. Jul. 8, 2003;42(26):7967-75.
Brown et al., Light at the end of the tunnel. J RNAi Gene Silencing. Jul. 28, 2006;2(2):175-7.
Bunnell et al., Targeted delivery of antisense oligonucleotides by molecular conjugates. Somat Cell Mol Genet. Nov. 1992;18(6):559-69.
Byrne et al., Novel hydrophobically modified asymmetric RNAi compounds (sd-rxRNA) demonstrate robust efficacy in the eye. J Ocul Pharmacol Ther. Dec. 2013;29(10):855-64. doi: 10.1089/jop.2013.0148. Epub Nov. 1, 2013.
Cardia et al., Novel self-delivering RNAi compounds with enhanced cellular updatake and distribution properties. Keystone RNAi Silencing Conference. Jan. 14-19, 2010. Poster. 1 Page.
Castera et al., MDM2 as a modifier gene in retinoblastoma. J Natl Cancer Inst. Dec. 1, 2010;102(23):1805-8. doi: 10.1093/jnci/djq416. Epub Nov. 4, 2010.
Chen et al., Nanoparticles modified with tumor-targeting scFv deliver siRNA and miRNA for cancer therapy. Mol Ther. Sep. 2010;18(9):1650-6. doi: 10.1038/mt.2010.136. Epub Jul. 6, 2010.
Cheng et al., Connective tissue growth factor is a biomarker and mediator of kidney allograft fibrosis. Am J Transplant. Oct. 2006;6(10):2292-306. Epub Aug. 4, 2006.
Chintagumpala et al., Retinoblastoma: review of current management. Oncologist. Oct. 2007;12(10):1237-46.
Choi et al., Control of scarring in adult wounds using antisense transforming growth factor-beta 1 oligodeoxynucleotides. Immunol Cell Biol. Apr. 1996;74(2):144-50.
Choung et al., Chemical modification of siRNAs to improve serum stability without loss of efficacy. Biochem Biophys Res Commun. Apr. 14, 2006;342(3):919-27.
Chu et al., Potent RNAi by short RNA triggers. RNA. 2008;14:1714-9.
Cicha et al., Connective tissue growth factor is overexpressed in complicated atherosclerotic plaques and induces mononuclear cell chemotaxis in vitro. Arterioscler Thromb Vasc Biol. May 2005;25(5):1008-13. Epub Mar. 10, 2005.
Collins et al., A small interfering RNA screen for modulators of tumor cell motility identifies MAP4K4 as a promigratory kinase. Proc Natl Acad Sci U S A. Mar. 7, 2006; 103(10): 3775-3780.
Cordeiro et al., Novel antisense oligonucleotides targeting TGF-beta inhibit in vivo scarring and improve surgical outcome. Gene Ther. Jan. 2003;10(1):59-71.
Czauderna et al., ., Structural variations and stabilising modifications of synthetic siRNAs in mammalian cells. Nucleic Acids Res. Jun. 1, 2003;31(11):2705-16.
Daniels et al., Imatinib mesylate inhibits the profibrogenic activity of TGF-beta and prevents bleomycin-mediated lung fibrosis. J Clin Invest. Nov. 2004;114(9):1308-16.

De Smidt et al., Association of antisense oligonucleotides with lipoproteins prolongs the plasma half-life and modifies the tissue distribution. Nucleic Acids Res. Sep. 11, 1991;19(17):4695-700.
Debart et al., Chemical modifications to improve the cellular uptake of oligonucleotides. Curr Top Med Chem. 2007;7(7):727-37.
Distler et al., Imatinib mesylate reduces production of extracellular matrix and prevents development of experimental dermal fibrosis. Arthritis Rheum. Jan. 2007;56(1):311-22.
Dykxhoorn et al., The silent treatment: siRNAs as small molecule drugs. Gene Ther. Mar. 2006;13(6):541-52. Review.
Dziadzio et al., N-terminal connective tissue growth factor is a marker of the fibrotic phenotype in scleroderma. QJM. Jul. 2005;98(7):485-92. Epub Jun. 13, 2005.
Elbashir et al., Duplexes of 21-nucleotide RNAs mediate RNA interference in cultured mammalian cells. Nature. May 24, 2001;411(6836):494-8.
Elbashir et al., Functional anatomy of siRNAs for mediating efficient RNAi in *Drosophila melanogaster* embryo lysate. EMBO J. Dec. 3, 2001;20(23):6877-88.
Fedorov et al., Off-target effects by siRNA can induce toxic phenotype. RNA. Jul. 2006;12(7):1188-96. Epub May 8, 2006.
Ferentz et al., Disulfide-crosslinked oligonucleotides. Journal of the American Chemical Society. 1991;113 (10): 4000-4002.
Ferguson et al., Scar-free healing: from embryonic mechanisms to adult therapeutic intervention. Philos Trans R Soc Lond B Biol Sci. May 29, 2004;359(1445):839-50.
Fisher et al., Intracellular disposition and metabolism of fluorescently-labeled unmodified and modified oligonucleotides microinjected into mammalian cells. Nucleic Acids Res. Aug. 11, 1993;21(16):3857-65.
Futagami et al., Wound healing involves induction of cyclooxygenase-2 expression in rat skin. Lab Invest. Nov. 2002;82(11):1503-13.
Genbank Submission; NCBI, Accession No. NM_004834; Han et al.; Feb. 9, 2011.
Ginobbi et al., Folic acid-polylysine carrier improves efficacy of c-myc antisense oligodeoxynucleotides on human melanoma (M14) cells. Anticancer Res. Jan.-Feb. 1997;17(1A):29-35.
Gressner et al., Connective tissue growth factor in serum as a new candidate test for assessment of hepatic fibrosis. Clin Chem. Sep. 2006;52(9):1815-7. Epub Jul. 20, 2006.
Gressner et al., Connective tissue growth factor: a fibrogenic master switch in fibrotic liver diseases. Liver Int. Sep. 2008;28(8):1065-79. doi:10.1111/j.1478-3231.2008.01826.x.
Hagigit et al., Ocular antisense oligonucleotide delivery by cationic nanoemulsion for improved treatment of ocular neovascularization: an in-vivo study in rats and mice. J Control Release. Jun. 10, 2012;160(2):225-31. doi: 10.1016/j.jconrel.2011.11.022. Epub Nov. 27, 2011.
Hao et al., Electrically assisted delivery of macromolecules into the corneal epithelium. Exp Eye Res. Dec. 2009;89(6):934-41. doi: 10.1016/j.exer.2009.08.001. Epub Aug. 12, 2009.
Hao et al., Gene delivery to cornea. Brain Res Bull. Feb. 15, 2010;81(2-3):256-61. doi: 10.1016/j.brainresbull.2009.06.011. Epub Jun. 26, 2009. Review.
Hinton et al., Novel growth factors involved in the pathogenesis of proliferative vitreoretinopathy. Eye (Lond). Jul. 2002;16(4):422-8.
Holmes et al., Syntheses and oligonucleotide incorporation of nucleoside analogues containing pendant imidazolyl or amino functionalities—the search for sequence-specific artificial ribonucleases. Eur J Org Chem. Apr. 13, 2005;5171-83. DOI; 10.1002/ejoc.20050413.
Hosseini et al., Efficacy of a phosphorodiamidate morpholino oligomer antisense compound in the inhibition of corneal transplant rejection in a rat cornea transplant model. J Ocul Pharmacol Ther. Apr. 2012;28(2):194-201. doi: 10.1089/jop.2011.0135. Epub Dec. 7, 2011.
Ito et al., Expression of connective tissue growth factor in human renal fibrosis. Kidney Int. Apr. 1998;53(4):853-61.
Ito et al., Kinetics of connective tissue growth factor expression during experimental proliferative glomerulonephritis. J Am Soc Nephrol. Mar. 2001;12(3):472-84.

(56) References Cited

OTHER PUBLICATIONS

Jackson et al., Position-specific chemical modification of siRNAs reduces "off-target" transcript silencing. RNA. Jul. 2006;12(7):1197-1205. Epub May 8, 2006.

Kamens et al., Novel, chemically modified RNAi compounds with improved potency, stability and specificity. Keystone RNAi Silencing: Mechanism, Biology and Application Conference. Jan. 14-19, 2010. Poster. 1 Page.

Kim et al., Synthetic dsRNA Dicer substrates enhance RNAi potency and efficacy. Nat Biotechnol. Feb. 2005;23(2):222-6. Epub Dec. 26, 2004.

Kim et al., Systemic and specific delivery of small interfering RNAs to the liver mediated by apolipoprotein A-I. Mol Ther. Jun. 2007;15(6):1145-52. Epub Apr. 17, 2007.

Koitabashi et al., Plasma connective tissue growth factor is a novel potential biomarker of cardiac dysfunction in patients with chronic heart failure. Eur J Heart Fail. Apr. 2008;10(4):373-9. doi: 10.1016/j.ejheart.2008.02.011.

Kraynack et al., Small interfering RNAs containing full 2'-O-methylribonucleotide-modified sense strands display Argonaute2/eIF2C2-dependent activity. RNA. Jan. 2006;12(1):163-76. Epub Nov. 21, 2005.

Kryger et al., Temporal expression of the transforming growth factor-Beta pathway in the rabbit ear model of wound healing and scarring. J Am Coll Surg. Jul. 2007; 205(1): 78-88.

Kubo et al., Modified 27-nt dsRNAs with dramatically enhanced stability in serum and long-term RNAi activity. Oligonucleotides. 2007 Winter;17(4):445-64.

Layzer et al., In vivo activity of nuclease-resistant siRNAs. RNA. May 2004;10(5):766-71.

Leask et al., Connective tissue growth factor (CTGF, CCN2) gene regulation: a potent clinical bio-marker of fibroproliferative disease? J Cell Commun Signal. Jun. 2009;3(2):89-94. Epub Jan. 21, 2009.

Leask et al., Insights into the molecular mechanism of chronic fibrosis: the role of connective tissue growth factor in scleroderma. J Invest Dermatol. Jan. 2004;122(1):1-6.

Lee et al., Contributions of 3'-overhang to the dissociation of small interfering RNAs from the PAZ domain: molecular dynamics simulation study. J Mol Graph Model. Mar. 2007;25(6):784-93. Epub Jul. 11, 2006.

Letsinger et al., Cholesteryl-conjugated oligonucleotides: synthesis, properties, and activity as inhibitors of replication of human immunodeficiency virus in cell culture. Proc Natl Acad Sci U S A. Sep. 1989;86(17):6553-6.

Leuschner et al., Cleavage of the siRNA passenger strand during RISC assembly in human cells. EMBO Reports 2006;7(3):314-20.

Li et al., A new approach of delivering siRNA to the cornea and its application for inhibiting herpes simplex keratitis. Curr Mol Med. 2014;14(9):1215-25. Database Embase Abstract only. Accession No. EMB-2015893176.

Li et al., Inhibition of connective tissue growth factor by siRNA prevents liver fibrosis in rats. J Gene Med. Jul. 2006;8(7):889-900.

Li et al., Surface-modified LPD nanoparticles for tumor targeting. Ann N Y Acad Sci. Oct. 2006;1082:1-8.

Liu et al., Role of connective tissue growth factor in experimental radiation nephropathy in rats. Chin Med J (Engl). Oct. 5, 2008;121(19):1925-31.

Luo et al., Inhibition of connective tissue growth factor by small interfering RNA prevents renal fibrosis in rats undergoing chronic allograft nephropathy. Transplant Proc. Sep. 2008;40(7):2365-9. doi:10.1016/j.transproceed.2008.07.100.

Lynch et al., Role of platelet-derived growth factor in wound healing: synergistic effects with other growth factors. Proc Natl Acad Sci U S A. Nov. 1987;84(21):7696-700.

Macrae et al., Structure of Dicer and mechanistic implications for RNAi. Cold Spring Harb Symp Quant Biol. 2006;71:73-80.

Manoharan et al., Chemical modifications to improve uptake and bioavailability of antisense oligonucleotides. Ann N Y Acad Sci. Oct. 28, 1992;660:306-9.

Manoharan, Oligonucleotide conjugates as potential antisense drugs with improved uptake, biodistribution, targeted delivery, and mechanism of action. Antisense Nucleic Acid Drug Dev. Apr. 2002;12(2):103-28.

Martins et al., Sterol side chain length and structure affect the clearance of chylomicron-like lipid emulsions in rats and mice. J Lipid Res. Feb. 1998;39(2):302-12.

Mathews et al., Incorporating chemical modification constraints into a dynamic programming algorithm for prediction of RNA secondary structure. Proc Natl Acad Sci U S A. May 11, 2004;101(19):7287-92. Epub May 3, 2004.

McEvoy et al., Analysis of MDM2 and MDM4 single nucleotide polymorphisms, mRNA splicing and protein expression in retinoblastoma. PLoS One. 2012;7(8):e42739. doi: 10.1371/journal.pone.0042739. Epub Aug. 20, 2012.

Mescalchin et al., Cellular uptake and intracellular release are major obstacles to the therapeutic application of siRNA: novel options by phosphorothioate-stimulated delivery. Expert Opin Biol Ther. Oct. 2007;7(10):1531-8. Review.

Mori et al., Molecular mechanisms linking wound inflammation and fibrosis: knockdown of osteopontin leads to rapid repair and reduced scarring. J Exp Med. Jan. 21, 2008;205(1):43-51. doi: 10.1084/jem.20071412. Epub Jan. 7, 2008.

Murchison et al., Characterization of Dicer-deficient murine embryonic stem cells. Proc Natl Acad Sci U S A. Aug. 23, 2005;102(34):12135-40. Epub Aug. 12, 2005.

Niessen et al., Keratinocyte-derived growth factors play a role in the formation of hypertrophic scars. J Pathol. Jun. 2001;194(2):207-16.

Oberhauser et al., Effective incorporation of 2'-O-methyl-oligoribonucleotides into liposomes and enhanced cell association through modification with thiocholesterol. Nucleic Acids Res. Feb. 11, 1992;20(3):533-8.

Ortigão et al., Antisense effect of oligodeoxynucleotides with inverted terminal internucleotidic linkages: a minimal modification protecting against nucleolytic degradation. Antisense Res Dev. 1992 Summer;2(2):129-46.

Overhoff et al., Phosphorothioate-stimulated uptake of short interfering RNA by human cells. EMBO Rep. Dec. 2005;6(12):1176-81.

Paradis et al., Expression of connective tissue growth factor in experimental rat and human liver fibrosis. Hepatology. Oct. 1999;30(4):968-76.

Parrish et al., Functional anatomy of a dsRNA trigger: differential requirement for the two trigger strands in RNA interference. Mol Cell. Nov. 2000;6(5):1077-87.

Pavco et al., Robust Intradermal efficacy with novel chemically modified self-delivering RNAi compounds. Keystone RNAi Silencing Conference: Mechanism, Biology and Application Conference. Jan. 14-19, 2010. Poster. 1 Page.

Rajeev et al., 2'-modified-2-thiothymidineoligonucleotides. Org Lett. Aug. 21, 2003;5(17):3005-8.

Reish et al., Scar Treatments: Preclinical and Clinical Studies. J Am Coll Surg. Apr. 2008;206(4):719-30.

Rozners et al., Expanding functionality of RNA: synthesis and properties of RNA containing imidazole modified tandem G-U wobble base pairs. Chem Commun (Camb). Dec. 14, 2005;(46):5778-80.

Rump et al., Preparation of conjugates of oligodeoxynucleotides and lipid structures and their interaction with low-density lipoprotein. Bioconjug Chem. May-Jun. 1998;9(3):341-9.

Sadick et al., TGF-beta1 antisense therapy modulates expression of matrix metalloproteinases in keloid-derived fibroblasts. Int J Mol Med. Jul. 2008;22(1):55-60.

Salomon et al., Modified dsRNAs that are not processed by Dicer maintain potency and are incorporated into the RISC. Nucleic Acids Res. Jun. 2010;38(11):3771-9. doi: 10.1093/nar/gkq055. Epub Feb. 18, 2010.

Sato et al., Serum levels of connective tissue growth factor are elevated in patients with systemic sclerosis: association with extent of skin sclerosis and severity of pulmonary fibrosis. J Rheumatol. Jan. 2000;27(1):149-54.

Sato et al., Tumor targeting and imaging of intraperitoneal tumors by use of antisense oligo-DNA complexed with dendrimers and/or avidin in mice. Clin Cancer Res. Nov. 2001;7(11):3606-12.

(56) References Cited

OTHER PUBLICATIONS

Seela et al., Oligodeoxyribonucleotides containing 1,3-propanediol as nucleoside substitute. Nucleic Acids Res. Apr. 10, 1987;15(7):3113-29.

Seifert et al., Keloid scarring: bench and bedside. Arch Dermatol Res. Apr. 2009;301(4):259-72. doi: 10.1007/s00403-009-0952-8. Epub Apr. 10, 2009.

Semizarov et al., Specificity of short interfering RNA determined through gene expression signatures. Proc Natl Acad Sci U S A. May 27, 2003;100(11):6347-52. Epub May 13, 2003.

Shah et al., Neutralisation of TGF-beta 1 and TGF-beta 2 or exogenous addition of TGF-beta 3 to cutaneous rat wounds reduces scarring. J Cell Sci. Mar. 1995;108 ( Pt 3):985-1002.

Sherwood et al., A sequential, multiple-treatment, targeted approach to reduce wound healing and failure of glaucoma filtration surgery in a rabbit model (an American Ophthalmological Society thesis). Trans Am Ophthalmol Soc. 2006;104:478-92.

Shi, Mammalian RNAi for the masses. Trends Genet. Jan. 2003;19(1):9-12.

Shi-Wen et al., Regulation and function of connective tissue growth factor/CCN2 in tissue repair, scarring and fibrosis. Cytokine Growth Factor Rev. Apr. 2008;19(2):133-44. doi: 10.1016/j.cytogfr.2008. 01.002.

Shoeman et al., Fluorescence microscopic comparison of the binding of phosphodiester and phosphorothioate (antisense) oligodeoxyribonucleotides to subcellular structures, including intermediate filaments, the endoplasmic reticulum, and the nuclear interior. Antisense Nucleic Acid Drug Dev. Aug. 1997;7(4):291-308.

Sisco et al., Antisense inhibition of connective tissue growth factor (CTGF/CCN2) mRNA limits hypertrophic scarring without affecting wound healing in vivo. Wound Repair Regen. Sep.-Oct. 2008;16(5):661-73. doi:10.1111/j.1524-475X.2008.00416.x.

Sisco et al., Antisense oligonucleotides against transforming growth factor-beta delay wound healing in a rabbit ear model. J Amer. Coll. Surgeons. Sep. 2005;210(3):560.

Snead et al., RNA interference trigger variants: getting the most out of RNA for RNA interference-based therapeutics. Nucleic Acid Ther. Jun. 2012;22(3):139-46. doi: 10.1089/nat.2012.0361. Review.

Soutschek et al., Therapeutic silencing of an endogenous gene by systemic administration of modified siRNAs. Nature. Nov. 11, 2004;432(7014):173-8.

Sriram et al., Reduction of corneal scarring in rabbits by targeting the TGFB1 pathway with a triple siRNA combination. Adv Biosci Biotechnol. Jan. 1, 2013;4(10):47-55.

Sriram et al., Triple combination of siRNAs targeting TGFβ1, TGFβ2, and CTGF enhances reduction of collagen I and smooth muscle actin in corneal fibroblasts. Invest Ophthalmol Vis Sci. Dec. 17, 2013;54(13):8214-23. doi: 10.1167/iovs.13-12758.

Stein et al., A specificity comparison of four antisense types: morpholino, 2'-O-methyl RNA, DNA, and phosphorothioate DNA. Antisense Nucleic Acid Drug Dev. Jun. 1997;7(3):151-7.

Sui et al., A DNA vector-based RNAi technology to suppress gene expression in mammalian cells. Proc Natl Acad Sci U S A. Apr. 16, 2002;99(8):5515-20.

Summerton et al., Morpholino and phosphorothioate antisense oligomers compared in cell-free and in-cell systems. Antisense Nucleic Acid Drug Dev. Apr. 1997;7(2):63-70.

Sun et al., Asymmetric RNA duplexes mediate RNA interference in mammalian cells. Nat Biotechnol. Dec. 2008;26(12):1379-82. doi: 10.1038/nbt.1512. Epub Nov. 23, 2008. 4 Pages.

Tang et al., An RNA interference-based screen identifies MAP4K4/ NIK as a negative regulator of PPARgamma, adipogenesis, and insulin-responsive hexose transport. Proc Natl Acad Sci U S A. Feb. 14, 2006;103(7):2087-92. Epub Feb. 3, 2006.

Toyono et al., Angiopoietin-like protein 2 is a potent hemangiogenic and lymphangiogenic factor in corneal inflammation. Invest Ophthalmol Vis Sci. Jun. 26, 2013;54(6):4278-85. doi: 10.1167/iovs.12-11497.

Uhlmann et al., Antisense oligonucleotides: a new therapeutic principle. Chem Rev. 1990;90(4):543-84.

Vaught et al., Expanding the chemistry of DNA for in vitro selection. J Am Chem Soc. Mar. 31, 2010;132(12):4141-51. doi: 10.1021/ja908035g.

Vermeulen et al., The contributions of dsRNA structure to Dicer specificity and efficiency. RNA. May 2005;11(5):674-82. Epub Apr. 5, 2005.

Villegas et al., Retinoblastoma. Curr Opin Ophthalmol. Nov. 2013;24(6):581-8. doi: 10.1097/ICU.0000000000000002.

Williams et al., Increased expression of connective tissue growth factor in fibrotic human liver and in activated hepatic stellate cells. J Hepatol. May 2000;32(5):754-61.

Wolfrum et al., Mechanisms and optimization of in vivo delivery of lipophilic siRNAs. Nat Biotechnol. Oct. 2007;25(10):1149-57. Epub Sep. 16, 2007.

Xiao et al., Effect of small interfering RNA on the expression of connective tissue growth factor and type I and III collagen in skin fibroblasts of patients with systemic sclerosis. Br J Dermatol. Dec. 2006;155(6):1145-53.

Xu et al., Retinoblastoma has properties of a cone precursor tumor and depends upon cone-specific MDM2 signaling. Cell. Jun. 12, 2009;137(6):1018-31. doi: 10.1016/j.cell.2009.03.051.

Xue et al., Mesodermal patterning defect in mice lacking the Ste20 NCK interacting kinase (NIK). Development. May 2001;128(9):1559-72.

Yamada et al., Synthesis and properties of oligonucleotides having a chemically stable 2-(trimethylsilyl)benzoyl group. Nucleic Acids Symp Ser (Oxf). 2008;(52):301-2. doi: 10.1093/nass/nrn152.

Yamada et al., Tranilast, a selective inhibitor of collagen synthesis in human skin fibroblasts. J Biochem. Oct. 1994;116(4):892-7.

Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.

Zhang et al., Inhibition of vascular endothelial growth factor expression in keloid fibroblasts by vector-mediated vascular endothelial growth factor shRNA: a therapeutic potential strategy for keloid. Arch Dermatol Res. Apr. 2008;300(4):177-84. doi:10.1007/s00403-007-0825-y. Epub Feb. 1, 2008.

Zhang et al., Mechanisms of hypoxic regulation of plasminogen activator inhibitor-1 gene expression in keloid fibroblasts. J Invest Dermatol. Nov. 2003;121(5):1005-12.

sd-rxRNA show robust uptake and silencing compared to rxRNAori in ARPE-19 cells

Examples of sd-rxRNA for Ocular Indications

| Gene | Generic Name | TEG ID | 2'F | Targeting site | Optimized lead sequence | Optimized lead sequence |
|---|---|---|---|---|---|---|
| CTGF | CTGF L1 | 17376 | 4 | 2295 | 21212 | mU.mU. G.mC.A.mC.mC.mU.mU.mU.mC.mU*mA*mA-chol<br>P.mU.fU.A.G.A.mAA.G.G.fU.G.fC.mA.mA*mA*fC*mA*mA*mG* G |
| | | | | | 21214 | mU.mU. G.mC.A.mC.mC.mU.mU.mU.mC.mU*mA*mA-chol<br>P.mU.fU.A.G.A.mAA.G.G.fU.G.fC.A.A*A*fC*A*mA*mG*G |
| | | | | | 21215 | mU.mU. G.mC.A.mC.mC.mU.mU.mU.mC.mU*mA*mA-chol<br>P.mU.fU.A.G.A.mAA.G.G.fU.G.fC.mA.A*mA*fC*A*mA*mG*G |
| | CTGF L2 | 20393 | 5 | 2296 | 21204 | G.mC.A.mC.mC.mU.mU.mU.mC.mU. A*mG*mA-TEG-Chl<br>P.mU. fC.fU.A.G.mA.A.mA.G.G.fU.G.mC*A*A*A*mC*A*U |
| | | | | | 21205 | G.mC.A.mC.mC.mU.mU.mU.mC.mU. A*mG*mA-TEG-Chl<br>P.mU. fC.fU.A.G.mA.A.mA.G.G.fU.G.mC*A*mA*A*mC*A*U |
| | | | | | 21227 | G.mC.A.mC.mC.mU.mU.mU.mC.mU. A*mG*mA-TEG-Chl<br>P.mU. fC.fU.A.G.mA.A.mA.G.G.fU.G.fC*mA*mA*mA*fC*mA*U |
| | CTGF L3 | 20392 | 13 | 2275 | 21381 | G.mU. G. A.mC.mC. A. A. A. A. G*mU*mA-TEG-Chl<br>P.mU. A.fC.fU.fU.fU.fU.G.G.fU.mC.A.mC*A*mC*mU*mC*mU*c. |
| | | | | | 21382 | G.mU. G. A.mC.mC. A. A. A. A. G*mU*mA.TEG.Chl<br>P.mU. A.fC.fU.fU.fU.fU.G.G.fU.fC. A.mC* A*fC*mU*fC*mU* C |
| | | | | | 21429 | G.mU. G. A.mC.mC. A. A. mA. A. G*mU*mA-TEG-Chl<br>P.mU. A.fC.fU.fU.fU.fU.G.G.fU.fC. A.mC* A*fC*mU*fC*mU* C |
| | | | | | 21430 | G.mU. G. A.mC.mC. A. A. mA. A. G*mU*mA-TEG-Chl<br>P.mU. A.fC.fU.fU.fU.fU.G.G.fU.mC. A.mC* A*mC*mU*mC*mU*c. |
| | | | | | 21383 | mG*mU*mG.mA.mC.mC.mA.mA.mA.mA.mG*mU*mA-TEG-Chl<br>P.mU. A.fC.fU.fU.fU.fU.G.G.fU.mC. A.mC* A*mC*mU*mC*mU*c. |
| | CTGF L4 | 17387 | 5 | 2299 | 21224 | mC.mC.mU.mU.mU.mC.mU.A. G.mU* mG*mA-TEG-Chl<br>P.mU.fC. A. A. fC.fU.A. G. A.mA. A. G. G*fU*mG*fC*mA*mA* A |
| PTGS2 | PTGS2 L1 | 20394 | 8 | 448 | 21228 | G. A.mU.mC. A.mC. A.mU.mU.mU. G*mA*mA-TEG-Chl<br>P.mU.fU.fC.A.mA.A.fU.G.fU.G.A.fU.fC*fU*mG*mC*mA*fU* G |
| | | | | | 21229 | G. A.mU.mC. A.mC. A.mU.mU.mU. G*mA*mA-TEG-Chl<br>P.mU.fU.fC.A.A.A.fU.G.fU.G.A.mU.mC*mU*G*G*A*mU*G |
| | | | | | 21230 | G. A.mU.mC. A.mC. A.mU.mU.mU. G*mA*mA-TEG-Chl<br>P.mU.fU.fC.A.A.A.fU.G.fU.G.A.fU.fC*fU*mG*mC*mA*fU* G |
| | PTGS2 L2 | 20395 | 8 | 449 | 21393 | G. A.mU.mC. A.mC. A.mU.mU.mU. G. A*mU*mA-TEG-Chl<br>P.mU. A.fU.fC. A. A. A.fU. G.fU. G. A.mU.mC*mU*mG*mG*mA*fU* G |
| | | | | | 21394 | G.A.mU.mC. A.mC. A.mU.mU.mU. G. A*mU*mA-TEG-Chl<br>P.mU.A.fU.fC. A. A. A.fU. G.fU. G. A.mU.fC*mU* G* G* A*fU* G |
| | | | | | 21233 | G.A.mU.mC. A.mC. A.mU.mU.mU. G. A*mU*mA-TEG-Chl<br>P.mU.A.fU.fC. A. A. A.fU. G.fU. G. A.fU.fC*fU*G*G*A*fU*G |
| | | | | | 21234 | G.A.mU.mC. A.mC. A.mU.mU.mU. G. A*mU*mA-TEG-Chl<br>P.mU.A.fU.fC. A. A. A.fU. G.fU. G. A.fU.fC*fU*mG*mG*mA*fU*G |
| rTGFB1 | TGFB1 rL1 | | | 1244 | 21360 | mC*mA*mC.mA.mC.mA.mG.mU.mA.mU.mA*mU*mA.TEG-Chl<br>P.mU.A.fU. A.fU. A.fC.fU. G.fU. G.mU. G*fU* G* A*mU*mG* U |
| hTGFb1 | TGFb1 hL3 | | | 1244 | 21374 | mC.mA.mC.mA.mC.mA.mG.mC.mA.mU.mA*mU*mA-TEG-Chl<br>P.mU.A.fU. A.fU. G.fC.fU. G.fU. G.fU. mG*fU*mA*fC*mU*fC*U |
| rTGFB2 | TGFB2 rL1 | | | 1660 | 21366 | mC*mG*mG.mU.mG.A.mC.mA.mA.mU.mG*mA*mA-TEG-Chl<br>P.mU.fU. fC.A.mfU. G.fU.fC. A.mC.mC. G*mU* G*mA*mU*mU* U |
| rTGFB2 | TGFB2 rL2 | | | 2056 | 21368 | mU. A.mU.mU. G.mC.mU.mC.mU. G.mC*mA*mA-TEG-Chl<br>P.mU.fU. G.fC. A.mG. A. G.fC. A. A.fU.mA*fC*mA*mG*mA*mG* G |
| hTGFb2 | TGFb2 hL3 | | | 2081 | 21379 | mU*mC*mA.mU.mC.mA.mG.mU.mG.mU.mU*mA*mA-TEG-Chl<br>P.mU.fU. A. A.fC. A.fC.fU. G. A.fU. G.A* A*fC*fC*mA*mA* G |
| | | | | | 21380 | mU*mC*mA.mU.mC.mA.mG.mU.mG.mU.mU*mA*mA-TEG-Chl<br>P.mU.fU. A. A.fC. A.fC.fU. G. A.fU. G.mA*mA*fC*fC*mA*mA* G |
| PPIB | PPIB | 18485 | 8 | 438 | 21352 | mA.mA.mA.mU.mU.mC.mC.mA.mU.mC.mG.mU*mG*mu.TEG-Chl<br>P.mA.fC. A.fC. G. A.fU. G. G.mA. A.fU.fU.fU*mG*fC*fU*mG*mU* U |
| Map4k4 | Map4k4 | 13966 | 5 | 2931 | 21777 | mC.mU. G.mU. G. G. A. A. G.mU.mC*mU* A.TEG-Chl |

Fig. 6

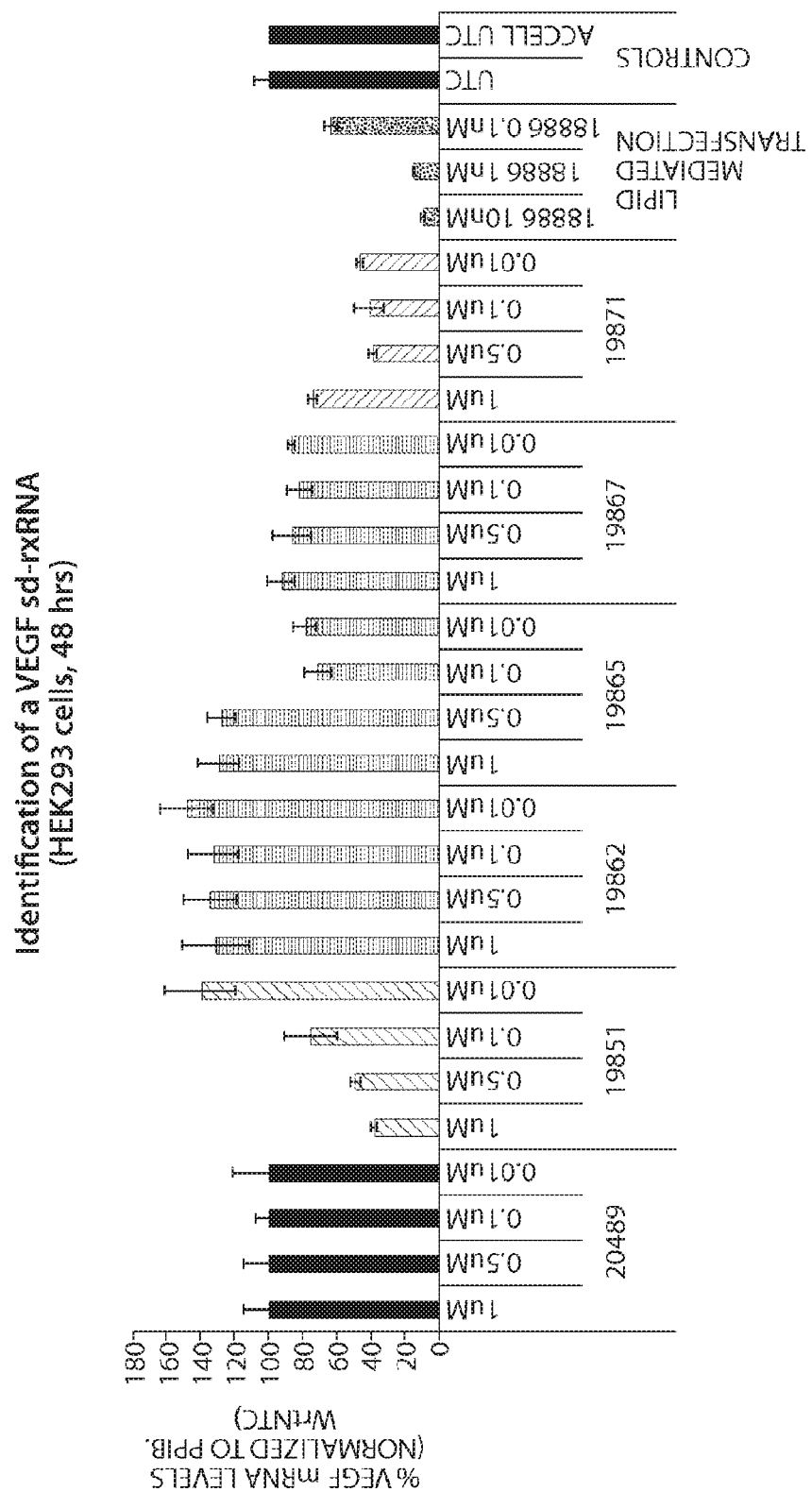

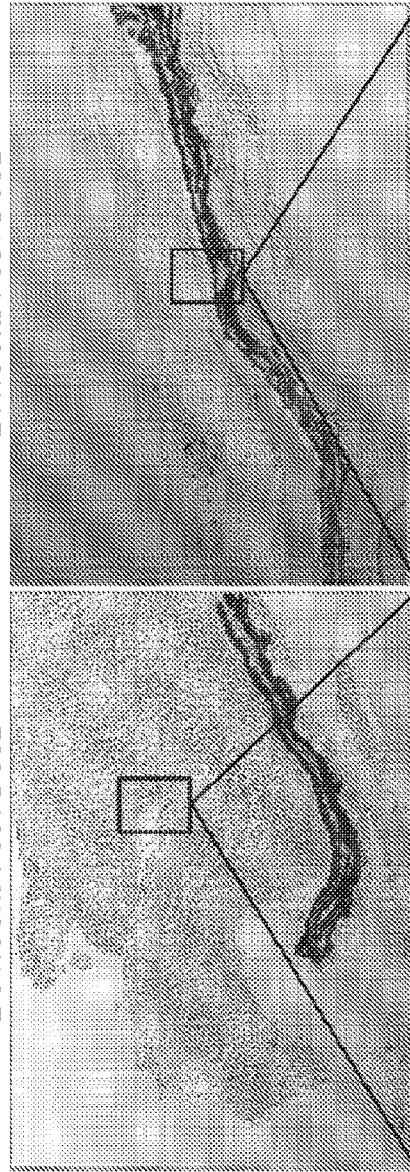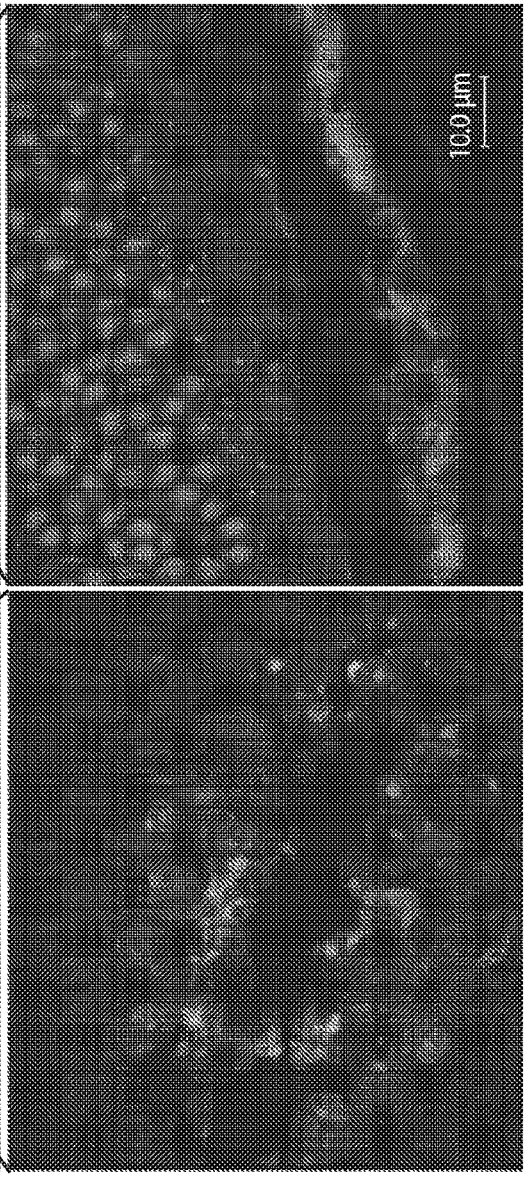
Fig. 8

Confocal Microscopy Reveals No Visible Delivery of
Conventional RNA Compounds to the Eye

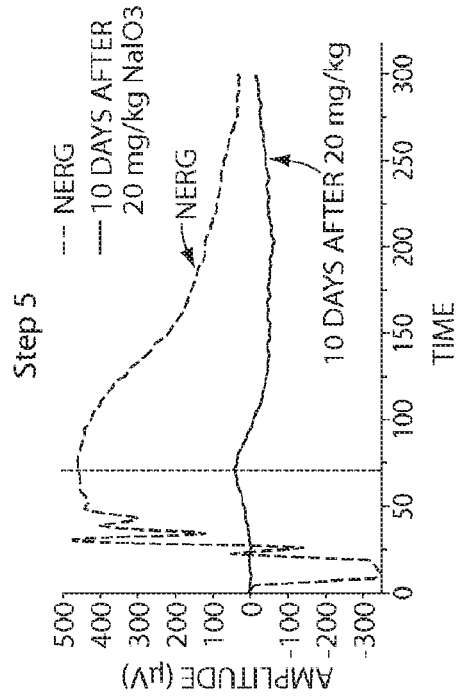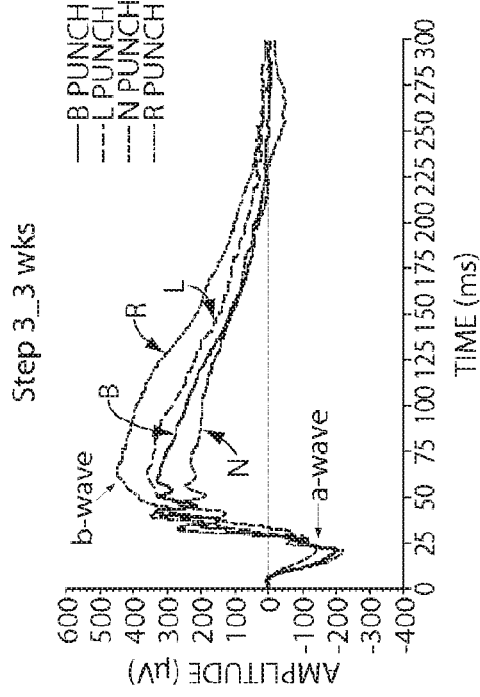
Fig. 17

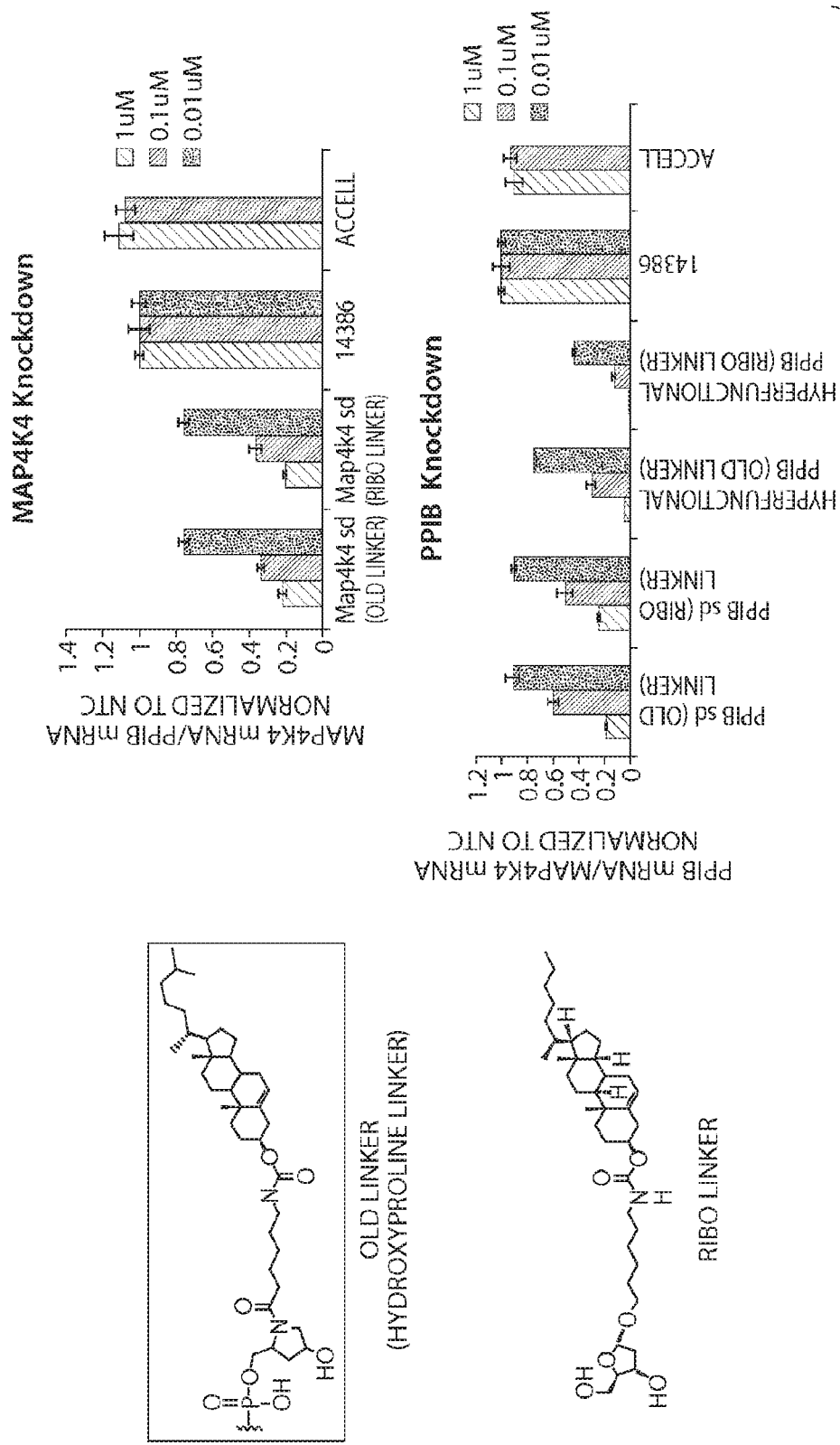

RNA INTERFERENCE IN OCULAR INDICATIONS

RELATED APPLICATIONS

This application is a continuation under 35 U.S.C. § 120 of U.S. patent application Ser. No. 14/728,653, filed on Jun. 2, 2015, entitled "RNA INTERFERENCE IN OCULAR INDICATIONS", which is a continuation under 35 U.S.C. § 120 of U.S. patent application Ser. No. 13/636,748, entitled "RNA INTERFERENCE IN OCULAR INDICATIONS," filed Feb. 5, 2013, which is a national stage filing under 35 U.S.C. § 371 of international application PCT/US2011/029849, filed Mar. 24, 2011, which was published under PTC Article 21(2) in English, and claims the benefit under 35 U.S.C. § 119(e) of the filing date of U.S. Provisional Application Ser. No. 61/317,254, entitled "RNA INTERFERENCE IN OCULAR INDICATIONS," filed on Mar. 24, 2010, and U.S. Provisional Application Ser. No. 61/317,621, entitled "RNA INTERFERENCE IN OCULAR INDICATIONS," filed on Mar. 25, 2010, the entire disclosures of each of which are incorporated by reference herein.

FIELD OF INVENTION

The invention pertains to the field of RNA interference (RNAi). The invention more specifically relates to ocular administration of nucleic acid molecules with improved in vivo delivery properties and their use in efficient gene silencing.

BACKGROUND OF INVENTION

Complementary oligonucleotide sequences are promising therapeutic agents and useful research tools in elucidating gene functions. However, prior art oligonucleotide molecules suffer from several problems that may impede their clinical development, and frequently make it difficult to achieve intended efficient inhibition of gene expression (including protein synthesis) using such compositions in vivo.

A major problem has been the delivery of these compounds to cells and tissues. Conventional double-stranded RNAi compounds, 19-29 bases long, form a highly negatively-charged rigid helix of approximately 1.5 by 10-15 nm in size. This rod type molecule cannot get through the cell-membrane and as a result has very limited efficacy both in vitro and in vivo. As a result, all conventional RNAi compounds require some kind of a delivery vehicle to promote their tissue distribution and cellular uptake. This is considered to be a major limitation of the RNAi technology.

There have been previous attempts to apply chemical modifications to oligonucleotides to improve their cellular uptake properties. One such modification was the attachment of a cholesterol molecule to the oligonucleotide. A first report on this approach was by Letsinger et al., in 1989. Subsequently, ISIS Pharmaceuticals, Inc. (Carlsbad, Calif.) reported on more advanced techniques in attaching the cholesterol molecule to the oligonucleotide (Manoharan, 1992).

With the discovery of siRNAs in the late nineties, similar types of modifications were attempted on these molecules to enhance their delivery profiles. Cholesterol molecules conjugated to slightly modified (Soutschek, 2004) and heavily modified (Wolfrum, 2007) siRNAs appeared in the literature. Yamada et al., 2008 also reported on the use of advanced linker chemistries which further improved cholesterol mediated uptake of siRNAs. In spite of all this effort, the uptake of these types of compounds appears to be inhibited in the presence of biological fluids resulting in highly limited efficacy in gene silencing in vivo, limiting the applicability of these compounds in a clinical setting.

SUMMARY OF INVENTION

Described herein are methods and compositions for efficient in vivo administration of sd-rxRNA® molecules to the eye. Surprisingly, intraocular (e.g., intravitreal and subretinal) administration of sd-rxRNA® molecules resulted in distribution and uptake of the sd-rxRNA® by all the cell layers in the retina. These molecules have widespread applications for treatment of disorders or conditions associated with the eye.

Aspects of the invention relate to methods for delivering a nucleic acid to an eye of a subject in need thereof, comprising administering to the eye of the subject an sd-rxRNA®, in an effective amount to promote RNA interference by the sd-rxRNA® in the eye. In some embodiments, the administration of the sd-rxRNA® is intravitreal.

In some embodiments, the method is for treating an ocular disorder. In certain embodiments, the ocular disorder is vascular leakage, neovascularization, age-related macular degeneration (AMD), choroidal neovascularization (wet AMD), geographic atrophy (advanced dry AMD), early-to-intermediate dry AMD, post surgical cystoid macular edema (CME), nonproliferative diabetic retinopathy (NPDR), diabetic macular edema (DME), macular edema secondary to retinal vein occlusion (RVO), proliferative diabetic retinopathy (PDR), glaucoma, neovascular glaucoma (NVG), retinopathy of prematurity (ROP), fibroproliferative retinal disease, proliferative vitreoretinopathy (PVR), epiretinal membranes/vitreomacular adhesions, retinal degenerative disease, retinitis pigmentosa, retinal vascular occlusive disorders, retinal vein occlusion, retinal artery occlusion, retinoblastoma, trabeculectomy failure due to scarring, or uveitis. In one embodiment, the ocular disorder is AMD. In another embodiment, the ocular disorder is DME. In yet another embodiment, the ocular disorder is PVR. In still another embodiment, the ocular disorder is trabeculectomy failure due to scarring.

In certain embodiments, the sd-rxRNA® is directed against a gene encoding for VEGF, MAP4K4, PDGF-B, SDF-1, IGTA5, ANG2, CTGF, HIF-1α, mTOR, SDF-1, PDGF-B, SPP1, PTGS2 (COX-2), TGFβ1, TGFβ2, complement factors 3 or 5, PDGFRa, PPIB, or myc, or a combination thereof.

In some embodiments, the sd-rxRNA® is directed against a gene encoding for VEGF. In certain embodiments, the sd-rxRNA® is directed against a sequence selected from the sequences within Table 2. In one embodiment, the sd-rxRNA® is directed against a sequence comprising at least 12 contiguous nucleotides of a sequence selected from the sequences within Table 2. In another embodiment the sd-rxRNA® comprises at least 12 contiguous nucleotides of a sequence selected from the sequences within Tables 3-8 or 10. In yet another embodiment, the sense strand of the sd-rxRNA® comprises at least 12 contiguous nucleotides of the sequence of SEQ ID NO: 1317 or SEQ ID NO: 1357. In still another embodiments, the antisense strand of the sd-rxRNA® comprises at least 12 contiguous nucleotides of the sequence of SEQ ID NO:1318 or SEQ ID NO:1358. In a further embodiment, the sense strand of the sd-rxRNA® comprises SEQ ID NO: 1317 and the antisense strand of the sd-rxRNA® comprises SEQ ID NO: 1318. In one embodiment, the sense strand of the sd-rxRNA® comprises SEQ ID NO:1357 and the antisense strand of the sd-rxRNA® comprises SEQ ID NO: 1358. In another embodiment, the sense strand of the sd-rxRNA® comprises SEQ ID NO: 1379 and the antisense strand of the sd-rxRNA® comprises SEQ ID NO: 1380. In yet another embodiment, the sense strand of the sd-rxRNA® comprises SEQ ID NO:1397 and the antisense strand of the sd-rxRNA® comprises SEQ ID NO:1398.

In certain embodiments, the sd-rxRNA® is directed against a gene encoding for CTGF. In one embodiment, the antisense strand of the sd-rxRNA® comprises at least 12 contiguous nucleotides of the sequence of SEQ ID NO:948 or SEQ ID NO:964. In another embodiment, the sense strand of the sd-rxRNA® comprises at least 12 contiguous nucleotides of the sequence of SEQ ID NO:947 or SEQ ID NO:963.

In some embodiments, two or more different sd-rxRNA® molecules that are directed against genes encoding for two or more different proteins are both administered to the eye of the subject. In one embodiment, the sd-rxRNA® molecules are directed against VEGF and CTGF. In another embodiment, the sd-rxRNA® molecules are directed against VEGF and PTGS2 (COX-2).

In certain aspects, the sd-rxRNA® of any one of the foregoing embodiments is hydrophobically modified. In some embodiments, the sd-rxRNA® is linked to one or more hydrophobic conjugates.

In certain aspects, the sd-rxRNA® of any one of the foregoing embodiments, includes at least one 5-methyl C or U modifications.

Other aspects of the invention relate to methods for delivering a nucleic acid to an eye of a subject in need thereof, including administering to the eye of the subject an rxRNAori, in an effective amount to promote RNA interference by the rxRNAori in the eye. In one embodiment, the rxRNAori is directed against VEGF. In another embodiment, the rxRNAori is directed against a sequence comprising at least 12 contiguous nucleotides of a sequence selected from the sequences within Table 2. In yet another embodiment, the sense strand of the rxRNAori comprises at least 12 contiguous nucleotides of the sequence of SEQ ID NO:13 or SEQ ID NO:28. In still another embodiment, the antisense strand of the rxRNAori comprises at least 12 contiguous nucleotides of the sequence of SEQ ID NO: 1377 or SEQ ID NO:1378.

Some aspects of the invention relate to sd-rxRNA® molecules directed against a sequence selected from the sequences within Table 2. Other aspects relate to sd-rxRNA® molecules directed against a sequence comprising at least 12 contiguous nucleotides of a sequence selected from the sequences within Table 2. Yet other aspects relate to sd-rxRNA® molecules that comprises at least 12 contiguous nucleotides of a sequence selected from the sequences within Tables 3-8 or 10. In some embodiments, the sense strand of the sd-rxRNA® comprises at least 12 contiguous nucleotides of the sequence of SEQ ID NO:1317, 1357, 1379 or 1397. In other embodiments, the antisense strand of the sd-rxRNA® comprises at least 12 contiguous nucleotides of the sequence of SEQ ID NO:1318, 1358, 1380 or 1398. In yet other embodiments, the antisense strand of the sd-rxRNA® comprises SEQ ID NO: 1318. In still other embodiments, the sense strand of the sd-rxRNA® comprises SEQ ID NO: 1357 and the antisense strand of the sd-rxRNA® comprises SEQ ID NO: 1358. In further embodiments, the sense strand of the sd-rxRNA® comprises SEQ ID NO:1379 and the antisense strand of the sd-rxRNA® comprises SEQ ID NO: 1380. In still further embodiments, the sense strand of the sd-rxRNA® comprises SEQ ID NO: 1397 and the antisense strand of the sd-rxRNA® comprises SEQ ID NO: 1398. In certain embodiments, the sd-rxRNA® is hydrophobically modified. In other embodiments, the sd-rxRNA® is linked to one or more hydrophobic conjugates. In certain other embodiments, the sd-rxRNA® includes at least one 5-methyl C or U modifications.

Other aspects of the invention relate to compositions comprising an sd-rxRNA® of any one of any one of the foregoing aspects or embodiments. In one embodiment, the composition further comprises an sd-rxRNA® that is directed against a gene encoding for a protein other than VEGF. In another embodiment, the composition comprises an sd-rxRNA® that is directed against a gene encoding for CTGF and/or PTGS2 (COX-2).

Aspects of the invention also relate to an rxRNAori that is directed against a sequence selected from the sequences within Table 2. Another aspect relates to an rxRNAori that is directed against a sequence comprising at least 12 contiguous nucleotides of a sequence selected from the sequences within Table 2. In one embodiment, the sense strand of the rxRNAori comprises at least 12 contiguous nucleotides of the sequence of SEQ ID NO: 13 or SEQ ID NO:28. In another embodiment, the antisense strand of the rxRNAori comprises at least 12 contiguous nucleotides of the sequence of SEQ ID NO: 1377 or SEQ ID NO: 1378.

Another aspect of the invention relates to a composition comprising an rxRNAori of any one of the foregoing aspects or embodiments. In one embodiment, the composition comprises an rxRNAori that is directed against a gene encoding for a protein other than VEGF. In another embodiment, the composition comprises an rxRNAori that is directed against a gene encoding for CTGF and/or PTGS2 (COX-2).

In some embodiments, the sd-rxRNA® within the composition is hydrophobically modified. In certain embodiments, the sd-rxRNA® is linked to one or more hydrophobic conjugates. In some embodiments, the sd-rxRNA® is linked to a lipophilic group. In certain embodiments, the lipophilic group is linked to the passenger strand of the sd-rxRNA®. In some embodiments, the sd-rxRNA® is linked to cholesterol, a long chain alkyl cholesterol analog, vitamin A, or vitamin E. In some embodiments, the sd-rxRNA® is attached to chloroformate.

The sd-rxRNA® can include at least one 2' O methyl or 2' fluoro modification and/or at least one 5-methyl C or U modification. In some embodiments, the sd-rxRNA® has a guide strand of 16-28 nucleotides in length. In certain embodiments, at least 40% of the nucleotides of the sd-rxRNA® are modified. The sd-rxRNA® can be attached to a linker which in certain embodiments is protonatable.

In some embodiments, the sd-rxRNA® contains at least two single stranded regions which can contain phosphorothioate modifications. In certain embodiments, the single stranded regions are located at the 3' end of the guide strand and the 5' end of the passenger strand.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 6 demonstrates non-limiting examples of sd-rxRNA® having ocular potential. The optimized lead molecules in FIG. 6 correspond to the following SEQ ID NOs, representing the sense and antisense strands, respectively: lead 21212: SEQ ID NOs 963 and 964; lead 21214: SEQ ID NOs 967 and 968; lead 21215: SEQ ID NOs 969 and 970; lead 21204: SEQ ID NOs 947 and 948; lead 21205: SEQ ID NOs 949 and 950; lead 21227: SEQ ID NOs 993 and 994; lead 21381: SEQ ID NOs 1011 and 1012; lead 21382: SEQ ID NOs 1013 and 1014; lead 21429: SEQ ID NOs 1023 and 1024; lead 21430: SEQ ID NOs 1025 and 1026; lead 21383: SEQ ID NOs 1015 and 1016; lead 21224: SEQ ID NOs 987 and 988; lead 21228: SEQ ID NOs 1399 and 1400; lead 21229: SEQ ID NOs 1401 and 1402; lead 21230: SEQ ID NOs 1403 and 1404; lead 21393: SEQ ID NOs 1405 and 1406; lead 21394: SEQ ID NOs 1407 and 1408; lead 21233: SEQ ID NOs 1409 and 1410; lead 21234: SEQ ID NOs 1411 and 1412; lead 21360: SEQ ID NOs 1413 and 1414; lead 21374: SEQ ID NOs 1304 and 1314; lead 21366: SEQ ID NOs 1415 and 1416; lead 21368: SEQ ID NOs 1417 and 1418; lead 21379: SEQ ID NOs 1155 and 1156; lead 21380: SEQ ID NOs 1157 and 1158; lead 21352: SEQ ID NOs 1419 and 1420; and lead 21777: SEQ ID NO:1421.

FIG. 7 demonstrates identification of VEGF sd-rxRNA®.

FIG. 8 demonstrates progression of sd-rxRNA® penetration to cell layers of the eye after intravitreal dosing. sd-rxRNA® penetrates the ganglion cell layer by 2-3 hours post dose. sd-rxRNA® penetrates to the retinal pigment epithelium (RPE) and outer segments of the photoreceptors by 24 hours post dose.

FIG. 17 reveals that sd-rxRNA® does not impair retinal function 3 weeks post dose.

FIG. 19 demonstrates that variation of linker chemistry does not influence silencing activity of sd-rxRNA® molecules in vitro. Two different linker chemistries were evaluated, a hydroxyproline linker and ribo linker, on multiple sd-rxRNA® molecules (targeting Map4k4 or PPIB) in passive uptake assays to determine linkers which favor self delivery. HeLa cells were transfected in the absence of a delivery vehicle (passive transfection) with sd-rxRNA® molecules at 1 uM, 0.1 uM or 0.01 uM for 48 hrs. Use of either linker results in an efficacious delivery of sd-rxRNA®.

DETAILED DESCRIPTION

Figure 1:
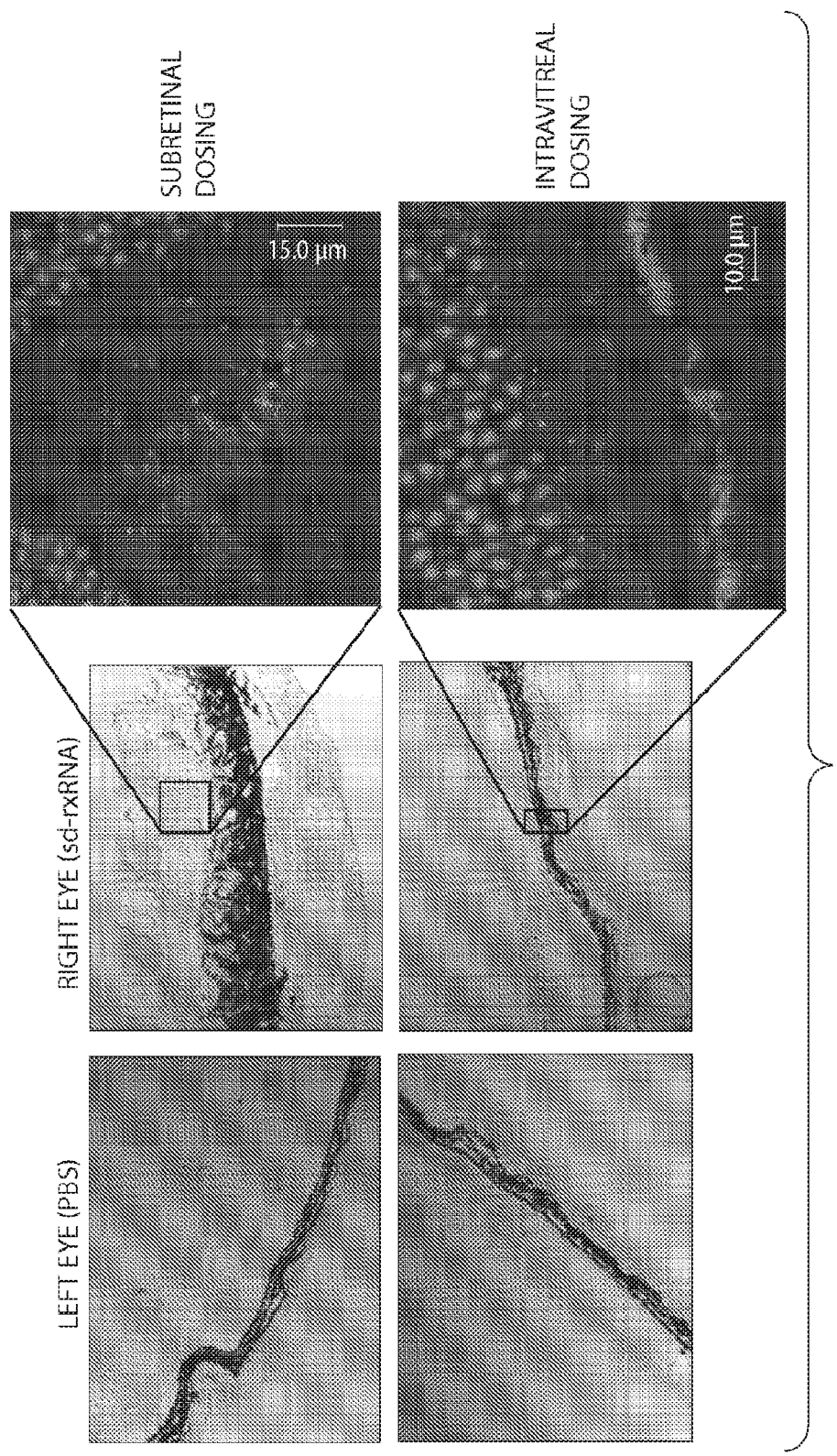
FIG. 1 presents a confocal triple overlay of DIC, DY547 and Hoechst indicating that by 24 hours after intravitreal or subretinal dosing, sd-rxRNA® has penetrated the entire retina.

Aspects of the invention relate to methods and compositions involved in gene silencing. The invention is based at least in part on the surprising discovery that delivery to the eye, including subretinal and intravitreal injection of sd-rxRNA® molecules results in efficient distribution and uptake by all cell layers in the retina, including the retinal pigment epithelium layer. Drastically better retinal uptake and distribution is observed for sd-rxRNA® molecules than for conventional RNAi compounds. Thus, sd-rxRNA® molecules represent a new class of therapeutic RNAi molecules with significant potential in treatment of ocular conditions or disorders.

sd-rxRNA® Molecules

Aspects of the invention relate to sd-rxRNA® molecules. As used herein, an "sd-rxRNA®" or an "sd-rxRNA® molecule" refers to a self-delivering RNA molecule such as those described in, and incorporated by reference from, PCT Publication No. WO2010/033247 (Application No. PCT/US2009/005247), filed on Sep. 22, 2009, and entitled "REDUCED SIZE SELF-DELIVERING RNAI COMPOUNDS." Briefly, an sd-rxRNA®, (also referred to as an sd-rxRNA$^{nano}$) is an isolated asymmetric double stranded nucleic acid molecule comprising a guide strand, with a minimal length of 16 nucleotides, and a passenger strand of 8-18 nucleotides in length, wherein the double stranded nucleic acid molecule has a double stranded region and a single stranded region, the single stranded region having 4-12 nucleotides in length and having at least three nucleotide backbone modifications. In preferred embodiments, the double stranded nucleic acid molecule has one end that is blunt or includes a one or two nucleotide overhang. sd-rxRNA® molecules can be optimized through chemical modification, and in some instances through attachment of hydrophobic conjugates.

In some embodiments, an sd-rxRNA® comprises an isolated double stranded nucleic acid molecule comprising a guide strand and a passenger strand, wherein the region of the molecule that is double stranded is from 8-15 nucleotides long, wherein the guide strand contains a single stranded region that is 4-12 nucleotides long, wherein the single stranded region of the guide strand contains 3, 4, 5, 6, 7, 8, 9, 10, 11 or 12 phosphorothioate modifications, and wherein at least 40% of the nucleotides of the double stranded nucleic acid are modified.

The polynucleotides of the invention are referred to herein as isolated double stranded or duplex nucleic acids, oligonucleotides or polynucleotides, nano molecules, nano RNA, sd-rxRNA$^{nano}$, sd-rxRNA® or RNA molecules of the invention.

sd-rxRNA® molecules are much more effectively taken up by cells compared to conventional siRNAs. These molecules are highly efficient in silencing of target gene expression and offer significant advantages over previously described RNAi molecules including high activity in the presence of serum, efficient self delivery, compatibility with a wide variety of linkers, and reduced presence or complete absence of chemical modifications that are associated with toxicity.

In contrast to single-stranded polynucleotides, duplex polynucleotides have traditionally been difficult to deliver to a cell as they have rigid structures and a large number of negative charges which makes membrane transfer difficult. sd-rxRNA® molecules however, although partially double-stranded, are recognized in vivo as single-stranded and, as such, are capable of efficiently being delivered across cell membranes. As a result the polynucleotides of the invention are capable in many instances of self delivery. Thus, the polynucleotides of the invention may be formulated in a manner similar to conventional RNAi agents or they may be delivered to the cell or subject alone (or with non-delivery type carriers) and allowed to self deliver. In one embodiment of the present invention, self delivering asymmetric double-stranded RNA molecules are provided in which one portion of the molecule resembles a conventional RNA duplex and a second portion of the molecule is single stranded.

The oligonucleotides of the invention in some aspects have a combination of asymmetric structures including a double stranded region and a single stranded region of 5 nucleotides or longer, specific chemical modification patterns and are conjugated to lipophilic or hydrophobic molecules. This class of RNAi like compounds have superior efficacy in vitro and in vivo. It is believed that the reduction in the size of the rigid duplex region in combination with phosphorothioate modifications applied to a single stranded region contribute to the observed superior efficacy.

The invention is based, at least in part, on the surprising discovery that sd-rxRNA® molecules can be delivered efficiently to the eye through either subretinal or intravitreal injection. Based on results generated in multiple different mammalian systems, including mouse, rat and rabbit, and as presented in the Examples section, drastically (several orders of magnitude) better ocular uptake and distribution is observed following administration of sd-rxRNA® molecules than following administration of conventional RNAi compounds.

Another surprising aspect of the invention is that sd-rxRNA® molecules are taken up by all cell layers in the retina, including the retinal pigment epithelium cell layer. Efficient sd-rxRNA® distribution is achieved through both subretinal and intravitreal injection and both means of administration are compatible with aspects of the invention. In some embodiments, intravitreal administration is preferred due to technical ease and widespread use in intraocular drug delivery.

As used herein, "ocular" refers to the eye, including any and all of its cells including muscles, nerves, blood vessels, tear ducts, membranes etc., as well as structures that are connected with the eye and its physiological functions. The terms ocular and eye are used interchangeably throughout this disclosure. Non-limiting examples of cell types within the eye include: cells located in the ganglion cell layer (GCL), the inner plexiform layer inner (IPL), the inner nuclear layer (INL), the outer plexiform layer (OPL), outer nuclear layer (ONL), outer segments (OS) of rods and cones, the retinal pigmented epithelium (RPE), the inner segments (IS) of rods and cones, the epithelium of the conjunctiva, the iris, the ciliary body, the corneum, and epithelium of ocular sebaceous glands.

In a preferred embodiment the RNAi compounds of the invention comprise an asymmetric compound comprising a duplex region (required for efficient RISC entry of 8-15 bases long) and single stranded region of 4-12 nucleotides long. In some embodiments, the duplex region is 13 or 14 nucleotides long. A 6 or 7 nucleotide single stranded region is preferred in some embodiments. The single stranded region of the new RNAi compounds also comprises 2-12 phosphorothioate internucleotide linkages (referred to as phosphorothioate modifications). 6-8 phosphorothioate internucleotide linkages are preferred in some embodiments. Additionally, the RNAi compounds of the invention also include a unique chemical modification pattern, which provides stability and is compatible with RISC entry. The combination of these elements has resulted in unexpected properties which are highly useful for delivery of RNAi reagents in vitro and in vivo.

The chemical modification pattern, which provides stability and is compatible with RISC entry includes modifications to the sense, or passenger, strand as well as the antisense, or guide, strand. For instance the passenger strand can be modified with any chemical entities which confirm stability and do not interfere with activity. Such modifications include 2' ribo modifications (O-methyl, 2' F, 2 deoxy and others) and backbone modification like phosphorothioate modifications. A preferred chemical modification pattern in the passenger strand includes Omethyl modification of C and U nucleotides within the passenger strand or alternatively the passenger strand may be completely Omethyl modified.

The guide strand, for example, may also be modified by any chemical modification which confirms stability without interfering with RISC entry. A preferred chemical modification pattern in the guide strand includes the majority of C and U nucleotides being 2' F modified and the 5' end being phosphorylated. Another preferred chemical modification pattern in the guide strand includes 2'Omethyl modification of position 1 and C/U in positions 11-18 and 5' end chemical phosphorylation. Yet another preferred chemical modification pattern in the guide strand includes 2'Omethyl modification of position 1 and C/U in positions 11-18 and 5' end chemical phosphorylation and 2'F modification of C/U in positions 2-10. In some embodiments the passenger strand and/or the guide strand contains at least one 5-methyl C or U modifications.

In some embodiments, at least 30% of the nucleotides in the sd-rxRNA® are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the sd-rxRNA® are modified. In some embodiments, 100% of the nucleotides in the sd-rxRNA® are modified.

The above-described chemical modification patterns of the oligonucleotides of the invention are well tolerated and actually improved efficacy of asymmetric RNAi compounds. It was also demonstrated experimentally herein that the combination of modifications to RNAi when used together in a polynucleotide results in the achievement of optimal efficacy in passive uptake of the RNAi. Elimination of any of the described components (Guide strand stabilization, phosphorothioate stretch, sense strand stabilization and hydrophobic conjugate) or increase in size in some instances results in sub-optimal efficacy and in some instances complete lost of efficacy. The combination of elements results in development of a compound, which is fully active following passive delivery to cells such as HeLa cells. The data in the Examples presented below demonstrates high efficacy of the oligonucleotides of the invention in vivo upon ocular administration.

The sd-rxRNA® can be further improved in some instances by improving the hydrophobicity of compounds using of novel types of chemistries. For example, one chemistry is related to use of hydrophobic base modifications. Any base in any position might be modified, as long as modification results in an increase of the partition coefficient of the base. The preferred locations for modification chemistries are positions 4 and 5 of the pyrimidines. The major advantage of these positions is (a) ease of synthesis and (b) lack of interference with base-pairing and A form helix formation, which are essential for RISC complex loading and target recognition. A version of sd-rxRNA® compounds where multiple deoxy Uridines are present without interfering with overall compound efficacy was used. In addition major improvement in tissue distribution and cellular uptake might be obtained by optimizing the structure of the hydrophobic conjugate. In some of the preferred embodiment the structure of sterol is modified to alter (increase/decrease) C17 attached chain. This type of modification results in significant increase in cellular uptake and improvement of tissue uptake prosperities in vivo.

dsRNA formulated according to the invention also includes rxRNAori. rxRNAori refers to a class of RNA molecules described in and incorporated by reference from PCT Publication No. WO2009/102427 (Application No. PCT/US2009/000852), filed on Feb. 11, 2009, and entitled, "MODIFIED RNAI POLYNUCLEOTIDES AND USES THEREOF."

In some embodiments, an rxRNAori molecule comprises a double-stranded RNA (dsRNA) construct of 12-35 nucleotides in length, for inhibiting expression of a target gene, comprising: a sense strand having a 5'-end and a 3'-end, wherein the sense strand is highly modified with 2'-modified ribose sugars, and wherein 3-6 nucleotides in the central portion of the sense strand are not modified with 2'-modified ribose sugars and, an antisense strand having a 5'-end and a 3'-end, which hybridizes to the sense strand and to mRNA of the target gene, wherein the dsRNA inhibits expression of the target gene in a sequence-dependent manner.

rxRNAori can contain any of the modifications described herein. In some embodiments, at least 30% of the nucleotides in the rxRNAori are modified. For example, at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% of the nucleotides in the rxRNAori are modified. In some embodiments, 100% of the nucleotides in the sd-rxRNA® are modified. In some embodiments, only the passenger strand of the rxRNAori contains modifications.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Thus, aspects of the invention relate to isolated double stranded nucleic acid molecules comprising a guide (antisense) strand and a passenger (sense) strand. As used herein, the term "double-stranded" refers to one or more nucleic acid molecules in which at least a portion of the nucleomonomers are complementary and hydrogen bond to form a double-stranded region. In some embodiments, the length of the guide strand ranges from 16-29 nucleotides long. In certain embodiments, the guide strand is 16, 17, 18, 19, 20, 21, 22, 23, 24, 25, 26, 27, 28, or 29 nucleotides long. The guide strand has complementarity to a target gene. Complementarity between the guide strand and the target gene may exist over any portion of the guide strand. Complementarity as used herein may be perfect complementarity or less than perfect complementarity as long as the guide strand is sufficiently complementary to the target that it mediates RNAi. In some embodiments complementarity refers to less than 25%, 20%, 15%, 10%, 5%, 4%, 3%, 2%, or 1% mismatch between the guide strand and the target. Perfect complementarity refers to 100% complementarity. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Moreover, not all positions of a siRNA contribute equally to target recognition. Mismatches in the center of the siRNA are most critical and essentially abolish target RNA cleavage. Mismatches upstream of the center or upstream of the cleavage site referencing the antisense strand are tolerated but significantly reduce target RNA cleavage. Mismatches downstream of the center or cleavage site referencing the antisense strand, preferably located near the 3' end of the antisense strand, e.g. 1, 2, 3, 4, 5 or 6 nucleotides from the 3' end of the antisense strand, are tolerated and reduce target RNA cleavage only slightly.

While not wishing to be bound by any particular theory, in some embodiments, the guide strand is at least 16 nucleotides in length and anchors the Argonaute protein in RISC. In some embodiments, when the guide strand loads into RISC it has a defined seed region and target mRNA cleavage takes place across from position 10-11 of the guide strand. In some embodiments, the 5' end of the guide strand is or is able to be phosphorylated. The nucleic acid molecules described herein may be referred to as minimum trigger RNA.

In some embodiments, the length of the passenger strand ranges from 8-15 nucleotides long. In certain embodiments, the passenger strand is 8, 9, 10, 11, 12, 13, 14 or 15 nucleotides long. The passenger strand has complementarity to the guide strand. Complementarity between the passenger strand and the guide strand can exist over any portion of the passenger or guide strand. In some embodiments, there is 100% complementarity between the guide and passenger strands within the double stranded region of the molecule.

Aspects of the invention relate to double stranded nucleic acid molecules with minimal double stranded regions. In some embodiments the region of the molecule that is double stranded ranges from 8-15 nucleotides long. In certain embodiments, the region of the molecule that is double stranded is 8, 9, 10, 11, 12, 13, 14 or 15 nucleotides long. In certain embodiments the double stranded region is 13 or 14 nucleotides long. There can be 100% complementarity between the guide and passenger strands, or there may be one or more mismatches between the guide and passenger strands. In some embodiments, on one end of the double stranded molecule, the molecule is either blunt-ended or has a one-nucleotide overhang. The single stranded region of the molecule is in some embodiments between 4-12 nucleotides long. For example the single stranded region can be 4, 5, 6, 7, 8, 9, 10, 11 or 12 nucleotides long. However, in certain embodiments, the single stranded region can also be less than 4 or greater than 12 nucleotides long. In certain embodiments, the single stranded region is at least 6 or at least 7 nucleotides long.

RNAi constructs associated with the invention can have a thermodynamic stability (ΔG) of less than −13 kkal/mol. In some embodiments, the thermodynamic stability (ΔG) is less than −20 kkal/mol. In some embodiments there is a loss of efficacy when (ΔG) goes below −21 kkal/mol. In some embodiments a (ΔG) value higher than −13 kkal/mol is compatible with aspects of the invention. Without wishing to be bound by any theory, in some embodiments a molecule with a relatively higher (ΔG) value may become active at a relatively higher concentration, while a molecule with a relatively lower (ΔG) value may become active at a relatively lower concentration. In some embodiments, the (ΔG) value may be higher than −9 kkcal/mol. The gene silencing effects mediated by the RNAi constructs associated with the invention, containing minimal double stranded regions, are unexpected because molecules of almost identical design but lower thermodynamic stability have been demonstrated to be inactive (Rana et al 2004).

Without wishing to be bound by any theory, results described herein suggest that a stretch of 8-10 bp of dsRNA or dsDNA will be structurally recognized by protein components of RISC or co-factors of RISC. Additionally, there is a free energy requirement for the triggering compound that it may be either sensed by the protein components and/or stable enough to interact with such components so that it may be loaded into the Argonaute protein. If optimal thermodynamics are present and there is a double stranded portion that is preferably at least 8 nucleotides then the duplex will be recognized and loaded into the RNAi machinery.

In some embodiments, thermodynamic stability is increased through the use of LNA bases. In some embodiments, additional chemical modifications are introduced. Several non-limiting examples of chemical modifications include: 5' Phosphate, 2'-O-methyl, 2'-O-ethyl, 2'-fluoro, ribothymidine, C-5 propynyl-dC (pdC) and C-5 propynyl-dU (pdU); C-5 propynyl-C (pC) and C-5 propynyl-U (pU); 5-methyl C, 5-methyl U, 5-methyl dC, 5-methyl dU methoxy, (2,6-diaminopurine), 5'-Dimethoxytrityl-N4-ethyl-2'-deoxyCytidine and MGB (minor groove binder). It should be appreciated that more than one chemical modification can be combined within the same molecule.

Molecules associated with the invention are optimized for increased potency and/or reduced toxicity. For example, nucleotide length of the guide and/or passenger strand, and/or the number of phosphorothioate modifications in the guide and/or passenger strand, can in some aspects influence potency of the RNA molecule, while replacing 2'-fluoro (2'F) modifications with 2'-O-methyl (2'OMe) modifications can in some aspects influence toxicity of the molecule. Specifically, reduction in 2'F content of a molecule is predicted to reduce toxicity of the molecule. The Examples section presents molecules in which 2'F modifications have been eliminated, offering an advantage over previously described RNAi compounds due to a predicted reduction in toxicity. Furthermore, the number of phosphorothioate modifications in an RNA molecule can influence the uptake of the molecule into a cell, for example the efficiency of passive uptake of the molecule into a cell. Preferred embodiments of molecules described herein have no 2'F modification and yet are characterized by equal efficacy in cellular uptake and tissue penetration. Such molecules represent a significant improvement over prior art, such as molecules described by Accell and Wolfrum, which are heavily modified with extensive use of 2'F.

In some embodiments, a guide strand is approximately 18-19 nucleotides in length and has approximately 2-14 phosphate modifications. For example, a guide strand can contain 2, 3, 4, 5, 6, 7, 8, 9, 10, 11, 12, 13, 14 or more than 14 nucleotides that are phosphate-modified. The guide strand may contain one or more modifications that confer increased stability without interfering with RISC entry. The phosphate modified nucleotides, such as phosphorothioate modified nucleotides, can be at the 3' end, 5' end or spread throughout the guide strand. In some embodiments, the 3' terminal 10 nucleotides of the guide strand contains 1, 2, 3, 4, 5, 6, 7, 8, 9 or 10 phosphorothioate modified nucleotides. The guide strand can also contain 2'F and/or 2'OMe modifications, which can be located throughout the molecule. In some embodiments, the nucleotide in position one of the guide strand (the nucleotide in the most 5' position of the guide strand) is 2'OMe modified and/or phosphorylated. C and U nucleotides within the guide strand can be 2'F modified. For example, C and U nucleotides in positions 2-10 of a 19 nt guide strand (or corresponding positions in a guide strand of a different length) can be 2'F modified. C and U nucleotides within the guide strand can also be 2'OMe modified. For example, C and U nucleotides in positions 11-18 of a 19 nt guide strand (or corresponding positions in a guide strand of a different length) can be 2'OMe modified. In some embodiments, the nucleotide at the most 3' end of the guide strand is unmodified. In certain embodiments, the majority of Cs and Us within the guide strand are 2'F modified and the 5' end of the guide strand is phosphorylated. In other embodiments, position 1 and the Cs or Us in positions 11-18 are 2'OMe modified and the 5' end of the guide strand is phosphorylated. In other embodiments, position 1 and the Cs or Us in positions 11-18 are 2'OMe modified, the 5' end of the guide strand is phosphorylated, and the Cs or Us in position 2-10 are 2'F modified.

In some aspects, an optimal passenger strand is approximately 11-14 nucleotides in length. The passenger strand may contain modifications that confer increased stability. One or more nucleotides in the passenger strand can be 2'OMe modified. In some embodiments, one or more of the C and/or U nucleotides in the passenger strand is 2'OMe modified, or all of the C and U nucleotides in the passenger strand are 2'OMe modified. In certain embodiments, all of the nucleotides in the passenger strand are 2'OMe modified. One or more of the nucleotides on the passenger strand can also be phosphate-modified such as phosphorothioate modified. The passenger strand can also contain 2' ribo, 2'F and 2 deoxy modifications or any combination of the above. As demonstrated in the Examples, chemical modification patterns on both the guide and passenger strand are well tolerated and a combination of chemical modifications is shown herein to lead to increased efficacy and self-delivery of RNA molecules.

Aspects of the invention relate to RNAi constructs that have extended single-stranded regions relative to double stranded regions, as compared to molecules that have been used previously for RNAi. The single stranded region of the molecules may be modified to promote cellular uptake or gene silencing. In some embodiments, phosphorothioate modification of the single stranded region influences cellular uptake and/or gene silencing. The region of the guide strand that is phosphorothioate modified can include nucleotides within both the single stranded and double stranded regions of the molecule. In some embodiments, the single stranded region includes 2-12 phosphorothioate modifications. For example, the single stranded region can include 2, 3, 4, 5, 6, 7, 8, 9, 10, 11, or 12 phosphorothioate modifications. In some instances, the single stranded region contains 6-8 phosphorothioate modifications.

Molecules associated with the invention are also optimized for cellular uptake. In RNA molecules described herein, the guide and/or passenger strands can be attached to a conjugate. In certain embodiments the conjugate is hydrophobic. The hydrophobic conjugate can be a small molecule with a partition coefficient that is higher than 10. The conjugate can be a sterol-type molecule such as cholesterol, or a molecule with an increased length polycarbon chain attached to C17, and the presence of a conjugate can influence the ability of an RNA molecule to be taken into a cell with or without a lipid transfection reagent. The conjugate can be attached to the passenger or guide strand through a hydrophobic linker. In some embodiments, a hydrophobic linker is 5-12C in length, and/or is hydroxypyrrolidine-based. In some embodiments, a hydrophobic conjugate is attached to the passenger strand and the CU residues of either the passenger and/or guide strand are modified. In some embodiments, at least 50%, 55%, 60%, 65%, 70%, 75%, 80%, 85%, 90% or 95% of the CU residues on the passenger strand and/or the guide strand are modified. In some aspects, molecules associated with the invention are self-delivering (sd). As used herein, "self-delivery" refers to the ability of a molecule to be delivered into a cell without the need for an additional delivery vehicle such as a transfection reagent.

Aspects of the invention relate to selecting molecules for use in RNAi. In some embodiments, molecules that have a double stranded region of 8-15 nucleotides can be selected for use in RNAi. In some embodiments, molecules are selected based on their thermodynamic stability ($\Delta G$). In some embodiments, molecules will be selected that have a ($\Delta G$) of less than −13 kkal/mol. For example, the ($\Delta G$) value may be −13, −14, −15, −16, −17, −18, −19, −21, −22 or less than −22 kkal/mol. In other embodiments, the ($\Delta G$) value may be higher than −13 kkal/mol. For example, the ($\Delta G$) value may be −12, −11, −10, −9, −8, −7 or more than −7 kkal/mol. It should be appreciated that $\Delta G$ can be calculated using any method known in the art. In some embodiments $\Delta G$ is calculated using Mfold, available through the Mfold internet site (mfold.bioinfo.rpi.edu/cgi-bin/rna-form1.cgi).

Methods for calculating $\Delta G$ are described in, and are incorporated by reference from, the following references: Zuker, M. (2003) Nucleic Acids Res., 31(13):3406-15; Mathews, D. H., Sabina, J., Zuker, M. and Turner, D. H. (1999) J. Mol. Biol. 288:911-940; Mathews, D. H., Disney, M. D., Childs, J. L., Schroeder, S. J., Zuker, M., and Turner, D. H. (2004) Proc. Natl. Acad. Sci. 101:7287-7292; Duan, S., Mathews, D. H., and Turner, D. H. (2006) Biochemistry 45:9819-9832; Wuchty, S., Fontana, W., Hofacker, I. L., and Schuster, P. (1999) Biopolymers 49:145-165.

In certain embodiments, the polynucleotide contains 5'- and/or 3'-end overhangs. The number and/or sequence of nucleotides overhang on one end of the polynucleotide may be the same or different from the other end of the polynucleotide. In certain embodiments, one or more of the overhang nucleotides may contain chemical modification(s), such as phosphorothioate or 2'-OMe modification.

In certain embodiments, the polynucleotide is unmodified. In other embodiments, at least one nucleotide is modified. In further embodiments, the modification includes a 2'-H or 2'-modified ribose sugar at the 2nd nucleotide from the 5'-end of the guide sequence. The "2nd nucleotide" is defined as the second nucleotide from the 5'-end of the polynucleotide.

As used herein, "2'-modified ribose sugar" includes those ribose sugars that do not have a 2'-OH group. "2'-modified ribose sugar" does not include 2'-deoxyribose (found in unmodified canonical DNA nucleotides). For example, the 2'-modified ribose sugar may be 2'-O-alkyl nucleotides, 2'-deoxy-2'-fluoro nucleotides, 2'-deoxy nucleotides, or combination thereof.

In certain embodiments, the 2'-modified nucleotides are pyrimidine nucleotides (e.g., C/U). Examples of 2'-O-alkyl nucleotides include 2'-O-methyl nucleotides, or 2'-O-allyl nucleotides.

In certain embodiments, the sd-rxRNA® polynucleotide of the invention with the above-referenced 5'-end modification exhibits significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the RNAi reagent or therapeutics.

As used herein, "off-target" gene silencing refers to unintended gene silencing due to, for example, spurious sequence homology between the antisense (guide) sequence and the unintended target mRNA sequence.

According to this aspect of the invention, certain guide strand modifications further increase nuclease stability, and/or lower interferon induction, without significantly decreasing RNAi activity (or no decrease in RNAi activity at all).

In some embodiments, the 5'-stem sequence may comprise a 2'-modified ribose sugar, such as 2'-O-methyl modified nucleotide, at the $2^{nd}$ nucleotide on the 5'-end of the polynucleotide and, in some embodiments, no other modified nucleotides. The hairpin structure having such modification may have enhanced target specificity or reduced off-target silencing compared to a similar construct without the 2'-O-methyl modification at said position.

Certain combinations of specific 5'-stem sequence and 3'-stem sequence modifications may result in further unexpected advantages, as partly manifested by enhanced ability to inhibit target gene expression, enhanced serum stability, and/or increased target specificity, etc.

In certain embodiments, the guide strand comprises a 2'-O-methyl modified nucleotide at the $2^{nd}$ nucleotide on the 5'-end of the guide strand and no other modified nucleotides.

In other aspects, the sd-rxRNA® structures of the present invention mediates sequence-dependent gene silencing by a microRNA mechanism. As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

microRNAs are involved in down-regulating target genes in critical pathways, such as development and cancer, in mice, worms and mammals. Gene silencing through a microRNA mechanism is achieved by specific yet imperfect base-pairing of the miRNA and its target messenger RNA (mRNA). Various mechanisms may be used in microRNA-mediated down-regulation of target mRNA expression.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNAs are expressed by endogenous genes in vivo and are processed from a hairpin or stem-loop precursor (pre-miRNA or pri-miRNAs) by Dicer or other RNAses. miRNAs can exist transiently in vivo as a double-stranded duplex but only one strand is taken up by the RISC complex to direct gene silencing.

In some embodiments a version of sd-rxRNA® compounds, which are effective in cellular uptake and inhibiting of miRNA activity are described. Essentially the compounds are similar to RISC entering version but large strand chemical modification patterns are optimized in the way to block cleavage and act as an effective inhibitor of the RISC action. For example, the compound might be completely or mostly Omethyl modified with the PS content described previously. For these types of compounds the 5' phosphorylation is not necessary. The presence of double stranded region is preferred as it is promotes cellular uptake and efficient RISC loading.

Another pathway that uses small RNAs as sequence-specific regulators is the RNA interference (RNAi) pathway, which is an evolutionarily conserved response to the presence of double-stranded RNA (dsRNA) in the cell. The dsRNAs are cleaved into ~20-base pair (bp) duplexes of small-interfering RNAs (siRNAs) by Dicer. These small RNAs get assembled into multiprotein effector complexes called RNA-induced silencing complexes (RISCs). The siRNAs then guide the cleavage of target mRNAs with perfect complementarity.

Some aspects of biogenesis, protein complexes, and function are shared between the siRNA pathway and the miRNA pathway. The subject single-stranded polynucleotides may mimic the dsRNA in the siRNA mechanism, or the microRNA in the miRNA mechanism.

In certain embodiments, the modified RNAi constructs may have improved stability in serum and/or cerebral spinal fluid compared to an unmodified RNAi constructs having the same sequence.

In certain embodiments, the structure of the RNAi construct does not induce interferon response in primary cells, such as mammalian primary cells, including primary cells from human, mouse and other rodents, and other non-human mammals. In certain embodiments, the RNAi construct may also be used to inhibit expression of a target gene in an invertebrate organism.

To further increase the stability of the subject constructs in vivo, the 3'-end of the hairpin structure may be blocked by protective group(s). For example, protective groups such as inverted nucleotides, inverted abasic moieties, or amino-end modified nucleotides may be used. Inverted nucleotides may comprise an inverted deoxynucleotide. Inverted abasic moieties may comprise an inverted deoxyabasic moiety, such as a 3',3'-linked or 5',5'-linked deoxyabasic moiety.

The RNAi constructs of the invention are capable of inhibiting the synthesis of any target protein encoded by target gene(s). The invention includes methods to inhibit expression of a target gene either in a cell in vitro, or in vivo. As such, the RNAi constructs of the invention are useful for treating a patient with a disease characterized by the overexpression of a target gene.

The target gene can be endogenous or exogenous (e.g., introduced into a cell by a virus or using recombinant DNA technology) to a cell. Such methods may include introduction of RNA into a cell in an amount sufficient to inhibit expression of the target gene. By way of example, such an RNA molecule may have a guide strand that is complementary to the nucleotide sequence of the target gene, such that the composition inhibits expression of the target gene.

The invention also relates to vectors expressing the nucleic acids of the invention, and cells comprising such vectors or the nucleic acids. The cell may be a mammalian cell in vivo or in culture, such as a human cell.

The invention further relates to compositions comprising the subject RNAi constructs, and a pharmaceutically acceptable carrier or diluent.

Another aspect of the invention provides a method for inhibiting the expression of a target gene in a mammalian cell, comprising contacting an eye cell with any of the subject RNAi constructs.

The method may be carried out in vitro, ex vivo, or in vivo, in, for example, mammalian cells in culture, such as a human cell in culture.

The target cells (e.g., mammalian cell) may be contacted in the presence of a delivery reagent, such as a lipid (e.g., a cationic lipid) or a liposome.

Another aspect of the invention provides a method for inhibiting the expression of a target gene in a mammalian cell, comprising contacting the mammalian cell with a vector expressing the subject RNAi constructs.

In one aspect of the invention, a longer duplex polynucleotide is provided, including a first polynucleotide that ranges in size from about 16 to about 30 nucleotides; a second polynucleotide that ranges in size from about 26 to about 46 nucleotides, wherein the first polynucleotide (the antisense strand) is complementary to both the second polynucleotide (the sense strand) and a target gene, and wherein both polynucleotides form a duplex and wherein the first polynucleotide contains a single stranded region longer than 6 bases in length and is modified with alternative chemical modification pattern, and/or includes a conjugate moiety that facilitates cellular delivery. In this embodiment, between about 40% to about 90% of the nucleotides of the passenger strand between about 40% to about 90% of the nucleotides of the guide strand, and between about 40% to about 90% of the nucleotides of the single stranded region of the first polynucleotide are chemically modified nucleotides.

In an embodiment, the chemically modified nucleotide in the polynucleotide duplex may be any chemically modified nucleotide known in the art, such as those discussed in detail above. In a particular embodiment, the chemically modified nucleotide is selected from the group consisting of 2' F modified nucleotides, 2'-O-methyl modified and 2'deoxy nucleotides. In another particular embodiment, the chemically modified nucleotides results from "hydrophobic modifications" of the nucleotide base. In another particular embodiment, the chemically modified nucleotides are phosphorothioates. In an additional particular embodiment, chemically modified nucleotides are combination of phosphorothioates, 2'-O-methyl, 2'deoxy, hydrophobic modifications and phosphorothioates. As these groups of modifications refer to modification of the ribose ring, back bone and nucleotide, it is feasible that some modified nucleotides will carry a combination of all three modification types.

In another embodiment, the chemical modification is not the same across the various regions of the duplex. In a particular embodiment, the first polynucleotide (the passenger strand), has a large number of diverse chemical modifications in various positions. For this polynucleotide up to 90% of nucleotides might be chemically modified and/or have mismatches introduced.

In another embodiment, chemical modifications of the first or second polynucleotide include, but not limited to, 5' position modification of Uridine and Cytosine (4-pyridyl, 2-pyridyl, indolyl, phenyl ($C_6H_5OH$); tryptophanyl (C8H6N)CH2CH(NH2)CO), isobutyl, butyl, aminobenzyl; phenyl; naphthyl, etc), where the chemical modification might alter base pairing capabilities of a nucleotide. For the guide strand an important feature of this aspect of the invention is the position of the chemical modification relative to the 5' end of the antisense and sequence. For example, chemical phosphorylation of the 5' end of the guide strand is usually beneficial for efficacy. O-methyl modifications in the seed region of the sense strand (position 2-7 relative to the 5' end) are not generally well tolerated, whereas 2'F and deoxy are well tolerated. The mid part of the guide strand and the 3' end of the guide strand are more permissive in a type of chemical modifications applied. Deoxy modifications are not tolerated at the 3' end of the guide strand.

A unique feature of this aspect of the invention involves the use of hydrophobic modification on the bases. In one embodiment, the hydrophobic modifications are preferably positioned near the 5' end of the guide strand, in other embodiments, they localized in the middle of the guides strand, in other embodiment they localized at the 3' end of the guide strand and yet in another embodiment they are distributed thought the whole length of the polynucleotide. The same type of patterns is applicable to the passenger strand of the duplex.

The other part of the molecule is a single stranded region. The single stranded region is expected to range from 7 to 40 nucleotides.

In one embodiment, the single stranded region of the first polynucleotide contains modifications selected from the group consisting of between 40% and 90% hydrophobic base modifications, between 40%-90% phosphorothioates, between 40%-90% modification of the ribose moiety, and any combination of the preceding.

Efficiency of guide strand (first polynucleotide) loading into the RISC complex might be altered for heavily modified polynucleotides, so in one embodiment, the duplex polynucleotide includes a mismatch between nucleotide 9, 11, 12, 13, or 14 on the guide strand (first polynucleotide) and the opposite nucleotide on the sense strand (second polynucleotide) to promote efficient guide strand loading.

More detailed aspects of the invention are described in the sections below.

Duplex Characteristics

Double-stranded oligonucleotides of the invention may be formed by two separate complementary nucleic acid strands. Duplex formation can occur either inside or outside the cell containing the target gene.

As used herein, the term "duplex" includes the region of the double-stranded nucleic acid molecule(s) that is (are) hydrogen bonded to a complementary sequence. Double-stranded oligonucleotides of the invention may comprise a nucleotide sequence that is sense to a target gene and a complementary sequence that is antisense to the target gene. The sense and antisense nucleotide sequences correspond to the target gene sequence, e.g., are identical or are sufficiently identical to effect target gene inhibition (e.g., are about at least about 98% identical, 96% identical, 94%, 90% identical, 85% identical, or 80% identical) to the target gene sequence.

In certain embodiments, the double-stranded oligonucleotide of the invention is double-stranded over its entire length, i.e., with no overhanging single-stranded sequence at either end of the molecule, i.e., is blunt-ended. In other embodiments, the individual nucleic acid molecules can be of different lengths. In other words, a double-stranded oligonucleotide of the invention is not double-stranded over its entire length. For instance, when two separate nucleic acid molecules are used, one of the molecules, e.g., the first molecule comprising an antisense sequence, can be longer than the second molecule hybridizing thereto (leaving a portion of the molecule single-stranded). Likewise, when a single nucleic acid molecule is used a portion of the molecule at either end can remain single-stranded.

In one embodiment, a double-stranded oligonucleotide of the invention contains mismatches and/or loops or bulges, but is double-stranded over at least about 70% of the length of the oligonucleotide. In another embodiment, a double-stranded oligonucleotide of the invention is double-stranded over at least about 80% of the length of the oligonucleotide. In another embodiment, a double-stranded oligonucleotide of the invention is double-stranded over at least about 90%-95% of the length of the oligonucleotide. In another embodiment, a double-stranded oligonucleotide of the invention is double-stranded over at least about 96%-98% of the length of the oligonucleotide. In certain embodiments, the double-stranded oligonucleotide of the invention contains at least or up to 1, 2, 3, 4, 5, 6, 7, 8, 9, 10, 11, 12, 13, 14, or 15 mismatches.

Modifications

The nucleotides of the invention may be modified at various locations, including the sugar moiety, the phosphodiester linkage, and/or the base.

In some embodiments, the base moiety of a nucleoside may be modified. For example, a pyrimidine base may be modified at the 2, 3, 4, 5, and/or 6 position of the pyrimidine ring. In some embodiments, the exocyclic amine of cytosine may be modified. A purine base may also be modified. For example, a purine base may be modified at the 1, 2, 3, 6, 7, or 8 position. In some embodiments, the exocyclic amine of adenine may be modified. In some cases, a nitrogen atom in a ring of a base moiety may be substituted with another atom, such as carbon. A modification to a base moiety may be any suitable modification. Examples of modifications are known to those of ordinary skill in the art. In some embodiments, the base modifications include alkylated purines or pyrimidines, acylated purines or pyrimidines, or other heterocycles.

In some embodiments, a pyrimidine may be modified at the 5 position. For example, the 5 position of a pyrimidine may be modified with an alkyl group, an alkynyl group, an alkenyl group, an acyl group, or substituted derivatives thereof. In other examples, the 5 position of a pyrimidine may be modified with a hydroxyl group or an alkoxyl group or substituted derivative thereof. Also, the $N^4$ position of a pyrimidine may be alkylated. In still further examples, the pyrimidine 5-6 bond may be saturated, a nitrogen atom within the pyrimidine ring may be substituted with a carbon atom, and/or the $O^2$ and $O^4$ atoms may be substituted with sulfur atoms. It should be understood that other modifications are possible as well.

In other examples, the $N^7$ position and/or $N^2$ and/or $N^3$ position of a purine may be modified with an alkyl group or substituted derivative thereof. In further examples, a third ring may be fused to the purine bicyclic ring system and/or a nitrogen atom within the purine ring system may be substituted with a carbon atom. It should be understood that other modifications are possible as well.

Non-limiting examples of pyrimidines modified at the 5 position are disclosed in U.S. Pat. Nos. 5,591,843, 7,205,297, 6,432,963, and 6,020,483; non-limiting examples of pyrimidines modified at the $N^4$ position are disclosed in U.S. Pat. No. 5,580,731; non-limiting examples of purines modified at the 8 position are disclosed in U.S. Pat. Nos. 6,355,787 and 5,580,972; non-limiting examples of purines modified at the $N^6$ position are disclosed in U.S. Pat. Nos. 4,853,386, 5,789,416, and 7,041,824; and non-limiting examples of purines modified at the 2 position are disclosed in U.S. Pat. Nos. 4,201,860 and 5,587,469, all of which are incorporated herein by reference.

Non-limiting examples of modified bases include $N^4,N^4$-ethanocytosine, 7-deazaxanthosine, 7-deazaguanosine, 8-oxo-$N^6$-methyladenine, 4-acetylcytosine, 5-(carboxyhydroxylmethyl) uracil, 5-fluorouracil, 5-bromouracil, 5-carboxymethylaminomethyl-2-thiouracil, 5-carboxymethylaminomethyl uracil, dihydrouracil, inosine, $N^6$-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, $N^6$-methyladenine, 7-methylguanine, 5-methylaminomethyl uracil, 5-methoxy aminomethyl-2-thiouracil, 5-methoxyuracil, 2-methylthio-$N^6$-isopentenyladenine, pseudouracil, 5-methyl-2-thiouracil, 2-thiouracil, 4-thiouracil, 5-methyluracil, 2-thiocytosine, and 2,6-diaminopurine. In some embodiments, the base moiety may be a heterocyclic base other than a purine or pyrimidine. The heterocyclic base may be optionally modified and/or substituted.

Sugar moieties include natural, unmodified sugars, e.g., monosaccharide (such as pentose, e.g., ribose, deoxyribose), modified sugars and sugar analogs. In general, possible modifications of nucleomonomers, particularly of a sugar moiety, include, for example, replacement of one or more of the hydroxyl groups with a halogen, a heteroatom, an aliphatic group, or the functionalization of the hydroxyl group as an ether, an amine, a thiol, or the like.

One particularly useful group of modified nucleomonomers are 2'-O-methyl nucleotides. Such 2'-O-methyl nucleotides may be referred to as "methylated," and the corresponding nucleotides may be made from unmethylated nucleotides followed by alkylation or directly from methylated nucleotide reagents. Modified nucleomonomers may be used in combination with unmethylated nucleomonomers. For example, an oligonucleotide of the invention may contain both methylated and unmethylated nucleomonomers.

Some exemplary modified nucleomonomers include sugar- or backbone-modified ribonucleotides. Modified ribonucleotides may contain a non-naturally occurring base (instead of a naturally occurring base), such as uridines or cytidines modified at the 5'-position, e.g., 5'-(2-amino)propyl uridine and 5'-bromo uridine; adenosines and guanosines modified at the 8-position, e.g., 8-bromo guanosine; deaza nucleotides, e.g., 7-deaza-adenosine; and N-alkylated nucleotides, e.g., N6-methyl adenosine. Also, sugar-modified ribonucleotides may have the 2'-OH group replaced by a H, alxoxy (or OR), R or alkyl, halogen, SH, SR, amino (such as $NH_2$, NHR, $NR_2$), or CN group, wherein R is lower alkyl, alkenyl, or alkynyl.

Modified ribonucleotides may also have the phosphodiester group connecting to adjacent ribonucleotides replaced by a modified group, e.g., of phosphorothioate group. More generally, the various nucleotide modifications may be combined.

Although the antisense (guide) strand may be substantially identical to at least a portion of the target gene (or genes), at least with respect to the base pairing properties, the sequence need not be perfectly identical to be useful, e.g., to inhibit expression of a target gene's phenotype. Generally, higher homology can be used to compensate for the use of a shorter antisense gene. In some cases, the antisense strand generally will be substantially identical (although in antisense orientation) to the target gene.

The use of 2'-O-methyl modified RNA may also be beneficial in circumstances in which it is desirable to minimize cellular stress responses. RNA having 2'-O-methyl nucleomonomers may not be recognized by cellular machinery that is thought to recognize unmodified RNA. The use of 2'-O-methylated or partially 2'-O-methylated RNA may avoid the interferon response to double-stranded nucleic acids, while maintaining target RNA inhibition. This may be useful, for example, for avoiding the interferon or other cellular stress responses, both in short RNAi (e.g., siRNA) sequences that induce the interferon response, and in longer RNAi sequences that may induce the interferon response.

Overall, modified sugars may include D-ribose, 2'-O-alkyl (including 2'-O-methyl and 2'-O-ethyl), i.e., 2'-alkoxy, 2'-amino, 2'-S-alkyl, 2'-halo (including 2'-fluoro), 2'-methoxyethoxy, 2'-allyloxy ($-OCH_2CH=CH_2$), 2'-propargyl, 2'-propyl, ethynyl, ethenyl, propenyl, and cyano and the like. In one embodiment, the sugar moiety can be a hexose and incorporated into an oligonucleotide as described (Augustyns, K., et al., *Nucl. Acids. Res.* 18:4711 (1992)). Exemplary nucleomonomers can be found, e.g., in U.S. Pat. No. 5,849,902, incorporated by reference herein.

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In certain embodiments, oligonucleotides of the invention comprise 3' and 5' termini (except for circular oligonucleotides). In one embodiment, the 3' and 5' termini of an oligonucleotide can be substantially protected from nucleases e.g., by modifying the 3' or 5' linkages (e.g., U.S. Pat. No. 5,849,902 and WO 98/13526). For example, oligonucleotides can be made resistant by the inclusion of a "blocking group." The term "blocking group" as used herein refers to substituents (e.g., other than OH groups) that can be attached to oligonucleotides or nucleomonomers, either as protecting groups or coupling groups for synthesis (e.g., FITC, propyl ($CH_2$—$CH_2$—$CH_3$), glycol (—O—$CH_2$—$CH_2$—O—) phosphate ($PO_3^{2-}$), hydrogen phosphonate, or phosphoramidite). "Blocking groups" also include "end blocking groups" or "exonuclease blocking groups" which protect the 5' and 3' termini of the oligonucleotide, including modified nucleotides and non-nucleotide exonuclease resistant structures.

Exemplary end-blocking groups include cap structures (e.g., a 7-methylguanosine cap), inverted nucleomonomers, e.g., with 3'-3' or 5'-5' end inversions (see, e.g., Ortiagao et al. 1992. *Antisense Res. Dev.* 2:129), methylphosphonate, phosphoramidite, non-nucleotide groups (e.g., non-nucleotide linkers, amino linkers, conjugates) and the like. The 3' terminal nucleomonomer can comprise a modified sugar moiety. The 3' terminal nucleomonomer comprises a 3'-O that can optionally be substituted by a blocking group that prevents 3'-exonuclease degradation of the oligonucleotide. For example, the 3'-hydroxyl can be esterified to a nucleotide through a 3'→3' internucleotide linkage. For example, the alkyloxy radical can be methoxy, ethoxy, or isopropoxy, and preferably, ethoxy. Optionally, the 3'→3'linked nucleotide at the 3' terminus can be linked by a substitute linkage. To reduce nuclease degradation, the 5' most 3'→5' linkage can be a modified linkage, e.g., a phosphorothioate or a P-alkyloxyphosphotriester linkage. Preferably, the two 5' most 3'→5' linkages are modified linkages. Optionally, the 5' terminal hydroxy moiety can be esterified with a phosphorus containing moiety, e.g., phosphate, phosphorothioate, or P-ethoxyphosphate.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein. However, it will be appreciated that the present invention is not intended to be limited to these protecting groups; rather, a variety of additional equivalent protecting groups can be readily identified using the above criteria and utilized in the method of the present invention. Additionally, a variety of protecting groups are described in *Protective Groups in Organic Synthesis*, Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceeded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "lower alkyl" is used to indicate those alkyl groups (cyclic, acyclic, substituted, unsubstituted, branched, or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —CH2-cyclobutyl, n-pentyl, sec-pentyl, isopentyl, tert-pentyl, cyclopentyl, —CH2-cyclopentyl, n-hexyl, sec-hexyl, cyclohexyl, —CH2-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$, wherein each occurrence of $R_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments described herein.

The terms "halo" and "halogen" as used herein refer to an atom selected from fluorine, chlorine, bromine, and iodine.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, unless otherwise specified, the term alkyl includes both "unsubstituted alkyls" and "substituted alkyls," the latter of which refers to alkyl moieties having independently selected substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, unless otherwise specified, the term alkenyl includes both "unsubstituted alkenyls" and "substituted alkenyls," the latter of which refers to alkenyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, unless otherwise specified, the term alkynyl includes both "unsubstituted alkynyls" and "substituted alkynyls," the latter of which refers to alkynyl moieties having independently selected substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with independently selected groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "heteroatom" includes atoms of any element other than carbon or hydrogen. Preferred heteroatoms are nitrogen, oxygen, sulfur and phosphorus.

The term "hydroxy" or "hydroxyl" includes groups with an —OH or —O⁻ (with an appropriate counterion).

The term "halogen" includes fluorine, bromine, chlorine, iodine, etc. The term "perhalogenated" generally refers to a moiety wherein all hydrogens are replaced by halogen atoms.

The term "substituted" includes independently selected substituents which can be placed on the moiety and which allow the molecule to perform its intended function. Examples of substituents include alkyl, alkenyl, alkynyl, aryl, $(CR'R'')_{0-3}NR'R''$, $(CR'R'')_{0-3}CN$, $NO_2$, halogen, $(CR'R'')_{0-3}C(halogen)_3$, $(CR'R'')_{0-3}CH(halogen)_2$, $(CR'R'')_{0-3}CH_2(halogen)$, $(CR'R'')_{0-3}CONR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-2}R'$, $(CR'R'')_{0-3}O(CR'R'')_{0-3}H$, $(CR'R'')_{0-3}COR'$, $(CR'R'')_{0-3}CO_2R'$, or $(CR'R'')_{0-3}OR'$ groups; wherein each R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —$(CH_2)_2O(CH_2)_2$— group.

The term "amine" or "amino" includes compounds or moieties in which a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups.

The term "ether" includes compounds or moieties which contain an oxygen bonded to two different carbon atoms or heteroatoms. For example, the term includes "alkoxyalkyl," which refers to an alkyl, alkenyl, or alkynyl group covalently bonded to an oxygen atom which is covalently bonded to another alkyl group.

The terms "polynucleotide," "nucleotide sequence," "nucleic acid," "nucleic acid molecule," "nucleic acid sequence," and "oligonucleotide" refer to a polymer of two or more nucleotides. The polynucleotides can be DNA, RNA, or derivatives or modified versions thereof. The polynucleotide may be single-stranded or double-stranded. The polynucleotide can be modified at the base moiety, sugar moiety, or phosphate backbone, for example, to improve stability of the molecule, its hybridization parameters, etc. The polynucleotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. The olynucleotide may comprise a modified sugar moiety (e.g., 2'-fluororibose, ribose, 2'-deoxyribose, 2'-O-methylcytidine, arabinose, and hexose), and/or a modified phosphate moiety (e.g., phosphorothioates and 5'-N-phosphoramidite linkages). A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA, and RNA-RNA hybrids, as well as "protein nucleic acids" (PNA) formed by conjugating bases to an amino acid backbone.

The term "base" includes the known purine and pyrimidine heterocyclic bases, deazapurines, and analogs (including heterocyclic substituted analogs, e.g., aminoethyoxy phenoxazine), derivatives (e.g., 1-alkyl-, 1-alkenyl-, heteroaromatic- and 1-alkynyl derivatives) and tautomers thereof. Examples of purines include adenine, guanine, inosine, diaminopurine, and xanthine and analogs (e.g., 8-oxo-N⁶-methyladenine or 7-diazaxanthine) and derivatives thereof. Pyrimidines include, for example, thymine, uracil, and cytosine, and their analogs (e.g., 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

In a preferred embodiment, the nucleomonomers of an oligonucleotide of the invention are RNA nucleotides. In another preferred embodiment, the nucleomonomers of an oligonucleotide of the invention are modified RNA nucleotides. Thus, the oligunucleotides contain modified RNA nucleotides.

The term "nucleoside" includes bases which are covalently attached to a sugar moiety, preferably ribose or deoxyribose. Examples of preferred nucleosides include ribonucleosides and deoxyribonucleosides. Nucleosides also include bases linked to amino acids or amino acid analogs which may comprise free carboxyl groups, free amino groups, or protecting groups. Suitable protecting groups are well known in the art (see P. G. M. Wuts and T. W. Greene, "Protective Groups in Organic Synthesis", $2^{nd}$ Ed., Wiley-Interscience, New York, 1999).

The term "nucleotide" includes nucleosides which further comprise a phosphate group or a phosphate analog.

The nucleic acid molecules may be associated with a hydrophobic moiety for targeting and/or delivery of the molecule to a cell. In certain embodiments, the hydrophobic moiety is associated with the nucleic acid molecule through a linker. In certain embodiments, the association is through non-covalent interactions. In other embodiments, the association is through a covalent bond. Any linker known in the art may be used to associate the nucleic acid with the hydrophobic moiety. Linkers known in the art are described in published international PCT applications, WO 92/03464, WO 95/23162, WO 2008/021157, WO 2009/021157, WO 2009/134487, WO 2009/126933, U.S. Patent Application Publication 2005/0107325, U.S. Pat. Nos. 5,414,077, 5,419,966, 5,512,667, 5,646,126, and 5,652,359, which are incorporated herein by reference. The linker may be as simple as a covalent bond to a multi-atom linker. The linker may be cyclic or acyclic. The linker may be optionally substituted. In certain embodiments, the linker is capable of being cleaved from the nucleic acid. In certain embodiments, the linker is capable of being hydrolyzed under physiological conditions. In certain embodiments, the linker is capable of being cleaved by an enzyme (e.g., an esterase or phosphodiesterase). In certain embodiments, the linker comprises a spacer element to separate the nucleic acid from the hydrophobic moiety. The spacer element may include one to thirty carbon or heteroatoms. In certain embodiments, the linker and/or spacer element comprises protonatable functional groups. Such protonatable functional groups may promote the endosomal escape of the nucleic acid molecule. The protonatable functional groups may also aid in the delivery of the nucleic acid to a cell, for example, neutralizing the overall charge of the molecule. In other embodiments, the linker and/or spacer element is biologically inert (that is, it does not impart biological activity or function to the resulting nucleic acid molecule).

In certain embodiments, the nucleic acid molecule with a linker and hydrophobic moiety is of the formulae described herein. In certain embodiments, the nucleic acid molecule is of the formula:

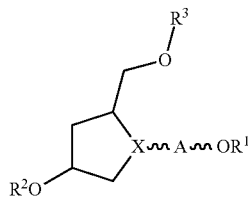

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the molecule is of the formula:

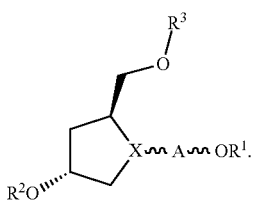

In certain embodiments, the molecule is of the formula:

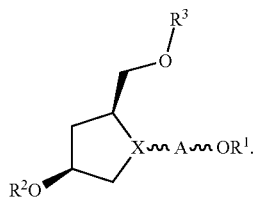

In certain embodiments, the molecule is of the formula:

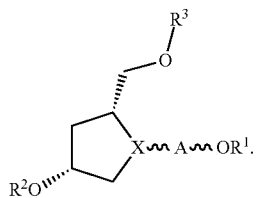

In certain embodiments, the molecule is of the formula:

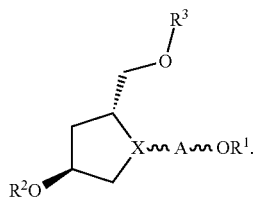

In certain embodiments, X is N. In certain embodiments, X is CH.

In certain embodiments, A is a bond. In certain embodiments, A is substituted or unsubstituted, cyclic or acyclic, branched or unbranched aliphatic. In certain embodiments, A is acyclic, substituted or unsubstituted, branched or unbranched aliphatic. In certain embodiments, A is acyclic, substituted, branched or unbranched aliphatic. In certain embodiments, A is acyclic, substituted, unbranched aliphatic. In certain embodiments, A is acyclic, substituted, unbranched alkyl. In certain embodiments, A is acyclic, substituted, unbranched $C_{1-20}$ alkyl. In certain embodiments, A is acyclic, substituted, unbranched $C_{1-12}$ alkyl. In certain embodiments, A is acyclic, substituted, unbranched $C_{1-10}$ alkyl. In certain embodiments, A is acyclic, substituted, unbranched $C_{1-8}$ alkyl. In certain embodiments, A is acyclic, substituted, unbranched $C_{1-6}$ alkyl. In certain embodiments, A is substituted or unsubstituted, cyclic or acyclic, branched or unbranched heteroaliphatic. In certain embodiments, A is acyclic, substituted or unsubstituted, branched or unbranched heteroaliphatic. In certain embodiments, A is acyclic, substituted, branched or unbranched heteroaliphatic. In certain embodiments, A is acyclic, substituted, unbranched heteroaliphatic.

In certain embodiments, A is of the formula:

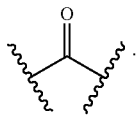 [SMILES: *C(*)=O]

In certain embodiments, A is of one of the formulae:
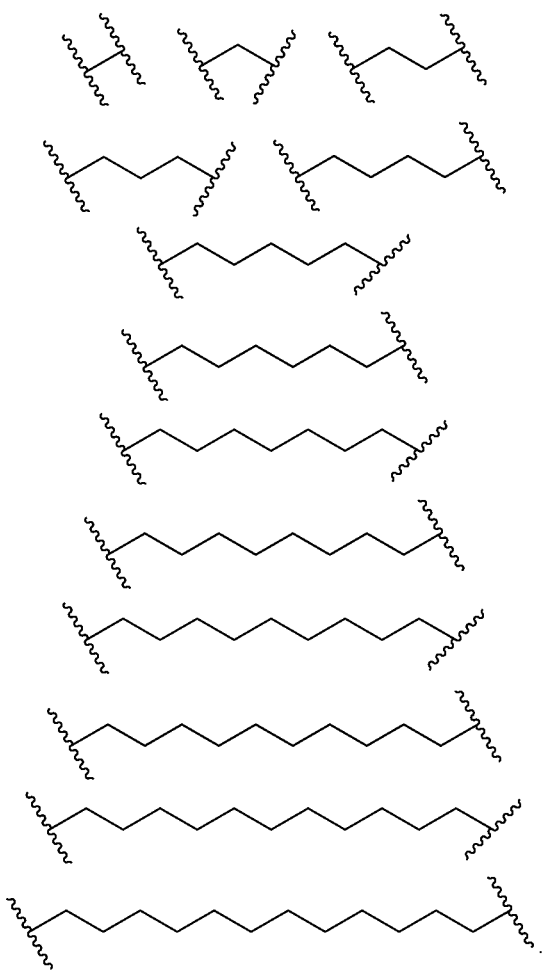
In certain embodiments, A is of one of the formulae:
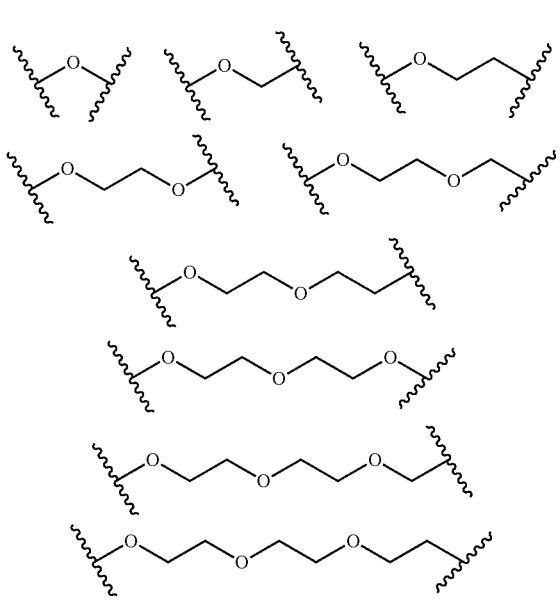
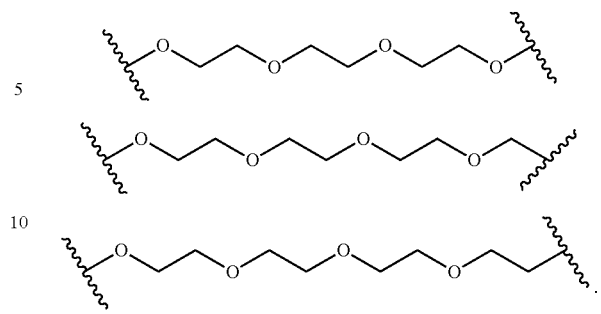
In certain embodiments, A is of one of the formulae:
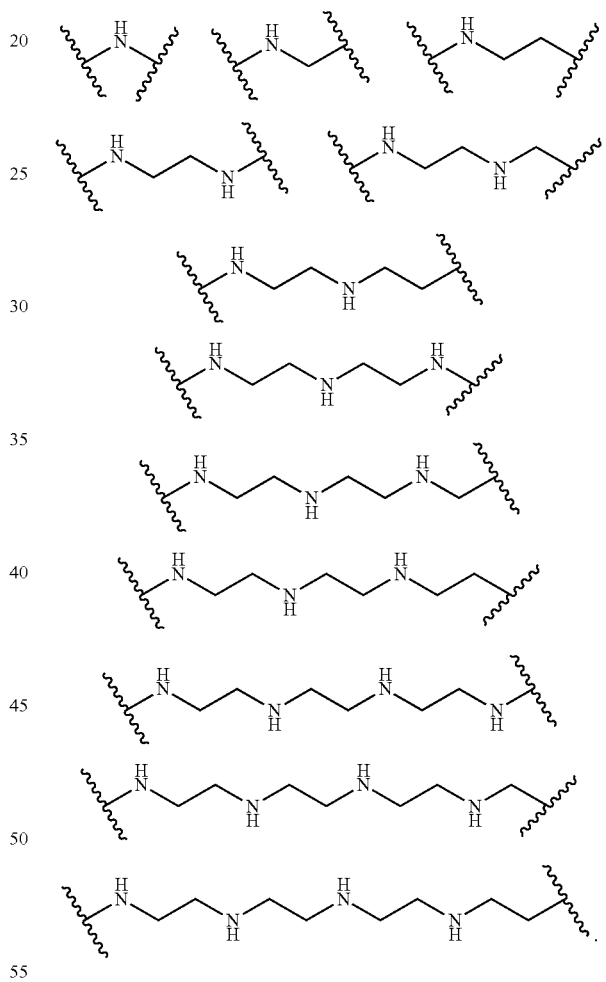
In certain embodiments, A is of the formula:
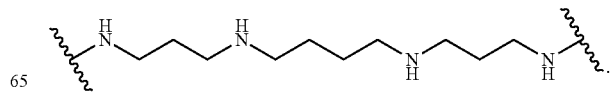

In certain embodiments, A is of the formula:

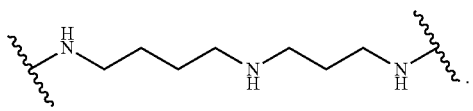 [SMILES: *NCCCCNCCCN*]

In certain embodiments, A is of the formula:

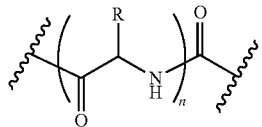

wherein
each occurrence of R is independently the side chain of a natural or unnatural amino acid; and
n is an integer between 1 and 20, inclusive. In certain embodiments, A is of the formula:

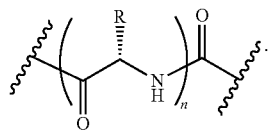

In certain embodiments, each occurrence of R is independently the side chain of a natural amino acid. In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

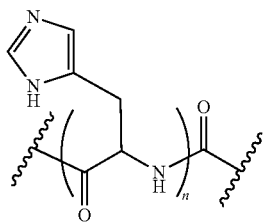

wherein n is an integer between 1 and 20, inclusive. In certain embodiments, A is of the formula:

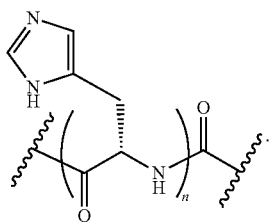

In certain embodiments, n is an integer between 1 and 15, inclusive. In certain embodiments, n is an integer between 1 and 10, inclusive. In certain embodiments, n is an integer between 1 and 5, inclusive.

In certain embodiments, A is of the formula:

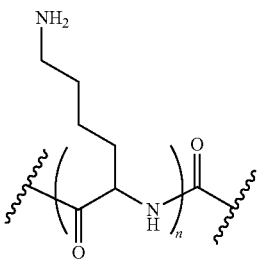

wherein n is an integer between 1 and 20, inclusive. In certain embodiments, A is of the formula:

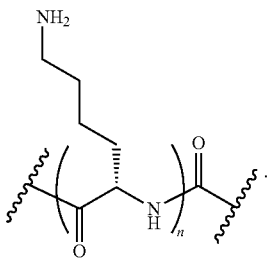

In certain embodiments, n is an integer between 1 and 15, inclusive. In certain embodiments, n is an integer between 1 and 10, inclusive. In certain embodiments, n is an integer between 1 and 5, inclusive.

In certain embodiments, the molecule is of the formula:

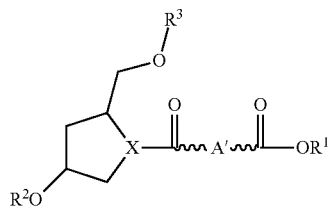

wherein X, $R^1$, $R^2$, and $R^3$ are as defined herein; and
A' is substituted or unsubstituted, cyclic or acyclic, branched or unbranched aliphatic; or substituted or unsubstituted, cyclic or acyclic, branched or unbranched heteroaliphatic.

In certain embodiments, A' is of one of the formulae:

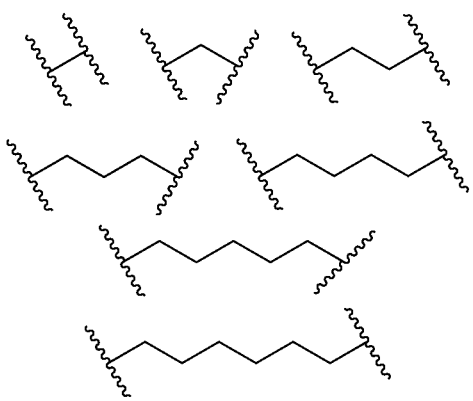

-continued

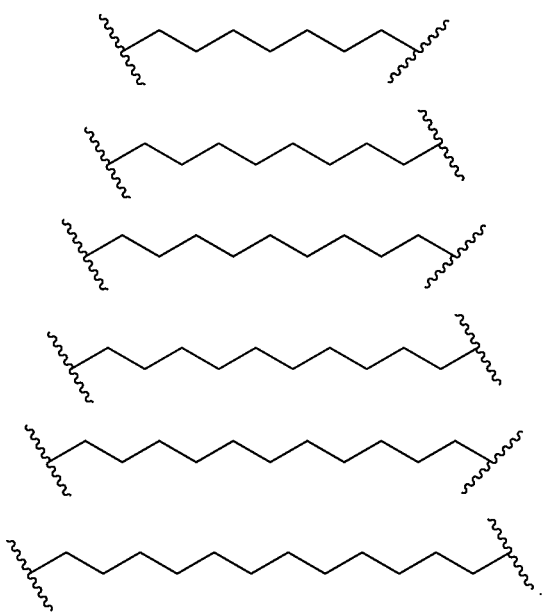

In certain embodiments, A is of one of the formulae:

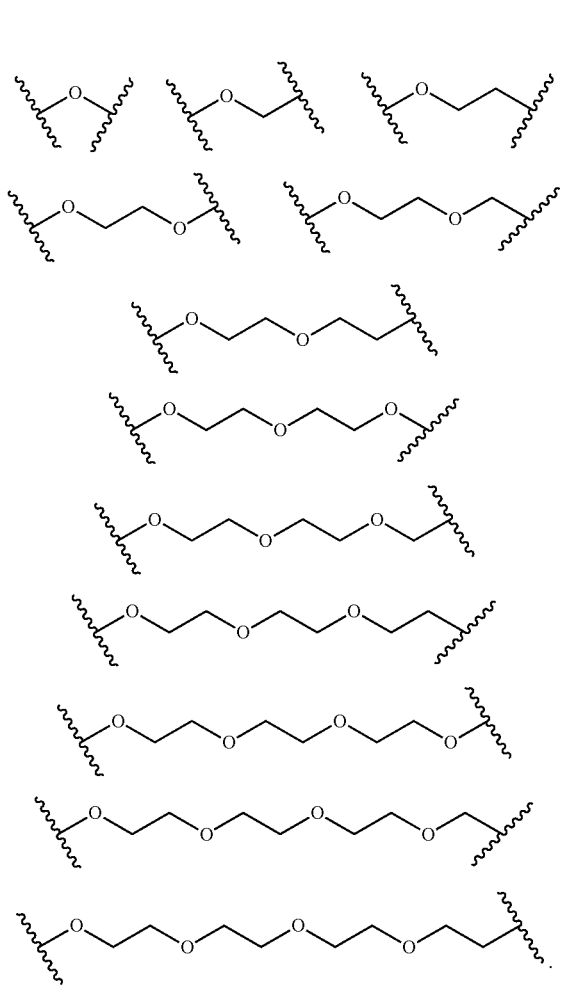

In certain embodiments, A is of one of the formulae:

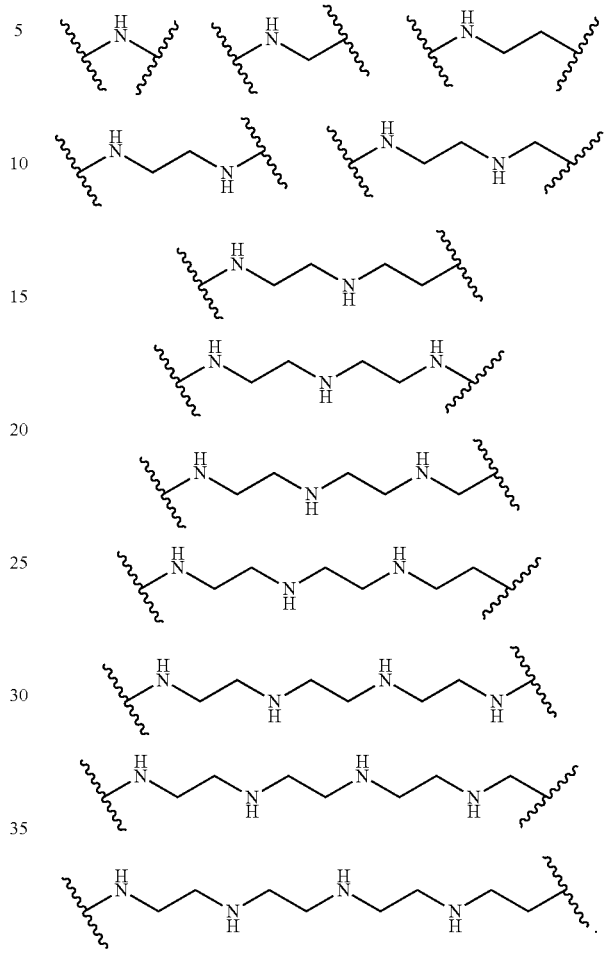

In certain embodiments, A is of the formula:

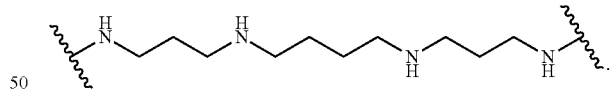

In certain embodiments, A is of the formula:

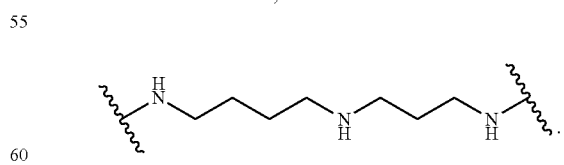

In certain embodiments, $R^1$ is a steroid. In certain embodiments, $R^1$ is a cholesterol. In certain embodiments, $R^1$ is a lipophilic vitamin. In certain embodiments, $R^1$ is a vitamin A.

In certain embodiments, $R^1$ is a vitamin E.

In certain embodiments, $R^1$ is of the formula:

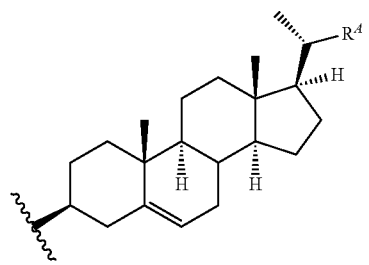

wherein $R^4$ is substituted or unsubstituted, cyclic or acyclic, branched or unbranched aliphatic; or substituted or unsubstituted, cyclic or acyclic, branched or unbranched heteroaliphatic.

In certain embodiments, $R^1$ is of the formula:

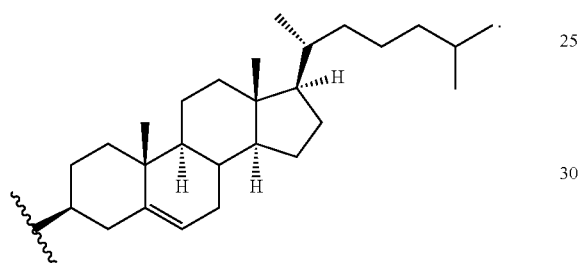

In certain embodiments, $R^1$ is of the formula:

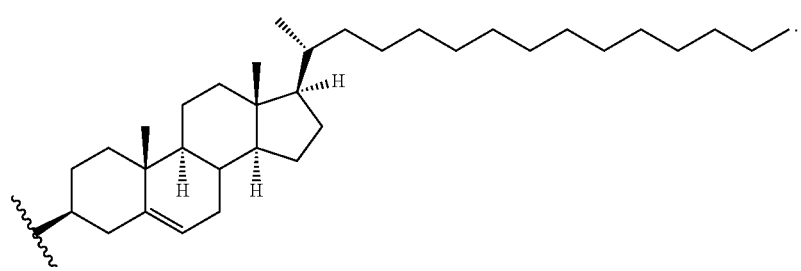

In certain embodiments, $R^1$ is of the formula:

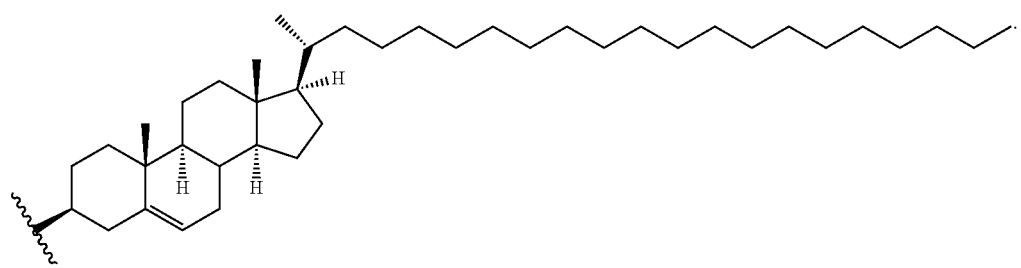

In certain embodiments, $R^1$ is of the formula:

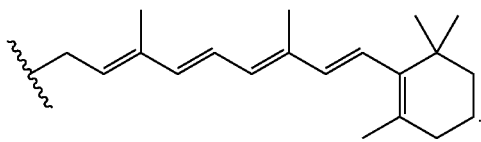 [SMILES: *C/C=C(C)/C=C/C=C(C)/C=C/C1=C(C)CCCC1(C)C]

In certain embodiments, $R^1$ is of the formula:

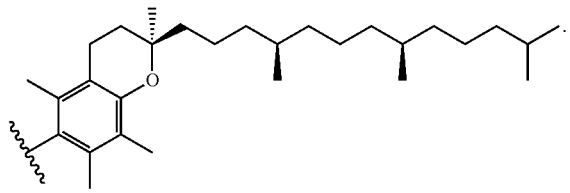 [SMILES: *c1c(C)c(C)c2c(c1C)CC[C@@](C)(CCC[C@H](C)CCC[C@H](C)CCCC(C)C)O2]

In certain embodiments, the nucleic acid molecule is of the formula:

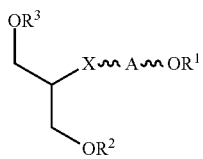

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the nucleic acid molecule is of the formula:

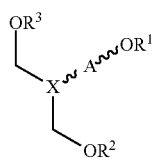

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid.

In certain embodiments, the nucleic acid molecule is of the formula:

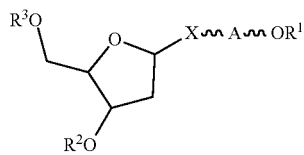

wherein

X is N or CH;

A is a bond; substituted or unsubstituted, cyclic or acyclic, branched or unbranched aliphatic; or substituted or unsubstituted, cyclic or acyclic, branched or unbranched heteroaliphatic;

$R^1$ is a hydrophobic moiety;

$R^2$ is hydrogen; an oxygen-protecting group; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; and $R^3$ is a nucleic acid. In certain embodiments, the nucleic acid molecule is of the formula:

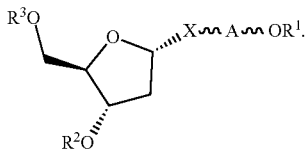

In certain embodiments, the nucleic acid molecule is of the formula:

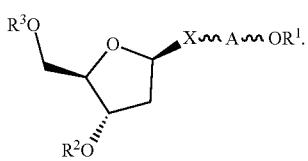

In certain embodiments, the nucleic acid molecule is of the formula:

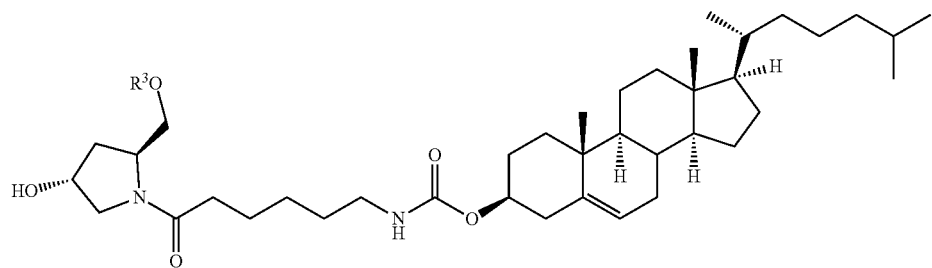

wherein R³ is a nucleic acid.

In certain embodiments, the nucleic acid molecule is of the formula:

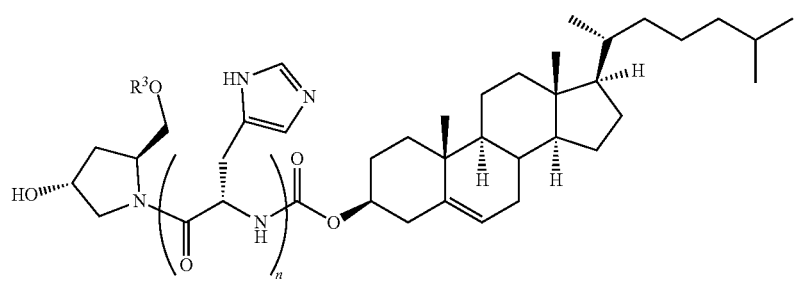

wherein R³ is a nucleic acid; and
n is an integer between 1 and 20, inclusive.

In certain embodiments, the nucleic acid molecule is of the formula:

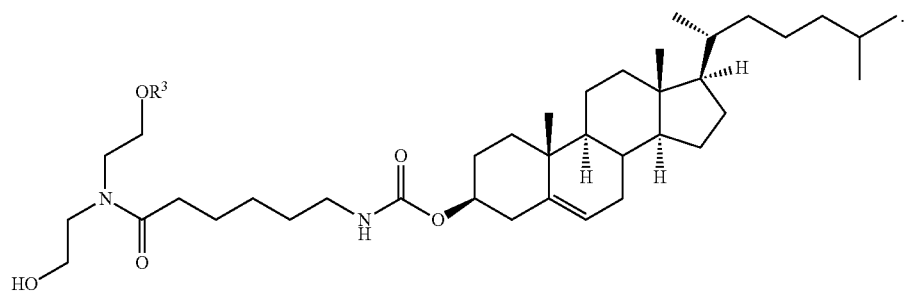

In certain embodiments, the nucleic acid molecule is of the formula:

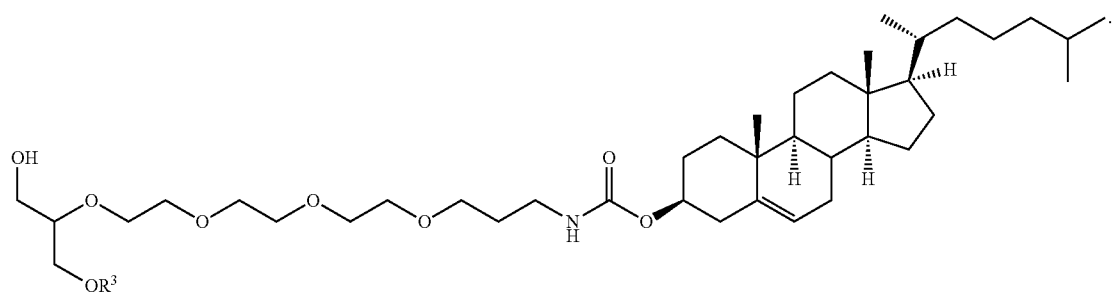

In certain embodiments, the nucleic acid molecule is of the formula:

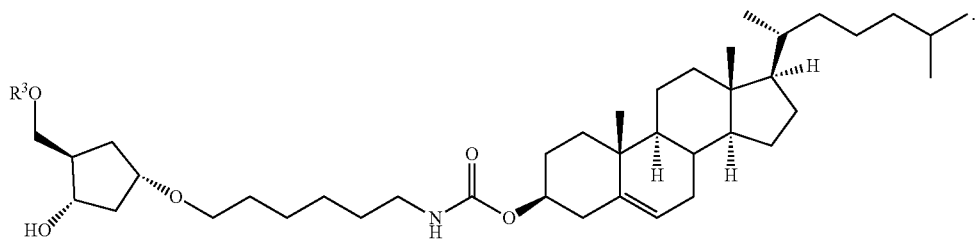

In certain embodiments, the nucleic acid molecule is of the formula:

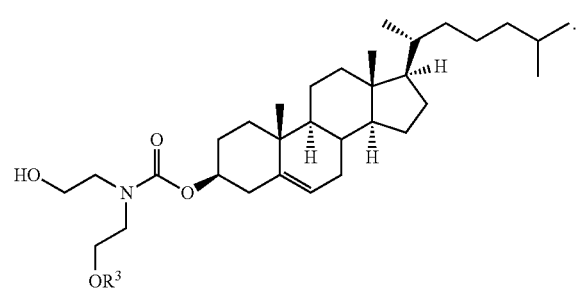

In certain embodiments, the nucleic acid molecule is of the formula:

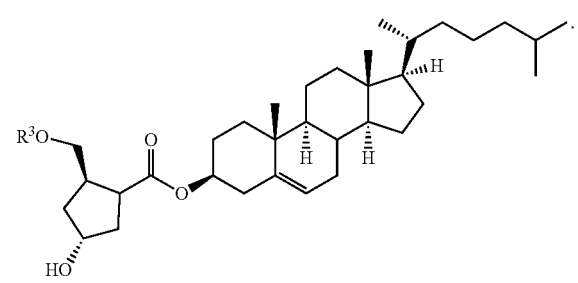

As used herein, the term "linkage" includes a naturally occurring, unmodified phosphodiester moiety (—O—(PO$^2$—)—O—) that covalently couples adjacent nucleomonomers. As used herein, the term "substitute linkage" includes any analog or derivative of the native phosphodiester group that covalently couples adjacent nucleomonomers. Substitute linkages include phosphodiester analogs, e.g., phosphorothioate, phosphorodithioate, and P-ethyoxyphosphodiester, P-ethoxyphosphodiester, P-alkyloxyphosphotriester, methylphosphonate, and nonphosphorus containing linkages, e.g., acetals and amides. Such substitute linkages are known in the art (e.g., Bjergarde et al. 1991. Nucleic Acids Res. 19:5843; Caruthers et al. 1991. Nucleosides Nucleotides. 10:47). In certain embodiments, non-hydrolizable linkages are preferred, such as phosphorothiate linkages.

In certain embodiments, oligonucleotides of the invention comprise hydrophobicly modified nucleotides or "hydrophobic modifications." As used herein "hydrophobic modifications" refers to bases that are modified such that (1) overall hydrophobicity of the base is significantly increased, and/or (2) the base is still capable of forming close to regular Watson-Crick interaction. Several non-limiting examples of base modifications include 5-position uridine and cytidine modifications such as phenyl, 4-pyridyl, 2-pyridyl, indolyl, and isobutyl, phenyl (C6H5OH); tryptophanyl (C8H6N) CH2CH(NH2)CO), Isobutyl, butyl, aminobenzyl; phenyl; and naphthyl.

Another type of conjugates that can be attached to the end (3' or 5' end), the loop region, or any other parts of the sd-rxRNA® might include a sterol, sterol type molecule, peptide, small molecule, protein, etc. In some embodiments, a sdrxRNA may contain more than one conjugates (same or different chemical nature). In some embodiments, the conjugate is cholesterol.

Another way to increase target gene specificity, or to reduce off-target silencing effect, is to introduce a 2'-modification (such as the 2'-O methyl modification) at a position corresponding to the second 5'-end nucleotide of the guide sequence. This allows the positioning of this 2'-modification in the Dicer-resistant hairpin structure, thus enabling one to design better RNAi constructs with less or no off-target silencing.

In one embodiment, a hairpin polynucleotide of the invention can comprise one nucleic acid portion which is DNA and one nucleic acid portion which is RNA. Antisense (guide) sequences of the invention can be "chimeric oligonucleotides" which comprise an RNA-like and a DNA-like region.

The language "RNase H activating region" includes a region of an oligonucleotide, e.g., a chimeric oligonucleotide, that is capable of recruiting RNase H to cleave the target RNA strand to which the oligonucleotide binds. Typically, the RNase activating region contains a minimal core (of at least about 3-5, typically between about 3-12, more typically, between about 5-12, and more preferably between about 5-10 contiguous nucleomonomers) of DNA or DNA-like nucleomonomers. (See, e.g., U.S. Pat. No. 5,849,902). Preferably, the RNase H activating region comprises about nine contiguous deoxyribose containing nucleomonomers.

The language "non-activating region" includes a region of an antisense sequence, e.g., a chimeric oligonucleotide, that does not recruit or activate RNase H. Preferably, a non-activating region does not comprise phosphorothioate DNA. The oligonucleotides of the invention comprise at least one non-activating region. In one embodiment, the non-activating region can be stabilized against nucleases or can provide specificity for the target by being complementary to the target and forming hydrogen bonds with the target nucleic acid molecule, which is to be bound by the oligonucleotide.

In one embodiment, at least a portion of the contiguous polynucleotides are linked by a substitute linkage, e.g., a phosphorothioate linkage.

In certain embodiments, most or all of the nucleotides beyond the guide sequence (2'-modified or not) are linked by phosphorothioate linkages. Such constructs tend to have improved pharmacokinetics due to their higher affinity for serum proteins. The phosphorothioate linkages in the non-guide sequence portion of the polynucleotide generally do not interfere with guide strand activity, once the latter is loaded into RISC.

Antisense (guide) sequences of the present invention may include "morpholino oligonucleotides." Morpholino oligonucleotides are non-ionic and function by an RNase H-independent mechanism. Each of the 4 genetic bases (Adenine, Cytosine, Guanine, and Thymine/Uracil) of the morpholino oligonucleotides is linked to a 6-membered morpholine ring. Morpholino oligonucleotides are made by joining the 4 different subunit types by, e.g., non-ionic phosphorodiamidate inter-subunit linkages. Morpholino oligonucleotides have many advantages including: complete resistance to nucleases (Antisense & Nucl. Acid Drug Dev. 1996. 6:267); predictable targeting (Biochemica Biophysica Acta. 1999. 1489:141); reliable activity in cells (Antisense & Nucl. Acid Drug Dev. 1997. 7:63); excellent sequence specificity (Antisense & Nucl. Acid Drug Dev. 1997. 7:151); minimal non-antisense activity (Biochemica Biophysica Acta. 1999. 1489:141); and simple osmotic or scrape delivery (Antisense & Nucl. Acid Drug Dev. 1997. 7:291). Morpholino oligonucleotides are also preferred because of their non-toxicity at high doses. A discussion of the preparation of morpholino oligonucleotides can be found in Antisense & Nucl. Acid Drug Dev. 1997. 7:187.

The chemical modifications described herein are believed, based on the data described herein, to promote single stranded polynucleotide loading into the RISC. Single stranded polynucleotides have been shown to be active in loading into RISC and inducing gene silencing. However, the level of activity for single stranded polynucleotides appears to be 2 to 4 orders of magnitude lower when compared to a duplex polynucleotide.

Figure 18:
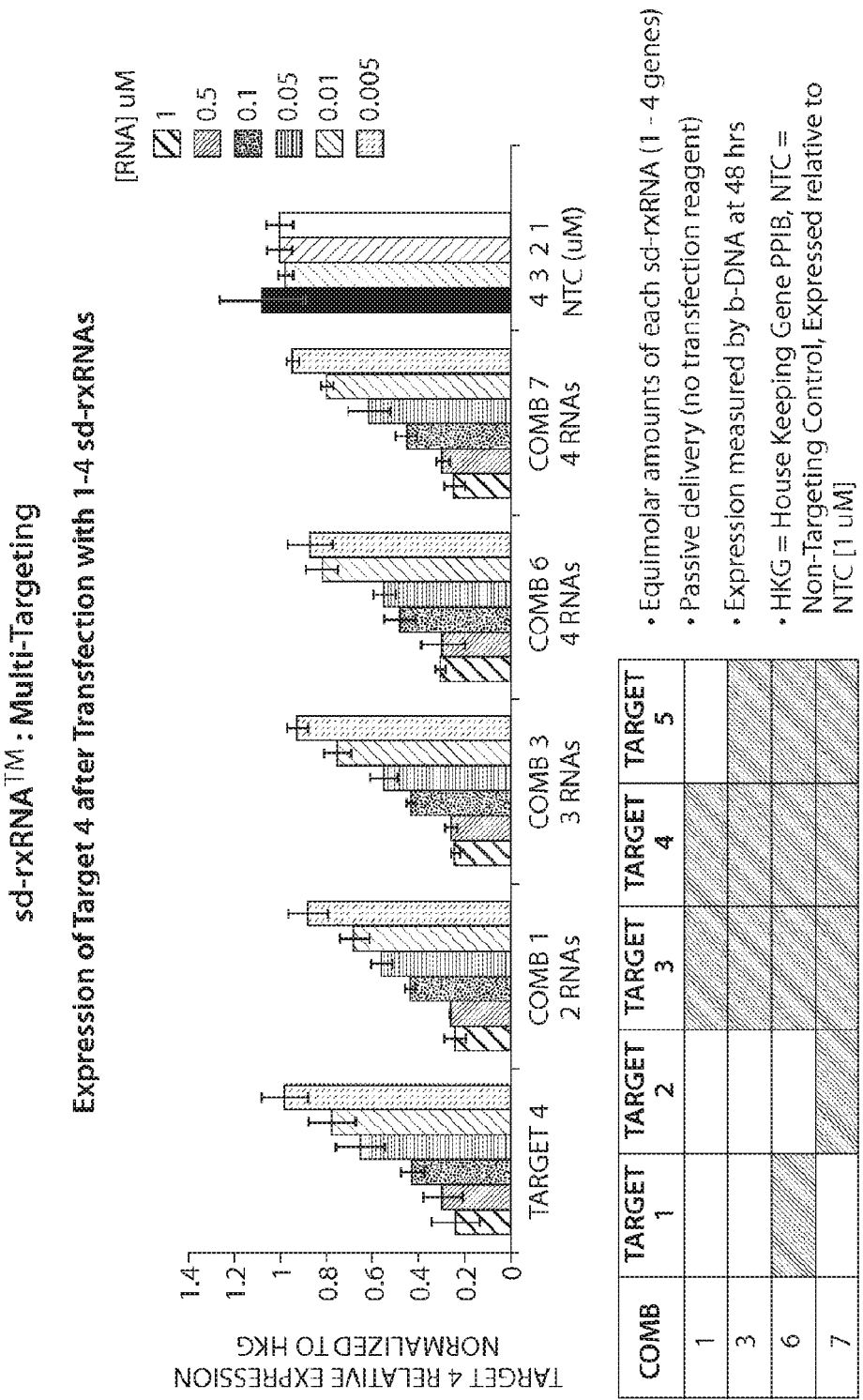
FIG. 18 demonstrates that multiple sd-rxRNA® constructs can be used to target multiple genes simultaneously.

The present invention provides a description of the chemical modification patterns, which may (a) significantly increase stability of the single stranded polynucleotide (b) promote efficient loading of the polynucleotide into the RISC complex and (c) improve uptake of the single stranded nucleotide by the cell. FIG. 18 provides some non-limiting examples of the chemical modification patterns which may be beneficial for achieving single stranded polynucleotide efficacy inside the cell. The chemical modification patterns may include combination of ribose, backbone, hydrophobic nucleoside and conjugate type of modifications. In addition, in some of the embodiments, the 5' end of the single polynucleotide may be chemically phosphorylated.

In yet another embodiment, the present invention provides a description of the chemical modifications patterns, which improve functionality of RISC inhibiting polynucleotides. Single stranded polynucleotides have been shown to inhibit activity of a preloaded RISC complex through the substrate competition mechanism. For these types of molecules, conventionally called antagomers, the activity usually requires high concentration and in vivo delivery is not very effective. The present invention provides a description of the chemical modification patterns, which may (a) significantly increase stability of the single stranded polynucleotide (b) promote efficient recognition of the polynucleotide by the RISC as a substrate and/or (c) improve uptake of the single stranded nucleotide by the cell. FIG. 6 provides some non-limiting examples of the chemical modification patterns that may be beneficial for achieving single stranded polynucleotide efficacy inside the cell. The chemical modification patterns may include combination of ribose, backbone, hydrophobic nucleoside and conjugate type of modifications.

The modifications provided by the present invention are applicable to all polynucleotides. This includes single stranded RISC entering polynucleotides, single stranded RISC inhibiting polynucleotides, conventional duplexed polynucleotides of variable length (15-40 bp), asymmetric duplexed polynucleotides, and the like. Polynucleotides may be modified with wide variety of chemical modification patterns, including 5' end, ribose, backbone and hydrophobic nucleoside modifications.

Synthesis

Oligonucleotides of the invention can be synthesized by any method known in the art, e.g., using enzymatic synthesis and/or chemical synthesis. The oligonucleotides can be synthesized in vitro (e.g., using enzymatic synthesis and chemical synthesis) or in vivo (using recombinant DNA technology well known in the art).

In a preferred embodiment, chemical synthesis is used for modified polynucleotides. Chemical synthesis of linear oligonucleotides is well known in the art and can be achieved by solution or solid phase techniques. Preferably, synthesis is by solid phase methods. Oligonucleotides can be made by any of several different synthetic procedures including the phosphoramidite, phosphite triester, H-phosphonate, and phosphotriester methods, typically by automated synthesis methods.

Oligonucleotide synthesis protocols are well known in the art and can be found, e.g., in U.S. Pat. No. 5,830,653; WO 98/13526; Stec et al. 1984. *J. Am. Chem. Soc.* 106:6077; Stec et al. 1985. *J. Org. Chem.* 50:3908; Stec et al. J. Chromatog. 1985. 326:263; LaPlanche et al. 1986. *Nucl. Acid. Res.* 1986. 14:9081; Fasman G. D., 1989. Practical Handbook of Biochemistry and Molecular Biology. 1989. CRC Press, Boca Raton, Fla.; Lamone. 1993. *Biochem. Soc. Trans.* 21:1; U.S. Pat. Nos. 5,013,830; 5,214,135; 5,525,719; Kawasaki et al. 1993. *J. Med. Chem.* 36:831; WO 92/03568; U.S. Pat. Nos. 5,276,019; and 5,264,423.

The synthesis method selected can depend on the length of the desired oligonucleotide and such choice is within the skill of the ordinary artisan. For example, the phosphoramidite and phosphite triester method can produce oligonucleotides having 175 or more nucleotides, while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543-584) provide references and outline procedures for making oligonucleotides with modified bases and modified phosphodiester linkages. Other exemplary methods for making oligonucleotides are taught in Sonveaux. 1994. "Protecting Groups in Oligonucleotide Synthesis"; Agrawal. *Methods in Molecular Biology* 26:1. Exemplary synthesis methods are also taught in "Oligonucleotide Synthesis—A Practical Approach" (Gait, M. J. IRL Press at Oxford University Press. 1984). Moreover, linear oligonucleotides of defined sequence, including some sequences with modified nucleotides, are readily available from several commercial sources.

The oligonucleotides may be purified by polyacrylamide gel electrophoresis, or by any of a number of chromatographic methods, including gel chromatography and high pressure liquid chromatography. To confirm a nucleotide sequence, especially unmodified nucleotide sequences, oligonucleotides may be subjected to DNA sequencing by any of the known procedures, including Maxam and Gilbert sequencing, Sanger sequencing, capillary electrophoresis sequencing, the wandering spot sequencing procedure or by using selective chemical degradation of oligonucleotides bound to Hybond paper. Sequences of short oligonucleotides can also be analyzed by laser desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

The quality of oligonucleotides synthesized can be verified by testing the oligonucleotide by capillary electrophoresis and denaturing strong anion HPLC (SAX-HPLC) using, e.g., the method of Bergot and Egan. 1992. *J. Chrom.* 599:35.

Other exemplary synthesis techniques are well known in the art (see, e.g., Sambrook et al., Molecular Cloning: a Laboratory Manual, Second Edition (1989); DNA Cloning, Volumes I and II (DN Glover Ed. 1985); Oligonucleotide Synthesis (M J Gait Ed, 1984; Nucleic Acid Hybridisation (B D Hames and S J Higgins eds. 1984); A Practical Guide to Molecular Cloning (1984); or the series, Methods in Enzymology (Academic Press, Inc.)).

In certain embodiments, the subject RNAi constructs or at least portions thereof are transcribed from expression vectors encoding the subject constructs. Any art recognized vectors may be use for this purpose. The transcribed RNAi constructs may be isolated and purified, before desired modifications (such as replacing an unmodified sense strand with a modified one, etc.) are carried out.

Delivery/Carrier

Uptake of Oligonucleotides by Cells

Oligonucleotides and oligonucleotide compositions are contacted with (i.e., brought into contact with, also referred to herein as administered or delivered to) and taken up by one or more cells or a cell lysate. The term "cells" includes prokaryotic and eukaryotic cells, preferably vertebrate cells, and, more preferably, mammalian cells. In a preferred embodiment, the oligonucleotide compositions of the invention are contacted with human cells.

Oligonucleotide compositions of the invention can be contacted with cells in vitro, e.g., in a test tube or culture dish, (and may or may not be introduced into a subject) or in vivo, e.g., in a subject such as a mammalian subject. In some embodiments, Oligonucleotides are administered topically or through electroporation. Oligonucleotides are taken up by cells at a slow rate by endocytosis, but endocytosed oligonucleotides are generally sequestered and not available, e.g., for hybridization to a target nucleic acid molecule. In one embodiment, cellular uptake can be facilitated by electroporation or calcium phosphate precipitation. However, these procedures are only useful for in vitro or ex vivo embodiments, are not convenient and, in some cases, are associated with cell toxicity.

In another embodiment, delivery of oligonucleotides into cells can be enhanced by suitable art recognized methods including calcium phosphate, DMSO, glycerol or dextran, electroporation, or by transfection, e.g., using cationic, anionic, or neutral lipid compositions or liposomes using methods known in the art (see e.g., WO 90/14074; WO 91/16024; WO 91/17424; U.S. Pat. No. 4,897,355; Bergan et al. 1993. *Nucleic Acids Research.* 21:3567). Enhanced delivery of oligonucleotides can also be mediated by the use of vectors (See e.g., Shi, Y. 2003. Trends Genet 2003 Jan. 19:9; Reichhart J M et al. Genesis. 2002. 34(1-2):1604, Yu et al. 2002. Proc. Natl. Acad Sci. USA 99:6047; Sui et al. 2002. Proc. Natl. Acad Sci. USA 99:5515) viruses, polyamine or polycation conjugates using compounds such as polylysine, protamine, or Ni, N12-bis (ethyl) spermine (see, e.g., Bartzatt, R. et al. 1989. *Biotechnol. Appl. Biochem.* 11:133; Wagner E. et al. 1992. *Proc. Natl. Acad. Sci.* 88:4255).

In certain embodiments, the sd-rxRNA® of the invention may be delivered by using various beta-glucan containing particles, referred to as GeRPs (glucan encapsulated RNA loaded particle), described in, and incorporated by reference from, U.S. Provisional Application No. 61/310,611, filed on Mar. 4, 2010 and entitled "Formulations and Methods for Targeted Delivery to Phagocyte Cells." Such particles are also described in, and incorporated by reference from US Patent Publications US 2005/0281781 A1, and US 2010/0040656, and in PCT publications WO 2006/007372, and WO 2007/050643. The sd-rxRNA® molecule may be hydrophobically modified and optionally may be associated with a lipid and/or amphiphilic peptide. In certain embodiments, the beta-glucan particle is derived from yeast. In certain embodiments, the payload trapping molecule is a polymer, such as those with a molecular weight of at least about 1000 Da, 10,000 Da, 50,000 Da, 100 kDa, 500 kDa, etc. Preferred polymers include (without limitation) cationic polymers, chitosans, or PEI (polyethylenimine), etc.

Glucan particles can be derived from insoluble components of fungal cell walls such as yeast cell walls. In some embodiments, the yeast is Baker's yeast. Yeast-derived glucan molecules can include one or more of β-(1,3)-Glucan, β-(1,6)-Glucan, mannan and chitin. In some embodiments, a glucan particle comprises a hollow yeast cell wall whereby the particle maintains a three dimensional structure resembling a cell, within which it can complex with or encapsulate a molecule such as an RNA molecule. Some of the advantages associated with the use of yeast cell wall particles are availability of the components, their biodegradable nature, and their ability to be targeted to phagocytic cells.

In some embodiments, glucan particles can be prepared by extraction of insoluble components from cell walls, for example by extracting Baker's yeast (Fleischmann's) with IM NaOH/pH 4.0 H2O, followed by washing and drying. Methods of preparing yeast cell wall particles are discussed in, and incorporated by reference from U.S. Pat. Nos. 4,810,646, 4,992,540, 5,082,936, 5,028,703, 5,032,401, 5,322,841, 5,401,727, 5,504,079, 5,607,677, 5,968,811, 6,242,594, 6,444,448, 6,476,003, US Patent Publications 2003/0216346, 2004/0014715 and 2010/0040656, and PCT published application WO02/12348.

Protocols for preparing glucan particles are also described in, and incorporated by reference from, the following references: Soto and Ostroff (2008), "Characterization of multilayered nanoparticles encapsulated in yeast cell wall particles for DNA delivery." *Bioconjug Chem* 19(4):840-8; Soto and Ostroff (2007), "Oral Macrophage Mediated Gene Delivery System," *Nanotech*, Volume 2, Chapter 5 ("Drug Delivery"), pages 378-381; and Li et al. (2007), "Yeast glucan particles activate murine resident macrophages to secrete proinflammatory cytokines via MyD88- and Syk kinase-dependent pathways." *Clinical Immunology* 124(2): 170-181.

Glucan containing particles such as yeast cell wall particles can also be obtained commercially. Several non-limiting examples include: Nutricell MOS 55 from Biorigin (Sao Paolo, Brazil), SAF-Mannan (SAF Agri, Minneapolis, Minn.), Nutrex (Sensient Technologies, Milwaukee, Wis.), alkali-extracted particles such as those produced by Nutricepts (Nutricepts Inc., Burnsville, Minn.) and ASA Biotech, acid-extracted WGP particles from Biopolymer Engineering, and organic solvent-extracted particles such as Adjuvax™ from Alpha-beta Technology, Inc. (Worcester, Mass.) and microparticulate glucan from Novogen (Stamford, Conn.).

Glucan particles such as yeast cell wall particles can have varying levels of purity depending on the method of production and/or extraction. In some instances, particles are alkali-extracted, acid-extracted or organic solvent-extracted to remove intracellular components and/or the outer mannoprotein layer of the cell wall. Such protocols can produce particles that have a glucan (w/w) content in the range of 50%-90%. In some instances, a particle of lower purity, meaning lower glucan w/w content may be preferred, while in other embodiments, a particle of higher purity, meaning higher glucan w/w content may be preferred.

Glucan particles, such as yeast cell wall particles, can have a natural lipid content. For example, the particles can contain 1%, 2%, 3%, 4%, 5%, 6%, 7%, 8%, 9%, 10%, 11%, 12%, 13%, 14%, 15%, 16%, 17%, 18%, 19%, 20% or more than 20% w/w lipid. In the Examples section, the effectiveness of two glucan particle batches are tested: YGP SAF and YGP SAF+L (containing natural lipids). In some instances, the presence of natural lipids may assist in complexation or capture of RNA molecules.

Glucan containing particles typically have a diameter of approximately 2-4 microns, although particles with a diameter of less than 2 microns or greater than 4 microns are also compatible with aspects of the invention.

The RNA molecule(s) to be delivered are complexed or "trapped" within the shell of the glucan particle. The shell or RNA component of the particle can be labeled for visualization, as described in, and incorporated by reference from, Soto and Ostroff (2008) *Bioconjug Chem* 19:840. Methods of loading GeRPs are discussed further below.

The optimal protocol for uptake of oligonucleotides will depend upon a number of factors, the most crucial being the type of cells that are being used. Other factors that are important in uptake include, but are not limited to, the nature and concentration of the oligonucleotide, the confluence of the cells, the type of culture the cells are in (e.g., a suspension culture or plated) and the type of media in which the cells are grown.

Encapsulating Agents

Encapsulating agents entrap oligonucleotides within vesicles. In another embodiment of the invention, an oligonucleotide may be associated with a carrier or vehicle, e.g., liposomes or micelles, although other carriers could be used, as would be appreciated by one skilled in the art. Liposomes are vesicles made of a lipid bilayer having a structure similar to biological membranes. Such carriers are used to facilitate the cellular uptake or targeting of the oligonucleotide, or improve the oligonucleotide's pharmacokinetic or toxicologic properties.

For example, the oligonucleotides of the present invention may also be administered encapsulated in liposomes, pharmaceutical compositions wherein the active ingredient is contained either dispersed or variously present in corpuscles consisting of aqueous concentric layers adherent to lipidic layers. The oligonucleotides, depending upon solubility, may be present both in the aqueous layer and in the lipidic layer, or in what is generally termed a liposomic suspension. The hydrophobic layer, generally but not exclusively, comprises phopholipids such as lecithin and sphingomyelin, steroids such as cholesterol, more or less ionic surfactants such as diacetylphosphate, stearylamine, or phosphatidic acid, or other materials of a hydrophobic nature. The diameters of the liposomes generally range from about 15 nm to about 5 microns.

The use of liposomes as drug delivery vehicles offers several advantages. Liposomes increase intracellular stability, increase uptake efficiency and improve biological activity. Liposomes are hollow spherical vesicles composed of lipids arranged in a similar fashion as those lipids which make up the cell membrane. They have an internal aqueous space for entrapping water soluble compounds and range in size from 0.05 to several microns in diameter. Several studies have shown that liposomes can deliver nucleic acids to cells and that the nucleic acids remain biologically active. For example, a lipid delivery vehicle originally designed as a research tool, such as Lipofectin or LIPOFECTAMINE™ 2000, can deliver intact nucleic acid molecules to cells.

Specific advantages of using liposomes include the following: they are non-toxic and biodegradable in composition; they display long circulation half-lives; and recognition molecules can be readily attached to their surface for targeting to tissues. Finally, cost-effective manufacture of liposome-based pharmaceuticals, either in a liquid suspension or lyophilized product, has demonstrated the viability of this technology as an acceptable drug delivery system.

In some aspects, formulations associated with the invention might be selected for a class of naturally occurring or chemically synthesized or modified saturated and unsaturated fatty acid residues. Fatty acids might exist in a form of triglycerides, diglycerides or individual fatty acids. In another embodiment, the use of well-validated mixtures of fatty acids and/or fat emulsions currently used in pharmacology for parenteral nutrition may be utilized.

Liposome based formulations are widely used for oligonucleotide delivery. However, most of commercially available lipid or liposome formulations contain at least one positively charged lipid (cationic lipids). The presence of this positively charged lipid is believed to be essential for obtaining a high degree of oligonucleotide loading and for enhancing liposome fusogenic properties. Several methods have been performed and published to identify optimal positively charged lipid chemistries. However, the commercially available liposome formulations containing cationic lipids are characterized by a high level of toxicity. In vivo limited therapeutic indexes have revealed that liposome formulations containing positive charged lipids are associated with toxicity (i.e. elevation in liver enzymes) at concentrations only slightly higher than concentration required to achieve RNA silencing.

Nucleic acids associated with the invention can be hydrophobically modified and can be encompassed within neutral nanotransporters. Further description of neutral nanotransporters is incorporated by reference from PCT Application PCT/US2009/005251, filed on Sep. 22, 2009, and entitled "Neutral Nanotransporters." Such particles enable quantitative oligonucleotide incorporation into non-charged lipid mixtures. The lack of toxic levels of cationic lipids in such neutral nanotransporter compositions is an important feature.

As demonstrated in PCT/US2009/005251, oligonucleotides can effectively be incorporated into a lipid mixture that is free of cationic lipids and such a composition can effectively deliver a therapeutic oligonucleotide to a cell in a manner that it is functional. For example, a high level of activity was observed when the fatty mixture was composed of a phosphatidylcholine base fatty acid and a sterol such as a cholesterol. For instance, one preferred formulation of neutral fatty mixture is composed of at least 20% of DOPC or DSPC and at least 20% of sterol such as cholesterol. Even as low as 1:5 lipid to oligonucleotide ratio was shown to be sufficient to get complete encapsulation of the oligonucleotide in a non charged formulation.

The neutral nanotransporters compositions enable efficient loading of oligonucleotide into neutral fat formulation. The composition includes an oligonucleotide that is modified in a manner such that the hydrophobicity of the molecule is increased (for example a hydrophobic molecule is attached (covalently or no-covalently) to a hydrophobic molecule on the oligonucleotide terminus or a non-terminal nucleotide, base, sugar, or backbone), the modified oligonucleotide being mixed with a neutral fat formulation (for example containing at least 25% of cholesterol and 25% of DOPC or analogs thereof). A cargo molecule, such as another lipid can also be included in the composition. This composition, where part of the formulation is build into the oligonucleotide itself, enables efficient encapsulation of oligonucleotide in neutral lipid particles.

In some aspects, stable particles ranging in size from 50 to 140 nm can be formed upon complexing of hydrophobic oligonucleotides with preferred formulations. It is interesting to mention that the formulation by itself typically does not form small particles, but rather, forms agglomerates, which are transformed into stable 50-120 nm particles upon addition of the hydrophobic modified oligonucleotide.

The neutral nanotransporter compositions of the invention include a hydrophobic modified polynucleotide, a neutral fatty mixture, and optionally a cargo molecule. A "hydrophobic modified polynucleotide" as used herein is a polynucleotide of the invention (i.e. sd-rxRNA®) that has at least one modification that renders the polynucleotide more hydrophobic than the polynucleotide was prior to modification. The modification may be achieved by attaching (covalently or non-covalently) a hydrophobic molecule to the polynucleotide. In some instances the hydrophobic molecule is or includes a lipophilic group.

The term "lipophilic group" means a group that has a higher affinity for lipids than its affinity for water. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible.

The hydrophobic molecule may be attached at various positions of the polynucleotide. As described above, the hydrophobic molecule may be linked to the terminal residue of the polynucleotide such as the 3' of 5'-end of the polynucleotide. Alternatively, it may be linked to an internal nucleotide or a nucleotide on a branch of the polynucleotide. The hydrophobic molecule may be attached, for instance to a 2'-position of the nucleotide. The hydrophobic molecule may also be linked to the heterocyclic base, the sugar or the backbone of a nucleotide of the polynucleotide.

The hydrophobic molecule may be connected to the polynucleotide by a linker moiety. Optionally the linker moiety is a non-nucleotidic linker moiety. Non-nucleotidic linkers are e.g. abasic residues (dSpacer), oligoethyleneglycol, such as triethyleneglycol (spacer 9) or hexaethylenegylcol (spacer 18), or alkane-diol, such as butanediol. The spacer units are preferably linked by phosphodiester or phosphorothioate bonds. The linker units may appear just once in the molecule or may be incorporated several times, e.g. via phosphodiester, phosphorothioate, methylphosphonate, or amide linkages.

Typical conjugation protocols involve the synthesis of polynucleotides bearing an aminolinker at one or more positions of the sequence, however, a linker is not required. The amino group is then reacted with the molecule being conjugated using appropriate coupling or activating reagents. The conjugation reaction may be performed either with the polynucleotide still bound to a solid support or following cleavage of the polynucleotide in solution phase. Purification of the modified polynucleotide by HPLC typically results in a pure material.

In some embodiments the hydrophobic molecule is a sterol type conjugate, a PhytoSterol conjugate, cholesterol conjugate, sterol type conjugate with altered side chain length, fatty acid conjugate, any other hydrophobic group conjugate, and/or hydrophobic modifications of the internal nucleoside, which provide sufficient hydrophobicity to be incorporated into micelles.

For purposes of the present invention, the term "sterols", refers or steroid alcohols are a subgroup of steroids with a hydroxyl group at the 3-position of the A-ring. They are amphipathic lipids synthesized from acetyl-coenzyme A via the HMG-CoA reductase pathway. The overall molecule is quite flat. The hydroxyl group on the A ring is polar. The rest of the aliphatic chain is non-polar. Usually sterols are considered to have an 8 carbon chain at position 17.

For purposes of the present invention, the term "sterol type molecules", refers to steroid alcohols, which are similar in structure to sterols. The main difference is the structure of the ring and number of carbons in a position 21 attached side chain.

For purposes of the present invention, the term "PhytoSterols" (also called plant sterols) are a group of steroid alcohols, phytochemicals naturally occurring in plants. There are more then 200 different known PhytoSterols For purposes of the present invention, the term "Sterol side chain" refers to a chemical composition of a side chain attached at the position 17 of sterol-type molecule. In a standard definition sterols are limited to a 4 ring structure carrying a 8 carbon chain at position 17. In this invention, the sterol type molecules with side chain longer and shorter than conventional are described. The side chain may branched or contain double back bones.

Thus, sterols useful in the invention, for example, include cholesterols, as well as unique sterols in which position 17 has attached side chain of 2-7 or longer then 9 carbons. In a particular embodiment, the length of the polycarbon tail is varied between 5 and 9 carbons. Such conjugates may have significantly better in vivo efficacy, in particular delivery to liver. These types of molecules are expected to work at concentrations 5 to 9 fold lower then oligonucleotides conjugated to conventional cholesterols.

Alternatively the polynucleotide may be bound to a protein, peptide or positively charged chemical that functions as the hydrophobic molecule. The proteins may be selected from the group consisting of protamine, dsRNA binding domain, and arginine rich peptides. Exemplary positively charged chemicals include spermine, spermidine, cadaverine, and putrescine.

In another embodiment hydrophobic molecule conjugates may demonstrate even higher efficacy when it is combined with optimal chemical modification patterns of the polynucleotide (as described herein in detail), containing but not limited to hydrophobic modifications, phosphorothioate modifications, and 2' ribo modifications.

In another embodiment the sterol type molecule may be a naturally occurring PhytoSterols. The polycarbon chain may be longer than 9 and may be linear, branched and/or contain double bonds. Some PhytoSterol containing polynucleotide conjugates may be significantly more potent and active in delivery of polynucleotides to various tissues. Some PhytoSterols may demonstrate tissue preference and thus be used as a way to delivery RNAi specifically to particular tissues.

The hydrophobic modified polynucleotide is mixed with a neutral fatty mixture to form a micelle. The neutral fatty acid mixture is a mixture of fats that has a net neutral or slightly net negative charge at or around physiological pH that can form a micelle with the hydrophobic modified polynucleotide. For purposes of the present invention, the term "micelle" refers to a small nanoparticle formed by a mixture of non charged fatty acids and phospholipids. The neutral fatty mixture may include cationic lipids as long as they are present in an amount that does not cause toxicity. In preferred embodiments the neutral fatty mixture is free of cationic lipids. A mixture that is free of cationic lipids is one that has less than 1% and preferably 0% of the total lipid being cationic lipid. The term "cationic lipid" includes lipids and synthetic lipids having a net positive charge at or around physiological pH. The term "anionic lipid" includes lipids and synthetic lipids having a net negative charge at or around physiological pH.

The neutral fats bind to the oligonucleotides of the invention by a strong but non-covalent attraction (e.g., an electrostatic, van der Waals, pi-stacking, etc. interaction).

The neutral fat mixture may include formulations selected from a class of naturally occurring or chemically synthesized or modified saturated and unsaturated fatty acid residues. Fatty acids might exist in a form of triglycerides, diglycerides or individual fatty acids. In another embodiment the use of well-validated mixtures of fatty acids and/or fat emulsions currently used in pharmacology for parenteral nutrition may be utilized.

The neutral fatty mixture is preferably a mixture of a choline based fatty acid and a sterol. Choline based fatty acids include for instance, synthetic phosphocholine derivatives such as DDPC, DLPC, DMPC, DPPC, DSPC, DOPC, POPC, and DEPC. DOPC (chemical registry number 4235-95-4) is dioleoylphosphatidylcholine (also known as dielaidoylphosphatidylcholine, dioleoyl-PC, dioleoylphosphocholine, dioleoyl-sn-glycero-3-phosphocholine, dioleylphosphatidylcholine). DSPC (chemical registry number 816-94-4) is distearoylphosphatidylcholine (also known as 1,2-Distearoyl-sn-Glycero-3-phosphocholine).

The sterol in the neutral fatty mixture may be for instance cholesterol. The neutral fatty mixture may be made up completely of a choline based fatty acid and a sterol or it may optionally include a cargo molecule. For instance, the neutral fatty mixture may have at least 20% or 25% fatty acid and 20% or 25% sterol.

For purposes of the present invention, the term "Fatty acids" relates to conventional description of fatty acid. They may exist as individual entities or in a form of two- and triglycerides. For purposes of the present invention, the term "fat emulsions" refers to safe fat formulations given intravenously to subjects who are unable to get enough fat in their diet. It is an emulsion of soy bean oil (or other naturally occurring oils) and egg phospholipids. Fat emulsions are being used for formulation of some insoluble anesthetics. In this disclosure, fat emulsions might be part of commercially available preparations like Intralipid, Liposyn, Nutrilipid, modified commercial preparations, where they are enriched with particular fatty acids or fully de novo-formulated combinations of fatty acids and phospholipids.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

50%-60% of the formulation can optionally be any other lipid or molecule. Such a lipid or molecule is referred to herein as a cargo lipid or cargo molecule. Cargo molecules include but are not limited to intralipid, small molecules, fusogenic peptides or lipids or other small molecules might be added to alter cellular uptake, endosomal release or tissue distribution properties. The ability to tolerate cargo molecules is important for modulation of properties of these particles, if such properties are desirable. For instance the presence of some tissue specific metabolites might drastically alter tissue distribution profiles. For example use of Intralipid type formulation enriched in shorter or longer fatty chains with various degrees of saturation affects tissue distribution profiles of these type of formulations (and their loads).

An example of a cargo lipid useful according to the invention is a fusogenic lipid. For instance, the zwiterionic lipid DOPE (chemical registry number 4004-5-1, 1,2-Dioleoyl-sn-Glycero-3-phosphoethanolamine) is a preferred cargo lipid.

Intralipid may be comprised of the following composition: 1 000 mL contain: purified soybean oil 90 g, purified egg phospholipids 12 g, glycerol anhydrous 22 g, water for injection q.s. ad 1 000 mL. pH is adjusted with sodium hydroxide to pH approximately 8. Energy content/L: 4.6 MJ (190 kcal). Osmolality (approx.): 300 mOsm/kg water. In another embodiment fat emulsion is Liposyn that contains 5% safflower oil, 5% soybean oil, up to 1.2% egg phosphatides added as an emulsifier and 2.5% glycerin in water for injection. It may also contain sodium hydroxide for pH adjustment. pH 8.0 (6.0-9.0). Liposyn has an osmolarity of 276 m Osmol/liter (actual).

Variation in the identity, amounts and ratios of cargo lipids affects the cellular uptake and tissue distribution characteristics of these compounds. For example, the length of lipid tails and level of saturability will affect differential uptake to liver, lung, fat and cardiomyocytes. Addition of special hydrophobic molecules like vitamins or different forms of sterols can favor distribution to special tissues which are involved in the metabolism of particular compounds. In some embodiments, vitamin A or E is used. Complexes are formed at different oligonucleotide concentrations, with higher concentrations favoring more efficient complex formation.

In another embodiment, the fat emulsion is based on a mixture of lipids. Such lipids may include natural compounds, chemically synthesized compounds, purified fatty acids or any other lipids. In yet another embodiment the composition of fat emulsion is entirely artificial. In a particular embodiment, the fat emulsion is more then 70% linoleic acid. In yet another particular embodiment the fat emulsion is at least 1% of cardiolipin. Linoleic acid (LA) is an unsaturated omega-6 fatty acid. It is a colorless liquid made of a carboxylic acid with an 18-carbon chain and two cis double bonds.

In yet another embodiment of the present invention, the alteration of the composition of the fat emulsion is used as a way to alter tissue distribution of hydrophobicly modified polynucleotides. This methodology provides for the specific delivery of the polynucleotides to particular tissues.

In another embodiment the fat emulsions of the cargo molecule contain more then 70% of Linoleic acid (C18H32O2) and/or cardiolipin.

Fat emulsions, like intralipid have been used before as a delivery formulation for some non-water soluble drugs (such as Propofol, re-formulated as Diprivan). Unique features of the present invention include (a) the concept of combining modified polynucleotides with the hydrophobic compound (s), so it can be incorporated in the fat micelles and (b) mixing it with the fat emulsions to provide a reversible carrier. After injection into a blood stream, micelles usually bind to serum proteins, including albumin, HDL, LDL and other. This binding is reversible and eventually the fat is absorbed by cells. The polynucleotide, incorporated as a part of the micelle will then be delivered closely to the surface of the cells. After that cellular uptake might be happening though variable mechanisms, including but not limited to sterol type delivery.

Complexing Agents

Complexing agents bind to the oligonucleotides of the invention by a strong but non-covalent attraction (e.g., an electrostatic, van der Waals, pi-stacking, etc. interaction). In one embodiment, oligonucleotides of the invention can be complexed with a complexing agent to increase cellular uptake of oligonucleotides. An example of a complexing agent includes cationic lipids. Cationic lipids can be used to deliver oligonucleotides to cells. However, as discussed above, formulations free in cationic lipids are preferred in some embodiments.

The term "cationic lipid" includes lipids and synthetic lipids having both polar and non-polar domains and which are capable of being positively charged at or around physiological pH and which bind to polyanions, such as nucleic acids, and facilitate the delivery of nucleic acids into cells. In general cationic lipids include saturated and unsaturated alkyl and alicyclic ethers and esters of amines, amides, or derivatives thereof. Straight-chain and branched alkyl and alkenyl groups of cationic lipids can contain, e.g., from 1 to about 25 carbon atoms. Preferred straight chain or branched alkyl or alkene groups have six or more carbon atoms. Alicyclic groups include cholesterol and other steroid groups. Cationic lipids can be prepared with a variety of counterions (anions) including, e.g., Cl⁻, Br⁻, I⁻, F⁻, acetate, trifluoroacetate, sulfate, nitrite, and nitrate.

Examples of cationic lipids include polyethylenimine, polyamidoamine (PAMAM) starburst dendrimers, Lipofectin (a combination of DOTMA and DOPE), Lipofectase, LIPOFECTAMINE™ (e.g., LIPOFECTAMINE™ 2000), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3-dioleyloxy-N-[2 (sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). The cationic lipid N-(1-(2,3-dioleyloxy)propyl)-N,N,N-trimethylammonium chloride (DOTMA), for example, was found to increase 1000-fold the antisense effect of a phosphorothioate oligonucleotide. (Vlassov et al., 1994, Biochimica et Biophysica Acta 1197:95-108). Oligonucleotides can also be complexed with, e.g., poly (L-lysine) or avidin and lipids may, or may not, be included in this mixture, e.g., steryl-poly (L-lysine).

Cationic lipids have been used in the art to deliver oligonucleotides to cells (see, e.g., U.S. Pat. Nos. 5,855,910; 5,851,548; 5,830,430; 5,780,053; 5,767,099; Lewis et al. 1996. *Proc. Natl. Acad. Sci. USA* 93:3176; Hope et al. 1998. *Molecular Membrane Biology* 15:1). Other lipid compositions which can be used to facilitate uptake of the instant oligonucleotides can be used in connection with the claimed methods. In addition to those listed supra, other lipid compositions are also known in the art and include, e.g., those taught in U.S. Pat. Nos. 4,235,871; 4,501,728; 4,837,028; 4,737,323.

In one embodiment lipid compositions can further comprise agents, e.g., viral proteins to enhance lipid-mediated transfections of oligonucleotides (Kamata, et al., 1994. *Nucl. Acids. Res.* 22:536). In another embodiment, oligonucleotides are contacted with cells as part of a composition comprising an oligonucleotide, a peptide, and a lipid as taught, e.g., in U.S. Pat. No. 5,736,392. Improved lipids have also been described which are serum resistant (Lewis, et al., 1996. *Proc. Natl. Acad. Sci.* 93:3176). Cationic lipids and other complexing agents act to increase the number of oligonucleotides carried into the cell through endocytosis.

In another embodiment N-substituted glycine oligonucleotides (peptoids) can be used to optimize uptake of oligonucleotides. Peptoids have been used to create cationic lipid-like compounds for transfection (Murphy, et al., 1998. *Proc. Natl. Acad. Sci.* 95:1517). Peptoids can be synthesized using standard methods (e.g., Zuckermann, R. N., et al. 1992. *J. Am. Chem. Soc.* 114:10646; Zuckermann, R. N., et al. 1992. *Int. J. Peptide Protein Res.* 40:497). Combinations of cationic lipids and peptoids, liptoids, can also be used to optimize uptake of the subject oligonucleotides (Hunag, et al., 1998. *Chemistry and Biology.* 5:345). Liptoids can be synthesized by elaborating peptoid oligonucleotides and coupling the amino terminal submonomer to a lipid via its amino group (Hunag, et al., 1998. *Chemistry and Biology.* 5:345).

It is known in the art that positively charged amino acids can be used for creating highly active cationic lipids (Lewis et al. 1996. *Proc. Natl. Acad. Sci. U.S.A.* 93:3176). In one embodiment, a composition for delivering oligonucleotides of the invention comprises a number of arginine, lysine, histidine or ornithine residues linked to a lipophilic moiety (see e.g., U.S. Pat. No. 5,777,153).

In another embodiment, a composition for delivering oligonucleotides of the invention comprises a peptide having from between about one to about four basic residues. These basic residues can be located, e.g., on the amino terminal, C-terminal, or internal region of the peptide. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine (can also be considered non-polar), asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Apart from the basic amino acids, a majority or all of the other residues of the peptide can be selected from the non-basic amino acids, e.g., amino acids other than lysine, arginine, or histidine. Preferably a preponderance of neutral amino acids with long neutral side chains are used.

In one embodiment, a composition for delivering oligonucleotides of the invention comprises a natural or synthetic polypeptide having one or more gamma carboxyglutamic acid residues, or γ-Gla residues. These gamma carboxyglutamic acid residues may enable the polypeptide to bind to each other and to membrane surfaces. In other words, a polypeptide having a series of γ-Gla may be used as a general delivery modality that helps an RNAi construct to stick to whatever membrane to which it comes in contact. This may at least slow RNAi constructs from being cleared from the blood stream and enhance their chance of homing to the target.

The gamma carboxyglutamic acid residues may exist in natural proteins (for example, prothrombin has 10 γ-Gla residues). Alternatively, they can be introduced into the purified, recombinantly produced, or chemically synthesized polypeptides by carboxylation using, for example, a vitamin K-dependent carboxylase. The gamma carboxyglutamic acid residues may be consecutive or non-consecutive, and the total number and location of such gamma carboxyglutamic acid residues in the polypeptide can be regulated/fine tuned to achieve different levels of "stickiness" of the polypeptide.

In one embodiment, the cells to be contacted with an oligonucleotide composition of the invention are contacted with a mixture comprising the oligonucleotide and a mixture comprising a lipid, e.g., one of the lipids or lipid compositions described supra for between about 12 hours to about 24 hours. In another embodiment, the cells to be contacted with an oligonucleotide composition are contacted with a mixture comprising the oligonucleotide and a mixture comprising a lipid, e.g., one of the lipids or lipid compositions described supra for between about 1 and about five days. In one embodiment, the cells are contacted with a mixture comprising a lipid and the oligonucleotide for between about three days to as long as about 30 days. In another embodiment, a mixture comprising a lipid is left in contact with the cells for at least about five to about 20 days. In another embodiment, a mixture comprising a lipid is left in contact with the cells for at least about seven to about 15 days.

For example, in one embodiment, an oligonucleotide composition can be contacted with cells in the presence of a lipid such as cytofectin CS or GSV (available from Glen Research; Sterling, Va.), GS3815, GS2888 for prolonged incubation periods as described herein.

In one embodiment, the incubation of the cells with the mixture comprising a lipid and an oligonucleotide composition does not reduce the viability of the cells. Preferably, after the transfection period the cells are substantially viable. In one embodiment, after transfection, the cells are between at least about 70% and at least about 100% viable. In another embodiment, the cells are between at least about 80% and at least about 95% viable. In yet another embodiment, the cells are between at least about 85% and at least about 90% viable.

In one embodiment, oligonucleotides are modified by attaching a peptide sequence that transports the oligonucleotide into a cell, referred to herein as a "transporting peptide." In one embodiment, the composition includes an oligonucleotide which is complementary to a target nucleic acid molecule encoding the protein, and a covalently attached transporting peptide.

The language "transporting peptide" includes an amino acid sequence that facilitates the transport of an oligonucleotide into a cell. Exemplary peptides which facilitate the transport of the moieties to which they are linked into cells are known in the art, and include, e.g., HIV TAT transcription factor, lactoferrin, Herpes VP22 protein, and fibroblast growth factor 2 (Pooga et al. 1998. *Nature Biotechnology.* 16:857; and Derossi et al. 1998. *Trends in Cell Biology.* 8:84; Elliott and O'Hare. 1997. *Cell* 88:223).

Oligonucleotides can be attached to the transporting peptide using known techniques, e.g., (Prochiantz, A. 1996. *Curr. Opin. Neurobiol.* 6:629; Derossi et al. 1998. *Trends Cell Biol.* 8:84; Troy et al. 1996. *J. Neurosci.* 16:253), Vives et al. 1997. *J. Biol. Chem.* 272:16010). For example, in one embodiment, oligonucleotides bearing an activated thiol group are linked via that thiol group to a cysteine present in a transport peptide (e.g., to the cysteine present in the β turn between the second and the third helix of the antennapedia homeodomain as taught, e.g., in Derossi et al. 1998. *Trends Cell Biol.* 8:84; Prochiantz. 1996. *Current Opinion in Neurobiol.* 6:629; Allinquant et al. 1995. J Cell Biol. 128:919). In another embodiment, a Boc-Cys-(Npys)OH group can be coupled to the transport peptide as the last (N-terminal) amino acid and an oligonucleotide bearing an SH group can be coupled to the peptide (Troy et al. 1996. *J. Neurosci.* 16:253).

In one embodiment, a linking group can be attached to a nucleomonomer and the transporting peptide can be covalently attached to the linker. In one embodiment, a linker can function as both an attachment site for a transporting peptide and can provide stability against nucleases. Examples of suitable linkers include substituted or unsubstituted $C_1$-$C_{20}$ alkyl chains, $C_2$-$C_{20}$ alkenyl chains, $C_2$-$C_{20}$ alkynyl chains, peptides, and heteroatoms (e.g., S, O, NH, etc.). Other exemplary linkers include bifunctional crosslinking agents such as sulfosuccinimidyl-4-(maleimidophenyl)-butyrate (SMPB) (see, e.g., Smith et al. Biochem J 1991. 276: 417-2).

In one embodiment, oligonucleotides of the invention are synthesized as molecular conjugates which utilize receptor-mediated endocytotic mechanisms for delivering genes into cells (see, e.g., Bunnell et al. 1992. *Somatic Cell and Molecular Genetics.* 18:559, and the references cited therein).

Targeting Agents

The delivery of oligonucleotides can also be improved by targeting the oligonucleotides to a cellular receptor. The targeting moieties can be conjugated to the oligonucleotides or attached to a carrier group (i.e., poly(L-lysine) or liposomes) linked to the oligonucleotides. This method is well suited to cells that display specific receptor-mediated endocytosis.

For instance, oligonucleotide conjugates to 6-phosphomannosylated proteins are internalized 20-fold more efficiently by cells expressing mannose 6-phosphate specific receptors than free oligonucleotides. The oligonucleotides may also be coupled to a ligand for a cellular receptor using a biodegradable linker. In another example, the delivery construct is mannosylated streptavidin which forms a tight complex with biotinylated oligonucleotides. Mannosylated streptavidin was found to increase 20-fold the internalization of biotinylated oligonucleotides. (Vlassov et al. 1994. *Biochimica et Biophysica Acta* 1197:95-108).

In addition specific ligands can be conjugated to the polylysine component of polylysine-based delivery systems. For example, transferrin-polylysine, adenovirus-polylysine, and influenza virus hemagglutinin HA-2 N-terminal fusogenic peptides-polylysine conjugates greatly enhance receptor-mediated DNA delivery in eucaryotic cells. Mannosylated glycoprotein conjugated to poly(L-lysine) in alveolar macrophages has been employed to enhance the cellular uptake of oligonucleotides. Liang et al. 1999. *Pharmazie* 54:559-566.

Because malignant cells have an increased need for essential nutrients such as folic acid and transferrin, these nutrients can be used to target oligonucleotides to cancerous cells. For example, when folic acid is linked to poly(L-lysine) enhanced oligonucleotide uptake is seen in promyelocytic leukaemia (HL-60) cells and human melanoma (M-14) cells. Ginobbi et al. 1997. *Anticancer Res.* 17:29. In another example, liposomes coated with maleylated bovine serum albumin, folic acid, or ferric protoporphyrin IX, show enhanced cellular uptake of oligonucleotides in murine macrophages, KB cells, and 2.2.15 human hepatoma cells. Liang et al. 1999. *Pharmazie* 54:559-566.

Liposomes naturally accumulate in the liver, spleen, and reticuloendothelial system (so-called, passive targeting). By coupling liposomes to various ligands such as antibodies are protein A, they can be actively targeted to specific cell populations. For example, protein A-bearing liposomes may be pretreated with H-2K specific antibodies which are targeted to the mouse major histocompatibility complex-encoded H-2K protein expressed on L cells. (Vlassov et al. 1994. *Biochimica et Biophysica Acta* 1197:95-108).

Other in vitro and/or in vivo delivery of RNAi reagents are known in the art, and can be used to deliver the subject RNAi constructs. See, for example, U.S. patent application publications 20080152661, 20080112916, 20080107694, 20080038296, 20070231392, 20060240093, 20060178327, 20060008910, 20050265957, 20050064595, 20050042227, 20050037496, 20050026286, 20040162235, 20040072785, 20040063654, 20030157030, WO 2008/036825, WO04/065601, and AU2004206255B2, just to name a few (all incorporated by reference).

Administration

The optimal course of administration or delivery of the oligonucleotides may vary depending upon the desired result and/or on the subject to be treated. As used herein "administration" refers to contacting cells with oligonucleotides and can be performed in vitro or in vivo. The dosage of oligonucleotides may be adjusted to optimally reduce expression of a protein translated from a target nucleic acid molecule, e.g., as measured by a readout of RNA stability or by a therapeutic response, without undue experimentation.

For example, expression of the protein encoded by the nucleic acid target can be measured to determine whether or not the dosage regimen needs to be adjusted accordingly. In addition, an increase or decrease in RNA or protein levels in a cell or produced by a cell can be measured using any art recognized technique. By determining whether transcription has been decreased, the effectiveness of the oligonucleotide in inducing the cleavage of a target RNA can be determined.

Any of the above-described oligonucleotide compositions can be used alone or in conjunction with a pharmaceutically acceptable carrier. As used herein, "pharmaceutically acceptable carrier" includes appropriate solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, it can be used in the therapeutic compositions. Supplementary active ingredients can also be incorporated into the compositions.

Oligonucleotides may be incorporated into liposomes or liposomes modified with polyethylene glycol or admixed with cationic lipids for parenteral administration. Incorporation of additional substances into the liposome, for example, antibodies reactive against membrane proteins found on specific target cells, can help target the oligonucleotides to specific cell types.

With respect to in vivo applications, the formulations of the present invention can be administered to a patient in a variety of forms adapted to deliver the construct to the eye. In preferred embodiments, parenteral administration is ocular. Ocular administration can be intravitreal, intracameral, subretinal, subconjunctival, or subtenon.

Pharmaceutical preparations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, or dextran, optionally, the suspension may also contain stabilizers. The oligonucleotides of the invention can be formulated in liquid solutions, preferably in physiologically compatible buffers such as Hank's solution or Ringer's solution. In addition, the oligonucleotides may be formulated in solid form and redissolved or suspended immediately prior to use. Lyophilized forms are also included in the invention.

The chosen method of delivery will result in entry into cells. In some embodiments, preferred delivery methods include liposomes (10-400 nm), hydrogels, controlled-release polymers, and other pharmaceutically applicable vehicles, and microinjection or electroporation (for ex vivo treatments).

The pharmaceutical preparations of the present invention may be prepared and formulated as emulsions. Emulsions are usually heterogeneous systems of one liquid dispersed in another in the form of droplets usually exceeding 0.1 µm in diameter. The emulsions of the present invention may contain excipients such as emulsifiers, stabilizers, dyes, fats, oils, waxes, fatty acids, fatty alcohols, fatty esters, humectants, hydrophilic colloids, preservatives, and anti-oxidants may also be present in emulsions as needed. These excipients may be present as a solution in either the aqueous phase, oily phase or itself as a separate phase.

Examples of naturally occurring emulsifiers that may be used in emulsion formulations of the present invention include lanolin, beeswax, phosphatides, lecithin and acacia. Finely divided solids have also been used as good emulsifiers especially in combination with surfactants and in viscous preparations. Examples of finely divided solids that may be used as emulsifiers include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

Examples of preservatives that may be included in the emulsion formulations include methyl paraben, propyl paraben, quaternary ammonium salts, benzalkonium chloride, esters of p-hydroxybenzoic acid, and boric acid. Examples of antioxidants that may be included in the emulsion formulations include free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

In one embodiment, the compositions of oligonucleotides are formulated as microemulsions. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain ($C_8$-$C_{12}$) mono, di, and tri-glycerides, polyoxyethylated glyceryl fatty acid esters, fatty alcohols, polyglycolized glycerides, saturated polyglycolized $C_8$-$C_{10}$ glycerides, vegetable oils and silicone oil.

Microemulsions are particularly of interest from the standpoint of drug solubilization and the enhanced absorption of drugs. Lipid based microemulsions (both oil/water and water/oil) have been proposed to enhance the oral bioavailability of drugs.

Microemulsions offer improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11:1385; Ho et al., *J. Pharm. Sci.*, 1996, 85:138-143). Microemulsions have also been effective in the transdermal delivery of active components in both cosmetic and pharmaceutical applications. It is expected that the microemulsion compositions and formulations of the present invention will facilitate the increased systemic absorption of oligonucleotides from the gastrointestinal tract, as well as improve the local cellular uptake of oligonucleotides within the gastrointestinal tract, vagina, buccal cavity and other areas of administration.

The useful dosage to be administered and the particular mode of administration will vary depending upon such factors as the cell type, or for in vivo use, the age, weight and the particular animal and region thereof to be treated, the particular oligonucleotide and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved. When lipids are used to deliver the oligonucleotides, the amount of lipid compound that is administered can vary and generally depends upon the amount of oligonucleotide agent being administered. For example, the weight ratio of lipid compound to oligonucleotide agent is preferably from about 1:1 to about 15:1, with a weight ratio of about 5:1 to about 10:1 being more preferred. Generally, the amount of cationic lipid compound which is administered will vary from between about 0.1 milligram (mg) to about 1 gram (g). By way of general guidance, typically between about 0.1 mg and about 10 mg of the particular oligonucleotide agent, and about 1 mg to about 100 mg of the lipid compositions, each per kilogram of patient body weight, is administered, although higher and lower amounts can be used.

The agents of the invention are administered to subjects or contacted with cells in a biologically compatible form suitable for pharmaceutical administration. By "biologically compatible form suitable for administration" is meant that the oligonucleotide is administered in a form in which any toxic effects are outweighed by the therapeutic effects of the oligonucleotide. In one embodiment, oligonucleotides can be administered to subjects. Examples of subjects include mammals, e.g., humans and other primates; cows, pigs, horses, and farming (agricultural) animals; dogs, cats, and other domesticated pets; mice, rats, and transgenic non-human animals.

Administration of an active amount of an oligonucleotide of the present invention is defined as an amount effective, at dosages and for periods of time necessary to achieve the desired result. For example, an active amount of an oligonucleotide may vary according to factors such as the type of cell, the oligonucleotide used, and for in vivo uses the disease state, age, sex, and weight of the individual, and the ability of the oligonucleotide to elicit a desired response in the individual. Establishment of therapeutic levels of oligonucleotides within the cell is dependent upon the rates of uptake and efflux or degradation. Decreasing the degree of degradation prolongs the intracellular half-life of the oligonucleotide. Thus, chemically-modified oligonucleotides, e.g., with modification of the phosphate backbone, may require different dosing.

The exact dosage of an oligonucleotide and number of doses administered will depend upon the data generated experimentally and in clinical trials. Several factors such as the desired effect, the delivery vehicle, disease indication, and the route of administration, will affect the dosage. Dosages can be readily determined by one of ordinary skill in the art and formulated into the subject pharmaceutical compositions. Preferably, the duration of treatment will extend at least through the course of the disease symptoms.

Dosage regimens may be adjusted to provide the optimum therapeutic response. For example, the oligonucleotide may be repeatedly administered, e.g., several doses may be administered daily or the dose may be proportionally reduced as indicated by the exigencies of the therapeutic situation. One of ordinary skill in the art will readily be able to determine appropriate doses and schedules of administration of the subject oligonucleotides, whether the oligonucleotides are to be administered to cells or to subjects.

Ocular administration of sd-rxRNA® molecules, including intravitreal intravitreal, intracameral, subretinal, subconjunctival, and subtenon administration, can be optimized through testing of dosing regimens. In some embodiments, a single administration is sufficient. To further prolong the effect of the administered sd-rxRNA®, the sd-rxRNA® can be administered in a slow-release formulation or device, as would be familiar to one of ordinary skill in the art. The hydrophobic nature of sd-rxRNA® compounds can enable use of a wide variety of polymers, some of which are not compatible with conventional oligonucleotide delivery.

In other embodiments, the sd-rxRNA® is administered multiple times. In some instances it is administered daily, bi-weekly, weekly, every two weeks, every three weeks, monthly, every two months, every three months, every four months, every five months, every six months or less frequently than every six months. In some instances, it is administered multiple times per day, week, month and/or year. For example, it can be administered approximately every hour, 2 hours, 3 hours, 4 hours, 5 hours, 6 hours, 7 hours, 8 hours, 9 hours 10 hours, 12 hours or more than twelve hours. It can be administered 1, 2, 3, 4, 5, 6, 7, 8, 9, 10 or more than 10 times per day.

Aspects of the invention relate to administering sd-rxRNA® or rxRNA ori molecules to a subject. In some instances the subject is a patient and administering the sd-rxRNA® molecule involves administering the sd-rxRNA® molecule in a doctor's office.

Figure 2:
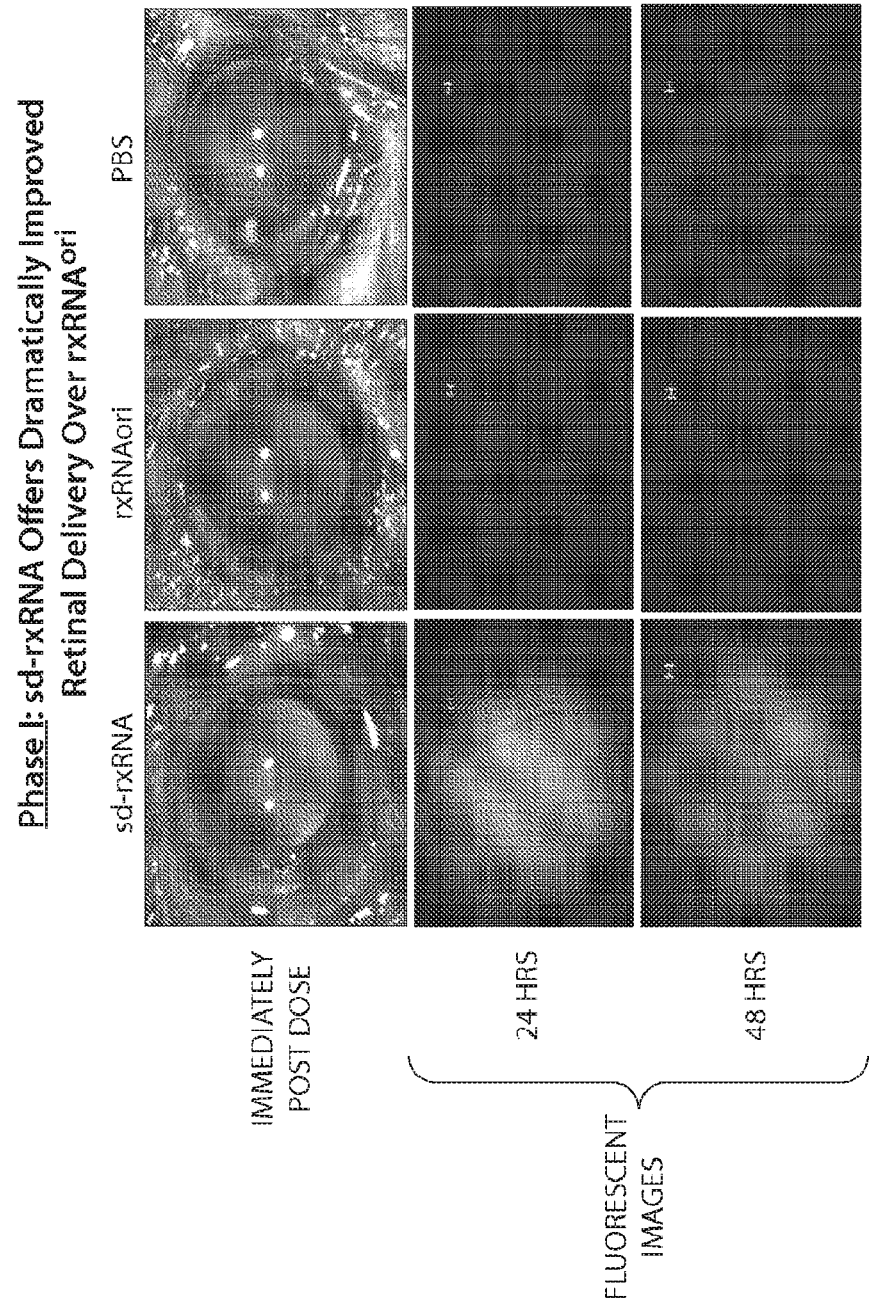
FIG. 2 demonstrates that sd-rxRNA® have improved retinal delivery over rxRNAori. Top panels represent images taken immediately post-dose, indicating intravitreal delivery of sd-rxRNA® and rxRNAori. Middle and bottom panels present fluorescent images taken 24 and 48 hours, respectively, after dosing, demonstrating retinal delivery of only sd-rxRNA®.
Figure 3:
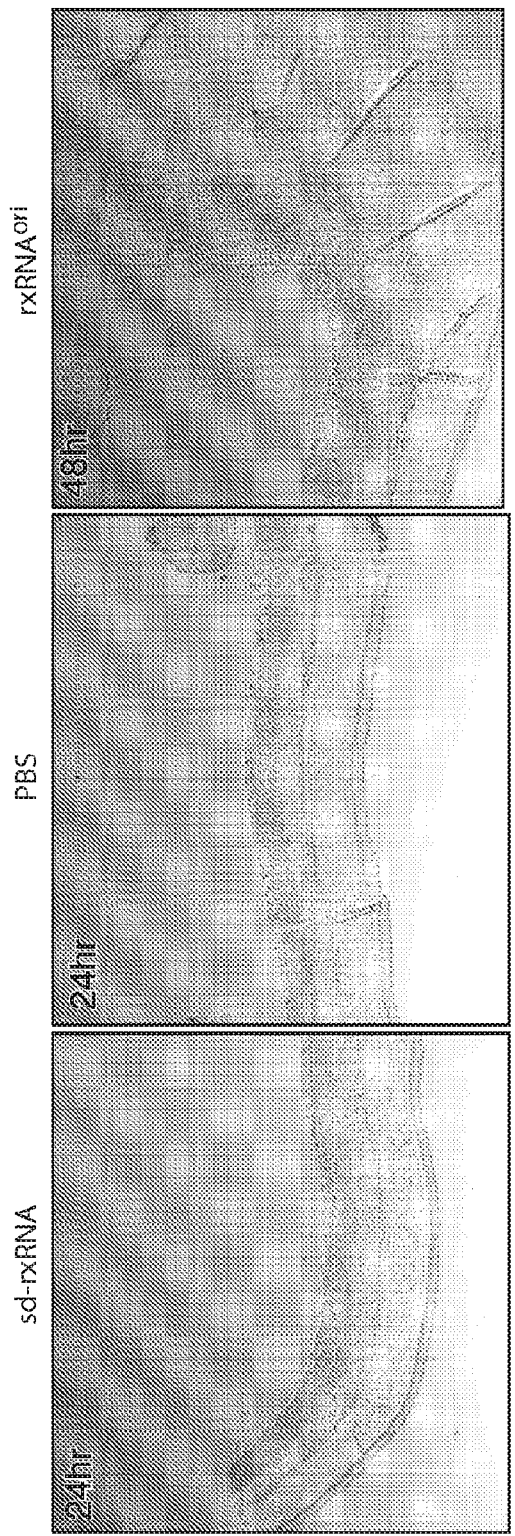
FIG. 3 demonstrates that a fluorescent signal is detected throughout the retina following intravitreal dosing of sd-rxRNA®, but not following dosing of PBS or rxRNAori.
Figure 4:
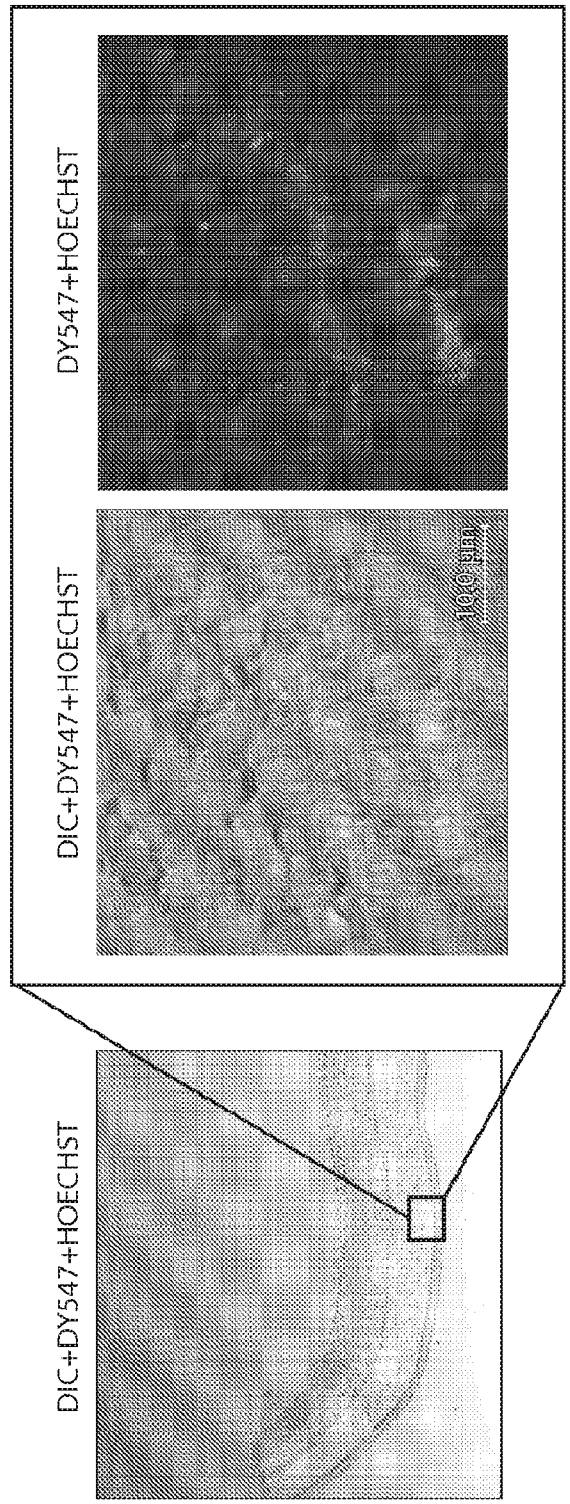
FIG. 4 demonstrates that sd-rxRNA® penetrates the retina to the outer segments of the photoreceptors.

FIG. 1 reveals uptake of sd-rxRNA® 24 hours post intravitreal or subretinal dosing. By 24 hours, sd-rxRNA® has penetrated the entire retina. FIG. 2 shows a comparison of retinal uptake of sd-rxRNA® and conventional RNAi compounds. While both are detected in the eye immediately after administration, after 48 hours, only the sd-rxRNA® is detected. FIG. 3 shows detection of sd-rxRNA® throughout the retina following intravitreal dosing, but not detection of conventional RNAi compounds. FIG. 4 shows that sd-rxRNA® penetrates the retina to the outer segments of the photoreceptors.

In some instances, the effective amount of sd-rxRNA® that is delivered through ocular administration is at least approximately 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more than 100 µg including any intermediate values.

sd-rxRNA® molecules administered through methods described herein are effectively targeted to all the cell types in the eye.

Physical methods of introducing nucleic acids include injection of a solution containing the nucleic acid, bombardment by particles covered by the nucleic acid, soaking the cell or organism in a solution of the nucleic acid, electroporation of cell membranes in the presence of the nucleic acid or topical application of a composition comprising the nucleic acid to the eye. A viral construct packaged into a viral particle would accomplish both efficient introduction of an expression construct into the cell and transcription of nucleic acid encoded by the expression construct. Other methods known in the art for introducing nucleic acids to cells may be used, such as lipid-mediated carrier transport, chemical-mediated transport, such as calcium phosphate, and the like. Thus the nucleic acid may be introduced along with components that perform one or more of the following activities: enhance nucleic acid uptake by the cell, inhibit annealing of single strands, stabilize the single strands, or other-wise increase inhibition of the target gene.

Assays of Oligonucleotide Stability

In some embodiments, the oligonucleotides of the invention are stabilized, i.e., substantially resistant to endonuclease and exonuclease degradation. An oligonucleotide is defined as being substantially resistant to nucleases when it is at least about 3-fold more resistant to attack by an endogenous cellular nuclease, and is highly nuclease resistant when it is at least about 6-fold more resistant than a corresponding oligonucleotide. This can be demonstrated by showing that the oligonucleotides of the invention are substantially resistant to nucleases using techniques which are known in the art.

One way in which substantial stability can be demonstrated is by showing that the oligonucleotides of the invention function when delivered to a cell, e.g., that they reduce transcription or translation of target nucleic acid molecules, e.g., by measuring protein levels or by measuring cleavage of mRNA. Assays which measure the stability of target RNA can be performed at about 24 hours post-transfection (e.g., using Northern blot techniques, RNase Protection Assays, or QC-PCR assays as known in the art). Alternatively, levels of the target protein can be measured. Preferably, in addition to testing the RNA or protein levels of interest, the RNA or protein levels of a control, non-targeted gene will be measured (e.g., actin, or preferably a control with sequence similarity to the target) as a specificity control. RNA or protein measurements can be made using any art-recognized technique. Preferably, measurements will be made beginning at about 16-24 hours post transfection. (M. Y. Chiang, et al. 1991. J Biol Chem. 266:18162-71; T. Fisher, et al. 1993. Nucleic Acids Research. 21 3857).

The ability of an oligonucleotide composition of the invention to inhibit protein synthesis can be measured using techniques which are known in the art, for example, by detecting an inhibition in gene transcription or protein synthesis. For example, Nuclease S1 mapping can be performed. In another example, Northern blot analysis can be used to measure the presence of RNA encoding a particular protein. For example, total RNA can be prepared over a cesium chloride cushion (see, e.g., Ausebel et al., 1987. Current Protocols in Molecular Biology (Greene & Wiley, New York)). Northern blots can then be made using the RNA and probed (see, e.g., Id.). In another example, the level of the specific mRNA produced by the target protein can be measured, e.g., using PCR. In yet another example, Western blots can be used to measure the amount of target protein present. In still another embodiment, a phenotype influenced by the amount of the protein can be detected. Techniques for performing Western blots are well known in the art, see, e.g., Chen et al. J. Biol. Chem. 271:28259.

In another example, the promoter sequence of a target gene can be linked to a reporter gene and reporter gene transcription (e.g., as described in more detail below) can be monitored. Alternatively, oligonucleotide compositions that do not target a promoter can be identified by fusing a portion of the target nucleic acid molecule with a reporter gene so that the reporter gene is transcribed. By monitoring a change in the expression of the reporter gene in the presence of the oligonucleotide composition, it is possible to determine the effectiveness of the oligonucleotide composition in inhibiting the expression of the reporter gene. For example, in one embodiment, an effective oligonucleotide composition will reduce the expression of the reporter gene.

A "reporter gene" is a nucleic acid that expresses a detectable gene product, which may be RNA or protein. Detection of mRNA expression may be accomplished by Northern blotting and detection of protein may be accomplished by staining with antibodies specific to the protein. Preferred reporter genes produce a readily detectable product. A reporter gene may be operably linked with a regulatory DNA sequence such that detection of the reporter gene product provides a measure of the transcriptional activity of the regulatory sequence. In preferred embodiments, the gene product of the reporter gene is detected by an intrinsic activity associated with that product. For instance, the reporter gene may encode a gene product that, by enzymatic activity, gives rise to a detectable signal based on color, fluorescence, or luminescence. Examples of reporter genes include, but are not limited to, those coding for chloramphenicol acetyl transferase (CAT), luciferase, beta-galactosidase, and alkaline phosphatase.

One skilled in the art would readily recognize numerous reporter genes suitable for use in the present invention. These include, but are not limited to, chloramphenicol acetyltransferase (CAT), luciferase, human growth hormone (hGH), and beta-galactosidase. Examples of such reporter genes can be found in F. A. Ausubel et al., Eds., Current Protocols in Molecular Biology, John Wiley & Sons, New York, (1989). Any gene that encodes a detectable product, e.g., any product having detectable enzymatic activity or against which a specific antibody can be raised, can be used as a reporter gene in the present methods.

One reporter gene system is the firefly luciferase reporter system. (Gould, S. J., and Subramani, S. 1988. Anal. Biochem., 7:404-408 incorporated herein by reference). The luciferase assay is fast and sensitive. In this assay, a lysate of the test cell is prepared and combined with ATP and the substrate luciferin. The encoded enzyme luciferase catalyzes a rapid, ATP dependent oxidation of the substrate to generate a light-emitting product. The total light output is measured and is proportional to the amount of luciferase present over a wide range of enzyme concentrations.

CAT is another frequently used reporter gene system; a major advantage of this system is that it has been an extensively validated and is widely accepted as a measure of promoter activity. (Gorman C. M., Moffat, L. F., and Howard, B. H. 1982. Mol. Cell. Biol., 2:1044-1051). In this system, test cells are transfected with CAT expression vectors and incubated with the candidate substance within 2-3 days of the initial transfection. Thereafter, cell extracts are prepared. The extracts are incubated with acetyl CoA and radioactive chloramphenicol. Following the incubation, acetylated chloramphenicol is separated from nonacetylated form by thin layer chromatography. In this assay, the degree of acetylation reflects the CAT gene activity with the particular promoter.

Another suitable reporter gene system is based on immunologic detection of hGH. This system is also quick and easy to use. (Selden, R., Burke-Howie, K. Rowe, M. E., Goodman, H. M., and Moore, D. D. (1986), Mol. Cell, Biol., 6:3173-3179 incorporated herein by reference). The hGH system is advantageous in that the expressed hGH polypeptide is assayed in the media, rather than in a cell extract. Thus, this system does not require the destruction of the test cells. It will be appreciated that the principle of this reporter gene system is not limited to hGH but rather adapted for use with any polypeptide for which an antibody of acceptable specificity is available or can be prepared.

In one embodiment, nuclease stability of a double-stranded oligonucleotide of the invention is measured and compared to a control, e.g., an RNAi molecule typically used in the art (e.g., a duplex oligonucleotide of less than 25 nucleotides in length and comprising 2 nucleotide base overhangs) or an unmodified RNA duplex with blunt ends.

The target RNA cleavage reaction achieved using the siRNAs of the invention is highly sequence specific. Sequence identity may determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10. Additionally, numerous commercial entities, such as Dharmacon, and Invitrogen provide access to algorithms on their website. The Whitehead Institute also offers a free siRNA Selection Program. Greater than 90% sequence identity, e.g., 91%, 92%, 93%, 94%, 95%, 96%, 97%, 98%, 99% or even 100% sequence identity, between the siRNA and the portion of the target gene is preferred. Alternatively, the siRNA may be defined functionally as a nucleotide sequence (or oligonucleotide sequence) that is capable of hybridizing with a portion of the target gene transcript. Examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Therapeutic Use

By inhibiting the expression of a gene, the oligonucleotide compositions of the present invention can be used to treat any disease involving the expression of a protein. Examples of diseases that can be treated by oligonucleotide compositions, just to illustrate, include: cancer, retinopathies, autoimmune diseases, inflammatory diseases (i.e., ICAM-1 related disorders, Psoriasis, Ulcerative Colitus, Crohn's disease), viral diseases (i.e., HIV, Hepatitis C), miRNA disorders, and cardiovascular diseases.

As discussed above, sd-rxRNA® molecules administered by methods described herein are effectively targeted to all the cell types in the eye.

Aspects of the invention relate to targeting sd-rxRNA® to various cell types in the eye, including, but not limited to, cells located in the ganglion cell layer (GCL), the inner plexiform layer inner (IPL), the inner nuclear layer (INL), the outer plexiform layer (OPL), outer nuclear layer (ONL), outer segments (OS) of rods and cones, the retinal pigmented epithelium (RPE), the inner segments (IS) of rods and cones, the epithelium of the conjunctiva, the iris, the ciliary body, the corneum, and epithelium of ocular sebaceous glands.

The sd-rxRNA® that is targeted to the eye may, in some instances target an eye-specific gene or a gene that is expressed at higher levels in the eye than in other tissues. As one of ordinary skill in the art would appreciate, publicly accessible databases can be used to identify genes that have eye-specific expression or increased expression in the eye relative to other tissues. Several non-limiting examples of such databases include TISGED (Tissue-Specific Genes Database) and the TiGER database for tissue-specific gene expression and regulation. In other embodiments, the sd-rxRNA® does not target an eye-specific gene. In other embodiments, the gene that is targeted does not have eye-specific expression or increased expression in the eye.

In some instances, an sd-rxRNA® that is targeted to the eye is used to ameliorate at least one symptom of a condition or disorder associated with the eye. Several non-limiting examples of conditions or disorders associated with the eye include: vascular leakage/neovascularization (e.g., angiographic cystoid macular edema, macular edema secondary to retinal vein occlusion (RVO), glaucoma or neovascular glaucoma (NVG), retinopathy of prematurity (ROP); fibroproliferative diseases (e.g., proliferative vitreoretinopathy (PVR), epiretinal membranes/vitreomacular adhesions; age-related macular degeneration (AMD) (e.g., choroidal neovascularization (wet AMD), geographic atrophy (advanced dry AMD), early-to-intermediate dry AMD); diabetic retinopathy (e.g., nonproliferative diabetic retinopathy (NPDR), diabetic macular edema (DME), proliferative diabetic retinopathy (PDR); retinal degenerative diseases (and related diseases); retinal vascular occlusive diseases (e.g., retinal vein occlusion, retinal artery occlusion) and other retinal diseases; retinal detachment; inflammatory diseases such as uveitis (including panuveitis) or choroiditis (including multifocal choroiditis) of unknown cause (idiopathic) or associated with a systemic (e.g., autoimmune) disease; episcleritis or scleritis; Birdshot retinochoroidopathy; vascular diseases (retinal ischemia, retinal vasculitis, choroidal vascular insufficiency, choroidal thrombosis); neovascularization of the optic nerve; optic neuritis; blepharitis; keratitis; rubeosis iritis; Fuchs' heterochromic iridocyclitis; chronic uveitis or anterior uveitis; conjunctivitis; allergic conjunctivitis (including seasonal or perennial, vernal, atopic, and giant papillary); keratoconjunctivitis sicca (dry eye syndrome); iridocyclitis; iritis; scleritis; episcleritis; corneal edema; scleral disease; ocular cicatrcial pemphigoid; pars planitis; Posner Schlossman syndrome; Behcet's disease; Vogt-Koyanagi-Harada syndrome; hypersensitivity reactions; conjunctival edema; conjunctival venous congestion; periorbital cellulitis; acute dacryocystitis; non-specific vasculitis; sarcoidosis; keratoconjunctivitis sicca, a condition also known as dry-eye, keratitis sicca, sicca syndrome, xeropthalmia, and dry eye syndrome (DES), which can arise from decreased tear production and/or increased tear film evaporation due to abnormal tear composition; a disorder associated with the autoimmune diseases rheumatoid arthritis, lupus erythematosus, diabetes mellitus, and Sjogren's syndrome. In some embodiments, sd-rxRNA® is administered as a method of wound healing. Non-limiting examples of conditions or disorders associated with the eye are incorporated by reference from US Patent Publication 20100010082 and U.S. Pat. No. 6,331,313.

Neovascularization/Vascular Leakage

Aspects of the invention relate to treating diseases and conditions associated with neovascularization and/or vascular leakage. Of these conditions, wet AMD and DME are most prevalent, PDR and macular edema secondary to RVO are of lower prevalence, and rare neovascular conditions include ROP and neovascular glaucoma. Vascular leakage is considered to be the driving force behind DME, while both vascular leakage and neovascularization drive PDR. Oligonucleotide compositions of the present invention can be selected based on the etiology of a particular disease or condition. For example, a composition comprising an antiangiogenic oligonucleotide affecting vascular permeability may be chosen to treat DME, while one affecting proliferation may be chosen to treat PDR. Alternatively, oligonucleotide compositions may comprise a combination of anti-angiogenic agents, for example, an sd-rxRNA® that inhibits function of a target that affects vascular permeability and an sd-rxRNA® that inhibits function of a target that affects proliferation, such that both etiological aspects of the condition are targeted.

In certain embodiments, the sd-rxRNA® is used to treat neovascularization and/or vascular permeability. In some embodiments, the sd-rxRNA® targets Vascular Endothelial Growth Factor (VEGF), an inhibitor of vascular permeability. VEGF is a canonical and clinically validated target for treatment of wet AMD and approval is expected for DME and RVO-associated ME. VEGF proteins are growth factors that bind to tyrosine kinase receptors and are implicated in multiple disorders such as cancer, age-related macular degeneration, rheumatoid arthritis and diabetic retinopathy. Members of this protein family include VEGF-A, VEGF-B, VEGF-C and VEGF-D. Representative Genbank accession numbers providing DNA and protein sequence information for human VEGF proteins are NM_001171623.1 (VEGF-A), U43368 (VEGF-B), X94216 (VEGF-C), and D89630 (VEGF-D).

Aspects of the invention relate to rxRNAori directed against VEGF. As described in the Examples section, over 100 optimal rxRNA ori sequences for VEGF were identified herein (Tables 2 and 9). An rxRNAori can be directed against a sequence comprising at least 12 contiguous nucleotides of a sequence within Table 2 or 9. For example, an rxRNAori can be directed against a sequence comprising 12, 13, 14, 15, 16, 17, 18, 19, 20, 21, 22, 23, 24, or 25 contiguous nucleotides of a sequence within Table 2 or 9. In some embodiments, an rxRNAori is directed against a sequence comprising at least 12 contiguous nucleotides of SEQ ID NO:13 (AUCACCAUCGACAGAACAGUC-CUUA) or SEQ ID NO: 28 (CCAUGCAGAUUAUGCG-GAUCAAACA). The sense strand of the rxRNAori molecule can comprise at least 12 contiguous nucleotides of a sequence selected from the sequences presented in Table 2. In some embodiments, the sense strand of the rxRNAori comprises at least 12 contiguous nucleotides of the sequence of SEQ ID NO: 13 or SEQ ID NO: 28. The antisense strand of the rxRNAori can be complementary to at least 12 contiguous nucleotides of a sequence selected from the sequences within Table 2. In some embodiments, the antisense strand of the rxRNAori comprises at least 12 contiguous nucleotides of SEQ ID NO:1377 (UAAGGACU-GUUCUGUCGAUGGUGAU) or SEQ ID NO:1378 (UGUUUGAUCCGCAUAAUCUGCAUGG).

Non-limiting examples of an rxRNAori directed against VEGF include an rxRNAori comprising a sense strand that comprises the sequence of SEQ ID NO: 13 and an antisense strand that comprises the sequence of SEQ ID NO: 1377 or an rxRNAori comprising a sense strand that comprises the sequence of SEQ ID NO:28 and an antisense strand that comprises the sequence of SEQ ID NO: 1378. It should be appreciated that a variety of modifications patterns are compatible with rxRNAori. Aspects of the invention encompass rxRNAori directed against VEGF, wherein the rxRNAori is modified or unmodified. In some embodiments, the rxRNAori is administered to the eye.

Ori sequences can also be converted to sd-rxRNA® molecules to target VEGF in the eye. It should be appreciated that the disclosed ori sequences represent non-limiting examples of sequences within VEGF for sd-rxRNA® development. Variations in length and modifications of these sequences, as well as other sequences within VEGF are also compatible with development of sd-rxRNA® molecules. An sd-rxRNA® can be directed against a sequence selected from the sequences within Table 2 or 9. For example, an sd-rxRNA® can be directed against a sequence comprising at least 12 contiguous nucleotides of a sequence selected from the sequences within Table 2 or 9. In some embodiments, an sd-rxRNA® can be directed against a sequence comprising 12, 13, 14, 15, 16, 17, 18, 19, 20, 21, 22, 23, 24 or 25 contiguous nucleotides of a sequence selected from the sequences within Table 2 or 9.

In some embodiments, an sd-rxRNA® directed against VEGF comprises at least 12 nucleotides of a sequence selected from the sequences within Table 8. In some embodiments, the sense strand of the sd-rxRNA® comprises at least 12 contiguous nucleotides of the sequence of SEQ ID NO: 1317 (AGAACAGUCCUUA) or SEQ ID NO:1357 (UGCGGAUCAAACA) and/or the antisense strand of the sd-rxRNA® comprises at least 12 contiguous nucleotides of the sequence of SEQ ID NO: 1318 (UAAGGACUGUUCUGUCGAU) or SEQ ID NO:1358 (UGUUUGAUCCGCAUAAUCU). In certain embodiments, an sd-rxRNA® directed against VEGF includes a sense strand comprising SEQ ID NO:1317 and an antisense strand comprising SEQ ID NO:1318. Various chemical modification patterns are compatible with sd-rxRNA®. Non-limiting examples of modified forms of SEQ ID NO:1317 and SEQ ID NO:1318 are represented by SEQ ID NOs 1379 (A. G. A. A.mC. A. G.mU.mC.mC.mU.mU. A.Chl) and 1380 (P.mU. A. A. G. G. A.fC.fU. G.fU.fU.fC.fU* G*fU*fC* G* A* U), respectively.

In certain embodiments, an sd-rxRNA® directed against VEGF includes a sense strand comprising SEQ ID NO:1357 and an antisense strand comprising SEQ ID NO:1358. Non-limiting examples of modified forms of SEQ ID NO: 1357 and SEQ ID NO: 1358 are represented by SEQ ID NOs 1397 (mU. G.mC. G. G. A.mU.mC. A. A. A.mC. A.Chl) and 1398 (P.mU. G.fU.fU.fU. G. A.fU.fC.fC. G.fC. A*fU* A* A*fU*fC* U), respectively. In certain embodiments, the sd-rxRNA® comprises SEQ ID NOs 1397 and 1398. It should be appreciated that other modifications patterns of sd-rxRNA® molecules disclosed herein are also compatible with aspects of the invention.

Described herein are also sd-rxRNA® molecules directed against genes that encode for proteins other than VEGF. Non-limiting examples of such sd-rxRNA® molecules are provided in Tables 3-7. In some embodiments, an sd-rxRNA® comprises at least 12 contiguous nucleotides of a sequence selected from the sequences within Tables 3-7.

In some embodiments, the sd-rxRNA® is directed against CTGF. Non-limiting examples of sd-rxRNA® molecules directed against CTGF are provided in Table 5. In some embodiments, the sense strand of an sd-rxRNA® directed against CTGF comprises at least 12 contiguous nucleotides of the sequence of SEQ ID NO: 1422 (GCACCUUUCUAGA) and an antisense strand of an sd-rxRNA® directed against CTGF comprises at least 12 contiguous nucleotides of the sequence of SEQ ID NO: 1423 (UCUAGAAAGGUGCAAACAU). Non-limiting examples of modified forms of SEQ ID NOs 1422 and 1423 are represented by SEQ ID NOs:947 (G.mC. A.mC.mC.mU. mU.mU.mC.mU. A*mG*mA.TEG-Chl) and 948 (P.mU.fC.fU. A. G.mA. A.mA. G. G.fU. G.mC* A* A* A*mC* A* U.), respectively. In some embodiments, the sense strand of an sd-rxRNA® directed against CTGF comprises at least 12 contiguous nucleotides of the sequence of SEQ ID NO: 1424 (UUGCACCUUUCUAA) and an antisense strand of an sd-rxRNA® directed against CTGF comprises at least 12 contiguous nucleotides of the sequence of SEQ ID NO: 1425 (UUAGAAAGGUGCAAACAAGG). Non-limiting examples of modified forms of SEQ ID Nos 1424 and 1425 and represented by SEQ ID NOs 963 (mU.mU. G.mC. A.mC.mC.mU.mU.mU.mC.mU*mA*mA.TEG-Chl) and 964 (P.mU.fU. A. G. A.mA. A. G. G.fU. G.fC.mA.mA*mA*fC*mA*mA*mG* G.).

In some embodiments, the sense strand of the sd-rxRNA® directed against CTGF comprises at least 12 contiguous nucleotides of the sequence of SEQ ID NO:947 or SEQ ID NO:963. In certain embodiments, the sd-rxRNA® directed against CTGF includes a sense strand comprising the sequence of SEQ ID NO:963 and an antisense strand comprising the sequence of SEQ ID NO:964. In other embodiments, the sd-rxRNA® directed against CTGF includes a sense strand comprising the sequence of SEQ ID NO:947 and an antisense strand comprising the sequence of SEQ ID NO:948.

sd-rxRNA® can be hydrophobically modified. For example, the sd-rxRNA® can be linked to one or more hydrophobic conjugates. In some embodiments, the sd-rxRNA® includes at least one 5-methyl C or U modifications.

Aspects of the invention relate to compositions comprising rxRNAori and/or sd-rxRNA® nucleic acids described herein. A composition can comprise one or more rxRNAori and/or sd-rxRNA®. In some embodiments, a composition comprises multiple different rxRNAoris that are directed to genes encoding for different proteins and/or multiple different sd-rxRNA® molecules that are directed to genes encoding for different proteins. In some embodiments, a composition comprises sd-rxRNA® directed to VEGF as well as sd-rxRNA® directed against another gene such as a gene encoding for CTGF or PTGS2 (COX-2).

In some embodiments, one or more sd-rxRNA® targets IGTA5, ANG2, CTGF, COX-2, complement factors 3 or 5, or a combination thereof.

In some embodiments, the sd-rxRNA® targets Connective tissue growth factor (CTGF), also known as Hypertrophic chondrocyte-specific protein 24. CTGF is a secreted heparin-binding protein that has been implicated in wound healing and scleroderma. Connective tissue growth factor is active in many cell types including fibroblasts, myofibroblasts, endothelial and epithelial cells. Representative Genbank accession number providing DNA and protein sequence information for human CTGF are NM_001901.2 and M92934.

In some embodiments, the sd-rxRNA® targets Osteopontin (OPN), also known as Secreted phosphoprotein 1 (SPP1), Bone Sinaloprotein 1 (BSP-1), and early T-lymphocyte activation (ETA-1). SPP1 is a secreted glycoprotein protein that binds to hydroxyapatite. OPN has been implicated in a variety of biological processes including bone remodeling, immune functions, chemotaxis, cell activation and apoptosis. Osteopontin is produced by a variety of cell types including fibroblasts, preosteoblasts, osteoblasts, osteocytes, odontoblasts, bone marrow cells, hypertrophic chondrocytes, dendritic cells, macrophages, smooth muscle, skeletal muscle myoblasts, endothelial cells, and extraosseous (non-bone) cells in the inner ear, brain, kidney, deciduum, and placenta. Representative Genbank accession number providing DNA and protein sequence information for human Osteopontin are NM_000582.2 and X13694.

In some embodiments, the sd-rxRNA® targets Transforming growth factor β (TGFβ) proteins, for which three isoforms exist in mammals (TGFβ1, TGFβ2, TGFβ3). TGFβ proteins are secreted proteins belonging to a superfamily of growth factors involved in the regulation of many cellular processes including proliferation, migration, apoptosis, adhesion, differentiation, inflammation, immuno-suppression and expression of extracellular proteins. These proteins are produced by a wide range of cell types including epithelial, endothelial, hematopoietic, neuronal, and connective tissue cells. Representative Genbank accession numbers providing DNA and protein sequence information for human TGFβ1, TGFβ2 and TGFβ3 are BT007245, BC096235, and X14149, respectively. Within the TGFβ family, TGFβ1 and TGFβ2 but not TGFβ3 represent suitable targets. In some embodiments, the sd-rxRNA® targets Cyclooxygenase-2 (COX-2), also called Prostaglandin G/H synthase 2 (PTGS2). COX-2 is involved in lipid metabolism and biosynthesis of prostanoids and is implicated in inflammatory disorders such as rheumatoid arthritis. A representative Genbank accession number providing DNA and protein sequence information for human COX-2 is AY462100.

In other embodiments, the sd-rxRNA® targets HIF-1α, a component of the HIF-1 transcription factor. HIF-1α is a key regulator of the cellular response to hypoxia, acting upstream of VEGF-dependent and VEGF-independent pro-angiogenic pathways and pro-fibrotic pathways. HIF-1α inhibitors are effective in laser CNV and OIR models. A representative Genbank accession number providing DNA and protein sequence information for human HIF 1α is U22431.

In some embodiments, the sd-rxRNA® targets mTOR. mTOR is a serine/threonine kinase component of the PI3K/Akt/mTOR pathway, and is a regulator or cell growth, proliferation, survival, transcription and translation. mTOR inhibitors have both anti-angiogenic (effective in laser CNV and OIR models) and anti-fibrotic activity. Rapamycin and other mTOR inhibitors are being used in clinical trials for AMD and DME. A representative Genbank accession number providing DNA and protein sequence information for human mTOR is L34075.

In some embodiments, the sd-rxRNA® targets SDF-1 (stromal derived factor-1), which is a soluble factor that stimulates homing of hematopoietic stem cells and endothelial progenitor cells to tissues. SDF-1 acts synergistically with VEGF to drive pathologic neovascularization, and inhibition of SDF-1 signaling suppresses neovascularization in OIR, laser CNV, and VEGF-induced rodent models.

In certain embodiments, the sd-rxRNA® targets PDGF-B (platelet-derived growth factor B). Retinal overexpression of PDGF-B in transgenic mice leads to fibrovascular proliferation, and inhibition of PDGF-B signaling enhances efficacy of anti-VEGF treatment in laser CNV model. Dual inhibition of PDGF-B and VEGF can promote regression of NV. Representative Genbank accession numbers providing DNA and protein sequence information for human PDGF genes and proteins include X03795 (PDGFA), X02811 (PDGFB), AF091434 (PDGFC), AB033832 (PDGFD).

In some embodiments, the sd-rxRNA® targets TIE1 (tyrosine kinase with immunoglobulin-like and EGF-like domains).

In other embodiments, the sd-rxRNA® targets VEGFR1 (vascular endothelial growth factor receptor 1), also referred to as FLT1 (fms-related tyrosine kinase 1). This gene encodes a member of the vascular endothelial growth factor receptor (VEGFR) family. VEGFR family members are receptor tyrosine kinases (RTKs) which contain an extracellular ligand-binding region with seven immunoglobulin (Ig)-like domains, a transmembrane segment, and a tyrosine kinase (TK) domain within the cytoplasmic domain. This protein binds to VEGFR-A, VEGFR-B and placental growth factor and plays an important role in angiogenesis and vasculogenesis. Representative Genbank accession numbers providing DNA and protein sequence information for human VEGFR1 genes and proteins include NM_001159920, NP_001153392, NM_001160030, NP_001153502, NM_001160031, NP_001153503, NM_002019, and NP_002010.

In certain embodiments, the sd-rxRNA® targets VEGFR2 (vascular endothelial growth factor receptor 2), also referred to as KDR (kinase insert domain receptor). This receptor, known as kinase insert domain receptor, is a type III receptor tyrosine kinase. It functions as the main mediator of VEGF-induced endothelial proliferation, survival, migration, tubular morphogenesis and sprouting. The signaling and trafficking of this receptor are regulated by multiple factors, including Rab GTPase, P2Y purine nucleotide receptor, integrin alphaVbeta3, T-cell protein tyrosine phosphatase, etc. Representative Genbank accession numbers providing DNA and protein sequence information for human VEGFR2 genes and proteins include NM_002253 and NP_002244. In some embodiments, treatment of neovascularization and/or vascular leakage may include the use of a combination of sd-rxRNA® molecules, each sd-rxRNA® targeting a different gene. For example, an sd-rRNA targeting VEGF and an sd-rxRNA® targeting HIF-1α can be used. As another example, an sd-rRNA® targeting mTOR and an sd-rxRNA® targeting SDF-1 can be used. As yet another example, an sd-rRNA® targeting VEGF, an sd-rxRNA® targeting mTOR, and an sd-rRNA® targeting PDGF-B can be used.

Wet AMD (Choroidal Neovascularization (CNV))

Aspects of the invention relate to treating choroidal vascularization, the fastest progressing form of AMD (~1 million cases in the U.S.), which results from inappropriate growth of new blood vessels from the choroid into the subretinal space and leakage of fluid from these vessels. If untreated, 75% of patients will progress to legal blindness within three years. Intravitreal anti-VEGF agents can rapidly improve vision by inhibiting CNV lesion growth and vascular leakage from CNV lesions; however, existing anti-VEGFs may not cause regression of existing lesions in most patients.

In certain embodiments, the sd-rxRNA® is used to treat CNV. In some embodiments, the sd-rxRNA® targets VEGF. In other embodiments, the sd-rxRNA® targets HIF-1α, mTOR, PDGF-B, SDF-1, IGTA5, ANG2, CTGF, COX-2, or complement factors 3 or 5. In some embodiments, treatment of CNV includes the use of a combination of sd-rxRNA® molecules, each sd-rxRNA® targeting a different gene.

Diabetic Macular Edema (DME)

DME results from vascular leakage from retinal vessels leading to vision-threatening buildup of fluid in the macula, occurring in ~2-5% of diabetic patients. The current standard of care is focal or grid laser photocoagulation. Intravitreal anti-VEGF agents and corticosteroids have been shown to be effective, but are not yet approved.

In certain embodiments, the sd-rxRNA® is used to treat DMA. In some embodiments, the sd-rxRNA® targets VEGF. In other embodiments, the sd-rxRNA® targets HIF-1α, mTOR, PDGF-B, SDF-1, IGTA5, ANG2, CTGF, COX-2, or complement factors 3 or 5. In some embodiments, treatment of DME includes the use of a combination of sd-rxRNA® molecules, each sd-rxRNA® targeting a different gene.

Proliferative Diabetic Retinopathy (PDR)

PDR is associated with chronic retinal ischemia. Retinal neovascularization occurs secondary to retinal ischemia and can lead to vitreous hemorrhage, fibrovascular proliferation, and traction retinal detachment.

In certain embodiments, the sd-rxRNA® is used to treat PDR. In some embodiments, the sd-rxRNA® targets VEGF. In other embodiments, the sd-rxRNA® targets HIF-1α, mTOR, PDGF-B, SDF-1, IGTA5, ANG2, CTGF, COX-2, or complement factors 3 or 5. In some embodiments, treatment of PDR includes the use of a combination of sd-rxRNA® molecules, each sd-rxRNA® targeting a different gene.

Macular Edema Secondary to RVO

RVO can occur in ischemic and non-ischemic forms. Ischemic RVO can lead to several vision threatening complications, including macular edema, retinal ischemia, and neovascularization. Non-ischemic RVO has a more favorable prognosis and the most common vision-threatening complication is macular edema.

In certain embodiments, the sd-rxRNA® is used to treat macular edema secondary to RVO. In some embodiments, the sd-rxRNA® targets VEGF. In other embodiments, the sd-rxRNA® targets HIF-1α, mTOR, PDGF-B, SDF-1, IGTA5, ANG2, CTGF, COX-2, or complement factors 3 or 5. In some embodiments, treatment of macular edema secondary to RVO includes the use of a combination of sd-rxRNA® molecules, each sd-rxRNA® targeting a different gene.

Iris Neovascularization/Neovascular Glaucoma (NVG)

NVG is a rare disorder that develops in eyes suffering from severe, chronic ocular ischemia. The most common causes are advanced PDR or ischemic CRVO. Iris neovascularization occurs due to ischemia, and eventually obstructs trabecular meshwork leading to a severe secondary glaucoma.

In certain embodiments, the sd-rxRNA® is used to treat iris neovascularization and/or NVG. In some embodiments, the sd-rxRNA® targets VEGF. In other embodiments, the sd-rxRNA® targets HIF-1α, mTOR, PDGF-B, SDF-1, IGTA5, ANG2, CTGF, COX-2, or complement factors 3 or 5. In some embodiments, treatment of iris neovascularization and/or NVG includes the use of a combination of sd-rxRNA® molecules, each sd-rxRNA® targeting a different gene.

Proliferative Retinal Diseases

Proliferative retinal diseases include proliferative vitreoretinopathy, proliferative diabetic retinopathy (PDR), epiretinal membranes (transparent layers of cells that can grow over the surface of the macula, causing retinal traction), and wet AMD.

In certain embodiment, the sd-rxRNA® is used to treat proliferative retinal diseases. In some embodiments, the sd-rxRNA® targets TGFβ, while in other embodiments, the sd-rxRNA® targets CTGF. In still other embodiments, multiple sd-rxRNA® molecules target PDGFRα, mTOR, IGTA5, or a combination thereof. In yet other embodiments, multiple sd-rxRNA® molecules targets TGFβ and at least one of CTGF, PDGFRα, mTOR, IGTA5, or a combination thereof. In further embodiments, multiple sd-rxRNA® molecules target CTGF and at least one of TGFβ, PDGFRα, mTOR, IGTA5, or a combination thereof. In certain embodiments, treatment of proliferative retinal diseases includes the use of a combination of sd-rxRNA® molecules, each sd-rxRNA® targeting a different gene.

Dry AMD

In certain embodiments, the sd-rxRNA® is used to treat dry AMD, including geographic atrophy (GA) (a form of advanced AMD that progresses more slowly than wet AMD) and early-to-intermediate dry AMD (early stages of dry AMD that precedes GA or CNV). In some embodiments, the sd-rxRNA® targets Alu transcription. In other embodiments, the sd-rxRNA® targets transcription factors or other molecules that inhibit or regulate expression of DICER (an endoribonuclease in the RNase III family that cleaves double-stranded RNA (dsRNA) and pre-microRNA (miRNA) into short double-stranded RNA fragments called small interfering RNA (siRNA) about 20-25 nucleotides long).

Cystoid Macular Edema

Cystoid macular edema is an accumulation of intraretinal fluid in erofoveal cysts following surgery. In certain embodiments, the sd-rxRNA® is used to treat cystoid macular edema. In some embodiments, the sd-rxRNA® targets COX-2 (cyclooxygenase-2) enzyme.

Retinitis Pigmentosa

Retinitis pigmentosa is an inherited retinal degenerative disease caused by mutations in several known genes. In certain embodiments, the sd-rxRNA® is used to treat retinitis pigmentosa. In some embodiments, the sd-rxRNA® targets NADPH oxidase.

Glaucoma

Glaucoma is a slowly progressive disease characterized by degeneration of the optic nerve. There is an initial vision loss in the periphery with central vision loss at advanced stages of the disease. The best understood risk factor for glaucoma-related vision loss is intraocular pressure (IOP). Trabeculectomy is a surgical procedure designed to create a channel or bleb though the sclera to allow excess fluid to drain from the anterior of the eye, leading to reduced IOP. The most common cause of trabeculectomy failure is blockage of the bleb by scar tissue.

In certain embodiments, the sd-rxRNA® is used to prevent formation of scar tissue resulting from a trabeculectomy. In some embodiments, the sd-rxRNA® targets CTGF, while in other embodiments, the sd-rxRNA® targets TGFβ. In still other embodiments, multiple sd-rxRNA® molecules target both CTGF and TGFβ. In some embodiments, scar tissue formation is prevented by the use of a combination of sd-rxRNA® molecules, one targeting CTGF and one targeting TGFβ.

Uveitis

Uveitis is a broad group of disorders characterized by inflammation of the middle layer of the eye, called the uvea, which is composed of the choroid, ciliary body, and iris. The disorders are categorized anatomically as anterior, intermediate, posterior, or panuveitis, and are categorized pathologically as infectious or non-infectious.

In certain embodiments, the sd-rxRNA® is used to treat uveitis. In some embodiments, the sd-rxRNA® targets a cytokine, for example TNFα. In other embodiments, the sd-rxRNA® targets IL-1, IL-6, IL-15, IL-17, IL-2R, or CTLA-4. In still other embodiments, the sd-rxRNA® targets adhesion molecules, including VLA-4, VCAM-1, LFA-1, ICAM-1, CD44, or osteopontin. In yet another embodiment, the sd-rxRNA® targets at least one of TNFα, IL-1, IL-6, IL-15, IL-17, IL-2R, CTLA-4, VLA-4, VCAM-1, LFA-1, ICAM-1, CD44, and osteopontin. In some embodiments, scar tissue formation is prevented by the use of a combination of sd-rxRNA® molecules, each targeting a different gene.

Retinoblastoma (Rb)

Retinoblastoma is a rapidly developing cancer in the cells of retina. In certain embodiments, the sd-rxRNA® is used to treat retinoblastoma. In some embodiments, the sd-rxRNA® targets HMGA2, a nuclear protein thought to have a role in neoplastic transformation.

In certain embodiments, sd-rxRNA® molecules of the present invention can be used for multi-gene silencing. In some embodiments, a combination of sd-rxRNA® molecules is used to target multiple, different genes. For example, when used for the treatment of a neovascular disorder, a sd-rxRNA® molecules targeting VEGF can be used together with a sd-rxRNA® targeting HIF-1α. As another example, when used for the treatment of uveitis, a sd-rxRNA® targeting TNFα, a sd-rxRNA® targeting VCAM-1, and a sd-rxRNA® targeting IL-2R can be used in combination.

In some embodiments, multiple sd-rxRNA® molecules can be used to target VEGF, IGTA5, ANG2, CTGF, COX-2, complement factor 3, complement factor 5, HIF-1α, mTOR, SDF-1, PDGF-β, Alu, NADPH oxidase, TGF-β, IL-1, IL-6, IL-15, IL-17, IL-2R, CTLA-4, VLA-4, VCAM-1, LFA-1, ICAM-1, CD44, osteopontin (SPP1), or any combination thereof. In some embodiments, such multi-target gene silencing can be used to treat more than one disease or condition, if so needed.

In some embodiments, the sd-rxRNA® targets MAP4K4. MAP4K4 is a mammalian serine/threonine protein kinase that belongs to a group of protein kinases related to *Saccharomyces cerevisiae* Sterile 20 (STE20). MAP4K4 (also known as NIK for Nck interacting kinase) was first identified in a mouse screen for proteins that interact with the SH3 domain of Nck (Su et al. (1997). Since its discovery, MAP4K4 has been and continues to be linked to wide range of physiological functions.

Approaches for RNAi-mediated inhibition of MAP4K4 expression are described in, and incorporated by reference from, U.S. Provisional Application Ser. No. 61/199,661, entitled "Inhibition of MAP4K4 through RNAi," filed on Nov. 19, 2008, and PCT application PCT/US2009/006211, filed on Nov. 19, 2009 and entitled "Inhibition of MAP4K4 through RNAi." sd-rxRNA® molecules targeting MAP4K4 are compatible with aspects of the invention. In some embodiments an sd-rxRNA® molecule targeting VEGF and an sd-rxRNA® molecule targeting MAP4K4 can be administered together.

Table 1 presents non-limiting examples of sd-rxRNA® targets and areas in which they can be applied.

TABLE 1

Examples of sd-rxRNA ® targets and applications

| Target | Area of Interest | Possible Indications |
| --- | --- | --- |
| VEGF | Neovascularization | i) AMD/DME |
| Map4K4 | Inflammation | i) Geographic Atrophy |
| CTGF | Angiogenesis, Fibrosis/Scarring | i)AMD/DME<br>ii)Proliferative Vitreoretinopathy<br>iii)Prevention of Trabeculectomy Failure |
| PTGS2 (COX-2) | Inflammation | i)Cystoid Macular Edema (Post Surgery),<br>ii)Geographic Atrophy |
| TGFβ | Fibrosis/Scarring | i)Proliferative Vitreoretinopathy<br>ii)Prevention of Trabeculectomy Failure<br>iii)Diabetic Retinopathy |
| VEGF/COX-2 | Neovascularization/ inflamation | i) AMD/DME<br>ii) Geographic Atrophy<br>iii) Proliferative Vitreoretinopathy<br>iv) Prevention of Trabeculectomy Failure |
| VEGF/CTGF | Neovascularization/fibrosis | i) AMD/DME<br>ii) Geographic Atrophy<br>iii) Proliferative Vitreoretinopathy<br>iv) Prevention of Trabeculectomy Failure |
| VEGF/MAP4K4 | Neovascularization/ inflamation | i) AMD/DME<br>ii) Geographic Atrophy<br>iii) Proliferative Vitreoretinopathy<br>iv) Prevention of Trabeculectomy Failure |

In one embodiment, in vitro treatment of cells with oligonucleotides can be used for ex vivo therapy of cells removed from a subject or for treatment of cells which did not originate in the subject, but are to be administered to the subject (e.g., to eliminate transplantation antigen expression on cells to be transplanted into a subject). In addition, in vitro treatment of cells can be used in non-therapeutic settings, e.g., to evaluate gene function, to study gene regulation and protein synthesis or to evaluate improvements made to oligonucleotides designed to modulate gene expression or protein synthesis. In vivo treatment of cells can be useful in certain clinical settings where it is desirable to inhibit the expression of a protein. The subject nucleic acids can be used in RNAi-based therapy in any animal having RNAi pathway, such as human, non-human primate, non-human mammal, non-human vertebrates, rodents (mice, rats, hamsters, rabbits, etc.), domestic livestock animals, pets (cats, dogs, etc.), *Xenopus*, fish, insects (*Drosophila*, etc.), and worms (*C. elegans*), etc.

The invention provides methods for inhibiting or preventing in a subject, a disease or condition associated with an aberrant or unwanted target gene expression or activity, by administering to the subject a nucleic acid of the invention. If appropriate, subjects are first treated with a priming agent so as to be more responsive to the subsequent RNAi therapy. Subjects at risk for a disease which is caused or contributed to by aberrant or unwanted target gene expression or activity can be identified by, for example, any or a combination of diagnostic or prognostic assays known in the art. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject.

In another aspect, the invention pertains to methods of modulating target gene expression, protein expression or activity for therapeutic purposes. Accordingly, in an exemplary embodiment, the methods of the invention involve contacting a cell capable of expressing target gene with a nucleic acid of the invention that is specific for the target gene or protein (e.g., is specific for the mRNA encoded by said gene or specifying the amino acid sequence of said protein) such that expression or one or more of the activities of target protein is modulated. These methods can be performed in vitro (e.g., by culturing the cell with the agent), in vivo (e.g., by administering the agent to a subject), or ex vivo. The subjects may be first treated with a priming agent so as to be more responsive to the subsequent RNAi therapy if desired. As such, the present invention provides methods of treating a subject afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

Thus the therapeutic agents of the invention can be administered to subjects to treat (prophylactically or therapeutically) disorders associated with aberrant or unwanted target gene activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a therapeutic agent as well as tailoring the dosage and/or therapeutic regimen of treatment with a therapeutic agent. Pharmacogenomics deals with clinically significant hereditary variations in the response to drugs due to altered drug disposition and abnormal action in affected persons.

For the purposes of the invention, ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a protein" or "a nucleic acid molecule" refers to one or more of those compounds or at least one compound. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein or nucleic acid molecule is a compound that has been removed from its natural milieu. As such, "isolated" and "biologically pure" do not necessarily reflect the extent to which the compound has been purified. An isolated compound of the present invention can be obtained from its natural source, can be produced using molecular biology techniques or can be produced by chemical synthesis.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Ocular Administration of Sd-rxRNA® Molecules

Subretinal and intravitreal administration was found to be highly effective in delivering sd-rxRNA® molecules to all of the cell types in the eye. sd-rxRNA® targeting MAP4K4 or non-targeting (with or without a DY547 label) were injected by either subretinal or intravitreal administration. 5 and 10 μg doses were evaluated. No signs of inflammation were detected. Eyes looked healthy and no signs of cellular migration (indicative of inflammatory response) were observed.

Compound uptake was visualized by fundus microscopy. Mice were sacrificed at 24 and 48 hours, retinas were collected, fixed, and paraffin embedded and compound uptake and distribution was analyzed by confocal microscopy.

FIG. 1 demonstrates a confocal triple overlay of DIC, DY547 and Hoechst. As revealed by the staining, by 24 hours, sd-rxRNA® had penetrated the entire retina. FIG. 2 provides a comparison of delivery of sd-rxRNA® with traditional RNAi compounds. 10 μg of RNA in 1 μl of PBS was delivered intravitreally. White light fundus imaging verified that the retinas had normal ocular architecture with no hemorrhage or gross signs of inflammation. Fluorescent images were taken with a fundus camera (a camera with a low power microscope designed to photograph the interior surface of the eye). As revealed in FIG. 2, both sd-rxRNA® and traditional RNAi compounds were detected in the retina immediately after administration. However, after 24 and 48 hours, only the sd-rxRNA® molecule was detected.

FIG. 3 reveals that sd-rxRNA® was detected throughout the retina following intravitreal dosing of sd-rxRNA®, but not following dosing of PBS or traditional RNAi compounds.

FIG. 4 reveals that sd-rxRNA® penetrated the retina to the outer segments of the photoreceptors.

Figure 5A:
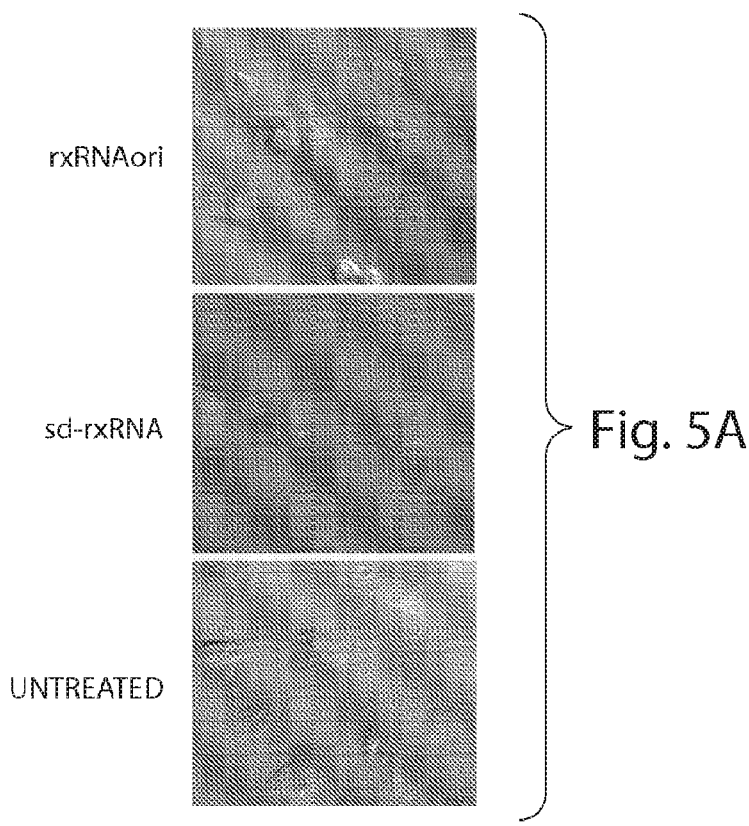
FIGS. 5A to 5B demonstrate robust uptake of and silencing by sd-rxRNA® in ARPE-19 cells, as compared to uptake of and silencing by rxRNAori in ARPE-19 cells.
Figure 5B:
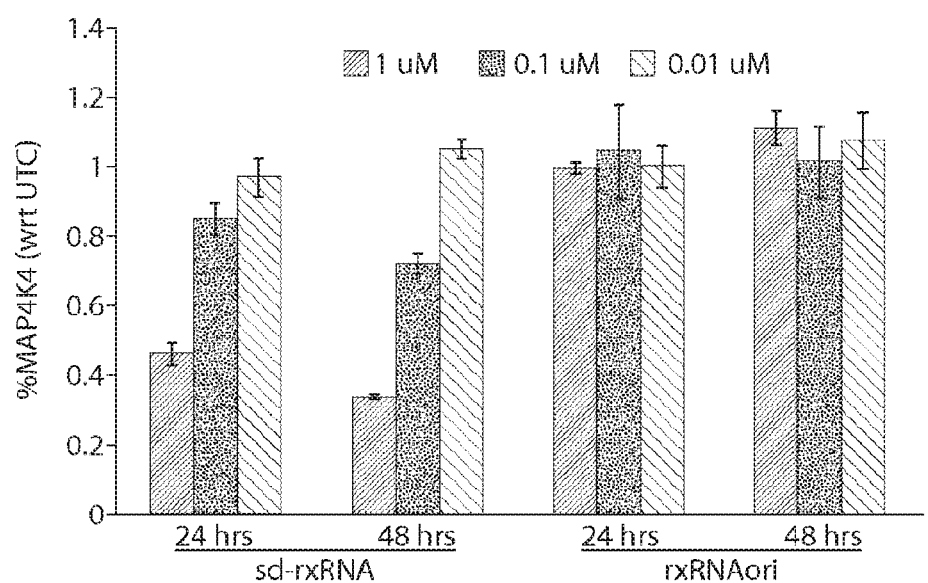

FIG. 5 reveals that in ARPE-19 cells, sd-rxRNA® shows robust uptake and silencing compared to rxRNAori.

FIG. 6 shows some non-limiting examples of sd-rxRNA® molecules for use in ocular indications.

The effectiveness of sd-rxRNA® directed to VEGF is demonstrated in FIG. 7 which shows the percentage of VEGF mRNA levels (normalized to PPIB) after doses of the VEGF-specific sd-rxRNA®.

FIG. 8 reveals efficient penetration of sd-rxRNA® following intravitreal dosing. Fluorescently-labeled RNAi compounds were administered to mouse eye using 1 μl intravitreal injection. By 2-3 hrs post injection, sd-rxRNA® was present in the ganglion cell layer and was present in the outer segments of the photoreceptors by 24 hrs post dosing. Fluorescence was detected using laser scanning confocal microscopy.

Figure 9A:
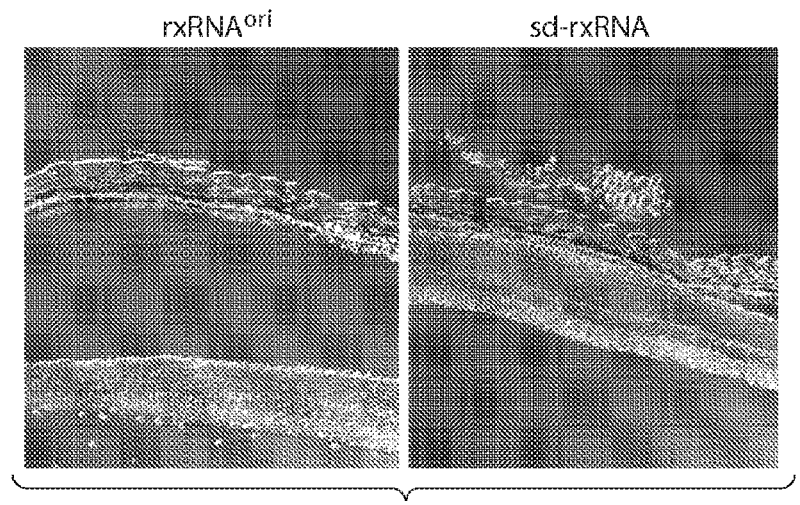
FIGS. 9A to 9B demonstrate by confocal microscopy that while sd-rxRNA® penetrates to the RPE and outer segments of the photoreceptors, there is no visible penetration of convention RNAi compounds.
Figure 9B:
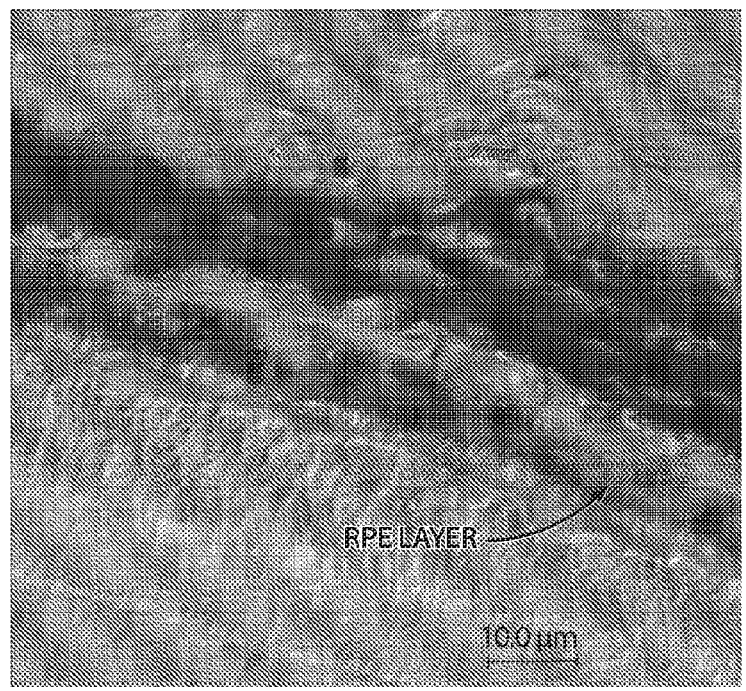

FIG. 9 reveals significant retinal uptake of sd-rxRNA® but not rxRNAori in vivo at 24 h. Fluorescently-tagged RNAi compounds were administered and whole eye mounts were prepared from eyes harvested at 24 h post dose. Whole eyes were fixed in 4% paraformaldehyde overnight followed by formalin fixing and paraffin embedding. Transverse sections were cut (5 μm thick), stained with Hoechst and visualized using a Leica SP5 Confocal Microscope. Images shown are a triple overlay of the Hoechst, DY547 (red tag on RNAi compound), and differential interference contract (DIC) images. Panel B shows a higher magnification view (scale bar is 10 μm) from the sd-rxRNA® sample shown in panel A, revealing delivery to the retinal pigment epithelium cells.

Figure 10:
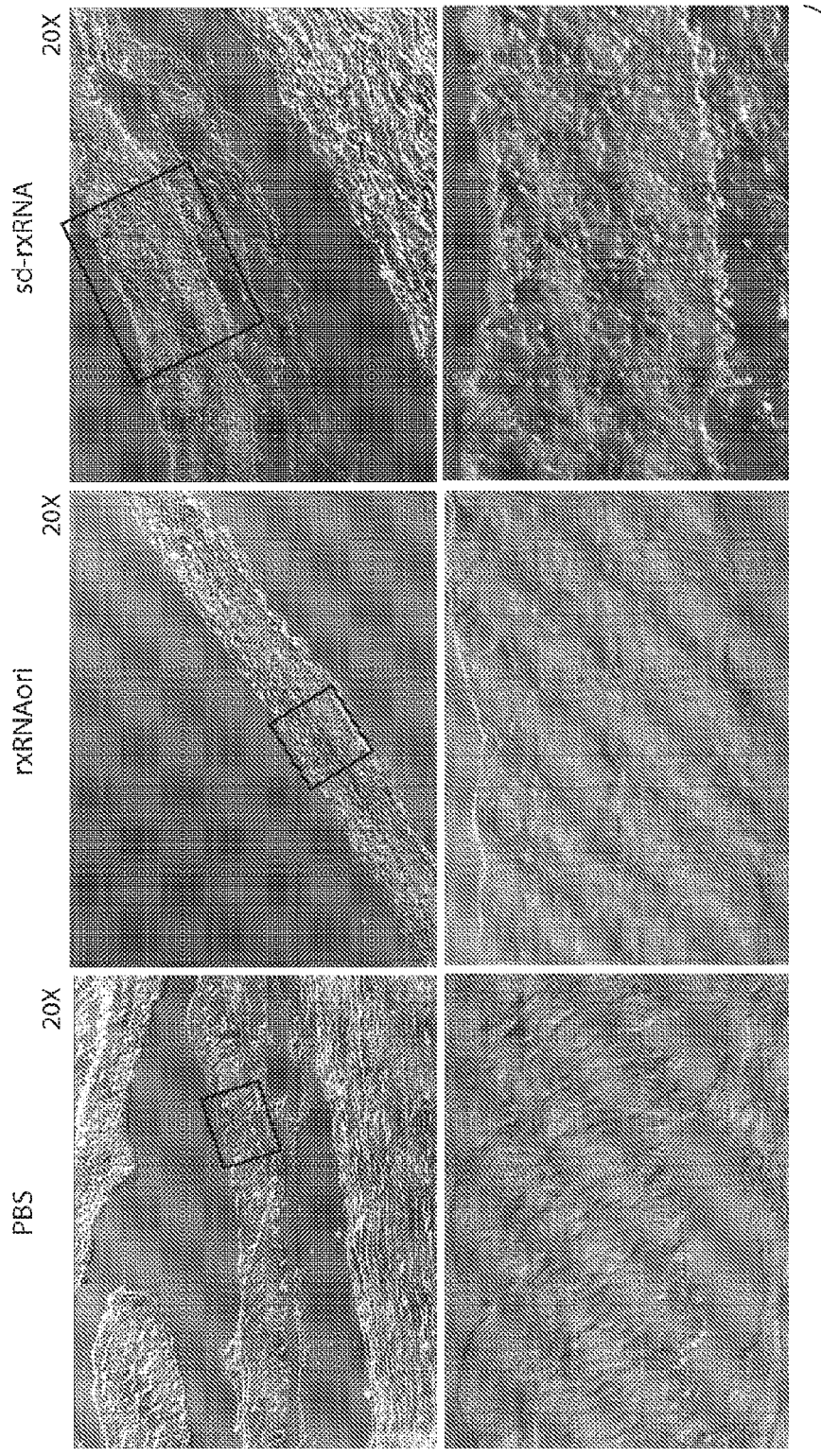
FIG. 10 demonstrates that fluorescent sd-rxRNA®, but not rxRNAori, can be detected in all rabbit retinal cell layers, 24 hours post dose.
Figure 11:
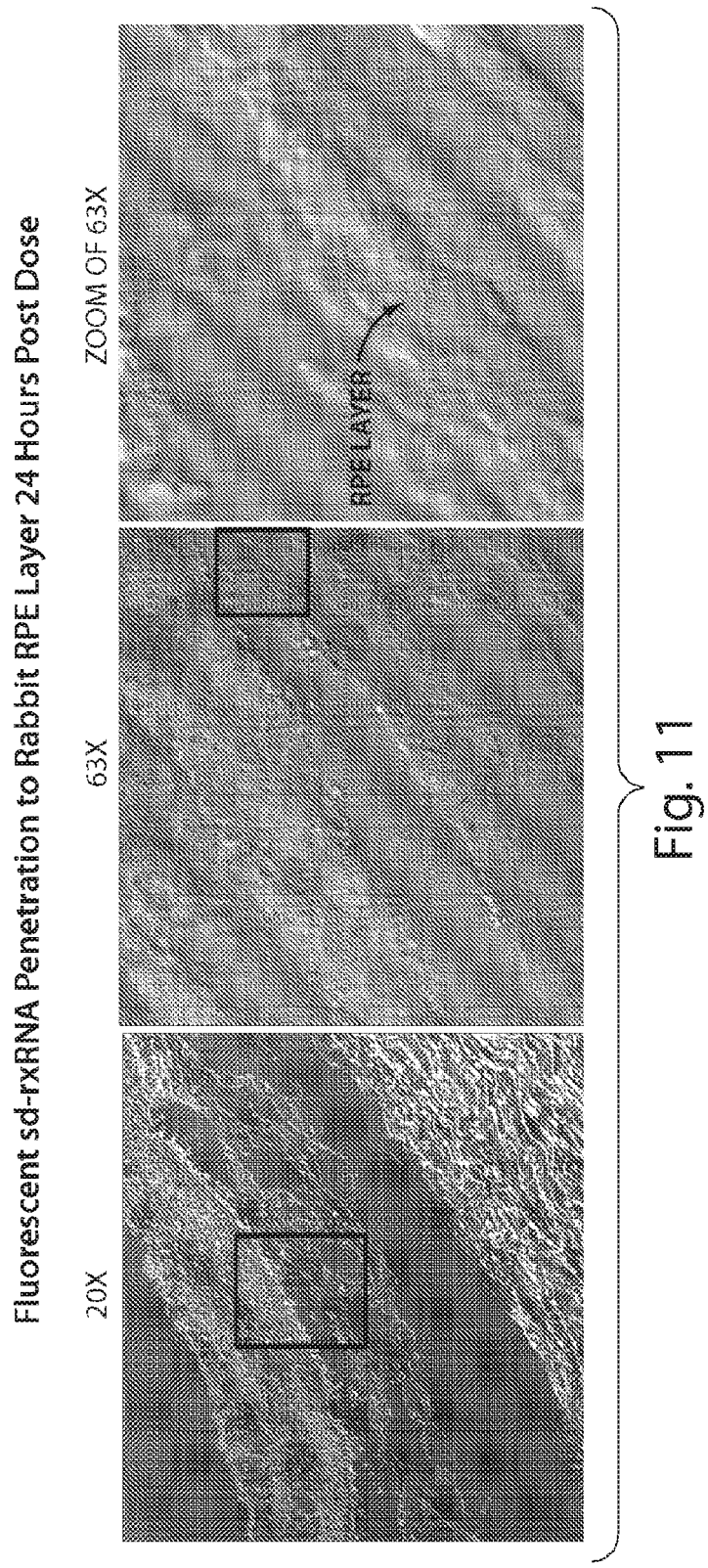
FIG. 11 presents confocal images at high magnification, demonstrating that sd-rxRNA® penetrates all rabbit retinal cell layers 24 hours post dose.

FIGS. 10 and 11 reveal significant retinal uptake of sd-rxRNA® in rabbit retina 24 h post dose. Fluorescently-labeled RNAi compounds (100 ug) were administered to rabbit eye via single intravitreal injection. At 24 h post injection whole eyes were harvested and frozen in optimal cutting temperature (OCT) gel. Frozen blocks were cut in sections were stained with Hoechst. sd-rxRNA® was present throughout the retinal cell layers following intravitreal dosing. Fluorescence was detected using laser scanning confocal microscopy.

Figure 12:
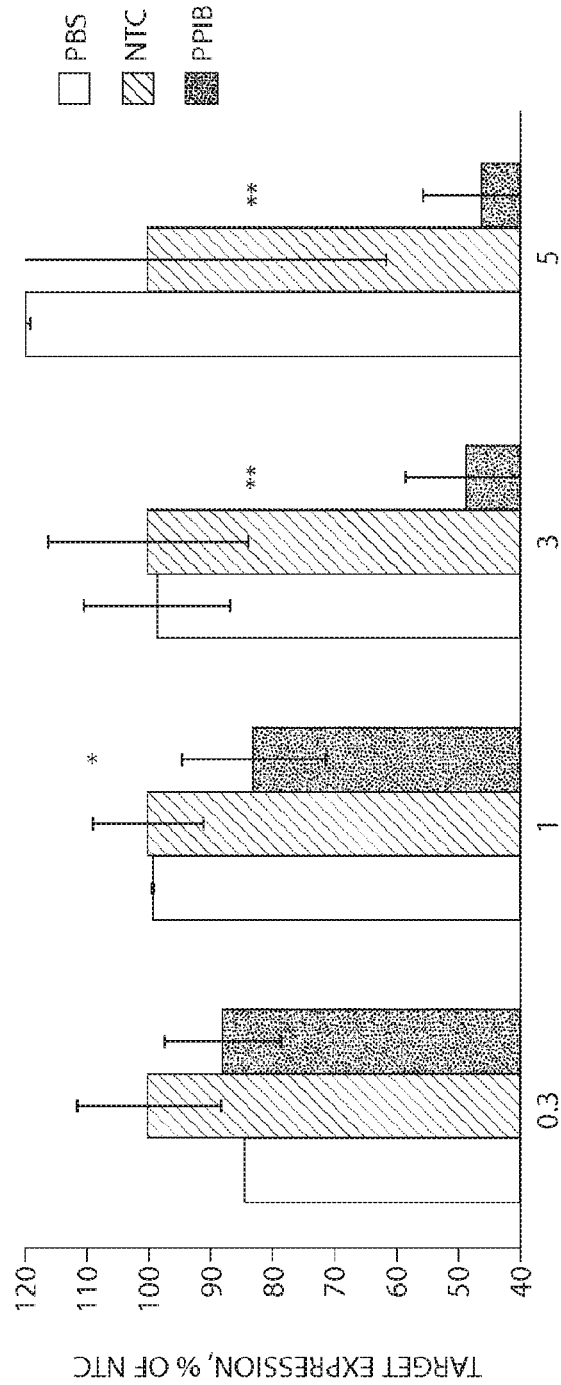
FIG. 12 demonstrates dose-dependent silencing in vivo by sd-rxRNA®, after intravitreal administration.

FIG. 12 reveals significant silencing of target mRNA following single intravitreal injection. sd-rxRNA® was administered by intravitreal injection (in 1 ul) to mouse eyes at indicated doses. Retinas were harvested at 48 hours, and mRNA levels quantified by QPCR and normalized to b-actin, n=5-8 (data from different studies was included, graphed+/−SD relative to NTC, *p≤0.05, **p≤0.01).

Figure 13:
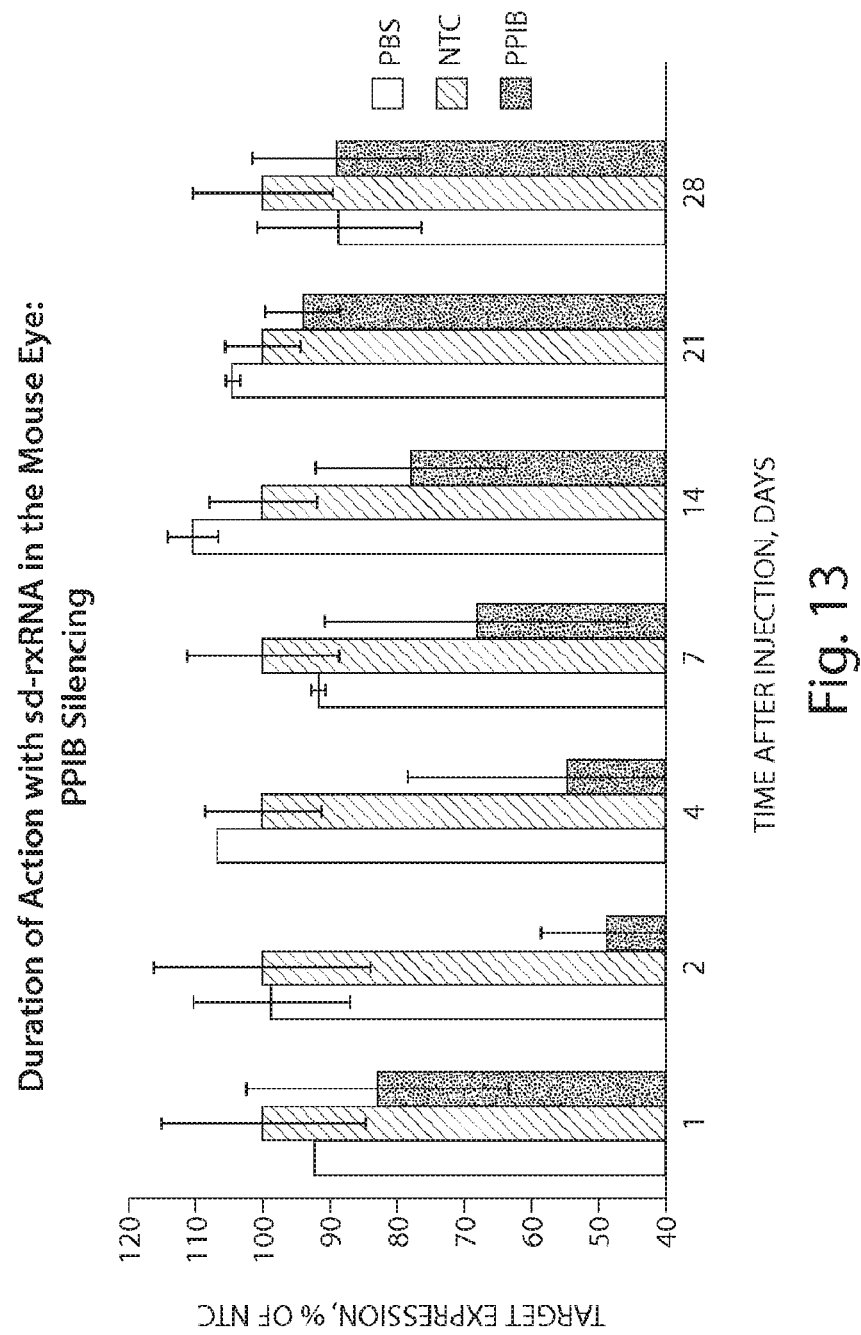
FIG. 13 demonstrates the duration of PPIB silencing by sd-rxRNA® in the mouse eye.

FIG. 13 reveals significant silencing of target mRNA following single intravitreal injection. 3 ug of PPIB or NTC sd-rxRNA® molecules were administered to mouse eyes by single intravitreal injection (1 ul). Retinas were harvested at 1, 2, 4, 7, 14, 21 and 28 days post injection. mRNA levels were quantified by qPCR and normalized to b-actin. Data was assembled from 6 different studies to enable sufficient 'n' for each data point (n=5-8) (graphed+/−SD relative to PBS in each study, *p≤0.01)

Figure 14:
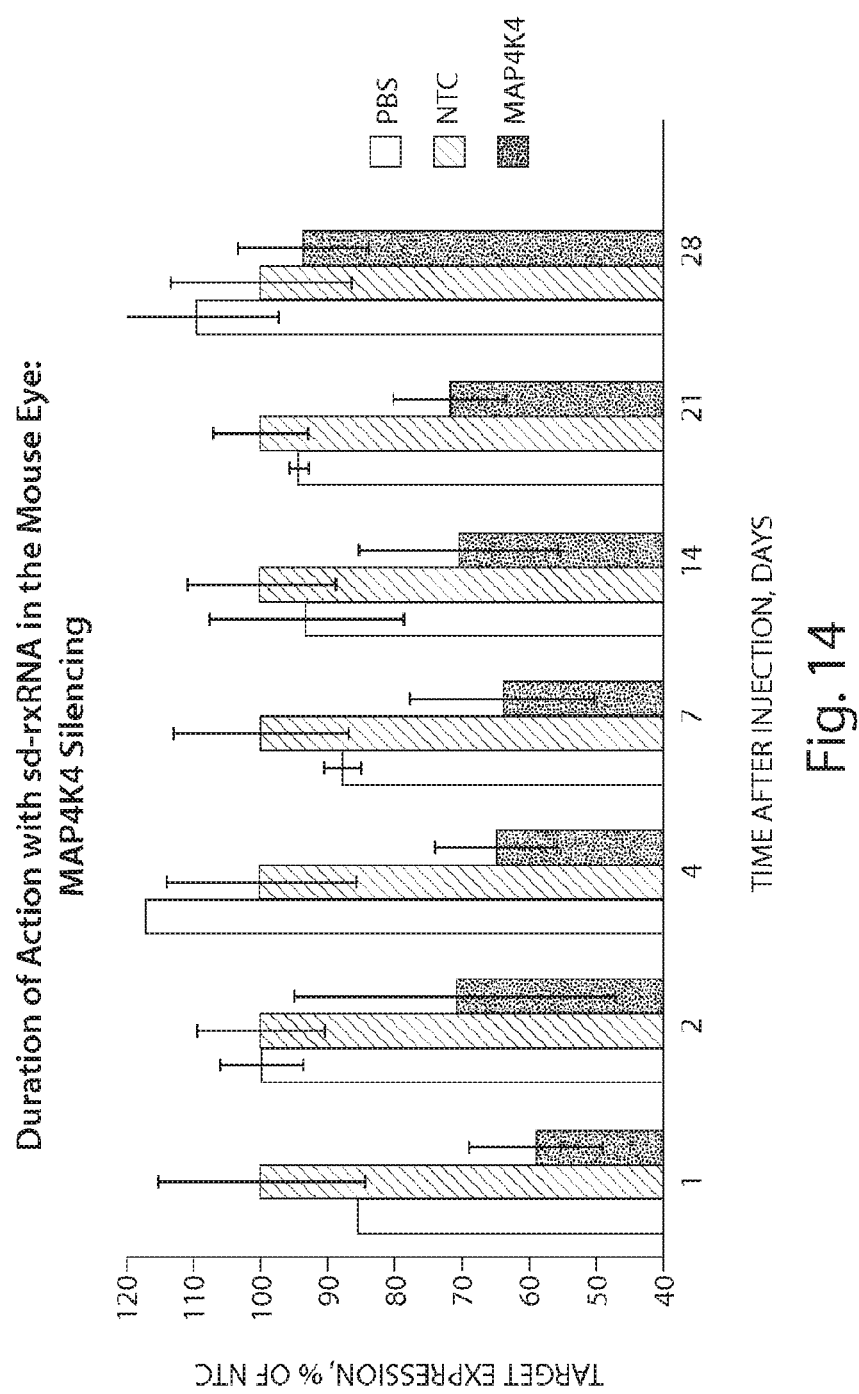
FIG. 14 demonstrates the duration of MAP4K4 silencing by sd-rxRNA® in the mouse eye.

FIG. 14 reveals significant silencing of target mRNA following single intravitreal injection. 3 ug of Map4K4 or NTC sd-rxRNA® molecules were administered to mouse eyes by single intravitreal injection (1 ul). Retinas were harvested at 1, 2, 4, 7, 14, 21 and 28 days post injection. mRNA levels were quantified by qPCR and normalized to b-actin. Data was assembled from 6 different studies to enable sufficient 'n' for each data point (n=5-8) (graphed+/−SD relative to PBS in each study, *p≤0.05, **p≤0.01).

Figure 15:
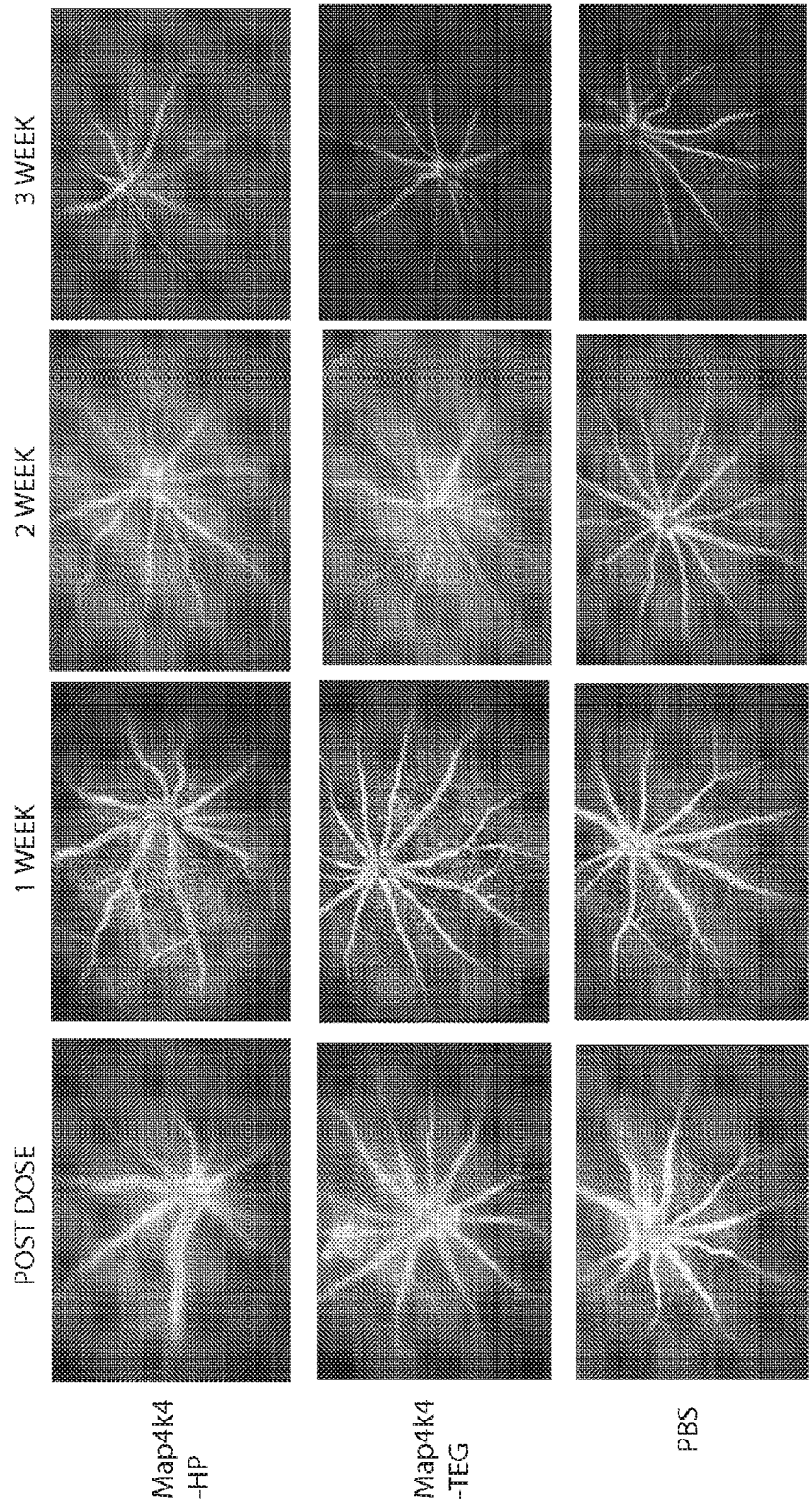
FIG. 15 demonstrates that sd-rxRNA® does not induce blood vessel leakage three weeks post dose.

FIG. 15 reveals that sd-rxRNA® did not induce blood vessel leakage three weeks post dose. sd-rxRNA® was administered by single intravitreal dosing (1 ul) of 5 μg of both Map4k4-TEG and Map4k4-HP sd-rxRNA® and PBS. Fluorescein-labeled dextran was administered subcutaneously prior to fluorescent fundus imaging 1, 2, and 3 weeks post dosing. Fluorescein angiography revealed no leakage of retinal blood vessels.

Figure 16:
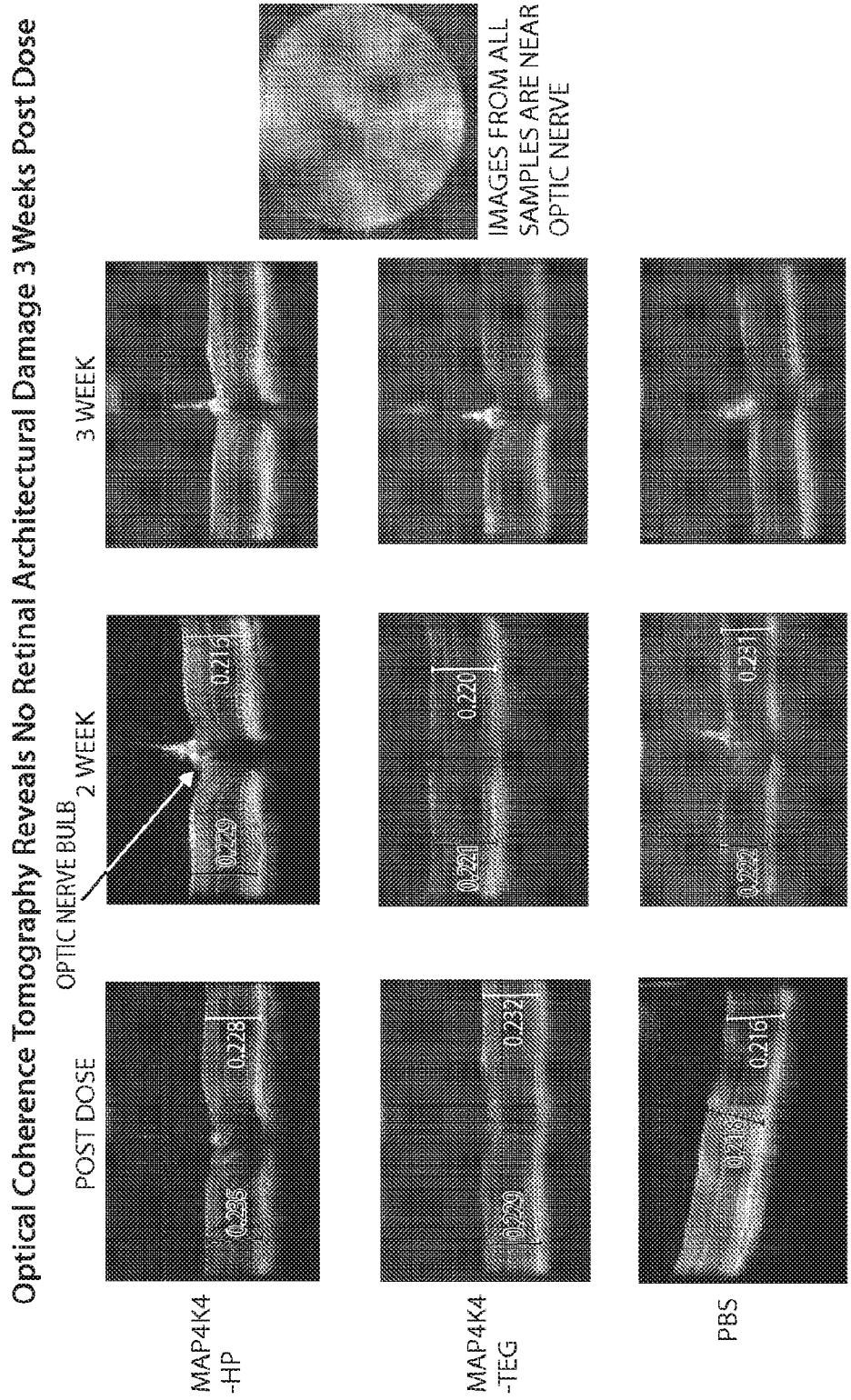
FIG. 16 demonstrates that sd-rxRNA® does not induce architectural damage three weeks post dose.

FIG. 16 reveals that sd-rxRNA® did not induce retinal architectural damage three weeks post dose. sd-rxRNA® was administered by single intravitreal dosing (1 ul) of 5 μg of both Map4k4-TEG and Map4k4-HP sd-rxRNA® and PBS. Optical coherence tomography was performed 2, and 3 weeks post dosing. Representative images show normal retinal architecture and thickness.

FIG. 17 reveals that sd-rxRNA® did not impair retinal function three weeks post dose. sd-rxRNA® was administered by single intravitreal dosing (1 ul) of 5 μg of both Map4k4-TEG and Map4k4-HP sd-rxRNA® and PBS. Scotopic electroretinography (ERG) recordings were taken three weeks post dosing and revealed similar retinal function following dosing with sd-rxRNA® and PBS. Photopic recordings were also collected with similar outcome.

FIG. 18 reveals a multi-targeted silencing approach with sd-rxRNA® molecules. The silencing activity of several sd-rxRNA® molecules was determined in cells treated with up to 4 sd-rxRNA® molecules targeting multiple genes of interest. When dosed in combination, sd-rxRNA® molecules retained their potent efficacy, demonstrating their potential for multi-targeting silencing.

Table 2 presents 25-mer sequences within VEGF. rxRNAoris and sd-rxRNA® molecules can be directed against sequences within Table 2. In some embodiments, rxRNAoris comprise the sequences presented in Table 2.

Table 3 presents non-limiting examples of sd-rxRNA® molecules directed against SPP1.

Table 4 presents non-limiting examples of sd-rxRNA® sequences directed against PTGS2 (COX-2).

Table 5 presents non-limiting examples of sd-rxRNA® sequences directed against CTGF.

Table 6 presents non-limiting examples of sd-rxRNA® sequences directed against TGFβ2.

Table 7 presents non-limiting examples of sd-rxRNA® sequences directed against TGFβ1.

Example 2: Identification of Sd-rxRNA® Molecules Targeting VEGF

Optimal sequences for sd-rxRNA® development were identified using a sequence selection algorithm (Table 2). The algorithm selects sequences based on the following criteria: a GC content greater than 32% but less than 47%, homology to specific animal models (e.g., mouse or rat), avoidance of 5 or more U/U stretches and/or 2 or more G/C stretches, an off-target hit score of less than 500, and avoidance of sequences contained within the 5' UTR.

The sequences were developed initially as 25 nucleotide blunt-ended duplexes with O-methyl modification. Such sequences were screened in various cell lines to identify those were most efficient in reducing gene expression. Several concentrations of the RNA molecules, such as 0.025, 0.1 and 0.25 nM, were tested, and suitable concentrations were determined. Dose response curves were generated to determine the most potent sequences. Those sequences were developed into sd-rxRNA® molecules based on parameters described throughout the application.

Table 8 presents non-limiting examples of sd-rxRNA® sequences directed against VEGF.

Table 9 presents non-limiting examples of rxRNAori sequences directed against VEGF.

Table 10 presents results of optimization of sd-rxRNA® sequences directed against VEGF, using a variety of chemical modification patterns.

Example 3: Linker Chemistry

FIG. 19 demonstrates that variation of linker chemistry does not influence silencing activity of sd-rxRNA® molecules in vitro. Two different linker chemistries were evaluated, a hydroxyproline linker and ribo linker, on multiple sd-rxRNA® molecules (targeting Map4k4 or PPIB) in passive uptake assays to determine linkers which favor self delivery. HeLa cells were transfected in the absence of a delivery vehicle (passive transfection) with sd-rxRNA® molecules at 1 uM, 0.1 uM or 0.01 uM for 48 hrs. Use of either linker results in an efficacious delivery of sd-rxRNA®.

The ribo linker used in Example 1 had the following structure:

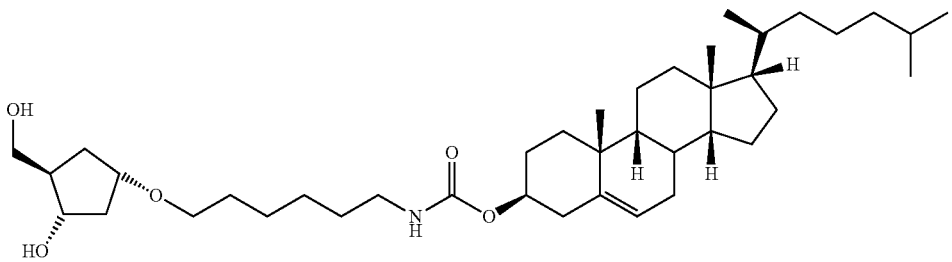

TABLE 2 hVEGF stealth sequences

| Oligo ID | Gene Region | Ref Pos | SEQ ID NO | 25-mer Sense Strand (position 25 of SS, replaced with A) | % Remaining Expression as Compared to NTC (100 pM) |
|---|---|---|---|---|---|
| 18832 | 3'UTR | 3471 | 1 | UAUCAUUUAUUUAUUGGUGCUACUA | 37% |
| 18811 | 3'UTR | 3199 | 2 | UUAAUUUUGCUAACACUCAGCUCUA | 37% |
| 18902 | 3'UTR | 2792 | 3 | CCUCACACCAUUGAAACCACUAGUA | 39% |
| 18830 | 3'UTR | 3429 | 4 | CUACAUACUAAAUCUCUCUCCUUUA | 41% |
| 18880 | CDS | 1343 | 5 | CCAACAUCACCAUGCAGAUUAUGCA | 42% |
| 18756 | CDS | 1389 | 6 | GCACAUAGGAGAGAUGAGCUUCCUA | 42% |
| 18913 | 3'UTR | 3163 | 7 | AUCGGUGACAGUCACUAGCUUAUCA | 42% |
| 18909 | 3'UTR | 3073 | 8 | UUUAUGAGAUGUAUCUUUUGCUCUA | 42% |
| 18831 | 3'UTR | 3430 | 9 | UACAUACUAAAUCUCUCUCCUUUUA | 43% |
| 18778 | 3'UTR | 2183 | 10 | UAACAGUGCUAAUGUUAUUGGUGUA | 43% |
| 18793 | 3'UTR | 2932 | 11 | UUGUGGAGGCAGAGAAAAGAGAAAA | 43% |
| 18898 | 3'UTR | 2210 | 12 | CACUGGAUGUAUUUGACUGCUGUGA | 46% |
| 18760 | 3'UTR | 1853 | 13 | AUCACCAUCGACAGAACAGUCCUUA | 46% |
| 18766 | 3'UTR | 1859 | 14 | AUCGACAGAACAGUCCUUAAUCCAA | 46% |
| 18908 | 3'UTR | 3072 | 15 | AUUUAUGAGAUGUAUCUUUUGCUCA | 46% |
| 18903 | 3'UTR | 2794 | 16 | UCACACCAUUGAAACCACUAGUUCA | 46% |
| 18834 | 3'UTR | 3476 | 17 | UUUAUUUAUUGGUGCUACUGUUUAA | 47% |
| 18828 | 3'UTR | 3427 | 18 | UUCUACAUACUAAAUCUCUCUCCUA | 48% |
| 18761 | 3'UTR | 1854 | 19 | UCACCAUCGACAGAACAGUCCUUAA | 48% |
| 18892 | 3'UTR | 1985 | 20 | CCUCUUGGAAUUGGAUUCGCCAUUA | 48% |
| 18764 | 3'UTR | 1857 | 21 | CCAUCGACAGAACAGUCCUUAAUCA | 48% |

TABLE 2-continued hVEGF stealth sequences

| Oligo ID | Gene Region | Ref Pos | SEQ ID NO | 25-mer Sense Strand (position

TABLE 2-continued hVEGF stealth sequences

| Oligo ID | Gene Region | Ref Pos | SEQ ID NO | 25-mer Sense Strand (position 25 of SS, replaced with A) | % Remaining Expression as Compared to NTC (100 pM) |
|---|---|---|---|---|---|
| 18767 | 3'UTR | 1860 | 59 | UCGACAGAACAGUCCUUAAUCCAGA | 60% |
| 18809 | 3'UTR | 3196 | 60 | UAUUUAAUUUUGCUAACACUCAGCA | 60% |
| 18816 | 3'UTR | 3251 | 61 | ACACAUUCCUUUGAAAUAAGGUUUA | 60% |
| 18867 | CDS | 1214 | 62 | CCCUGGUGGACAUCUUCCAGGAGUA | 60% |
| 18774 | 3'UTR | 1987 | 63 | UCUUGGAAUUGGAUUCGCCAUUUUA | 61% |
| 18882 | CDS | 1346 | 64 | ACAUCACCAUGCAGAUUAUGCGGAA | 61% |
| 18905 | 3'UTR | 2797 | 65 | CACCAUUGAAACCACUAGUUCUGUA | 61% |
| 18754 | CDS | 1385 | 66 | GCCAGCACAUAGGAGAGAUGAGCUA | 61% |
| 18822 | 3'UTR | 3366 | 67 | UAAAAUAGACAUUGCUAUUCUGUUA | 62% |
| 18763 | 3'UTR | 1856 | 68 | ACCAUCGACAGAACAGUCCUUAAUA | 62% |
| 18863 | 3'UTR | 3589 | 69 | UAAACAACGACAAAGAAAUACAGAA | 62% |
| 18835 | 3'UTR | 3477 | 70 | UUAUUUAUUGGUGCUACUGUUUAUA | 63% |
| 18893 | 3'UTR | 2009 | 71 | UUAUUUUCUUGCUGCUAAAUCACA | 63% |
| 18771 | 3'UTR | 1885 | 72 | AACCUGAAAUGAAGGAAGAGGAGAA | 63% |
| 18894 | 3'UTR | 2010 | 73 | UAUUUUUCUUGCUGCUAAAUCACCA | 64% |
| 18765 | 3'UTR | 1858 | 74 | CAUCGACAGAACAGUCCUUAAUCCA | 64% |
| 18796 | 3'UTR | 2936 | 75 | GGAGGCAGAGAAAAGAGAAAGUGUA | 65% |
| 18797 | 3'UTR | 2946 | 76 | AAAAGAGAAAGUGUUUUAUAUACGA | 65% |
| 18821 | 3'UTR | 3365 | 77 | AUAAAAUAGACAUUGCUAUUCUGUA | 65% |
| 18823 | 3'UTR | 3367 | 78 | AAAAUAGACAUUGCUAUUCUGUUUA | 66% |
| 18869 | CDS | 1231 | 79 | CAGGAGUACCCUGAUGAGAUCGAGA | 67% |
| 18781 | 3'UTR | 2187 | 80 | AGUGCUAAUGUUAUUGGUGUCUUCA | 67% |
| 18775 | 3'UTR | 2180 | 81 | AAUUAACAGUGCUAAUGUUAUUGGA | 67% |
| 18870 | CDS | 1232 | 82 | AGGAGUACCCUGAUGAGAUCGAGUA | 68% |
| 18815 | 3'UTR | 3248 | 83 | AGCACACAUUCCUUUGAAAUAAGGA | 68% |
| 18804 | 3'UTR | 3135 | 84 | AUUCAUGUUUCCAAUCUCUCUCUCA | 69% |
| 18799 | 3'UTR | 2950 | 85 | GAGAAAGUGUUUUAUAUACGGUACA | 69% |
| 18779 | 3'UTR | 2184 | 86 | AACAGUGCUAAUGUUAUUGGUGUCA | 69% |
| 18924 | 3'UTR | 3545 | 87 | UCUAGUGCAGUUUUCGAGAUAUUA | 69% |
| 18758 | CDS | 1394 | 88 | UAGGAGAGAUGAGCUUCCUACAGCA | 70% |
| 18782 | 3'UTR | 2188 | 89 | GUGCUAAUGUUAUUGGUGUCUUCAA | 70% |
| 18833 | 3'UTR | 3475 | 90 | AUUUAUUUAUUGGUGCUACUGUUUA | 70% |
| 18800 | 3'UTR | 3094 | 91 | UCUCUCUUGCUCUCUUAUUUGUACA | 70% |
| 18904 | 3'UTR | 2795 | 92 | CACACCAUUGAAACCACUAGUUCUA | 70% |
| 18845 | 3'UTR | 3515 | 93 | GGGAAAAGAUAUUAACAUCACGUCA | 71% |
| 18884 | CDS | 1348 | 94 | AUCACCAUGCAGAUUAUGCGGAUCA | 71% |

TABLE 2-continued hVEGF stealth sequences

| Oligo ID | Gene Region | Ref Pos | SEQ ID NO | 25-mer Sense Strand (position 25 of SS, replaced with A) | % Remaining Expression as Compared to NTC (100 pM) |
|---|---|---|---|---|---|
| 18818 | 3'UTR | 3356 | 95 | GUGAUUCUGAUAAAAUAGACAUUGA | 71% |
| 18814 | 3'UTR | 3247 | 96 | CAGCACACAUUCCUUUGAAAUAAGA | 71% |
| 18801 | 3'UTR | 3131 | 97 | UAAAAUUCAUGUUUCCAAUCUCUCA | 71% |
| 18873 | CDS | 1236 | 98 | GUACCCUGAUGAGAUCGAGUACAUA | 72% |
| 18802 | 3'UTR | 3133 | 99 | AAAUUCAUGUUUCCAAUCUCUCUCA | 72% |
| 18787 | 3'UTR | 2212 | 100 | CUGGAUGUAUUUGACUGCUGUGGAA | 72% |
| 18854 | 3'UTR | 3525 | 101 | AUUAACAUCACGUCUUUGUCUCUAA | 72% |
| 18901 | 3'UTR | 2791 | 102 | UCCUCACACCAUUGAAACCACUAGA | 73% |
| 18753 | CDS | 1384 | 103 | GGCCAGCACAUAGGAGAGAUGAGCA | 73% |
| 18820 | 3'UTR | 3364 | 104 | GAUAAAAUAGACAUUGCUAUUCUGA | 73% |
| 18807 | 3'UTR | 3194 | 105 | GAUAUUUAAUUUUGCUAACACUCAA | 73% |
| 18772 | 3'UTR | 1886 | 106 | ACCUGAAAUGAAGGAAGAGGAGACA | 74% |
| 18803 | 3'UTR | 3134 | 107 | AAUUCAUGUUUCCAAUCUCUCUCUA | 74% |
| 18844 | 3'UTR | 3514 | 108 | GGGGAAAAGAUAUUAACAUCACGUA | 75% |
| 18888 | CDS | 1411 | 109 | CUACAGCACAACAAAUGUGAAUGCA | 75% |
| 18895 | 3'UTR | 2077 | 110 | ACACACCCACCCACAUACAUACAUA | 76% |
| 18858 | 3'UTR | 3553 | 111 | AGUUUUUCGAGAUAUUCCGUAGUAA | 77% |
| 18889 | 3'UTR | 1981 | 112 | GGUCCCUCUUGGAAUUGGAUUCGCA | 77% |
| 18856 | 3'UTR | 3551 | 113 | GCAGUUUUUCGAGAUAUUCCGUAGA | 78% |
| 18931 | 3'UTR | 3588 | 114 | UUAAACAACGACAAAGAAAUACAGA | 78% |
| 18808 | 3'UTR | 3195 | 115 | AUAUUUAAUUUUGCUAACACUCAGA | 78% |
| 18825 | 3'UTR | 3423 | 116 | AGAAUUCUACAUACUAAAUCUCUCA | 78% |
| 18864 | 3'UTR | 3590 | 117 | AAACAACGACAAAGAAAUACAGAUA | 78% |
| 18881 | CDS | 1345 | 118 | AACAUCACCAUGCAGAUUAUGCGGA | 79% |
| 18906 | 3'UTR | 2798 | 119 | ACCAUUGAAACCACUAGUUCUGUCA | 79% |
| 18868 | CDS | 1229 | 120 | UCCAGGAGUACCCUGAUGAGAUCGA | 79% |
| 18897 | 3'UTR | 2196 | 121 | GUUAUUGGUGUCUUCACUGGAUGUA | 79% |
| 18788 | 3'UTR | 2213 | 122 | UGGAUGUAUUUGACUGCUGUGGACA | 79% |
| 18896 | 3'UTR | 2195 | 123 | UGUUAUUGGUGUCUUCACUGGAUGA | 79% |
| 18784 | 3'UTR | 2190 | 124 | GCUAAUGUUAUUGGUGUCUUCACUA | 79% |
| 18847 | 3'UTR | 3518 | 125 | AAAGAUAUUAACAUCACGUCUUUA | 80% |
| 18852 | 3'UTR | 3523 | 126 | AUAUUAACAUCACGUCUUUGUCUCA | 80% |
| 18850 | 3'UTR | 3521 | 127 | AGAUAUUAACAUCACGUCUUUGUCA | 80% |
| 18917 | 3'UTR | 3264 | 128 | AAAUAAGGUUUCAAUAUACAUCUAA | 81% |
| 18871 | CDS | 1234 | 129 | GAGUACCCUGAUGAGAUCGAGUACA | 81% |
| 18837 | 3'UTR | 3479 | 130 | AUUUAUUGGUGCUACUGUUUAUCCA | 81% |
| 18910 | 3'UTR | 3130 | 131 | AUAAAAUUCAUGUUUCCAAUCUCUA | 81% |

TABLE 2-continued hVEGF stealth sequences

| Oligo ID | Gene Region | Ref Pos | SEQ ID NO | 25-mer Sense Strand (position 25 of SS, replaced with A) | % Remaining Expression as Compared to NTC (100 pM) |
| --- | --- | --- | --- | --- | --- |
| 18875 | CDS | 1338 | 132 | GGAGUCCAACAUCACCAUGCAGAUA | 82% |
| 18923 | 3'UTR | 3544 | 133 | CUCUAGUGCAGUUUUUCGAGAUAUA | 82% |
| 18853 | 3'UTR | 3524 | 134 | UAUUAACAUCACGUCUUUGUCUCUA | 82% |
| 18876 | CDS | 1339 | 135 | GAGUCCAACAUCACCAUGCAGAUUA | 82% |
| 18824 | 3'UTR | 3422 | 136 | GAGAAUUCUACAUACUAAAUCUCUA | 84% |
| 18768 | 3'UTR | 1862 | 137 | GACAGAACAGUCCUUAAUCCAGAAA | 84% |
| 18891 | 3'UTR | 1983 | 138 | UCCCUCUUGGAAUUGGAUUCGCCAA | 85% |
| 18842 | 3'UTR | 3484 | 139 | UUGGUGCUACUGUUUAUCCGUAAUA | 85% |
| 18838 | 3'UTR | 3480 | 140 | UUUAUUGGUGCUACUGUUUAUCCGA | 86% |
| 18925 | 3'UTR | 3546 | 141 | CUAGUGCAGUUUUUCGAGAUAUUCA | 87% |
| 18859 | 3'UTR | 3554 | 142 | GUUUUUCGAGAUAUUCCGUAGUACA | 88% |
| 18885 | CDS | 1351 | 143 | ACCAUGCAGAUUAUGCGGAUCAAAA | 88% |
| 18857 | 3'UTR | 3552 | 144 | CAGUUUUUCGAGAUAUUCCGUAGUA | 88% |
| 18849 | 3'UTR | 3520 | 145 | AAGAUAUUAACAUCACGUCUUUGUA | 88% |
| 18755 | CDS | 1387 | 146 | CAGCACAUAGGAGAGAUGAGCUUCA | 88% |
| 18927 | 3'UTR | 3548 | 147 | AGUGCAGUUUUUCGAGAUAUUCCGA | 88% |
| 18786 | 3'UTR | 2194 | 148 | AUGUUAUUGGUGUCUUCACUGGAUA | 89% |
| 18926 | 3'UTR | 3547 | 149 | UAGUGCAGUUUUUCGAGAUAUUCCA | 91% |
| 18928 | 3'UTR | 3549 | 150 | GUGCAGUUUUUCGAGAUAUUCCGUA | 91% |
| 18757 | CDS | 1391 | 151 | ACAUAGGAGAGAUGAGCUUCCUACA | 91% |
| 18848 | 3'UTR | 3519 | 152 | AAAGAUAUUAACAUCACGUCUUUGA | 92% |
| 18921 | 3'UTR | 3542 | 153 | GUCUCUAGUGCAGUUUUUCGAGAUA | 93% |
| 18907 | 3'UTR | 3070 | 154 | CUAUUUAUGAGAUGUAUCUUUUGCA | 93% |
| 18783 | 3'UTR | 2189 | 155 | UGCUAAUGUUAUUGGUGUCUUCACA | 93% |
| 18918 | 3'UTR | 3296 | 156 | AUAUAUAUUUGGCAACUUGUAUUUA | 93% |
| 18851 | 3'UTR | 3522 | 157 | GAUAUUAACAUCACGUCUUUGUCUA | 94% |
| 18890 | 3'UTR | 1982 | 158 | GUCCCUCUUGGAAUUGGAUUCGCCA | 95% |
| 18827 | 3'UTR | 3425 | 159 | AAUUCUACAUACUAAAUCUCUCUCA | 95% |
| 18812 | 3'UTR | 3241 | 160 | GCUCCCCAGCACACAUUCCUUUGAA | 96% |
| 18773 | 3'UTR | 1887 | 161 | CCUGAAAUGAAGGAAGAGGAGACUA | 97% |
| 18855 | 3'UTR | 3526 | 162 | UUAACAUCACGUCUUUGUCUCUAGA | 98% |
| 18789 | 3'UTR | 2214 | 163 | GGAUGUAUUUGACUGCUGUGGACUA | 98% |
| 18826 | 3'UTR | 3424 | 164 | GAAUUCUACAUACUAAAUCUCUCUA | 98% |
| 18919 | 3'UTR | 3297 | 165 | UAUAUAUUUGGCAACUUGUAUUUGA | 98% |
| 18752 | CDS | 1381 | 166 | CAAGGCCAGCACAUAGGAGAGAUGA | 99% |
| 18914 | 3'UTR | 3165 | 167 | CGGUGACAGUCACUAGCUUAUCUUA | 100% |

TABLE 2-continued hVEGF stealth sequences

| Oligo ID | Gene Region | Ref Pos | SEQ ID NO | 25-mer Sense Strand (position 25 of SS, replaced with A) | % Remaining Expression as Compared to NTC (100 pM) |
|---|---|---|---|---|---|
| 18930 | 3'UTR | 3587 | 168 | UUUAAACAACGACAAAGAAAUACAA | 101% |
| 18911 | 3'UTR | 3161 | 169 | UGAUCGGUGACAGUCACUAGCUU TABLE 3-continued SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14092 | 612 | 199 | mU.G.G.A.mC.mU.G. A.G.G.mU.mC.A.Chl | 200 | P.mU.G.A.fC.fC.fU.fC.A. G.fU.mC.mC.A.mU*A* A*A*mC*C. | n/a |
| 14093 | 481 | 201 | G.A.G.mU.mC.mU.mC. A.mC.mC.A.mU.mU.Chl | 202 | P.mA.A.fU.G.G.fU.G.A. G.A.mC.mU.mC* A*mU*mC*A*G*A. | n/a |
| 14094 | 614 | 203 | G.A.mC.mU.G.A.G. G.mU.mC.A.A.A.Chl | 204 | P.mU.fU.fU.G. A.fC.fC.fU.fC.A. G.mU.mC*mC*A*mU* A*A*A. | n/a |
| 14095 | 951 | 205 | mU.mC.A.mC.A. G.mC.mC.A.mU.G.A. A.Chl | 206 | P.mU.fU.fC.A.fU.G. G.fC.fU.G.mU.G.A*A* A*mU*mU*mC*A. | 89% |
| 14096 | 482 | 207 | A.G.mU.mC.mU.mC. A.mC.mC. A.mU.mU.mC.Chl | 208 | P.mG.A.A.fU.G.G.fU.G. A.G.A.mC.mU*mC* A*mU*mC*A*G. | 87% |
| 14097 | 856 | 209 | A.A.G.mC.G.G.A.A. A.G.mC.mC.A.Chl | 210 | P.mU.G. G.fC.fU.fU.fC.fC. G.mC.mU.mU*A*mU* A*mU*A*A. | 88% |
| 14098 | 857 | 211 | A.G.mC.G.G.A.A.A. G.mC.mC.A.A.Chl | 212 | P.mU.fU.G. G.fC.fU.fU.fU.fC.fC. G.mC.mU*mU*A*mU* A*mU*A. | 113% |
| 14099 | 365 | 213 | A.mC.mC.A.mC.A.mU. G.G.A.mU.G.A.Chl | 214 | P.mU.fC.A.fU.fC.fC.A.fU. G.fU.G.G.mU*mC* A*mU*G*G*C. | 98% |
| 14100 | 359 | 215 | G.mC.mC.A.mU.G. A.mC.mC.A.mC. A.mU.Chl | 216 | P.mA.fU.G.fU.G.G.fU.fC. A.fU.G. G.mC*mU*mU*mU*mC* G*U. | 84% |
| 14101 | 357 | 217 | A.A.G.mC.mC.A.mU. G.A.mC.mC.A.mC.Chl | 218 | P.mG.fU.G.G.fU.fC.A.fU. G. G.mC.mU*mU*mU*mC* G*mU*mU*G. | 88% |
| 14102 | 858 | 219 | G.mC.G.G.A.A.A. G.mC.mC.A.A.mU.Chl | 220 | P.mA.fU.fU.G. G.fC.fU.fU.fU.fC.mC. G.mC*mU*mU*A*mU* A*U. | n/a |
| 14103 | 1012 | 221 | A.A.A.mU.mU.mU.mC. G.mU. A.mU.mU.mU.Chl | 222 | P.mA.A.fU.A.fC.G.A. A.A.mU.mU.mU*mC*A* G*G*mU*G. | 93% |
| 14104 | 1014 | 223 | A.mU.mU.mU.mC. G.mU. A.mU.mU.mU.mC.mU.Chl | 224 | P.mA.G.A.A.A.fU.A.fC. G.A.A. A.mU*mU*mU*mC*A* G*G. | 89% |
| 14105 | 356 | 225 | A.A.A.G.mC.mC. A.mU.G.A.mC.mC. A.Chl | 226 | P.mU.G.G.fU.fC.A.fU.G. G.fC.mU.mU.mU*mC* G*mU*mU*G*G. | 85% |
| 14106 | 368 | 227 | A.mC.A.mU.G.G. A.mU.G.A.mU. A.mU.Chl | 228 | P.mA.fU.A.fU.fC. A.fU.fC.fC.A.mU.G.mU* G*G*mU*mC*A*U. | 67% |
| 14107 | 1011 | 229 | G.A.A. A.mU.mU.mU.mC. G.mU.A.mU.mU.Chl | 230 | P.mA.A.fU.A.fC.G.A.A. A.fU.mU.mU.mC*A*G* G*mU*G*U. | 87% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14108 | 754 | 231 | G.mC.G.mC.mC.mU.mU.mC.mU.G.A.mU.mU.Chl | 232 | P.mA.A.fU.fC.A.G.A.A.G.G.mC.G.mC*G*mU*mU*mC*A*G. | 73% |
| 14109 | 1021 | 233 | A.mU.mU.mU.mC.mU.mC.A.mU.G.A.A.mU.Chl | 234 | P.mA.fU.fU.fC.A.fU.G.A.G.A.A.mU*A*mC*G*A*A*A. | 128% |
| 14110 | 1330 | 235 | mC.mU.mC.mU.mC.A.mU.G.A.A.mU.A.G.Chl | 236 | P.mC.fU.A.fU.fU.fC.A.fU.G.A.G.A.G*A*A*mU*A*A*C. | 101% |
| 14111 | 346 | 237 | A.A.G.mU.mC.mC.A.A.mC.G.A.A.A.Chl | 238 | P.mU.fU.fU.fC.G.fU.fU.G.G.A.mC.mU*A*mC*mU*mU*G*G. | 59% |
| 14112 | 869 | 239 | A.mU.G.A.mU.G.A.G.A.G.mC.A.A.Chl | 240 | P.mU.fU.G.fC.fU.fC.fU.fC.A.fU.mC.A.mU*mU*G*G*mC*mU*U. | 89% |
| 14113 | 701 | 241 | G.mC.G.A.G.G.A.G.mU.mU.G.A.A.Chl | 242 | P.mU.fU.fC.A.A.fC.fU.fC.fC.fU.mC.G.mC*mU*mU*mU*mC*mC*A. | 95% |
| 14114 | 896 | 243 | mU.G.A.mU.mU.G.A.mU.A.G.mU.mC.A.Chl | 244 | P.mU.G.A.fC.fU.A.fU.fC.A.A.mU.mC.A.mC*A*mU*mC*G*G. | 87% |
| 14115 | 1035 | 245 | A.G.A.mU.A.G.mU.G.mC.A.mU.mC.mU.Chl | 246 | P.mA.G.A.fU.G.fC.A.fC.fU.A.mU.mC.mU*A*A*mU*mU*mC*A. | 82% |
| 14116 | 1170 | 247 | A.mU.G.mU.G.mU.A.mU.mC.mU.A.mU.mU.Chl | 248 | P.mA.A.fU.A.G.A.fU.A.fC.A.mC.A.mU*mU*mC*A*A*mC*C. | 36% |
| 14117 | 1282 | 249 | mU.mU.mC.mU.A.mU.A.G.A.A.G.A.A.Chl | 250 | P.mU.fU.fC.fU.fU.fC.fU.A.fU.A.G.A.A*mU*G*A*A*mC*A. | 91% |
| 14118 | 1537 | 251 | mU.mU.G.mU.mC.mC.A.G.mC.A.A.mU.mU.Chl | 252 | P.mA.A.fU.fU.G.fC.fU.G.G.A.mC.A.A*mC*mC*G*mU*G*G. | 152% |
| 14119 | 692 | 253 | A.mC.A.mU.G.G.A.A.A.G.C.mG.A.Chl | 254 | P.mU.fC.G.fC.fU.fU.fU.fC.fC.A.mU.G.mU*G*mU*G*A*G*G. | n/a |
| 14120 | 840 | 255 | G.mC.A.G.mU.mC.mC.A.G.A.mU.mU.A.Chl | 256 | P.mU.A.A.fU.fC.fU.G.G.A.fC.mU.G.mC*mU*mU*G*mU*G*G. | 87% |
| 14121 | 1163 | 257 | mU.G.G.mU.mU.G.A.A.mU.G.mU.G.mU.Chl | 258 | P.mA.fC.A.fC.A.fU.fU.fC.A.A.mC.mC.A*A*mU*A*A*A*C. | 31% |
| 14122 | 789 | 259 | mU.mU.A.mU.G.A.A.A.mC.G.A.G.mU.Chl | 260 | P.mA.fC.fU.fC.G.fU.fU.fU.fC.A.mU.A.A*mC*mU*G*mU*mC*C. | 96% |
| 14123 | 841 | 261 | mC.A.G.mU.mC.mC.A.G.A.mU.mU.A.mU.Chl | 262 | P.mA.fU.A.A.fU.fC.fU.G.G.A.mC.mU.G*mC*mU*mU*G*mU*G. | 110% |
| 14124 | 852 | 263 | A.mU.A.mU.A.A.G.mC.G.G.A.A.A.Chl | 264 | P.mU.fU.fU.fC.fC.G.fC.fU.fU.A.mU.A.mU*A*A*mU*mC*mU*G. | 91% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14125 | 209 | 265 | mU.A.mC.mC.A. G.mU.mU.A.A.mC. A.Chl | 266 | P.mU.G.fU.fU.fU.A. A.fC.fU.G.G.mU.A*mU* G*G*mC*A*C. | 110% |
| 14126 | 1276 | 267 | mU.G.mU.mU.mC. A.mU.mU.mC.mU. A.mU.A.Chl | 268 | P.mU.A.fU.A.G.A.A.fU. G.A.A.mC.A*mU*A*G* A*mC.A. | n/a |
| 14127 | 137 | 269 | mC.mC.G.A.mC.mC.A. A.G.G.A.A.A.Chl | 270 | P.mU.fU.fU.fC.fC.fU.fU. G.G.fU.mC.G.G*mC* G*mU*mU*mU*G. | 71% |
| 14128 | 711 | 271 | G.A.A.mU.G.G.mU. G.mC.A.mU.A.mC.Chl | 272 | P.mG.fU.A.fU.G.fC. A.fC.fC.A.mU.mU.mC* A*A*mC*mU*mC*C. | 115% |
| 14129 | 582 | 273 | A.mU.A.mU.G.A.mU. G.G.mC.mC.G.A.Chl | 274 | P.mU.fC.G.G.fC.fC. A.fU.fC.A.mU.A.mU* G*mU*G*mU*mC*U. | 97% |
| 14130 | 839 | 275 | A.G.mC.A. G.mU.mC.mC.A.G. A.mU.mU.Chl | 276 | P.mA.A.fU.fC.fU.G.G. A.fC.fU.G.mC.mU*mU* G*mU*G*G*C. | 102% |
| 14131 | 1091 | 277 | G.mC.A.mU.mU.mU.A. G.mC.A.A.A.Chl | 278 | P.mU.fU.fU.G.A.fC.fU.A. A.A.mU.G.mC*A*A*A* G*mU*G. | 10% |
| 14132 | 884 | 279 | A.G.mC. A.mU.mU.mC.mC.G. A.mU.G.mU.Chl | 280 | P.mA.fC.A.fU.fC.G.G.A. A.fU.G.mC.mU*mC* A*mU*mU*G*C. | 93% |
| 14133 | 903 | 281 | mU.A.G.mU.mC.A.G. G.A.A.mC.mU.mU.Chl | 282 | P.mA.A.G.fU.fU.fC.fC.fU. G.A.mC.mU.A*mU*mC* A*A*mU*C. | 97% |
| 14134 | 1090 | 283 | mU.G.mC. A.mU.mU.mU.A. G.mU.mC.A.A.Chl | 284 | P.mU.fU.G.A.fC.fU.A.A. A.fU.G.mC.A*A*A* G*mU*G*A. | 39% |
| 14135 | 474 | 285 | G.mU.mC.mU.G. A.mU.G.A. G.mU.mU.mC.mU.Chl | 286 | P.mA.G.A.fC.fU.fC. A.fU.fC.A.G.A.mC*mU* G*G*mU*G*A. | 99% |
| 14136 | 575 | 287 | mU.A.G.A.mC.A.mC. A.mU.A.mU.G.A.Chl | 288 | P.mU.fC.A.fU.A.fU.G.fU. G.fU.mC.mU.A*mC*mU* G*mU*G*G. | 108% |
| 14137 | 671 | 289 | mC.A.G.A.mC.G.A.G. G.A.mC.A.mU.Chl | 290 | P.mA.fU.G.fU.fC.fC.fU.fC. G.fU.mC.mU.G*mU*A* G*mC*A*U. | 98% |
| 14138 | 924 | 291 | mC.A.G.mC.mC.G.mU. G.A.A.mU.mU.mC.Chl | 292 | P.mG.A.A.fU.fU.fC.A.fC. G.G.mC.mU.G* A*mC*mU*mU*mU*G. | 100% |
| 14139 | 1185 | 293 | A.G.mU.mC.mU.G.G. A.A.A.mU.A.A.Chl | 294 | P.mU.fU.A.fU.fU.fU.fC.fC. A.G.A.mC.mU*mC*A* A*A*mU*A. | 47% |
| 14140 | 1221 | 295 | A.G.mU.mU.mU. G.mU.G. G.mC.mU.mU.mC.Chl | 296 | P.mG.A.A.G.fC.fC.A.fC. A.A.A.mC.mU*A*A* A*mC*mU*A. | 100% |
| 14141 | 347 | 297 | A.G.mU.mC.mC.A. A.mC.G.A.A.A.G.Chl | 298 | P.mC.fU.fU.fU.fC. G.fU.fU.G.G. A.mC.mU*mU* A*mC*mU*mU*G. | 103% |
| 14142 | 634 | 299 | A.A.G.mU.mU.mU.mC. G.mC.A.G.A.mC.Chl | 300 | P.mG.fU.fC.fU.G.fC.G.A. A. A.mC.mU.mU*mC*mU* mU*A*G*A. | 100% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14143 | 877 | 301 | A.G.mC.A.A.mU.G.A.G.mC.A.mU.mU.Chl | 302 | P.mA.A.fU.G.fC.fU.fC.A.fU.fU.G.mC.mU*mC*mU*mC*A*mU*C. | 104% |
| 14144 | 1033 | 303 | mU.mU.A.G.A.mU.A.G.mU.G.mC.A.mU.Chl | 304 | P.mA.fU.G.fC.A.fC.fU.A.fU.fC.mU.A.A*mU*mU*mC*A*mU*G. | 95% |
| 14145 | 714 | 305 | mU.G.G.mU.G.mC.A.mU.A.mC.A.A.G.Chl | 306 | P.mC.fU.fU.G.fU.A.fU.G.fC.A.mC.mC.A*mU*mU*mC*A*A*C. | 101% |
| 14146 | 791 | 307 | A.mU.G.A.A.A.mC.G.A.G.mU.mC.A.Chl | 308 | P.mU.G.A.fC.fU.fC.G.fU.fU.fU.mC.A.mU*A*A*mC*mU*G*U. | 100% |
| 14147 | 813 | 309 | mC.mC.A.G.A.G.mU.G.mC.mU.G.A.A.Chl | 310 | P.mU.fU.fC.A.G.fC.A.fC.fU.fC.mU.G.G*mU*mC*A*mU*mC*C. | 97% |
| 14148 | 939 | 311 | mC.A.G.mC.mC.A.mU.G.A.A.mU.mU.mU.Chl | 312 | P.mA.A.fU.fU.fC.A.fU.G.G.mC.mU.G*mU*G*G*A*A*U. | 109% |
| 14149 | 1161 | 313 | A.mU.mU.G.G.mU.mU.G.A.A.mU.G.mU.Chl | 314 | P.mA.fC.A.fU.fU.fC.A.A.fC.fC.A.A.mU*A*A*A*mC*mU*G. | 34% |
| 14150 | 1164 | 315 | G.G.mU.mU.G.A.A.mU.G.mU.G.mU.A.Chl | 316 | P.mU.A.fC.A.fC.A.fU.fU.fC.A.A.mC.mC*A*A*mU*A*A*A. | n/a |
| 14151 | 1190 | 317 | G.G.A.A.A.mU.A.A.mC.mU.A.A.mU.Chl | 318 | P.mA.fU.fU.A.G.fU.fU.A.fU.fU.mU.mC.mC*A*G*A*mC*mU*C. | n/a |
| 14152 | 1333 | 319 | mU.mC.A.mU.G.A.mU.A.G.A.A.A.Chl | 320 | P.mU.fU.fU.fC.fU.A.fU.fU.fC.A.mU.G.A*G*A*G*A*A*U. | 31% |
| 14153 | 537 | 321 | G.mC.mC.A.G.mC.A.A.mC.mC.G.A.A.Chl | 322 | P.mU.fU.fC.G.G.fU.fU.G.fC.fU.G.G.mC*A*G*G*mU*mC*C. | n/a |
| 14154 | 684 | 323 | mC.A.mC.mC.mU.mC.A.mC.A.mC.A.mU.G.Chl | 324 | P.mC.A.fU.G.fU.G.fU.G.A.G.G.mU.G*A*mU*G*mU*mC*C. | 100% |
| 14155 | 707 | 325 | A.G.mU.mU.G.A.A.mU.G.G.mU.G.mC.Chl | 326 | P.mG.fC.A.fC.fC.A.fU.fU.fC.A.A.mC.mU*mC*mC*mU*mC*G*C. | 99% |
| 14156 | 799 | 327 | A.G.mU.mC.A.G.mC.mU.G.G.A.mU.G.Chl | 328 | P.mC.A.fU.fC.fC.A.G.fC.fU.G.A.mC.mU*mC*G*mU*mU*mU*C. | 95% |
| 14157 | 853 | 329 | mU.A.mU.A.A.G.mC.G.G.A.A.A.G.Chl | 330 | P.mC.fU.fU.fU.fC.fC.G.fC.fU.fU.A.mU.A*mU*A*A*mU*mC*U. | 106% |
| 14158 | 888 | 331 | mU.mU.mC.mC.G.A.mU.G.mU.G.A.mU.mU.Chl | 332 | P.mA.A.fU.fC.A.fC.A.fU.fC.G.G.A.A*mU*G*mC*mU*mC*A. | 88% |
| 14159 | 1194 | 333 | A.mU.A.A.mC.mU.A.A.mU.G.mU.G.mU.Chl | 334 | P.mA.fC.A.fC.A.fU.fU.A.G.fU.mU.A.mU*mU*mU*mC*mC*A*G. | 95% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14160 | 1279 | 335 | mU.mC.A.mU.mU.mC.mU.A.mU.A.G.A.A.Chl | 336 | P.mU.fU.fC.fU.A.fU.A.G.A.A.mU.G.A*A*mC*A*mU*A*G. | 15% |
| 14161 | 1300 | 337 | A.A.mC.mU.A.mU.mC.A.mC.mU.G.mU.A.Chl | 338 | P.mU.A.fC.A.G.fU.G.A.fU.A.G.mU.mU*mU*G*mC*A*mU*U. | 86% |
| 14162 | 1510 | 339 | G.mU.mC.A.A.mU.mU.G.mC.mU.mU.A.mU.Chl | 340 | P.mA.fU.A.A.G.fC.A.A.fU.fU.G.A.mC*A*mC*mC*A*mC*C. | 86% |
| 14163 | 1543 | 341 | A.G.mC.A.A.mU.mU.A.A.mU.A.A.A.Chl | 342 | P.mU.fU.fU.A.fU.fU.A.A.fU.fU.G.mC.mU*G*G*A*mC*A*A. | 110% |
| 14164 | 434 | 343 | A.mC.G.A.mC.mU.mC.mU.G.A.mU.G.A.Chl | 344 | P.mU.fC.A.fU.fC.A.G.A.G.fU.mC.G.mU*mU*mC*G*A*G*U. | 134% |
| 14165 | 600 | 345 | mU.A.G.mU.G.mU.G.G.mU.mU.mU.A.mU.Chl | 346 | P.mA.fU.A.A.A.fC.fC.A.fC.A.mC.mU.A*mU*mC*A*mC*mC*U. | 102% |
| 14166 | 863 | 347 | A.A.G.mC.mC.A.A.mU.G.A.mU.G.A.Chl | 348 | P.mU.fC.A.fU.fC.A.fU.fU.G.mC.mU.mU*mU*mC*mC*G*mC*U. | 93% |
| 14167 | 902 | 349 | A.mU.A.G.mU.mC.A.G.G.A.A.mC.mU.Chl | 350 | P.mA.G.fU.fU.fC.fC.fU.G.A.fC.mU.A.mU*mC*A*A*mU*mC*A. | 101% |
| 14168 | 921 | 351 | A.G.mU.mC.A.mC.mC.G.mU.G.A.A.Chl | 352 | P.mU.fU.fC.A.fC.G.G.fC.fU.G.A.mC.mU*mU*mU*G*G*A*A. | 98% |
| 14169 | 154 | 353 | A.mC.mU.A.mC.mC.A.mU.mU.A.G.A.A.Chl | 354 | P.mU.fU.fC.fU.fC.A.fU.G.G.fU.A.G.mU*G*A*G*mU*mU*U. | n/a |
| 14170 | 217 | 355 | A.A.A.mC.A.G.G.mC.mU.G.A.mU.mU.Chl | 356 | P.mA.A.fU.fC.A.G.fC.fC.fU.G.mU.mU*A*mC*mU*G*G. | 66% |
| 14171 | 816 | 357 | G.A.G.mU.G.mC.mU.G.A.A.A.mC.mC.Chl | 358 | P.mG.G.fU.fU.fU.fC.A.G.fC.A.mC.mU.mC*mU*G*G*mU*mC*A. | 102% |
| 14172 | 882 | 359 | mU.G.A.G.mC.A.mU.mU.mC.mC.G.A.mU.Chl | 360 | P.mA.fU.fC.G.G.A.A.fU.G.fC.mU.mC.A*mU*mU*G*mC*mU*C. | 103% |
| 14173 | 932 | 361 | A.A.mU.mU.mC.mC.mC.A.G.mC.mC.A.Chl | 362 | P.mU.G.G.fC.fU.G.fU.G.G.A.A.mU.mU*mC*A*mC*G*G*C. | n/a |
| 14174 | 1509 | 363 | mU.G.mU.mC.A.A.mU.mU.G.mC.mU.mU.A.Chl | 364 | P.mU.A.A.G.fC.A.A.fU.fU.G.A.mC.A*mC*mC*A*mC*mC*A. | n/a |
| 14175 | 157 | 365 | A.mC.mC.A.mU.G.A.G.A.A.mU.mU.G.Chl | 366 | P.mC.A.A.fU.fU.fC.fU.fC.A.fU.G.G.mU*A*G*mU*G*A*G. | 109% |
| 14176 | 350 | 367 | mC.mC.A.A.mC.G.A.A.G.mC.mC.A.Chl | 368 | P.mU.G.G.fC.fU.fU.fU.fC.G.fU.mU.G.G*A*mC*mU*mU*A*C. | 95% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14177 | 511 | 369 | mC.mU.G.G.mU.mC. A.mC.mU.G. A.mU.mU.Chl | 370 | P.mA.A.fU.fC.A.G.fU.G. A.fC.mC.A. G*mU*mU*mC*A*mU* C. | 100% |
| 14178 | 605 | 371 | mU.G.G.mU.mU.mU. A.mU.G.G. A.mC.mU.Chl | 372 | P.mA.G.fU.fC.fC.A.fU.A. A.A.mC.mC.A.mC* A*mC*mU*A*U. | 99% |
| 14179 | 811 | 373 | G.A.mC.mC.A.G.A. G.mU.G.mC.mU.G.Chl | 374 | P.mC.A.G.fC. A.fC.fU.fC.fU.G. G.mU.mC* A*mU*mC*mC*A*G. | 88% |
| 14180 | 892 | 375 | G.A.mU.G.mU.G. A.mU.mU.G.A.mU. A.Chl | 376 | P.mU.A.fU.fC.A.A.fU.fC. A.fC.A.mU.mC*G*G* A*A*mU*G. | 76% |
| 14181 | 922 | 377 | G.mU.mC.A.G.mC.mC. G.mU.G.A.A.mU.Chl | 378 | P.mA.fU.fU.fC.A.fC.G. G.fC.fU.G. A.mC*mU*mU*mU*G* G*A. | 59% |
| 14182 | 1169 | 379 | A.A.mU.G.mU.G.mU. A.mU.mC.mU.A.mU.Chl | 380 | P.mA.fU.A.G.fU.A.fC. A.fC.A.mU.mU*mC*A* A*mC*mC.A. | 69% |
| 14183 | 1182 | 381 | mU.mU.G.A. G.mU.mC.mU.G.G.A. A.A.Chl | 382 | P.mU.fU.fU.fC.fC.A.G. A.fC.fU.mC.A.A*mU* A*G*A*U. | n/a |
| 14184 | 1539 | 383 | G.mU.mC.mC.A.G.mC. A.A.mU.mU.A.A.Chl | 384 | P.mU.fU.A.A.fU.fU. G.fC.fU.G.G.A.mC*A* A*mC*mC*G*U. | 77% |
| 14185 | 1541 | 385 | mC.mC.A.G.mC.A. A.mU.mU.A.A.mU. A.Chl | 386 | P.mU.A.fU.fU.A.A.fU.fU. G.fC.mU.G.G*A*mC* A*A*mC*C. | n/a |
| 14186 | 427 | 387 | G.A.mC.mU.mC.G.A. A.mC.G.A.mC.mU.Chl | 388 | P.mA.G.fU.fC.G.fU.fU.fC. G.A.G.mU.mC*A* A*mU*G*G*A. | 69% |
| 14187 | 533 | 389 | A.mC.mC.mU. G.mC.mC.A.G.mC.A. A.mC.Chl | 390 | P.mG.fU.fU.G.fC.fU.G. G.fC.A.G. G.mU*mC*mC*G*mU* G*G. | 78% |
| 18538 | 496 | 391 | G.A.mU.G.A. A.mU.mC.mU.G.A.mU. A.Chl | 392 | P.mU.A.fU.fC.A.G. A.fU.fU.fC.A.fU.fC*A* G*A*A*fU*G. | 74% |
| 18539 | 496 | 393 | mU.G.A.mU.G.A. A.mU.mC.mU.G.A.mU. A.Chl | 394 | P.mU.A.fU.fC.A.G. A.fU.fU.fC.A.fU.fC*A* G*A*A*fU*G. | 72% |
| 18540 | 175 | 395 | A.mU.mU.mU. G.mC.mU.mU.mU.mU. G.mC.A.Chl | 396 | P.mU.G.fC.A.A.A.A. G.fC.A.A.A.fU*fC* A*fC*fU*fG*C. | 98% |
| 18541 | 175 | 397 | G.A.mU.mU.mU. G.mC.mU.mU.mU.mU. G.mC.A.Chl | 398 | P.mU.G.fC.A.A.A.A. G.fC.A.A.A.fU*fC* A*fC*fU*fG*C. | 28% |
| 18542 | 172 | 399 | G.mU.G. A.mU.mU.mU. G.mC.mU.mU.mU.A.Chl | 400 | P.mU.A.A.A.G.fC.A.A. A.fU.fC.A.fC*fU*G*fC* A*A*U. | 24% |
| 18543 | 172 | 401 | A.G.mU.G. A.mU.mU.mU. G.mC.mU.mU.mU.A.Chl | 402 | P.mU.A.A.A.G.fC.A.A. A.fU.fC.A.fC*fU*G*fC* A*A*U. | 14% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 18544 | 1013 | 403 | A.A.mU.mU.mU.mC. G.mU.A.mU.mU.mU. A.Chl | 404 | P.mU.A.A.A.fU.A.fC.G. A.A.A.fU.fU*fU*fC*A* G*G*U. | 100% |
| 18545 | 1013 | 405 | A.A.A.mU.mU.mU.mC. G.mU.A.mU.mU.mU. A.Chl | 406 | P.mU.A.A.A.fU.A.fC.G. A.A.A.fU.fU*fU*fC*A* G*G*U. | 109% |
| 18546 | 952 | 407 | mC.A.mC.A.G.mC.mC. A.mU.G.A.A.A.Chl | 408 | P.mU.fU.fU.C.A.fU.G. G.fC.fU.G.fU.G*A*A* A*fU*fU*C. | 32% |
| 18547 | 952 | 409 | mU.mC.A.mC.A. G.mC.mC.A.mU.G.A. A.A.Chl | 410 | P.mU.fU.fU.C.A.fU.G. G.fC.fU.G.fU.G*A*A* A*fU*fU*C. | 33% |
| 18548 | 174 | 411 | G.A.mU.mU.mU. mC.mU.mU.mU.mU. G.A.Chl | 412 | P.mU.fC.A.A.A.A.G.fC. A.A.fU.fC*A*fC*fU* G*fC*A. | 57% |
| 18549 | 174 | 413 | mU.G.A.mU.mU.mU. G.mC.mU.mU.mU.mU. G.A.Chl | 414 | P.mU.fC.A.A.A.A.G.fC. A.A.fU.fC*A*fC*fU* G*fC*A. | 53% |
| 18550 | 177 | 415 | mU.mU. G.mC.mU.mU.mU.mU. G.mC.mC.mU.A.Chl | 416 | P.mU.A.G.G.fC.A.A.A. A.G.fC.A*A*fU*fC* A*fC*U. | 97% |
| 18551 | 177 | 417 | mU.mU.mU. G.mC.mU.mU.mU.mU. G.mC.mC.mU.A.Chl | 418 | P.mU.A.G.G.fC.A.A.A. A.G.fC.A*A*fU*fC* A*fC*U. | 103% |
| 18552 | 1150 | 419 | mU.mU.mU.mC.mU.mC. A.G.mU.mU.mU.A. A.Chl | 420 | P.mU.fU.A.A.A.fC.fU.G. A.G.A.A.A*G*A* G*fC*A. | 96% |
| 18553 | 1089 | 421 | mU.mU.G.mC. A.mU.mU.mU.A. G.mU.mC.A.Chl | 422 | P.mU.G.A.fC.fU.A.A. A.fU.G.fC.A.A*A* G*fU*G*A*G. | 94% |
| 18554 | 1086 | 423 | A.mC.mU.mU.mU. G.mC.A.mU.mU.mU.A. A.Chl | 424 | P.mU.fU.A.A.A.fU.G.fC. A.A.A.G.fU*G*A*G* A*A*A. | n/a |
| 18555 | 1093 | 425 | A.mU.mU.mU.A. G.mU.mC.A.A.A.A. A.Chl | 426 | P.mU.fU.fU.fU.fU.G. A.fC.fU.A.A.A.fU*G*fC* A*A*G. | n/a |
| 18556 | 1147 | 427 | mU.mU.mC.mU.mU.mU. mC.mU.mC.A.G.mU. A.Chl | 428 | P.mU.A.fC.fU.G.A.G.A. A.A.G.A.A*G*fC* A*fU*fU*U. | n/a |
| 18557 | 1148 | 429 | mU.mC.mU.mU.mU.mC. mU.mC.A.G.mU.mU. A.Chl | 430 | P.mU.A.A.fC.fU.G.A.G. A.A.A.G.A*A*G*fC* A*fU*U. | 66% |
| 18558 | 1128 | 431 | G.A.A.A.G.A.G.A. A.mC.A.mU.A.Chl | 432 | P.mU.A.fU. G.fU.fU.fC.fU.fC.fU.fU. fC*A*fU*fU*fU*G. | 16% |
| 18559 | 1087 | 433 | mC.mU.mU.mU.G.mC. A.mU.mU.mU.A.G. A.Chl | 434 | P.mU.fC.fU.A.A.A.fU. G.fC.A.A.A.G*fU*G* A*G*A*A. | 28% |
| 18560 | 1088 | 435 | mU.mU.mU.G.mC. A.mU.mU.mU.A.G.mU. A.Chl | 436 | P.mU.A.fC.fU.A.A.A.fU. G.fC.A.A.A*G*fU*G* A*G*A. | n/a |
| 18561 | 1083 | 437 | mC.mU.mC. A.mC.mU.mU.mU. G.mC.A.mU.A.Chl | 438 | P.mU.A.fU.G.fC.A.A.A. G.fU.G.A.G*A*A* A*fU*fU*G. | 53% |

TABLE 3-continued

SPP1 (Accession Number NM_000582.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 18562 | 1081 | 439 | mU.mU.mC.mU.mC. A.mC.mU.mU.mU. G.mC.A.Chl | 440 | P.mU.G.fC.A.A.A.G.fU. G.A.G.A.A*A*fU*fU* G*fU*A. | 89% |
| 18563 | 555 | 441 | mC.A.mC.mU.mC.mC. A.G.mU.mU.mU.G.mU. A.Chl | 442 | P.mU.A.fC.A.A.fC.fU.G. G.A.G.fU.G*A*A*A* A*fC*fU. | 33% |
| 18564 | 1125 | 443 | A.A.mU.G.A.A.A.G. A.G.A.A.Chl | 444 | P.mU.fU.fU.fC.fU.fC.fU.fU .fU.fC.A.fU.fU*fU*fU* G*fC*fU*A. | n/a |
| 18565 | 168 | 445 | mU.G.mC.A.G.mU.G. A.mU.mU.mU.mG. A.Chl | 446 | P.mU.fC.A.A.A.fU.fC. A.fC.fU.G.fC.A* A*fU*fU*fC*fU*C. | 14% |
| 18566 | 1127 | 447 | mU.G.A.A.A.G.A.G. A.A.mC.A.A.Chl | 448 | P.mU.fU. G.fU.fU.fC.fU.fC.fU.fU.fU. fC.A*fU*fU*fU*fU*G* C. | 27% |
| 18567 | 1007 | 449 | A.mC.mC.mU.G.A.A. A.mU.mU.mU.mC.A.Chl | 450 | P.mU.G.A.A. A.fU.fU.fU.fC.A.G.G.fU* G*fU*fU*fU*A*U. | 129% |
| 18568 | 164 | 451 | G.A.A.mU.mU.G.mC. A.G.mU.G.A.A.Chl | 452 | P.mU.fU.fC.A.fC.fU.G.fC. A.A.fU.fU.fC*fU*fC* A*fU*G*G. | 47% |
| 18569 | 222 | 453 | G.G.mC.mU.G. A.mU.mU.mC.mU.G.G. A.Chl | 454 | P.mU.fC.fC.A.G.A. A.fU.fC.A.G.fC.fC*fU* G*fU*fU*fU*A. | n/a |
| 20612 | 172 | 455 | A.G.mU.G. A.mU.mU.mU. G.mC.mU.mU.mU.A.Chl | 456 | P.mU.A.A.A.G.fC.A.A. A.fU.mC.A.mC*mU* G*mC*A*U. | n/a |
| 20613 | 172 | 457 | A.G.mU.G. A.mU.mU.mU. G.mC.mU.mU.mU.A.Chl | 458 | P.mU.A.A.A.G.fC.A.A. A.fU.fC.A.mC*fU* G*mC*A*U. | n/a |
| 20614 | 172 | 459 | A.G.mU.G. A.mU.mU.mU. G.mC.mU.mU.mU.A.Chl | 460 | P.mU.A.A.A.G.C.A.A. A.U.mC.A.mC*mU* G*mC*A*U. | 101% |
| 20615 | 172 | 461 | A.G.mU.G. A.mU.mU.mU. G.mC.mU.mU.mU.A.Chl | 462 | P.mU.A.A.A.G.fC.A.A. A.fU.mC. A.mC*mU*mG*mC*mA* mA*U. | 104% |

Key
Chl = cholesterol with hydroxyprolinol linker
TEG-chl = cholesterol with TEG linker
m = 2'Ome
f = 2'fluoro
* = phosphorothioate llinkage
. = phosphodiester linkage

TABLE 4

PTGS2 (Accession Number NM_000963.2) sd-rxRNA® sequences

| Oligo Number | Start Site | SEQ ID NO | Sense sequence | SEQ ID NO | Antisense sequence | % remaining expression (1 uM A549) |
|---|---|---|---|---|---|---|
| 14422 | 451 | 463 | mC.A.mC. A.mU.mU.mU.G. A.mU.mU.G.A.Chl | 464 | P.mU.fC.A.A.fU.fC.A. A.A.fU.G.mU.G* A*mU*mC*mU*G*G. | 72% |

TABLE 4-continued

PTGS2 (Accession Number NM_000963.2) sd-rxRNA ® sequences

| | | | | | | |
|---|---|---|---|---|---|---|
| 14423 | 1769 | 465 | mC.A.mC.mU.G.mC.mU.mC.A.A.mU.mU.Chl | 466 | P.mA.A.fU.fU.G.A.G.G.fC.A.G.mU.G*mU*mU*G*A*mU*G. | 71% |
| 14424 | 1464 | 467 | A.A.A.mU.A.mC.mC.A.G.mU.mC.mU.mU.Chl | 468 | P.mA.A.G.A.fC.fU.G.G.fU.A.mU.mU.mU*mC*A*mU*mC*mU*G. | 74% |
| 14425 | 453 | 469 | mC.A.mU.mU.mU.G.A.mU.mU.G.A.mC.A.Chl | 470 | P.mU.G.fU.fC.A.A.fU.fC.A.A.A.mU.G*mU*G*A*mU*mC*U. | 83% |

| | | | | | | % remaining expression (1 um PC-3) |
|---|---|---|---|---|---|---|
| 17388 | 285 | 471 | G.A.A.A.A.mC.mU.G.mC.mU.mC.A.A.Chl | 472 | P.mU.fU.G.A.G.fC.A.G.fU.fU.fU.fU.fC*fU*fC*fC*A*fU*A. | 88% |
| 17389 | 520 | 473 | A.mC.mC.mU.mC.mU.mC.mC.mU.A.mU.mU.A.Chl | 474 | P.mU.A.A.fU.A.G.G.A.G.A.G.G.fU*fU*A*G*A*G*A. | 25% |
| 17390 | 467 | 475 | mU.mC.mC.A.mC.mC.A.A.mC.A.mU.mU.A.Chl | 476 | P.mU.fU.A.A.G.fU.fU.G.G.fU.G.G.A*fC*fU*G*fU*fC*A. | 68% |
| 17391 | 467 | 477 | G.mU.mC.mC.A.mC.mC.A.A.mC.mU.mU.A.Chl | 478 | P.mU.fU.A.A.G.fU.fU.G.G.fU.G.G.A*fC*fU*G*fU*fC*A. | 101% |
| 17392 | 524 | 479 | mC.mU.mC.mC.mU.A.mU.mU.A.mU.A.mC.A.Chl | 480 | P.mU.G.fU.A.fU.A.A.fU.A.G.G.A.G*A*G*G*fU*fU*A. | 49% |
| 17393 | 448 | 481 | G.A.mU.mC.A.mC.A.mU.mU.mU.G.A.A.Chl | 482 | P.mU.fU.fC.A.A.A.fU.G.fU.G.A.fU.fC*fU*G*G*A*fU*G. | 29% |
| 17394 | 448 | 483 | A.G.A.mU.mC.A.mC.A.mU.mU.mU.G.A.A.Chl | 484 | P.mU.fU.fC.A.A.A.fU.G.fU.G.A.fU.fC*fU*G*G*A*fU*G. | 31% |
| 17395 | 519 | 485 | A.mC.mC.mU.mC.mU.mC.mC.mU.A.mU.A.Chl | 486 | P.mU.A.fU.A.G.G.A.G.A.G.G.fU.fU*A*G*A*G*A*A. | 12% |
| 17396 | 437 | 487 | G.mU.mU.G.A.mC.A.mU.mC.mC.A.G.A.Chl | 488 | P.mU.fC.fU.G.G.A.fU.G.fU.fC.A.A.fC*A*fC*A*fU*A*A. | 86% |
| 17397 | 406 | 489 | mC.mC.mU.mU.mC.mC.mU.mU.mC.G.A.A.A.Chl | 490 | P.mU.fU.fU.fC.G.A.A.G.G.A.A.G*G*A*A*fU*G*U. | 23% |
| 17398 | 339 | 491 | A.mC.mU.mC.mC.A.A.A.mC.A.mC.A.A.Chl | 492 | P.mU.fU.G.fU.G.fU.fU.fU.G.G.A.G.fU*G*G*G*fU*fU*U. | 102% |
| 17399 | 339 | 493 | mC.A.mC.mU.mC.mC.A.A.A.mC.A.mC.A.A.Chl | 494 | P.mU.fU.G.fU.G.fU.fU.fU.G.G.A.G.fU*G*G*G*fU*fU*U. | 55% |

TABLE 4-continued

PTGS2 (Accession Number NM_000963.2) sd-rxRNA ® sequences

| | | | | | | |
|---|---|---|---|---|---|---|
| 17400 | 338 | 495 | mC.A.mC.mU.mC.mC.A.A.A.mC.A.mC.A.Chl | 496 | P.mU.G.fU.G.fU.fU.fU.G.G.A.G.fU.G*G*G*fU*fU*C. | 62% |
| 17401 | 468 | 497 | mC.mC.A.mC.mC.A.A.mC.mU.mU.A.mC.A.Chl | 498 | P.mU.G.fU.A.A.G.fU.fU.G.G.fU.G.G*A*fC*fU*G*fU*C. | 61% |
| 17402 | 468 | 499 | mU.mC.mC.A.mC.mC.A.A.mC.mU.mU.A.mC.A.Chl | 500 | P.mU.G.fU.A.A.G.fU.fU.G.G.fU.G.G*A*fC*fU*G*fU*C. | 179% |
| 17403 | 1465 | 501 | A.A.mU.A.mC.mC.A.G.mU.mC.mU.mU.A.Chl | 502 | P.mU.A.A.G.A.fC.fU.G.G.fU.A.fU.fU*fU*fC*A*fU*fC*U. | 30% |
| 17404 | 243 | 503 | G.A.mC.mC.A.G.mU.A.mU.A.A.G.A.Chl | 504 | P.mU.fC.fU.fU.A.fU.A.fC.fU.G.G.fU.fC*A*A*A*fU*fC*C. | 32% |
| 17405 | 1472 | 505 | G.mU.mC.mU.mU.mU.mUA.A.mU.G.A.A.Chl | 506 | P.mU.fU.fC.A.fU.fU.A.A.A.A.G.A.fC*fU*G*G*fU*A*U. | 15% |
| 17406 | 2446 | 507 | A.A.mU.mU.mU.mC.A.mU.G.mU.mC.mU.A.Chl | 508 | P.mU.A.G.A.fC.A.fU.G.A.A.A.fU.fU*A*fC*fU*G*G*U. | 142% |
| 17407 | 449 | 509 | A.mU.mC.A.mC.A.mU.mU.mU.G.A.mU.A.Chl | 510 | P.mU.A.fU.fC.A.A.A.fU.G.fU.G.A.fU*fC*fU*G*G*A*U. | 54% |
| 17408 | 449 | 511 | G.A.mU.mC.A.mC.A.mU.mU.mU.G.A.mU.A.Chl | 512 | P.mU.A.fU.fC.A.A.A.fU.G.fU.G.A.fU*fC*fU*G*G*A*U. | 27% |
| 17409 | 444 | 513 | mU.mC.mC.A.G.A.mU.mC.A.mC.A.mU.A.Chl | 514 | P.mU.A.fU.G.fU.G.A.fU.fC.fU.G.G.A*fU*G*fU*fC*A*A. | 49% |
| 17410 | 1093 | 515 | mU.A.mC.mU.G.A.mU.A.G.G.A.G.A.Chl | 516 | P.mU.fC.fU.fC.fC.fU.A.fU.fC.A.G.fU.A*fU*fU*A*G*fC*C. | 32% |
| 17411 | 1134 | 517 | G.mU.G.mC.A.A.mC.A.mC.mU.fU.G.A.Chl | 518 | P.mU.fC.A.A.G.fU.G.fU.fU.G.mC.A.fC*A*fU*A*A*fU*C. | 70% |
| 17412 | 244 | 519 | A.mC.mC.A.G.mU.A.mU.A.A.G.mU.A.Chl | 520 | P.mU.A.fC.fU.fU.A.fU.A.fC.fU.G.G.fU*fC*A*A*A*fU*C. | 63% |
| 17413 | 1946 | 521 | G.A.A.G.mU.mC.mU.A.G.A.fC.mU.fU.fC*fU*A*mU.G.A.A.Chl | 522 | P.mU.fU.fC.A.fU.fU.A.G.A.fC.mU.fU.fC*fU*fC*A*G*U. | 19% |
| 17414 | 638 | 523 | A.A.G.A.A.G.A.A.A.G.mU.mU.A.Chl | 524 | P.mU.A.A.fC.fU.fU.fU.fC.fU.fU.fC.fU.fU*A*G*A*A*G*C. | 27% |
| 17415 | 450 | 525 | mU.mC.A.mC.A.mU.mU.mU.G.A.mU.mU.A.Chl | 526 | P.mU.A.A.fU.fC.A.A.A.fU.G.fU.G.A*fU*fC*fU*G*G*A. | 216% |
| 17416 | 450 | 527 | A.mU.mC.A.mC.A.mU.mU.mU.G.A.mU.mU.A.Chl | 528 | P.mU.A.A.fU.fC.A.A.A.fU.G.fU.G.A*fU*fC*fU*G*G*A. | 32% |

TABLE 4-continued

PTGS2 (Accession Number NM_000963.2) sd-rxRNA ® sequences

| | | | | | | |
|---|---|---|---|---|---|---|
| 17417 | 452 | 529 | A.mC.A.mU.mU.G.A.mU.mG.A.A.Chl | 530 | P.mU.fU.fC.A.A.fU.fC.A.A.A.fU.G.fU*G*A*fU*fC*fU*G. | 99% |
| 17418 | 452 | 531 | mC.A.mC.A.mU.mU.G.A.mU.mG.A.A.Chl | 532 | P.mU.fU.fC.A.A.fU.fC.A.A.A.fU.G.fU*G*A*fU*fC*fU*G. | 54% |
| 17419 | 454 | 533 | A.mU.mU.mU.G.A.mU.mU.G.A.mC.A.A.Chl | 534 | P.mU.fU.G.fU.fC.A.A.fU.fC.A.A.A.fU*G*fU*G*A*fU*C. | 86% |
| 17420 | 454 | 535 | mC.A.mU.mU.mU.G.A.mU.mU.G.A.mC.A.A.Chl | 536 | P.mU.fU.G.fU.fC.A.A.fU.fC.A.A.A.fU*G*fU*G*A*fU*C. | 89% |
| 17421 | 1790 | 537 | mC.A.mU.mC.mU.G.mC.A.A.mU.A.A.A.Chl | 538 | P.mU.fU.fU.A.fU.fU.G.fC.A.G.A.fU.G*A*G*A*G*A*C. | 55% |
| 17422 | 1790 | 539 | mU.mC.A.mU.mC.mU.G.mC.A.A.mU.A.A.A.Chl | 540 | P.mU.fU.fU.A.fU.fU.G.fC.A.G.A.fU.G*A*G*A*G*A*C. | 62% |
| 21180 | 448 | 541 | G.A.mU.mC.A.mC.A.mU.mU.mU.G.A.A.TEG-Chl | 542 | P.mU.fU.fC.A.mA.A.fU.G.fU.G.A.mU.mC*mU*G*G*A*mU*G. | 76% |
| 21181 | 448 | 543 | G.A.mU.mC.A.mC.A.mU.mU.mU.G.A.A.TEG-Chl | 544 | P.mU.fU.fC.A.mA.A.fU.G.fU.G.A.fU.fC*fU*mG*mG*mA*fU*G. | 37% |
| 21182 | 448 | 545 | G.A.mU.mC.A.mC.A.mU.mU.mU.G*mA*mA.TEG-Chl | 546 | P.mU.fU.fC.A.A.A.fU.G.fU.G.A.fU.fC*fU*G*G*A*fU*G. | 29% |
| 21183 | 448 | 547 | mG*mA*mU.mC.A.mC.A.mU.mU.mU.G*mA*mA.TEG-Chl | 548 | P.mU.fU.fC.A.A.A.fU.G.fU.G.A.fU.fC*fU*G*G*A*fU*G. | 46% |
| 21184 | 448 | 549 | mG*mA*mU.mC.mA.mC.mA.mU.mU.mU.mG*mA*mA.TEG-Chl | 550 | P.mU.fU.fC.A.A.A.fU.G.fU.G.A.fU.fC*fU*G*G*A*fU*G. | 60% |
| 21185 | 449 | 551 | G.A.mU.mC.A.mC.A.mU.mU.mU.G.A.mU.A.TEG-Chl | 552 | P.mU.A.fU.fC.A.A.A.fU.G.fU.G.A.fU.fC*fU*G*G*A*fU*G. | 27% |
| 21186 | 449 | 553 | G.A.mU.mC.A.mC.A.mU.mU.mU.G.A.mU.A.TEG-Chl | 554 | P.mU.A.fU.fC.A.A.A.fU.G.fU.G.A.mU.mC*mU*G*G*A*mU*G. | 57% |
| 21187 | 449 | 555 | G.A.mU.mC.A.mC.A.mU.mU.mU.G.A.mU.A.TEG-Chl | 556 | P.mU.A.fU.fC.A.mA.A.fU.G.fU.G.A.mU.mC*mU*G*G*A*mU*G. | 54% |
| 21188 | 449 | 557 | G.A.mU.mC.A.mC.A.mU.mU.mU.G.A.mU.A.TEG-Chl | 558 | P.mU.A.fU.fC.A.A.A.fU.G.fU.G.A.mU.mC*mU*mG*mG*mA*mU*G. | 66% |
| 21189 | 449 | 559 | G.A.mU.mC.A.mC.A.mU.mU.mU.G.A.mU.A.TEG-Chl | 560 | P.mU.A.fU.fC.A.mA.A.fU.G.fU.G.A.mU.mC*mU*mG*mG*mA*mU*G. | 44% |

TABLE 4-continued

PTGS2 (Accession Number NM_000963.2) sd-rxRNA ® sequences

| | | | | | | |
|---|---|---|---|---|---|---|
| 21190 | 449 | 561 | G.A.mU.mC.<br>A.mC.<br>A.mU.mU.mU.G.<br>A.mU.A.TEG-Chl | 562 | P.mU.A.fU.fC.A.A.<br>A.fU.G.fU.G.<br>A.fU.fC*fU*mG*mG*m<br>A*fU*G. | 52% |
| 21191 | 449 | 563 | G.A.mU.mC.<br>A.mC.<br>A.mU.mU.mU.G.<br>A.mU.A.TEG-Chl | 564 | P.mU.A.fU.fC.A.mA.<br>A.fU.G.fU.G.<br>A.fU.fC*fU*mG*mG*m<br>A*fU*G. | 41% |
| 21192 | 449 | 565 | G.A.mU.mC.<br>A.mC.<br>A.mU.mU.mU.G.<br>A.mU.A.TEG-Chl | 566 | P.mU.A.fU.fC.A.A.<br>A.fU.G.fU.G.<br>A.fU.mC*fU*mG*mG*<br>mA*fU*G. | 98% |
| 21193 | 449 | 567 | G.A.mU.mC.<br>A.mC.<br>A.mU.mU.mU.G.<br>A*mU*mA.TEG-Chl | 568 | P.mU.A.fU.fC.A.A.<br>A.fU.G.fU.G.<br>A.fU*fC*fU*G*G*A*<br>U. | 93% |
| 21194 | 449 | 569 | mG*mA*mU.mC.<br>A.mC.<br>A.mU.mU.mU.G.<br>A*mU*mA.TEG-Chl | 570 | P.mU.A.fU.fC.A.A.<br>A.fU.G.fU.G.<br>A.fU*fC*fU*G*G*A*<br>U. | 119% |
| 21195 | 449 | 571 | mG*mA*mU.mC.m<br>A.mC.mA.mU.mU.<br>mU.mG.mA*mU*m<br>A.TEG-Chl | 572 | P.mU.A.fU.fC.A.A.<br>A.fU.G.fU.G.<br>A.fU*fC*fU*G*G*A*<br>U. | 292% |
| 20620 | 449 | 573 | G.A.mU.mC.<br>A.mC.<br>A.mU.mU.mU.G.<br>A.mU.A.Chl-TEG | 574 | P.mU.A.fU.fC.A.A.<br>A.fU.G.fU.G.<br>A.mU*mC*mU*G*G*<br>A*U. | 24% |
| 20621 | 449 | 575 | G.A.mU.mC.<br>A.mC.<br>A.mU.mU.mU.G.<br>A.mU.A.Chl-TEG | 576 | P.mU.A.fU.fC.A.A.<br>A.fU.G.fU.G.<br>A.mU*fC*mU*G*G*<br>A*U. | 5% |
| 20622 | 449 | 577 | G.A.mU.mC.<br>A.mC.<br>A.mU.mU.mU.G.<br>A.mU.A.Chl-TEG | 578 | P.mU.A.U.C.A.A.A.<br>U.G.U.G.<br>A.mU*mC*mU*G*G*<br>A*U. | 25% |
| 20623 | 449 | 579 | G.A.mU.mC.<br>A.mC.<br>A.mU.mU.mU.G.<br>A.mU.A.Chl-TEG | 580 | P.mU.A.fU.fC.A.A.<br>A.fU.G.fU.G.<br>A.mU*mC*mU*mG*m<br>G*mA*U. | 14% |
| 20588 | 448 | 581 | G.A.mU.mC.<br>A.mC.<br>A.mU.mU.mU.G.<br>A.A.Chl-TEG | 582 | P.mU.fU.fC.A.A.A.fU.<br>G.fU.G.A.mU.mC*mU*<br>G*G*A*mU*G. | 17% |
| 20589 | 448 | 583 | G.A.mU.mC.<br>A.mC.<br>A.mU.mU.mU.G.<br>A.A.Chl-TEG | 584 | P.mU.fU.fC.A.A.A.fU.<br>G.fU.G.A.mU.fC*mU*<br>G*G*A*fU*G. | 40% |
| 20590 | 448 | 585 | G.A.mU.mC.<br>A.mC.<br>A.mU.mU.mU.G.<br>A.A.Chl-TEG | 586 | P.mU.U.C.A.A.A.U.<br>G.U.G.A.mU.mC*mU*<br>G*G*A*mU*G. | 34% |
| 20591 | 448 | 587 | G.A.mU.mC.<br>A.mC.<br>A.mU.mU.mU.G.<br>A.A.Chl-TEG | 588 | P.mU.fU.fC.A.A.A.fU.<br>G.fU.G.<br>A.fU.fC*fU*mG*mG*m<br>A*fU*G. | n/a |

Key
Chl = cholesterol with hydroxyprolinol linker
TEG-chl = cholesterol with TEG linker
m = 2'Ome
f = 2'fluoro
* = phosphorothioate llinkage
. = phosphodiester linkage

TABLE 5

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 13980 | 1222 | 589 | A.mC.A.G.G.A.A.G.A.mU.G.mU.A.Chl | 590 | P.mU.A.fC.A.fU.fC.fU.fU.fC.fC.mU.G.mU*A*G*mU*A*mC.A. | 98% |
| 13981 | 813 | 591 | G.A.G.mU.G.G.A.G.mC.G.mC.mC.mU.Chl | 592 | P.mA.G.G.fC.G.fC.fU.fC.fC.A.mC.mU.mC*mU*G*mU*G*G*U. | 82% |
| 13982 | 747 | 593 | mC.G.A.mC.mU.G.G.A.A.G.A.mC.A.Chl | 594 | P.mU.G.fU.fC.fU.fU.fC.fC.A.G.mU.mC.G*G*mU*A*A*G*C. | 116% |
| 13983 | 817 | 595 | G.G.A.G.mC.G.mC.mC.mU.G.mU.mU.mC.Chl | 596 | P.mG.A.A.fC.A.G.G.fC.G.fC.mU.mC.mC*A*mC*mU*mC*mU*G. | 97% |
| 13984 | 1174 | 597 | G.mC.mC.A.mU.mU.A.mC.A.A.mC.mU.G.Chl | 598 | P.mC.A.G.fU.fU.G.fU.A.A.fU.G.G.mC*A*G*G*mC*A*C. | 102% |
| 13985 | 1005 | 599 | G.A.G.mU.mU.mU.mC.mU.G.G.mC.mU.Chl | 600 | P.mA.G.fC.fC.A.G.A.A.G.mC.mU.mC*A*A*A*mC*mU*U. | 114% |
| 13986 | 814 | 601 | A.G.mU.G.G.A.G.mC.G.mC.mC.mU.G.Chl | 602 | P.mC.A.G.G.fC.G.fC.fU.fC.fC.A.mC.mU*mC*mU*G*mU*G. | 111% |
| 13987 | 816 | 603 | mU.G.G.A.G.mC.G.mC.mC.mU.G.mU.mU.Chl | 604 | P.mA.A.fC.A.G.G.fC.G.fC.fU.fC.mC.A*mC*mU*mC*mU*G*U. | 102% |
| 13988 | 1001 | 605 | G.mU.mU.mU.G.A.G.mC.mU.mU.mU.mC.mU.Chl | 606 | P.mA.G.A.A.A.G.fC.fU.fC.A.A.A.mC*mU*mU*G*A*mU*A. | 99% |
| 13989 | 1173 | 607 | mU.G.mC.mC.A.mU.mU.A.mC.A.A.mC.mU.Chl | 608 | P.mA.G.fU.fU.G.fU.A.A.fU.G.G.mC.A*G*G*mC*A*mC*A. | 107% |
| 13990 | 749 | 609 | A.mC.mU.G.G.A.A.G.A.mC.A.mC.G.Chl | 610 | P.mC.G.fU.G.fU.fC.fU.fU.fC.fC.A.G.mU*mC*G*G*mU*A*A. | 91% |
| 13991 | 792 | 611 | A.A.mC.mU.G.mC.mC.mU.G.G.mU.mC.mC.Chl | 612 | P.mG.G.A.fC.fC.A.G.G.fC.A.G.mU.mU*G*G*mC*mU*mC*U. | 97% |
| 13992 | 1162 | 613 | A.G.A.mC.mC.mU.mU.G.mU.G.mC.mC.mU.G.Chl | 614 | P.mC.A.G.G.fC.A.fC.A.A.G.G.mU.mC*mU*mU*G*A*mU*G*A. | 107% |
| 13993 | 811 | 615 | mC.A.G.A.G.mU.G.G.A.G.mC.G.mC.Chl | 616 | P.mG.fC.G.fC.fU.fC.fC.A.fC.fU.mC.mU.G*mU*G*mU*mC*U. | 113% |
| 13994 | 797 | 617 | mC.mC.mU.G.G.mU.mC.mC.A.G.A.mC.mC.Chl | 618 | P.mG.G.fU.fC.fU.G.G.A.fC.fC.A.G.G*mC*A*G*mU*mU*G. | n/a |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
| --- | --- | --- | --- | --- | --- | --- |
| 13995 | 1175 | 619 | mC.mC.A.mU.mU. A.mC.A.A.mC.mU. G.mU.Chl | 620 | P.mA.fC.A.G.fU.fU. G.fU.A.A.mU.G. G*mC*A*G*G*mC* A. | 113% |
| 13996 | 1172 | 621 | mC.mU.G.mC.mC. A.mU.mU.A.mC.A. A.mC.Chl | 622 | P.mG.fU.fU.G.fU.A. A.fU.G.G.mC.A.G* G*mC*A*mC*A*G. | 110% |
| 13997 | 1177 | 623 | A.mU.mU.A.mC. A.A.mC.mU. G.mU.mC.mC.Chl | 624 | P.mG.A.fC.A. G.fU.fU.G.fU.A.A.mU* G*G*mC*A*G. | 105% |
| 13998 | 1176 | 625 | mC.A.mU.mU. A.mC.A.A.mC.mU. G.mU.mC.Chl | 626 | P.mG.A.fC.A.G.fU.fU. G.fU.A.A.mU.G* G*mC*A*G*G*C. | 89% |
| 13999 | 812 | 627 | A.G.A.G.mU.G. G.A.G.mC. G.mC.mC.Chl | 628 | P.mG.G.fC. G.fC.fU.fC.fC. A.fC.mU.mC.mU* G*mU*G*mU*C. | 99% |
| 14000 | 745 | 629 | A.mC.mC.G. A.mC.mU.G.G.A. A.G.A.Chl | 630 | P.mU.fC.fU.fU.fC.fC.A. G.fU.fC.G.G.mU*A* A*G*mC*mC*G. | n/a |
| 14001 | 1230 | 631 | A.mU.G.mU. A.mC.G.G.A.G. A.mC.A.Chl | 632 | P.mU.G.fU.fC.fU.fC.fC. G.fU.A.mC. A.mU*mC*mU*mU*m C*mC*U. | 106% |
| 14002 | 920 | 633 | G.mC.mC.mU.mU. G.mC.G.A.A. G.mC.mU.Chl | 634 | P.mA.fC.fU.fU.fC. G.fC.A.A.G. G.mC*mC*mU*G* A*mC*C. | 93% |
| 14003 | 679 | 635 | G.mC.mU.G.mC. G.A.G.G.A. G.mU.G.Chl | 636 | P.mC. A.fC.fU.fC.fC.fU.fC. G.fC.A.G.mC* A*mU*mU*mU*mC* C. | 102% |
| 14004 | 992 | 637 | G.mC.mC.mU. A.mU.mC.A.A. G.mU.mU.mU.Chl | 638 | P.mA.A.A.fC.fU.fU.G. A.fU.A.G. G.mC*mU*mU*G*G* A*G. | 100% |
| 14005 | 1045 | 639 | A. A.mU.mU.mC.mU. G.mU.G.G.A. G.mU.Chl | 640 | P.mA.fC.fU.fC.fC.A.fC. A.G.A.A.mU.mU*mU* A*G*mC*mU*C. | 104% |
| 14006 | 1231 | 641 | mU.G.mU.A.mC. G.G.A.G.A.mC. A.mU.Chl | 642 | P.mA.fU. G.fU.fC.fU.fC.fC.G.fU. A.mC. A*mU*mC*mU*mU*m C*C. | 87% |
| 14007 | 991 | 643 | A.G.mC.mC.mU. A.mU.mC.A.A. G.mU.mU.Chl | 644 | P.mA.A.fC.fU.fU.G. A.fU.A.G. G.mC.mU*mU*G*G* A*G*A. | 101% |
| 14008 | 998 | 645 | mC.A.A. G.mU.mU.mU.G. A. G.mC.mU.mU.Chl | 646 | P.mA.A.G.fC.fU.fC.A. A.A.fC.mU.mU.G* A*mU*A*G*G*C. | 98% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 14009 | 1049 | 647 | mC.mU.G.mU.G. G.A.G.mU.A.mU. G.mU.Chl | 648 | P.mA.fC.A.fU. A.fC.fU.fC.fC.A.mC.A. G*A*mU*mU*mU* A. | 98% |
| 14010 | 1044 | 649 | A.A. A.mU.mU.mC.mU. G.mU.G.G.A. G.Chl | 650 | P.mC.fU.fC.fC.A.fC.A. G.A.A.mU.mU.mU*A* G*mC*mU*mC*G. | 93% |
| 14011 | 1327 | 651 | mU.mU.mU.mC.A. G.mU.A.G.mC. A.mC.A.Chl | 652 | P.mU.G.fU.G.fC.fU. A.fC.fU.G.A.A. A*mU*mC* A*mU*mU*U. | 95% |
| 14012 | 1196 | 653 | mC.A.A.mU.G. A.mC. A.mU.mC.mU.mU. mU.Chl | 654 | P.mA.A.A.G.A.fU. G.fU.fC.A.mU.mU. G*mU*mC*mU*mC*m C*G. | 101% |
| 14013 | 562 | 655 | A.G.mU. A.mC.mC.A.G.mU. G.mC.A.mC.Chl | 656 | P.mG.fU.G.fC.A.fC.fU. G.G.fU. A.mC.mU*mU*G*mC* A*G*C. | 66% |
| 14014 | 752 | 657 | G.G.A.A.G. A.mC.A.mC. G.mU.mU.mU.Chl | 658 | P.mA.A.A.fC.G.fU. G.fU.fC.fU.mU.mC.mC* A*G*mU*mC*G*G. | 95% |
| 14015 | 994 | 659 | mC.mU.A.mU.mC. A.A. G.mU.mU.mU.G. A.Chl | 660 | P.mU.fC.A.A. A.fC.fU.fU.G.A.mU.A. G*G*mC*mU*mU*G* G. | 85% |
| 14016 | 1040 | 661 | A.G.mC.mU.A.A. A.mU.mU.mC.mU. G.mU.Chl | 662 | P.mA.fC.A.G.A. A.fU.fU.fU.A. G.mC.mU*mC*G* G*mU*A*U. | 61% |
| 14017 | 1984 | 663 | A.G.G.mU.A.G. A.A.mU.G.mU.A. A.Chl | 664 | P.mU.fU.A.fC. A.fU.fU.fC.fU. A.mC.mC.mU*A*mU* G*G*mU*G. | 32% |
| 14018 | 2195 | 665 | A.G.mC.mU.G. A.mU.mC.A. G.mU.mU.mU.Chl | 666 | P.mA.A.A.fC.fU.G. A.fU.fC.A.G.mC.mU* A*mU*A*mU*A*G. | 86% |
| 14019 | 2043 | 667 | mU.mU.mC.mU. G.mC.mU.mC.A.G. A.mU.A.Chl | 668 | P.mU.A.fU.fC.fU.G.A. G.fC.A.G.A. A*mU*mU*mU*mC*m C*A. | 81% |
| 14020 | 1892 | 669 | mU.mU. A.mU.mC.mU.A.A. G.mU.mU.A.A.Chl | 670 | P.mU.fU.A.A.fC.fU.fU. A.G.A.mU.A. A*mC*mU*G*mU*A* C. | 84% |
| 14021 | 1567 | 671 | mU.A.mU.A.mC. G.A.G.mU.A. A.mU.A.Chl | 672 | P.mU.A.fU.fU. A.fC.fU.fC.G.fU.A.mU. A*A*G*A*mU*G*C. | 72% |
| 14022 | 1780 | 673 | G.A.mC.mU.G.G. A.mC.A. G.mC.mU.mU.Chl | 674 | P.mA.A.G.fC.fU. G.fU.fC.fC.A. G.mU.mC*mU*A* A*mU*mC*G. | 65% |
| 14023 | 2162 | 675 | A.mU.G. G.mC.mC.mU.mU. mU.A.mU.mU. A.Chl | 676 | P.mU.A.A.fU.A.A.A. G.G.fC.mC. A.mU*mU*mU* G*mU*mC. | 80% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 14024 | 1034 | 677 | A.mU.A.mC.mC. G.A.G.mC.mU.A. A.A.Chl | 678 | P.mU.fU.fU.A. G.fC.fU.fC.G.G.mU. A.mU* G*mU*mC*mU*mU* C. | 91% |
| 14025 | 2264 | 679 | mU.mU.G.mU.mU. G.A.G.A.G.mU. G.mU.Chl | 680 | P.mA.fC. A.fC.fU.fC.fU.fC.A. A.mC.A.A*A*mU*A* A*A*C. | 58% |
| 14026 | 1032 | 681 | A.mC.A.mU. A.mC.mC.G.A. G.mC.mU.A.Chl | 682 | P.mU.A.G.fC.fU.fC.G. G.fU.A.mU. G.mU*mC*mU*mU*m C*A*U. | 106% |
| 14027 | 1535 | 683 | A.G.mC.A.G.A. A.A.G.G.mU.mU. A.Chl | 684 | P.mU.A. A.fC.fC.fU.fU.fU.fC.fU. G.mC.mU*G*G*mU* A*mC*C. | 67% |
| 14028 | 1694 | 685 | A.G.mU.mU. G.mU.mU.mC.mC. mU.mU.A.A.Chl | 686 | P.mU.fU.A.A.G.G.A. A.fC.A.A.mC.mU*mU* G*A*mC*mU*C. | 94% |
| 14029 | 1588 | 687 | A.mU.mU.mU.G. A.A.G.mU.G.mU. A.A.Chl | 688 | P.mU.fU.A.fC. A.fC.fU.fU.fC.A.A. A.mU*A*G*mC*A* G*G. | 97% |
| 14030 | 928 | 689 | A.A.G.mC.mU.G. A.mC.mC.mU.G.G. A.Chl | 690 | P.mU.fC.fC.A.G. G.fU.fC.A. G.mC.mU.mU*mC* G*mC*A*A*G. | 100% |
| 14031 | 1133 | 691 | G.G.mU.mC. A.mU.G.A.A.G.A. A.G.Chl | 692 | P.mC.fU.fU.fC.fU.fU.fC. A.fU.G. A.mC.mC*mU*mC* G*mC*mC*G. | 82% |
| 14032 | 912 | 693 | A.mU.G. G.mU.mC.A.G. G.mC.mC.mU.mU. Chl | 694 | P.mA.A.G.G.fC.fC.fU. G.A.fC.mC.A.mU* G*mC*A*mC*A*G. Chl | 84% |
| 14033 | 753 | 695 | G.A.A.G.A.mC. A.mC. G.mU.mU.mU. G.Chl | 696 | P.mC.A.A.A.fC.G.fU. G.fU.fC.mU.mU.mC*m C*A*G*mU*mC*G. | 86% |
| 14034 | 918 | 697 | A.G. G.mC.mC.mU.mU. G.mC.G.A.A. G.Chl | 698 | P.mC.fU.fU.fC.G.fC.A. A.G.G.mC.mC.mU*G* A*mC*mC*A*U. | 88% |
| 14035 | 744 | 699 | mU.A.mC.mC.G. A.mC.mU.G.G.A. A.G.Chl | 700 | P.mC.fU.fU.fC.fC.A. G.fU.fC.G.G.mU.A*A* G*mC*mC*G*C. | 95% |
| 14036 | 466 | 701 | A.mC.mC.G.mC. A.A.G.A.mU.mC. G.G.Chl | 702 | P.mC.fC.G. A.fU.fC.fU.fU.G.fC.G. G.mU*mU*G* G*mC*mC*G. | 73% |
| 14037 | 917 | 703 | mC.A.G. G.mC.mC.mU.mU. G.mC.G.A.A.Chl | 704 | P.mU.fU.fC.G.fC.A.A. G.G.fC.mC.mU.G* A*mC*mC*A*mU*G. | 86% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 14038 | 1038 | 705 | mC.G.A.G.mC.mU.A.A.A.mU.mU.mC.mU.Chl | 706 | P.mA.G.A.A.fU.fU.fU.A.G.fC.mU.mC.G*G*mU*A*mU*G*U. | 84% |
| 14039 | 1048 | 707 | mU.mC.mU.G.mU.G.G.A.G.mU.A.mU.G.Chl | 708 | P.mC.A.fU.A.fC.fU.fC.fC.A.fC.A.G.A*A*mU*mU*mU*A*G. | 87% |
| 14040 | 1235 | 709 | mC.G.G.A.G.A.mC.A.mU.G.G.mC.A.Chl | 710 | P.mU.G.fC.fC.A.fU.fU.fC.fU.fC.mC.G*mU*A*mC*A*mU*C. | 100% |
| 14041 | 868 | 711 | A.mU.G.A.mC.A.A.mC.G.mC.mC.mU.mC.Chl | 712 | P.mG.A.G.G.fC.G.fU.fU.G.fU.mC.A.mU*mU*G*G*mU*A*A. | 104% |
| 14042 | 1131 | 713 | G.A.G.G.mU.mC.A.mU.G.A.A.G.A.Chl | 714 | P.mU.fC.fU.fU.fC.A.fU.G.A.fC.mC.mU.mC*G*mC*mC*G*mU*C. | 85% |
| 14043 | 1043 | 715 | mU.A.A.A.mU.mU.mC.mU.G.mU.G.G.A.Chl | 716 | P.mU.fC.fC.A.fC.A.G.A.A.fU.mU.mU.A*G*mC*mU*mC*G*G. | 74% |
| 14044 | 751 | 717 | mU.G.G.A.A.G.A.mC.A.mC.G.mU.mU.Chl | 718 | P.mA.A.fC.G.fU.G.fU.fC.fU.fU.mC.mC.A*G*mU*mC*G*G*U. | 84% |
| 14045 | 1227 | 719 | A.A.G.A.mU.G.mU.A.mC.G.G.A.G.Chl | 720 | P.mC.fU.fC.fC.G.fU.A.fC.A.fU.mC.mU.mU*mC*mC*mU*G*mU*A. | 99% |
| 14046 | 867 | 721 | A.A.mU.G.A.mC.A.A.mC.G.mC.mC.mU.Chl | 722 | P.mA.G.G.fC.G.fU.fU.G.fU.fC.A.mU.mU*G*G*mU*A*A*C. | 94% |
| 14047 | 1128 | 723 | G.G.mC.G.A.G.G.mU.mC.A.mU.G.A.Chl | 724 | P.mU.fC.A.fU.G.A.fC.fC.fU.fC.G.mC.mC*G*mU*mC*A*G*G. | 89% |
| 14048 | 756 | 725 | G.A.mC.A.mC.G.mU.mU.mU.G.G.mC.mC.Chl | 726 | P.mG.G.fC.fC.A.A.A.fC.G.fU.G.mU.mC*mU*mU*mC*mC*A*G. | 93% |
| 14049 | 1234 | 727 | A.mC.G.G.A.G.A.mC.A.mU.G.G.mC.Chl | 728 | P.mG.fC.fC.A.fU.G.fU.fC.fU.fC.mC.G.mU*A*mC*A*mU*mC*U. | 100% |
| 14050 | 916 | 729 | mU.mC.A.G.G.mC.mC.mU.mU.G.mC.G.A.Chl | 730 | P.mU.fC.G.fC.A.A.G.G.fC.fC.mU.G.A*mC*mC*A*mU*G*C. | 96% |
| 14051 | 925 | 731 | G.mC.G.A.A.G.fC.fU.fU.mC.G.mC*A*A*G*mC*C. | 732 | P.mA.G.G.fU.fC.A.G.fC.fU.fU.mC.G.mC*A*A*G*mC*C. | 80% |
| 14052 | 1225 | 733 | G.G.A.A.G.A.mU.G.mU.A.mC.G.G.Chl | 734 | P.mC.fC.G.fU.A.fC.A.fU.fC.fU.mU.mC.mC*mU*G*mU*A*G*U. | 96% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 14053 | 445 | 735 | G.mU.G. A.mC.mU.mU.mC. G. G.mC.mU.mC.Chl | 736 | P.mG.A.G.fC.fC.G.A. A.G.fU.mC.A.mC*A* G*A*A*G*A. | 101% |
| 14054 | 446 | 737 | mU.G. A.mC.mU.mU.mC. G. G.mC.mU.mC.mC.Chl | 738 | P.mG.G.A.G.fC.fC.G. A.A.G.mU.mC.A.mC* A*G*A*A*G. | 93% |
| 14055 | 913 | 739 | mU.G.G.mU.mC. A.G. G.mC.mC.mU.mU. G.Chl | 740 | P.mC.A.A.G. G.fC.fC.fU.G.A.mC.mC. A*mU*G*mC*A*mC* A. | 67% |
| 14056 | 997 | 741 | mU.mC.A.A. G.mU.mU.mU.G. A.G.mC.mU.Chl | 742 | P.mA.G.fC.fU.fC.A.A. A.fC.fU.mU.G.A*mU* A*G*mC*U. | 92% |
| 14057 | 277 | 743 | G.mC.mC.A.G.A. A.mC.mU.G.mC.A. G.Chl | 744 | P.mC.fU.G.fC.A. G.fU.fU.fC.fU.G. G.mC*mC*G*A*mC* G*G. | 84% |
| 14058 | 1052 | 745 | mU.G.G.A.G.mU. A.mU.G.mU. A.mC.mC.Chl | 746 | P.mG.G.fU.A.fC.A.fU. A.fC.fU.mC.mC.A*mC* A*G*A*A*U. | n/a |
| 14059 | 887 | 747 | G.mC.mU.A.G.A. G.A.A.G.mC.A. G.Chl | 748 | P.mC.fU. G.fC.fU.fU.fC.fU.fC.fU. A.G.mC*mC*mU* G*mC*A*G. | 80% |
| 14060 | 914 | 749 | G.G.mU.mC.A.G. G.mC.mC.mU.mU. G.mC.Chl | 750 | P.mG.fC.A.A.G. G.fC.fC.fU.G. A.mC.mC*A*mU* G*mC*A*C. | 112% |
| 14061 | 1039 | 751 | G.A.G.mC.mU.A. A. A.mU.mU.mC.mU. G.Chl | 752 | P.mC.A.G.A. A.fU.fU.fU.A. G.mC.mU.mC*G* G*mU*A*mU*G. | 104% |
| 14062 | 754 | 753 | A.A.G.A.mC. A.mC. G.mU.mU.mU.G. G.Chl | 754 | P.mC.fC.A.A.A.fC. G.fU. G.fU.mC.mU.mU*mC* mC*A*G*mU*C. | 109% |
| 14063 | 1130 | 755 | mC.G.A.G. G.mU.mC.A.mU. G.A.A.G.Chl | 756 | P.mC.fU.fU.fC.A.fU.G. A.fC.fC.mU.mC. G*mC*mC* G*mU*mC*A. | 103% |
| 14064 | 919 | 757 | G. G.mC.mC.mU.mU. G.mC.G.A.A. G.mC.Chl | 758 | P.mG.fC.fU.fU.fC.G.fC. A.A.G.G.mC.mC*U* G*A*mC*mC*A. | 109% |
| 14065 | 922 | 759 | mC.mU.mU.G.mC. G.A.A.G.mC.mU. G.A.Chl | 760 | P.mU.fC.A. G.fC.fU.fU.fC.G.fC.A. A.G*G*mC*mC*mU* G*A. | 106% |
| 14066 | 746 | 761 | mC.mC.G. A.mC.mU.G.G.A. A.G.A.mC.Chl | 762 | P.mG.fU.fC.fU.fU.fC.fC. A.G.fU.mC.G.G*mU* A*A*G*mC*C. | 106% |
| 14067 | 993 | 763 | mC.mC.mU. A.mU.mC.A.A. G.mU.mU.mU. G.Chl | 764 | P.mC.A.A.A.fC.fU.fU. G.A.fU.A.G. G*mC*mU*mU*G*G* A. | 67% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 14068 | 825 | 765 | mU.G.mU.mC.mC.A.A.G.A.mC.mC.mU.Chl | 766 | P.mA.G.G.fU.fC.fU.fU.G.G.A.A.mC.A*G*G*mC*G*mC*U. | 93% |
| 14069 | 926 | 767 | mC.G.A.A.G.mC.mU.G.A.mC.mC.mU.G.Chl | 768 | P.mC.A.G.G.fU.fC.A.G.fC.fU.mU.mC.G*mC*A*A*G*G*C. | 95% |
| 14070 | 923 | 769 | mU.mU.G.mC.G.A.A.G.mC.mU.G.A.mC.Chl | 770 | P.mG.fU.fC.A.G.fC.fU.fU.fC.G.mC.A.A*G*G*mC*mC*mU*G. | 95% |
| 14071 | 866 | 771 | mC.A.A.mU.G.A.mC.A.A.mC.G.mC.mC.Chl | 772 | P.mG.G.fC.G.fU.fU.G.fU.fC.A.mU.mU.G*G*mU*A*A*mC*C. | 132% |
| 14072 | 563 | 773 | G.mU.A.mC.mC.A.G.mU.G.mC.A.mC.G.Chl | 774 | P.mC.G.fU.G.fC.A.fC.fU.G.G.mU.A.mC*mU*mU*G*mC*A*G. | n/a |
| 14073 | 823 | 775 | mC.mC.mU.G.mU.mU.mC.mC.A.A.G.A.mC.Chl | 776 | P.mG.fU.fC.fU.G.G.A.A.fC.A.G.G*mC*G*mC*mU*mC*C. | 98% |
| 14074 | 1233 | 777 | mU.A.mC.G.G.A.G.A.mC.A.mU.G.G.Chl | 778 | P.mC.fC.A.fU.G.fU.fC.fU.fC.fC.G.mU.A*mC*A*mU*mC*mU*U. | 109% |
| 14075 | 924 | 779 | mU.G.mC.G.A.A.G.mC.mU.G.A.mC.mC.Chl | 780 | P.mG.G.fU.fC.A.G.fC.fU.fU.fC.G.mC.A*A*G*G*mC*mC*U. | 95% |
| 14076 | 921 | 781 | mC.mC.mU.mU.G.mC.G.A.A.G.mC.mU.G.Chl | 782 | P.mC.A.G.fC.fU.fU.fC.G.fC.A.A.G.G*mC*mC*mU*G*A*C. | 116% |
| 14077 | 443 | 783 | mC.mU.G.mU.G.A.mC.mU.mU.mC.G.G.mC.Chl | 784 | P.mG.fC.fC.G.A.A.G.fU.fC.A.mC.A.G*A*A*G*A*G*G. | 110% |
| 14078 | 1041 | 785 | G.mC.mU.A.A.A.mU.mU.mC.mU.mU.A.mU.G.Chl | 786 | P.mC.A.fC.A.G.A.A.fU.fU.fU.A.G.mC*mU*mC*G*G*mU*A. | 99% |
| 14079 | 1042 | 787 | mC.mU.A.A.A.mU.mU.mC.mU.mU.A.mU.G.G.Chl | 788 | P.mC.fC.A.fC.A.G.A.A.fU.fU.fU.A.G*mC*mU*mC*G*G*U. | 109% |
| 14080 | 755 | 789 | A.G.A.mC.A.mC.G.mU.mU.mU.G.mC.Chl | 790 | P.mG.fC.fC.A.A.A.fC.G.fU.G.mU.mC.mU*mU*mC*mC*A*G*U. | 121% |
| 14081 | 467 | 791 | mC.mC.G.mC.A.A.G.A.mU.mC.G.mC.Chl | 792 | P.mG.fC.C.fG.A.U.fC.fU.fU.fG.C.mG.G*mU*mU*G*G*mC*C. | 132% |
| 14082 | 995 | 793 | mU.A.mU.mC.A.A.G.mU.mU.mU.G.A.G.Chl | 794 | P.mC.fU.fC.A.A.A.fC.fU.fU.G.A.mU.A*G*G*mC*mU*mU*G. | 105% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 14083 | 927 | 795 | G.A.A.G.mC.mU. G.A.mC.mC.mU.G. G.Chl | 796 | P.mC.fC.A.G.G.fU.fC. A.G.fC.mU.mU.mC* G*mC*A*A*G*G. | 114% |
| 17356 | 1267 | 797 | A.mC.A.mU.mU. A.A.mC.mU.mC. A.mU.A.Chl | 798 | P.mU.A.fU.G.A. G.mU.fU.A.A.fU. G.fU*fC*fU*fC*fU*fC* A. | 120% |
| 17357 | 1267 | 799 | G.A.mC. A.mU.mU.A. A.mC.mU.mC. A.mU.A.Chl | 800 | P.mU.A.fU.G.A. GmU..fU.A.A.fU. G.fU*fC*fU*fC*fU*fC* A. | 56% |
| 17358 | 1442 | 801 | mU.G.A.A.G.A. A.mU.G.mU.mU. A.A.Chl | 802 | P.mU.fU.A.A.fC. A.fU.fU.fC.fU.fU.fC.A* A*A*fC*fC*A*G. | 34% |
| 17359 | 1442 | 803 | mU.mU.G.A.A.G. A.A.mU. G.mU.mU.A.A.Chl | 804 | P.mU.fU.A.A.fC. A.fU.fU.fC.fU.fU.fC.A* A*A*fC*fC*A*G. | 31% |
| 17360 | 1557 | 805 | G.A.mU.A.G.mC. A.mU.mC.mU.mU. A.A.Chl | 806 | P.mU.fU.A.A.G.A.fU. G.fC.fU.A.fU.fC*fU*G* A*fU*G*A. | 59% |
| 17361 | 1557 | 807 | A.G.A.mU.A. G.mC. A.mU.mC.mU.mU. A.A.Chl | 808 | P.mU.fU.A.A.G.A.fU. G.fC.fU.A.fU.fC*fU*G* A*fU*G*A. | 47% |
| 17362 | 1591 | 809 | mU.G.A.A.G.mU. G.mU.A. A.mU.mU.A.Chl | 810 | P.mU.A.A.fU.fU.A.fC. A.fC.fU.fU.fC.A*A* A*fU*A*G*C. | 120% |
| 17363 | 1599 | 811 | A.A.mU.mU.G.A. G.A.A.G.A. A.Chl | 812 | P.mU.fU.fC.fC.fU.fU.fC.f U.fC.A.A.fU.fU*A*fC* A*fC*fU*U. | 71% |
| 17364 | 1601 | 813 | mU.mU.G.A.G.A. A.G.G.A.A.A. A.Chl | 814 | P.mU.fU.fU.fU.fC.fC.fU. fU.fC.fU.fC.A. A*fU*fU*A*fC*A*C. | 62% |
| 17365 | 1732 | 815 | mC. A.mU.mU.mC.mU. G.A.mU.mU.mC. G.A.Chl | 816 | P.mU.fC.G.A.A.fU.fC. A.G.A.A.fU.G*fU*fC* A*G*A*G. | 99% |
| 17366 | 1734 | 817 | mU.mU.mC.mU.G. A.mU.mU.mC.G. A.A.A.Chl | 818 | P.mU.fU.fU.fC.G.A. A.fU.fC.A.G.A.A*fU* G*fU*fC*A*G. | 97% |
| 17367 | 1770 | 819 | mC.mU.G.mU.mC. G.A.mU.mU.A.G. A.A.Chl | 820 | P.mU.fU.fC.fU.A. A.fU.fC.G.A.fC.A.G* G*A*fU*fU*fC*C. | 45% |
| 17368 | 1805 | 821 | mU.mU.mU. G.mC.mC.mU. G.mU.A.A.mC. A.Chl | 822 | P.mU.G.fU.fU.A.fC.A. G.G.fC.A.A. A*fU*fU*fC*A*fC*U. | 71% |
| 17369 | 1805 | 823 | A.mU.mU.mU. G.mC.mC.mU. G.mU.A.A.mC. A.Chl | 824 | P.mU.G.fU.fU.A.fC.A. G.G.fC.A.A. A*fU*fU*fC*A*fC*U. | 67% |
| 17370 | 1815 | 825 | A.mC.A.A. G.mC.mC.A.G. A.mU.mU.A.Chl | 826 | P.mU.A.A.fU.fC.fU.G. G.fC.fU.fU.G.fU*fU* A*fC*A*G*G. | 65% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 17371 | 1815 | 827 | A.A.mC.A.A. G.mC.mC.A.G. A.mU.mU.A.Chl | 828 | P.mU.A.A.fU.fC.fU.G. G.fC.fU.fU.G.fU*fU* A*fC*A*G*G. | 35% |
| 17372 | 2256 | 829 | mC.A. G.mU.mU.mU. A.mU.mU.mU. G.mU.A.Chl | 830 | P.mU.A.fC.A.A.A.fU. A.A.A.fC.fU. G*fU*fC*fC*G*A*A. | 113% |
| 17373 | 2265 | 831 | mU.G.mU.mU.G. A.G.A.G.mU. G.mU.A.Chl | 832 | P.mU.A.fC. A.fC.fU.fC.fU.fC.A. A.fC.A*A*A*fU*A* A*A. | 35% |
| 17374 | 2265 | 833 | mU.mU.G.mU.mU. G.A.G.A.G.mU. G.mU.A.Chl | 834 | P.mU.A.fC. A.fC.fU.fC.fU.fC.A. A.fC.A*A*A*fU*A* A*A. | 31% |
| 17375 | 2295 | 835 | mU.G.mC. A.mC.mC.mU.mU. mU.mC.mU.A. A.Chl | 836 | P.mU.fU.A.G.A.A.A. G.G.fU.G.fC.A*A* A*fC*A*fU*G. | 34% |
| 17376 | 2295 | 837 | mU.mU.G.mC. A.mC.mC.mU.mU. mU.mC.mU.A. A.Chl | 838 | P.mU.fU.A.G.A.A.A. G.G.fU.G.fC.A*A* A*fC*A*fU*G. | 28% |
| 17377 | 1003 | 839 | mU.mU.G.A. G.mC.mU.mU.mU. mC.mU.G.A.Chl | 840 | P.mU.fC.A.G.A.A.A. G.fC.fU.fC.A.A* A*fC*fU*fU*G*A. | 67% |
| 17378 | 2268 | 841 | mU.G.A.G.A. G.mU.G.mU.G. A.mC.A.Chl | 842 | P.mU.G.fU.fC.A.fC. A.fC.fU.fC.fU.fC.A* A*fC*A*A*A*U. | 42% |
| 17379 | 2272 | 843 | A.G.mU.G.mU.G. A.mC.mC.A.A.A. A.Chl | 844 | P.mU.fU.fU.fU.G. G.fU.fC.A.fC. A.fC.fU*fC*fU*fC*A* A*C. | 35% |
| 17380 | 2272 | 845 | G.A.G.mU.G.mU. G.A.mC.mC.A.A. A.A.Chl | 846 | P.mU.fU.fU.fU.G. G.fU.fC.A.fC. A.fC.fU*fC*fU*fC*A* A*C. | 29% |
| 17381 | 2273 | 847 | G.mU.G.mU.G. A.mC.mC.A.A.A. A.A.Chl | 848 | P.mU.fU.fU.fU.fU.G. G.fU.fC.A.fC. A.fC*fU*fC*fU*fC*A* A. | 42% |
| 17382 | 2274 | 849 | mU.G.mU.G. A.mC.mC.A.A.A. A.G.A.Chl | 850 | P.mU.fC.fU.fU.fU.G. G.fU.fC.A.fC. A*fC*fU*fC*fU*fC*A. | 42% |
| 17383 | 2274 | 851 | G.mU.G.mU.G. A.mC.mC.A.A.A. A.G.A.Chl | 852 | P.mU.fC.fU.fU.fU.G. G.fU.fC.A.fC. A*fC*fU*fC*fU*fC*A. | 37% |
| 17384 | 2275 | 853 | G.mU.G. A.mC.mC.A.A.A. A.G.mU.A.Chl | 854 | P.mU.A.fC.fU.fU.fU.fU. G.G.fU.fC.A.fC* A*fC*fU*fC*fU*C. | 24% |
| 17385 | 2277 | 855 | G.A.mC.mC.A.A. A.A.G.mU.mU.A. A.Chl | 856 | P.mU.fU.A. A.fC.fU.fU.fU.fU.G. G.fU.fC*A*fC* A*fC*fU*C. | 27% |
| 17386 | 2296 | 857 | G.mC. A.mC.mC.mU.mU. | 858 | P.mU.fC.fU.A.G.A.A. A.G.G.fU.G.fC*A*A* | 23% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| | | | mU.mC.mU.A.G.A.Chl | | A*fC*A*U. | |
| 17387 | 2299 | 859 | mC.mC.mU.mU.mU.mC.mU.A.G.mU.mU.G.A.Chl | 860 | P.mU.fC.A.A.fC.fU.A.G.A.A.G.G*fU*G*fC*A*A. | 46% |
| 21138 | 2296 | 861 | G.mC.A.mC.mC.mU.mU.mU.mC.mU.A.G.A.TEG-Chl | 862 | P.mU.fC.fU.A.G.mA.A.G.G.fU.G.mC*A*A*mC*A*U. | 42% |
| 21139 | 2296 | 863 | G.mC.A.mC.mC.mU.mU.mU.mC.mU.A.G.A.TEG-Chl | 864 | P.mU.fC.fU.A.G.mA.A.mA.G.G.fU.G.mC*A*A*mC*A*U. | 32% |
| 21140 | 2296 | 865 | G.mC.A.mC.mC.mU.mU.mU.mC.mU.A.G.A.TEG-Chl | 866 | P.mU.fC.fU.A.G.A.A.G.G.fU.G.mC*A*mA*A*mC*A*U. | 41% |
| 21141 | 2296 | 867 | G.mC.A.mC.mC.mU.mU.mU.mC.mU.A.G.A.TEG-Chl | 868 | P.mU.fC.fU.A.G.mA.A.G.G.fU.G.mC*A*mA*A*mC*A*U. | 51% |
| 21142 | 2296 | 869 | G.mC.A.mC.mC.mU.mU.mU.mC.mU.A.G.A.TEG-Chl | 870 | P.mU.fC.fU.A.G.mA.A.mA.G.G.fU.G.mC*A*mA*A*mC*A*U. | 25% |
| 21143 | 2296 | 871 | G.mC.A.mC.mC.mU.mU.mU.mC.mU.A.G.A.TEG-Chl | 872 | P.mU.fC.fU.A.G.A.A.G.G.fU.G.fC*mA*mA*mA*fC*mA*U. | 61% |
| 21144 | 2296 | 873 | G.mC.A.mC.mC.mU.mU.mU.mC.mU.A.G.A.TEG-Chl | 874 | P.mU.fC.fU.A.G.A.mA.G.G.fU.G.fC*mA*mA*mA*fC*mA*U. | 49% |
| 21145 | 2296 | 875 | G.mC.A.mC.mC.mU.mU.mU.mC.mU.A.G.A.TEG-Chl | 876 | P.mU.fC.fU.A.G.mA.A.mA.G.G.fU.G.fC*mA*mA*mA*fC*mA*U. | 46% |
| 21146 | 2296 | 877 | G.mC.A.mC.mC.mU.mU.mU.mC.mU.mU.A*mG*mA.TEG-Chl | 878 | P.mU.fC.fU.A.G.A.A.G.G.fU.G.fC*A*A*A*fC*A*U. | 37% |
| 21147 | 2296 | 879 | mG*mC*A.mC.mC.mU.mU.mU.mC.mU.A*mG*mA.TEG-Chl | 880 | P.mU.fC.fU.A.G.A.A.G.G.fU.G.fC*A*A*A*fC*A*U. | 43% |
| 21148 | 2296 | 881 | mG*mC*mA.mC.mC.mU.mU.mU.mC.mU.mA*mG*mA.TEG-Chl | 882 | P.mU.fC.fU.A.G.A.A.G.G.fU.G.fC*A*A*A*fC*A*U. | 29% |
| 21149 | 2275 | 883 | G.mU.G.A.mC.mC.A.A.A.A.G*mU*mA.TEG-Chl | 884 | P.mU.A.fC.fU.fU.fU.fU.G.G.fU.fC.A.fC*A*fC*fU*fC*fU*C. | 138% |
| 21150 | 2275 | 885 | mG*mU*G.A.mC.mC.A.A.mA.A.G*mU*mA.TEG-Chl | 886 | P.mU.A.fC.fU.fU.fU.fU.G.G.fU.fC.A.fC*A*fC*fU*fC*fU*C. | 116% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 21151 | 2275 | 887 | mG*mU*mG.mA. mC.mC.mA.mA.mA. mA.mG*mU*mA.TEG-Chl | 888 | P.mU.A.fC.fU.fU.fU.fU. G.G.fU.fC.A.fC* A*fC*fU*fC*fU*C. | 105% |
| 21152 | 2295 | 889 | mU.mU.G.mC. A.mC.mC.mU.mU. mU.mC.mU.A. A.TEG-Chl | 890 | P.mU.fU.A.G.A.mA.A. G.G.fU.G.fC.A.A* A*fC*A*fA*G*G. | 46% |
| 21153 | 2295 | 891 | mU.mU.G.mC. A.mC.mC.mU.mU. mU.mC.mU.A. A.TEG-Chl | 892 | P.mU.fU.A.G.mA. A.mA.G.G.fU.G.fC.A. A*A*fC*A*fA*G*G. | 28% |
| 21154 | 2295 | 893 | mU.mU.G.mC. A.mC.mC.mU.mU. mU.mC.mU.A. A.TEG-Chl | 894 | P.mU.fU.mA.G.mA. A.mA.G.mG.fU.G.fC. A.A*A*fC*A*fA*G* G. | 28% |
| 21155 | 2295 | 895 | mU.mU.G.mC. A.mC.mC.mU.mU. mU.mC.mU.A. A.TEG-Chl | 896 | P.mU.fU.A.G.A.mA.A. G.G.fU.G.mC.A.A* A*mC*A*mA*G*G. | 60% |
| 21156 | 2295 | 897 | mU.mU.G.mC. A.mC.mC.mU.mU. mU.mC.mU.A. A.TEG-Chl | 898 | P.mU.fU.A.G.A.mA.A. G.G.fU.G.fC. A.mA*mA*fC*mA*fA* mG*G. | 54% |
| 21157 | 2295 | 899 | mU.mU.G.mC. A.mC.mC.mU.mU. mU.mC.mU.A. A.TEG-Chl | 900 | P.mU.fU.A.G.A.mA.A. G.G.fU. G.fC.mA.mA*mA*fC*m A*fA*mG*G. | 40% |
| 21158 | 2295 | 901 | mU.mU.G.mC. A.mC.mC.mU.mU. mU.mC.mU.A. A.TEG-Chl | 902 | P.mU.fU.A.G.A.mA.A. G.G.fU.G.fC. A.mA*mA*fC*mA*mA* mG*G. | n/a |
| 21159 | 2295 | 903 | mU.mU.G.mC. A.mC.mC.mU.mU. mU.mC.mU.A. A.TEG-Chl | 904 | P.mU.fU.A.G.A.mA.A. G.G.fU.G.fC. A.mA*mA*mC*mA*mA *mG*G. | 41% |
| 21160 | 2295 | 905 | mU.mU.G.mC. A.mC.mC.mU.mU. mU.mC.mU.A. A.Chl-TEG | 906 | P.mU.fU.A.G.A.mA.A. G.G.fU.G.fC.mA. A*mA*mC*mA*mA*m G*mG. | 65% |
| 21161 | 2295 | 907 | mU.mU.G.mC. A.mC.mC.mU.mU. mU.mC.mU.A. A.TEG-Chl | 908 | P.mU.fU.A.G.A.mA.A. G.G.fU.G.fC.A.A* A*fC*A*mA*mG*G. | 43% |
| 21162 | 2295 | 909 | mU.mU.G.mC. A.mC.mC.mU.mU. mU.mC.mU.A. A.TEG-Chl | 910 | P.mU.fU.A.G.A.mA.A. G.G.fU.G.fC.mA. A*mA*fC*A*mA*mG* G. | 41% |
| 21163 | 2295 | 911 | mU.mU.G.mC. A.mC.mC.mU.mU. mU.mC.mU.A* A*TEG-Chl | 912 | P.mU.fU.A.G.A.A.A. G.G.fU.G.fC.A.A* A*fC*A*A*G*G. | 32% |
| 21164 | 2295 | 913 | mU.mU.G.mC. A.mC.mC.mU.mU. mU.mC.mU.mA*m A*TEG-Chl | 914 | P.mU.fU.A.G.A.A.A. G.G.fU.G.fC.A.A* A*fC*A*A*G*G. | 39% |
| 21165 | 2295 | 915 | mU*mU*G.mC. A.mC.mC.mU.mU. | 916 | P.mU.fU.A.G.A.A.A. G.G.fU.G.fC.A.A* | 28% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| | | | mU.mC.mU.mA.mA*TEG-Chl | | A*fC*A*A*G*G. | |
| 21166 | 2295 | 917 | mU.mU.mG.mC.mA.mC.mC.mU.mU.mC.mU.mA*mA*TEG-Chl | 918 | P.mU.fU.A.G.A.A.A.G.G.fU.G.fC.A.A*A*fC*A*A*G*G. | 27% |
| 21167 | 2299 | 919 | mC.mC.mU.mU.mU.mC.mU.A.G.mU.mU.G.A.TEG-Chl | 920 | P.mU.fC.A.A.fC.fU.A.G.A.mA.A.G*fU*G*fC*A*A. | 49% |
| 21168 | 2299 | 921 | mC.mC.mU.mU.mU.mC.mU.A.G.mU.mU.G.A.TEG-Chl | 922 | P.mU.fC.A.A.fC.fU.A.G.A.mA.A.G*mU*G*mC*A*A. | 53% |
| 21169 | 2299 | 923 | mC.mC.mU.mU.mU.mC.mU.A.G.mU.mU.G.A.TEG-Chl | 924 | P.mU.fC.A.A.fC.fU.A.G.mA.A.A.mG.G*fU*G*fC*A*A. | 47% |
| 21170 | 2299 | 925 | mC.mC.mU.mU.mU.mC.mU.A.G.mU.mU.G.A.TEG-Chl | 926 | P.mU.fC.A.A.fC.fU.A.G.mA.A.A.mG.G*mU*G*mC*A*A. | 70% |
| 21171 | 2299 | 927 | mC.mC.mU.mU.mU.mC.mU.A.G.mU.mU.G.A.TEG-Chl | 928 | P.mU.fC.A.A.fC.fU.A.G.A.mA.A.G*mU*G*mC*A*mA*A. | 65% |
| 21172 | 2299 | 929 | mC.mC.mU.mU.mU.mC.mU.A.G.mU.mU.G.A.TEG-Chl | 930 | P.mU.fC.A.A.fC.fU.A.G.A.mA.A.G*mU*G*mC*mA*mA*A. | 43% |
| 21173 | 2299 | 931 | mC.mC.mU.mU.mU.mC.mU.A.G.mU.mU.G.A.TEG-Chl | 932 | P.mU.fC.A.A.fC.fU.A.G.A.mA.A.G.mG*mU*mG*mC*mA*mA*A. | 52% |
| 21174 | 2299 | 933 | mC.mC.mU.mU.mU.mC.mU.A.G.mU.mU.G.A.TEG-Chl | 934 | P.mU.fC.A.A.fC.fU.A.G.A.mA.A.G.G*mU*mG*mC*mA*mA*A. | 47% |
| 21175 | 2299 | 935 | mC.mC.mU.mU.mU.mC.mU.A.G.mU.mU.G.A.TEG-Chl | 936 | P.mU.fC.A.A.fC.fU.A.G.A.mA.A.G.G*fU*mG*fC*mA*mA*A. | 35% |
| 21176 | 2299 | 937 | mC.mC.mU.mU.mU.mC.mU.A.G.mU.mU.G.A.TEG-Chl | 938 | P.mU.fC.A.A.fC.fU.A.G.mA.A.A.mG.G*fU*mG*fC*mA*mA*A. | 50% |
| 21177 | 2299 | 939 | mC.mC.mU.mU.mU.mC.mU.A.G.mU.mU*mG*mA.TEG-Chl | 940 | P.mU.fC.A.A.fC.fU.A.G.A.A.A.G.G*fU*G*fC*A*A*A. | 37% |
| 21178 | 2299 | 941 | mC*mC*mU.mU.mU.mC.mU.A.G.mU.mU*mG*mA.TEG-Chl | 942 | P.mU.fC.A.A.fC.fU.A.G.A.A.A.G.G*fU*G*fC*A*A*A. | 36% |
| 21179 | 2299 | 943 | mC*mC*mU.mU.mU.mC.mU.mA.mG.mU.mU*mG*mA.TEG-Chl | 944 | P.mU.fC.A.A.fC.fU.A.G.A.A.A.G.G*fU*G*fC*A*A*A. | 35% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 21203 | 2296 | 945 | G.mC.A.mC.mC.mU.mU.mU.mC.mU.A*mG*mA.TEG-Chl | 946 | P.mU.fC.fU.A.G.A.mA.A.G.G.fU.G.mC*A*A*A*mC*A*U. | 40% |
| 21204 | 2296 | 947 | G.mC.A.mC.mC.mU.mU.mU.mC.mU.A*mG*mA.TEG-Chl | 948 | P.mU.fC.fU.A.G.A.mA.A.mA.G.G.fU.G.mC*A*A*A*mC*A*U. | 28% |
| 21205 | 2296 | 949 | G.mC.A.mC.mC.mU.mU.mU.mC.mU.A*mG*mA.TEG-Chl | 950 | P.mU.fC.fU.A.G.A.mA.A.G.G.fU.G.mC*A*mA*A*mC*A*U. | 51% |
| 21206 | 2296 | 951 | mG*mC*A.mC.mC.mU.mU.mU.mC.mU.A*mG*mA.TEG-Chl | 952 | P.mU.fC.fU.A.G.A.mA.A.G.G.fU.G.mC*A*A*A*mC*A*U. | 46% |
| 21207 | 2296 | 953 | mG*mC*A.mC.mC.mU.mU.mU.mC.mU.A*mG*mA.TEG-Chl | 954 | P.mU.fC.fU.A.G.A.mA.A.mA.G.G.fU.G.mC*A*A*A*mC*A*U. | 29% |
| 21208 | 2296 | 955 | mG*mC*A.mC.mC.mU.mU.mU.mC.mU.A*mG*mA.TEG-Chl | 956 | P.mU.fC.fU.A.G.A.mA.A.mA.G.G.fU.G.mC*A*mA*A*mC*A*U. | 72% |
| 21209 | 2296 | 957 | mG*mC*mA.mC.mC.mU.mU.mU.mC.mU.mA*mG*mA.TEG-Chl | 958 | P.mU.fC.fU.A.G.A.mA.A.G.G.fU.G.mC*A*A*A*mC*A*U. | 89% |
| 21210 | 2296 | 959 | mG*mC*mA.mC.mC.mU.mU.mU.mC.mU.mA*mG*mA.TEG-Chl | 960 | P.mU.fC.fU.A.G.A.mA.A.mA.G.G.fU.G.mC*A*A*A*mC*A*U. | 65% |
| 21211 | 2296 | 961 | mG*mC*mA.mC.mC.mU.mU.mU.mC.mU.mA*mG*mA.TEG-Chl | 962 | P.mU.fC.fU.A.G.A.mA.A.mA.G.G.fU.G.mC*A*mA*A*mC*A*U. | 90% |
| 21212 | 2295 | 963 | mU.mU.G.mC.A.mC.mC.mU.mU.mU.mC.mU.mA*mA.TEG-Chl | 964 | P.mU.fU.A.G.A.mA.A.G.G.fU.G.fC.mA.mA*mA*fC*mA*mA*mG*G. | 60% |
| 21213 | 2295 | 965 | mU.mU.G.mC.A.mC.mC.mU.mU.mU.mC.mU.mA*mA.TEG-Chl | 966 | P.mU.fU.A.G.A.mA.A.G.G.fU.G.fC.A.mA*mA*mC*mA*mA*mG*G. | 63% |
| 21214 | 2295 | 967 | mU.mU.G.mC.A.mC.mC.mU.mU.mU.mC.mU.mA*mA.TEG-Chl | 968 | P.mU.fU.A.G.A.mA.A.G.G.fU.G.fC.A.A*A*fC*A*mA*mG*G. | 52% |
| 21215 | 2295 | 969 | mU.mU.G.mC.A.mC.mC.mU.mU.mU.mC.mU.mA*mA.TEG-Chl | 970 | P.mU.fU.A.G.A.mA.A.G.G.fU.G.fC.mA.A*mA*fC*A*mA*mG*G. | 45% |
| 21216 | 2295 | 971 | mU*mU*G.mC.A.mC.mC.mU.mU.mU.mC.mU*mA*mA.TEG-Chl | 972 | P.mU.fU.A.G.A.mA.A.G.G.fU.G.fC.mA.mA*mA*mA*fC*mA*mA*mG*G. | 65% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 21217 | 2295 | 973 | mU*mU*G.mC. A.mC.mC.mU.mU. mU.mC.mU*mA*m A.TEG-Chl | 974 | P.mU.fU.A.G.A.mA.A. G.G.fU.G.fC. A.mA*mA*mC*mA*mA *mG*G. | 69% |
| 21218 | 2295 | 975 | mU*mU*G.mC. A.mC.mC.mU.mU. mU.mC.mU*mA*m A.TEG-Chl | 976 | P.mU.fU.A.G.A.mA.A. G.G.fU.G.fC.A.A* A*fC*A*mA*mG*G. | 62% |
| 21219 | 2295 | 977 | mU*mU*G.mC. A.mC.mC.mU.mU. mU.mC.mU*mA*m A.TEG-Chl | 978 | P.mU.fU.A.G.A.mA.A. G.G.fU.G.fC.mA. A*mA*fC*A*mA*mG* G. | 54% |
| 21220 | 2295 | 979 | mU.mU.mG.mC.m A.mC.mC.mU.mU. mU.mC.mU*mA*m A.TEG-Chl | 980 | P.mU.fU.A.G.A.mA.A. G.G.fU. G.fC.mA.mA*mA*fC*m A*mA*mG*G. | 52% |
| 21221 | 2295 | 981 | mU.mU.mG.mC.m A.mC.mC.mU.mU. mU.mC.mU*mA*m A.TEG-Chl | 982 | P.mU.fU.A.G.A.mA.A. G.G.fU.G.fC. A.mA*mA*mC*mA*mA *mG*G. | 53% |
| 21222 | 2295 | 983 | mU.mU.mG.mC.m A.mC.mC.mU.mU. mU.mC.mU*mA*m A.TEG-Chl | 984 | P.mU.fU.A.G.A.mA.A. G.G.fU.G.fC.A.A* A*fC*A*mA*mG*G. | 43% |
| 21223 | 2295 | 985 | mU.mU.mG.mC.m A.mC.mC.mU.mU. mU.mC.mU*mA*m A.TEG-Chl | 986 | P.mU.fU.A.G.A.mA.A. G.G.fU.G.fC.mA. A*mA*fC*A*mA*mG* G. | 43% |
| 21224 | 2299 | 987 | mC.mC.mU.mU.m U.mC.mU.A. G.mU.mU*mG*mA. TEG-Chl | 988 | P.mU.fC.A.A.fC.fU.A. G.A.mA.A.G. G*fU*mG*fC*mA*mA* A. | 60% |
| 21225 | 2299 | 989 | mC*mC*mU.mU.m U.mC.mU.A. G.mU.mU*mG*mA. TEG-Chl | 990 | P.mU.fC.A.A.fC.fU.A. G.A.mA.A.G. G*fU*mG*fC*mA*mA* A. | 67% |
| 21226 | 2299 | 991 | mC*mC*mU.mU.m U.mC.mU.mA.mG. mU.mU*mG*mA.T EG-Chl | 992 | P.mU.fC.A.A.fC.fU.A. G.A.mA.A.G. G*fU*mG*fC*mA*mA* A. | 66% |
| 21227 | 2296 | 993 | G.mC. A.mC.mC.mU.mU. mU.mC.mU. A*mG*mA.TEG-Chl | 994 | P.mU.fC.fU.A.G.mA. A.mA.G.G.fU. G.fC*mA*mA*mA*fC* mA*U. | 49% |
| 20584 | 2296 | 995 | G.mC. A.mC.mC.mU.mU. mU.mC.mU.A.G. A.Chl-TEG | 996 | P.mU.fC.fU.A.G.A.A. A.G.G.mU.G.mC*A* A*A*mC*A*U. | 70% |
| 20585 | 2296 | 997 | G.mC. A.mC.mC.mU.mU. mU.mC.mU.A.G. A.Chl-TEG | 998 | P.mU.fC.fU.A.G.A.A. A.G.G.fU.G.mC*A* A*A*mC*A*U. | 15% |
| 20586 | 2296 | 999 | G.mC. A.mC.mC.mU.mU. mU.mC.mU.A.G. A.Chl-TEG | 1000 | P.mU.C.U.A.G.A.A. A.G.G.mU.G.mC*A* A*A*mC*A*U. | 30% |

TABLE 5-continued

CTGF (Accession Number: NM_001901.2) sd-rxRNA ® sequences

| Oligo Number | Start Site | SEQ ID NO | Sense sequence | SEQ ID NO | Antisense sequence | % remaining mRNA expression (1 uM sd-rxRNA ®, A549) |
|---|---|---|---|---|---|---|
| 20587 | 2296 | 1001 | G.mC.A.mC.mC.mU.mU.mU.mC.mU.A.G.A.Chl-TEG | 1002 | P.mU.fC.fU.A.G.A.A.A.G.G.fU.G.fC*mA*mA*mA*fC*mA*U. | 32% |
| 20616 | 2275 | 1003 | G.mU.G.A.mC.mC.A.A.A.A.G.mU.A.Chl-TEG | 1004 | P.mU.A.fC.fU.fU.fU.fU.G.G.fU.mC.A.mC*A*mC*mU*mC*mU*C. | 22% |
| 20617 | 2275 | 1005 | G.mU.G.A.mC.mC.A.A.A.A.G.mU.A.Chl-TEG | 1006 | P.mU.A.fC.fU.fU.fU.fU.G.G.fU.fC.A.mC*A*fC*mU*fC*mU*C. | 18% |
| 20618 | 2275 | 1007 | G.mU.G.A.mC.mC.A.A.A.A.G.mU.A.Chl-TEG | 1008 | P.mU.A.C.U.U.U.U.G.G.U.mC.A.mC*A*mC*mU*mC*mU*C. | 36% |
| 20619 | 2275 | 1009 | G.mU.G.A.mC.mC.A.A.A.A.G.mU.A.Chl-TEG | 1010 | P.mU.A.fC.fU.fU.fU.fU.G.G.fU.fC.A.mC*mA*mC*mU*mC*mU*C. | 28% |
| 21381 | 2275 | 1011 | G.mU.G.A.mC.mC.A.A.A.A.G*mU*mA.TEG-Chl | 1012 | P.mU.A.fC.fU.fU.fU.fU.G.G.fU.mC.A.mC*A*mC*mU*mC*mU*C. | 28% |
| 21382 | 2275 | 1013 | G.mU.G.A.mC.mC.A.A.A.A.G*mU*mA.TEG-Chl | 1014 | P.mU.A.fC.fU.fU.fU.fU.G.G.fU.fC.A.mC*A*fC*mU*fC*mU*C. | 28% |
| 21383 | 2275 | 1015 | mG*mU*mG.mA.mC.mC.mA.mA.mA.mA.mG*mU*mA.TEG-Chl | 1016 | P.mU.A.fC.fU.fU.fU.fU.G.G.fU.mC.A.mC*A*mC*mU*mC*mU*C. | 43% |
| 21384 | 2275 | 1017 | mG*mU*mG.mA.mC.mC.mA.mA.mA.mA.mG*mU*mA.TEG-Chl | 1018 | P.mU.A.fC.fU.fU.fU.fU.G.G.fU.fC.A.mC*A*fC*mU*fC*mU*C. | 50% |
| 20392 | 2275 | 1019 | G.mU.G.A.mC.mC.A.A.A.A.G.mU.A.TEG-Chl | 1020 | P.mU.A.fC.fU.fU.fU.fU.G.G.fU.fC.A.fC*A*fC*fU*fC*fU*C. | 28% |
| 20393 | 2296 | 1021 | G.mC.A.mC.mC.mU.mU.mU.mC.mU.A.G.A.TEG-Chl | 1022 | P.mU.fC.fU.A.G.A.A.A.G.G.fU.G.fC*A*A*fC*A*U. | 35% |
| 21429 | 2275 | 1023 | G.mU.G.A.mC.mC.A.A.A.A.G*mU*mA.Teg-Chl | 1024 | P.mU.A.fC.fU.fU.fU.fU.G.G.fU.fC.A.mC*A*fC*mU*fC*mU*C. | 36% |
| 21430 | 2275 | 1025 | G.mU.G.A.mC.mC.A.A.A.mA.A.G*mU*mA.Teg-Chl | 1026 | P.mU.A.fC.fU.fU.fU.fU.G.G.fU.mC.A.mC*A*mC*mU*mC*mU*C. | 31% |

Key
Chl = cholesterol with hydroxyprolinol linker
TEG-chl = cholesterol with TEG linker
m = 2'Ome
f = 2'fluoro
* = phosphorothioate llinkage
. = phosphodiester linkage

TABLE 6

TGfβ2 (Accession Number: Nm_001135599.1) sd-rxRNA sequences

| Oligo Number | Start Site | SEQ ID NO | Sense sequence | SEQ ID NO | Antisense sequence | % remaining expression (1 um, A549) |
|---|---|---|---|---|---|---|
| 14408 | 1324 | 1027 | G.G.mC.mU.mC.mU. mC.mC.mU.mU.mC. G.A.Chl | 1028 | P.mU.fC.G.A.A.G.G.A. G.A.G.mC.mC*A*mU*mU* mC*G*C. | 94% |
| 14409 | 1374 | 1029 | G.A.mC.A.G.G.A.A. mC.mC.mU.G.G.Chl | 1030 | P.mC.fC.A.G.G.fU.fU. fC.fC.fU.G.mU.mC*U* mU*A*mU*G. | n/a |
| 14410 | 946 | 1031 | mC.mC.A.A.G.G.A. G.G.mU.mU.mU.A. Chl | 1032 | P.mU.A.A.A.fC.fC.fU. fC.fC.fU.mU.G.G*mC* G*mU*A*G*U. | 90% |
| 14411 | 849 | 1033 | A.mU.mU.mU.mC.mC. A.mU.mC.mU.A.mC.A. Chl | 1034 | P.mU.G.fU.A.G.A.fU. G.G.A.A.A.mU*mC*A* mC*mC*mU*C. | 72% |
| 14412 | 852 | 1035 | mU.mC.mC.A.mU.mC. mU.A.mC.A.A.mC.A. Chl | 1036 | P.mU.G.fU.fU.G.fU.A. G.A.fU.G.G.A*A*A*mU* mC*A*C. | 76% |
| 14413 | 850 | 1037 | mU.mU.mU.mC.mC.A. mU.mC.mU.A.mC.A.A. Chl | 1038 | P.mU.fU.G.fU.A.G.A. fU.G.G.A.A.A*mU*mC* A*mC*mC*U. | 98% |
| 14414 | 944 | 1039 | mC.G.mC.mC.A.A.G. G.A.G.G.mU.mU.Chl | 1040 | P.mA.A.fC.fC.fU.fC. fC.fU.fU.G.G.mC.G* mU*A*G*mU.A*C. | 100% |
| 14415 | 1513 | 1041 | G.mU.G.G.mU.G.A. mU.mC.A.G.A.A.Chl | 1042 | P.mU.fU.fC.fU.G.A. fU.fC.A.fC.mC.A.mC* mU*G*G*mU*A*U. | n/a |
| 14416 | 1572 | 1043 | mC.mU.mC.mC.mU.G. mC.mU.A.A.mU.G.mU. Chl | 1044 | P.mA.fC.A.fU.fU.A.G. fC.A.G.G.A.G*A*mU* G*mU*G*G. | 100% |
| 14417 | 1497 | 1045 | A.mC.mC.mU.mC.mC. A.mC.A.mU.A.mU.A. Chl | 1046 | P.mU.A.fU.A.fU.G. G.A.G.G.mU*G*mC* mC*A*mU*C. | 73% |
| 14418 | 1533 | 1047 | A.A.G.mU.mC.mC.A. mC.mU.A.G.G.A.Chl | 1048 | P.MY.fC.fC.fU.A.G. fU.G.G.A.mC.mU.mU* mU*A*mU*A*G*U. | 98% |
| 14419 | 1514 | 1049 | mU.G.G.mU.G.A.mU. mC.A.G.A.A.A.Chl | 1050 | P.mU.fU.fU.fC.fU.G. A.fU.fC.A.mC.mC.A* mC*mU*G*G*mU*A. | 86% |
| 14420 | 1534 | 1051 | A.G.mU.mC.mC.A.mC. mU.A.G.G.A.A.Chl | 1052 | P.mU.fU.fC.fC.fU.A. G.fU.G.G.A.mC.mU*mU* mU*A*mU*A*G. | 99% |
| 14421 | 943 | 1053 | A.mC.G.mC.mC.A.A. G.G.A.G.G.mU.Chl | 1054 | P.mA.fC.fC.fU.fC.fC. fU.fU.G.G.mC.G.mU* A*G*mU*A*mC*U. | 41% |
| 18570 | 2445 | 1055 | mU.A.mU.mU.mU.A. mU.mU.G.mU.G.mU. A.Chl | 1056 | P.mU.A.fC.A.fC.A.A. fU.A.A.A.fU.A*A*fC* fU*fC*A*C. | 79% |
| 18571 | 2445 | 1057 | mU.mU.A.mU.mU.mU. A.mU.mU.G.mU.G.mU. A.Chl | 1058 | P.mU.A.fC.A.fC.A.A. fU.A.A.A.fU.A*A*fC* fU*fC*A*C. | 75% |
| 18572 | 2083 | 1059 | A.mU.C.A.G.mU.G. mU.mU.A.A.A.A.Chl | 1060 | P.mU.fU.fU.fU.A.A. fC.A.fC.fU.G.A.fU* G*A*A*fC*fC*A. | 47% |
| 18573 | 2083 | 1061 | mC.A.mU.mC.A.G.mU. G.mU.mU.A.A.A.A. Chl | 1062 | P.mU.fU.fU.fU.A.A. fC.A.fC.fU.G.A.fU* G*A*A*fC*fC*A. | 17% |

TABLE 6-continued

TGfβ2 (Accession Number: Nm_001135599.1) sd-rxRNA sequences

| Oligo Number | Start Site | SEQ ID NO | Sense sequence | SEQ ID NO | Antisense sequence | % remaining expression (1 um, A549) |
|---|---|---|---|---|---|---|
| 18574 | 2544 | 1063 | A.mU.G.G.mC.mU. A.A.G.G.A.A.Chl | 1064 | P.mU.fU.fC.fC.fU.fU. A.A.G.fC.A.U*fC*fC* A*fU*G*A. | 59% |
| 18575 | 2544 | 1065 | G.A.mU.G.G.mC.mU. mU.A.A.G.G.A.A. Chl | 1066 | P.mU.fU.fC.fC.fU.fU. A.A.G.fC.A.U*fC* fC*A*fU*G*A. | 141% |
| 18576 | 2137 | 1067 | mU.mU.G.mU.G.mU. mU.mC.mU.G.mU.mU. A.Chl | 1068 | P.mU.A.A.fC.A.G.A.A. fC.A.fC.A*A*fC*fU* fU*fC*C. | 77% |
| 18577 | 2137 | 1069 | mU.mU.mU.G.mU.G. mU.mU.mC.mU.mU.G.mU. mU.A.Chl | 1070 | P.mU.A.A.fC.A.G.A.A. fC.A.fC.A*A*fC* fU*fU*fC*C. | 59% |
| 18578 | 2520 | 1071 | A.A.A.mU.A.mC.mU. mU.mU.G.mC.mC.A. Chl | 1072 | P.mU.G.G.fC.A.A.A.G. fU.A.fU.fU.fU*G*G* fU*fC*fU*C. | 75% |
| 18579 | 2520 | 1073 | mC.A.A.A.mU.A.mC. mU.mU.mU.G.mC.mC. A.Chl | 1074 | P.mU.G.G.fC.A.A.A.G. fU.A.fU.fU.fU*G*G* fU*fC*fU*C. | 55% |
| 18580 | 3183 | 1075 | mC.mU.mU.G.mC.A. mC.mU.A.mC.A.A.A. Chl | 1076 | P.mU.fU.fU.G.fU.A.G. fU.G.fC.A.A.G*fU*fC* A*A*A*C. | 84% |
| 18581 | 3183 | 1077 | A.mC.mU.mU.G.mC.A. mC.mU.A.mC.A.A.A. Chl | 1078 | P.mU.fU.fU.G.fU.A.G. fU.G.fC.A.A.G*fU*fC* A*A*A*C. | 80% |
| 18582 | 2267 | 1079 | G.A.A.mU.mU.A. mU.mU.A.G.mU.A.Chl | 1080 | P.mU.A.fC.fU.A.A.fU. A.A.A.fU.fU.fC*fU* fU*fC*fC*A*G. | 82% |
| 18583 | 2267 | 1081 | A.G.A.A.mU.mU.mU. A.mU.mU.A.G.mU.A. Chl | 1082 | P.mU.A.fC.fU.A.A.fU. A.A.A.fU.fU.fC*fU* fU*fC*fC*A*G. | 67% |
| 18584 | 3184 | 1083 | mU.mU.G.mC.A.mC. mU.A.mC.A.A.A.A. Chl | 1084 | P.mU.fU.fU.fU.G.fU. A.G.fU.G.fC.A.A*G* fU*fC*A*A*A. | 77% |
| 18585 | 3184 | 1085 | mC.mU.mU.G.mC.A. mC.mU.A.mC.A.A.A. A.Chl | 1086 | P.mU.fU.fU.fU.G.fU. A.G.fU.G.fC.A.A*G* fU*fC*A*A*A. | 59% |
| 18586 | 2493 | 1087 | A.mU.A.A.A.A.mC.A. G.G.mU.G.A.Chl | 1088 | P.mU.fC.A.fC.fC.fU. G.fU.fU.fU.fU.A.fU* fU*fU*fU*fC*fC*A. | 84% |
| 18587 | 2493 | 1089 | A.A.mU.A.A.A.A.mC. A.G.G.mU.G.A.Chl | 1090 | P.mU.fC.A.fC.fC.fU. G.fU.fU.fU.fU.A.fU* fU*fU*fU*fC*fC*A. | 70% |
| 18588 | 2297 | 1091 | G.A.mC.A.A.mC.A.A. mC.A.A.mC.A.Chl | 1092 | P.mU.G.fU.fU.G.fU. fU.G.fU.fU.G.fU.fC* G*fU*fU*G*fU*U. | 40% |
| 18589 | 2046 | 1093 | A.mU.G.C.mU.mU.G. mU.A.A.mC.A.A.Chl | 1094 | P.mU.fU.G.fU.fU.A. fC.A.A.G.fC.A.fU*fC* A.fU*fC*G*U. | 39% |
| 18590 | 2531 | 1095 | mC.A.G.A.A.A.mC. mU.mC.A.mU.G.A.Chl | 1096 | P.mU.fC.A.fU.G.A.G. fU.fU.fU.fC.fU.G*G* fC*A*A*G. | 56% |
| 18591 | 2389 | 1097 | G.mU.A.mU.mU.G.mC. mU.A.mU.G.mC.A.Chl | 1098 | P.mU.G.fC.A.fU.A.G. fC.A.A.fU.A.fC*fU* A*A*A*A. | 64% |

TABLE 6-continued

TGfβ2 (Accession Number: Nm_001135599.1) sd-rxRNA sequences

| Oligo Number | Start Site | SEQ ID NO | Sense sequence | SEQ ID NO | Antisense sequence | % remaining expression (1 um, A549) |
|---|---|---|---|---|---|---|
| 18592 | 2530 | 1099 | mC.mC.A.G.A.A.A.mC.mU.mC.A.mU.A.Chl | 1100 | P.mU.A.fU.G.A.G.fU.fU.fU.fC.fU.G.G*fC*A*A*A*G*U. | 44% |
| 18593 | 2562 | 1101 | A.mC.mU.mC.A.A.A.mC.G.A.G.mC.A.Chl | 1102 | P.mU.G.fC.fU.fC.G.fU.fU.fU.G.A.G.fU*fU*fC*A*A*G*U. | 87% |
| 18594 | 2623 | 1103 | A.mU.A.mU.G.A.mC.mC.G.A.G.A.A.Chl | 1104 | P.mU.fU.fC.fU.fC.G.G.fU.fC.A.fU.A.fU*A*fU*A*A*C. | 69% |
| 18595 | 2032 | 1105 | mC.G.A.mC.G.A.mC.A.A.mC.G.A.A.Chl | 1106 | P.mU.fU.fC.G.fU.fU.G.fU.fC.G.fU.fC.G*fU*fC*A*fU*fC*A. | 55% |
| 18596 | 2809 | 1107 | G.mU.A.A.A.mC.mC.A.G.mU.G.A.A.Chl | 1108 | P.mU.fU.fC.A.fC.fU.G.G.fU.fU.fUA.fC*fU*A*A*A*fC*U. | 58% |
| 18597 | 2798 | 1109 | mU.mU.G.mU.mC.A.G.mU.mU.mU.A.G.A.Chl | 1110 | P.mU.fC.fU.A.A.A.fC.fU.G.A.fC.A.A*A*G*A*A*fC*C. | 38% |
| 18598 | 2081 | 1111 | mU.mC.A.mU.mC.A.G.mU.G.mU.mU.A.A.Chl | 1112 | P.mU.fU.A.A.fC.A.fC.fU.G.A.fU.G.A*A*fC*fC*A*G. | 25% |
| 18599 | 2561 | 1113 | A.A.mC.mU.mC.A.A.A.mC.G.A.G.A.Chl | 1114 | P.mU.fC.fU.fC.G.fU.fU.fU.G.A.G.fU.fU*fC*A*A*G*fU*U. | 57% |
| 18600 | 2296 | 1115 | mC.G.A.mC.A.A.mC.A.A.mC.A.A.A.Chl | 1116 | P.mU.fU.fU.G.fU.fU.G.fU.fU.G.fU.fC.G*fU*fU*G*fU*fU*C. | 69% |
| 18601 | 2034 | 1117 | A.mC.G.A.mC.A.A.mC.G.A.mU.G.A.Chl | 1118 | P.mU.fC.A.fU.fC.G.fU.fU.G.fU.fC.G.fU*fC*G*fU*fC*A*fU. | 22% |
| 18602 | 2681 | 1119 | G.mC.mU.G.mC.mC.mU.A.A.G.G.A.A.Chl | 1120 | P.mU.fU.fC.fC.fU.fU.A.G.G.fC.A.G.fC*fU*G*A*fU*A*C. | 43% |
| 18603 | 2190 | 1121 | A.mU.mU.mC.mU.A.mC.A.mU.mU.mU.mC.A.Chl | 1122 | P.mU.G.A.A.A.fU.G.fU.A.G.A.A.fU*A*A*G*G*fC*C. | 128% |
| 20604 | 2083 | 1123 | mC.A.mU.mC.A.G.mU.G.mU.mU.A.A.A.A.Chl | 1124 | P.mU.fU.fU.fU.A.A.fC.A.fC.fU.G.A.mU*G*A*A*mC*mC*A. | 19% |
| 20605 | 2083 | 1125 | mC.A.mU.mC.A.G.mU.G.mU.mU.A.A.A.A.Chl | 1126 | P.mU.fU.fU.fU.A.A.fC.A.fC.fU.G.A.mU*G*A*A*fC*mC*A. | 20% |
| 20606 | 2083 | 1127 | mC.A.mU.mC.A.G.mU.G.mU.mU.A.A.A.A.Chl | 1128 | P.mU.U.U.U.A.A.C.A.C.U.G.A.mU*G*A*A*mC*mC*A. | 82% |
| 20607 | 2083 | 1129 | mC.A.mU.mC.A.G.mU.G.mU.mU.A.A.A.A.Chl | 1130 | P.mU.fU.fU.fU.A.A.fC.A.fC.fU.G.A.fU*mG*mA*mA*fC*fC*A. | 59% |
| 21722 | 2081 | 1131 | mU.mC.A.mU.mC.A.G.mU.G.mU.mU.A.A.Chl | 1132 | P.mU.fU.A.A.fC.A.fC.fU.G.A.fU.G.A*A*mC*mC*A*A*G. | 34% |
| 21723 | 2081 | 1133 | mU.mC.A.mU.mC.A.G.mU.G.mU.mU.A.A.Chl | 1134 | P.mU.fU.A.A.fC.A.fC.fU.G.A.fU.G.mA*A*mC*mC*mA*mA*G. | 53% |

TABLE 6-continued

TGfβ2 (Accession Number: Nm_001135599.1) sd-rxRNA sequences

| Oligo Number | Start Site | SEQ ID NO | Sense sequence | SEQ ID NO | Antisense sequence | % remaining expression (1 um, A549) |
|---|---|---|---|---|---|---|
| 21724 | 2081 | 1135 | mU.mC.A.mU.mC.A.G. mU.G.mU.mU.A.A.Chl | 1136 | P.mU.fU.A.A.fC.A.fC. fU.G.A.mU.G.mA*mA* mC*mC*mA*mA*G. | 48% |
| 21725 | 2081 | 1137 | mU.mC.A.mU.mC.A.G. mU.G.mU.mU.A.A.Chl | 1138 | P.mU.fU.A.A.fC.A.fC. fU.G.A.fU.G.A*A*fC* fC*mA*mA*G. | 45% |
| 21726 | 2081 | 1139 | mU.mC.A.mU.mC.A.G. mU.G.mU.mU.A.A.Chl | 1140 | P.mU.fU.A.A.fC.A.fC. fU.G.A.fU.G.mA*mA* fC*fC*mA*mA*G. | 54% |
| 21727 | 2081 | 1141 | mU.mC.A.mU.mC.A.G. mU.G.mU.mU*mA*mA* TEG-Chl | 1142 | P.mU.fU.A.A.fC.A.fC. fU.G.A.fU.G.A*A*fC. fC*A*A*G. | 29% |
| 21728 | 2081 | 1143 | mU*mC*A.mU.mC.A.G. mU.G.mU.mU*mA*mA. TEG-Chl | 1144 | P.mU.fU.A.A.fC.A.fC. fU.G.A.fU.G.A*A*fC. fC*A.*A*G. | 27% |
| 21729 | 2081 | 1145 | mU*mC*mA.mU.mC.mA. mG.mU.mG.mU.mU*mA* mA.TEG-Chl | 1146 | P.mU.fU.A.A.fC.A.fC. fU.G.A.fU.G.A*A*fC* fC*A*A*G. | 30% |
| 21375 | 2081 | 1147 | mU.mC.A.mU.mC.A.G. mU.G.mU.mU*mA*mA. TEG-Chl | 1148 | P.mU.fU.A.A.fC.A.fC. fU.G.A.fU.G.A*A*mC* mC*A*A*G. | 29% |
| 21376 | 2081 | 1149 | mU.mC.A.mU.mC.A.G. mU.G.mU.mU*mA*mA. TEG-Chl | 1150 | P.mU.fU.A.A.fC.A.fC. fU.G.A.fU.G.A*A*fC* fC*mA*mA*G. | 30% |
| 21377 | 2081 | 1151 | mU.mC.A.mU.mC.A.G. mU.G.mU.mU*mA*mA. TEG-Chl | 1152 | P.mU.fU.A.A.fC.A.fC. fU.G.A.fU.G.mA*mA* fC*fC*mA*mA*G. | 37% |
| 21378 | 2081 | 1153 | mU*mC*mA.mU.mC.mA. mG.mU.mG.mU.mU*mA* mA.TEG-Chl | 1154 | P.mU.fU.A.A.fC.A.fC. fU.G.A.fU.G.A*A*.mC* mC*A*A*G. | 32% |
| 21379 | 2081 | 1155 | mU*mC*mA*mU.mC.mA. mG.mU.mG.mU.mU*mA* mA.TEG-Chl | 1156 | P.mU.fU.A.A.fC.A.fC. fU.G.A.fU.G.A*A*fC* fC*mA*mA*G. | 31% |
| 21380 | 2081 | 1157 | mU*mC*mA.mU.mC.mA. mG.mU.mG.mU.mU*mA* mA.TEG-Chl | 1158 | P.mU.fU.A.A.fC.A.fC. fU.G.A.fU.G.mA*mA* fC*fC*mA*mA*G. | 39% |

Key
Chl = cholesterol with hydroxyprolinol linker
TEG-chl = cholesterol with TEG linker
m = 2'Ome
f = 2'fluoro
*= phosphorothioate linkage
. = phosphodiester linkage

TABLE 7

TGFβ1 (Accession Number: NM_000660.3)

| Oligo Number | Start Site | SEQ ID NO | Sense sequence | SEQ ID NO | Antisense sequence | % remaining expression (1 uM A549) |
|---|---|---|---|---|---|---|
| 14394 | 1194 | 1159 | G.mC.mU.A.A.mU.G.G. mU.G.G.A.A.Chl | 1160 | P.mU.fU.fC.fC.A.fC.fC. A.fU.fU.A.G.mC*mC*G* mC*G*G. | 24% |
| 14395 | 2006 | 1161 | mU.G.A.mU.mC.G.mU. G.mC.G.mC.mU.mC.Chl | 1162 | P.mG.A.G.fC.G.fC.A.fC. G.A.mU.mC.A*mU*G*mU* mU*G*G. | 79% |

TABLE 7-continued

TGFβ1 (Accession Number: NM_000660.3)

| Oligo Number | Start Site | SEQ ID NO | Sense sequence | SEQ ID NO | Antisense sequence | % remaining expression (1 uM A549) |
|---|---|---|---|---|---|---|
| 14396 | 1389 | 1163 | mC.A.A.mU.mU.mC.mC. mU.G.mC.G.A.Chl | 1164 | P.mU.fC.G.fC.fC.A.G.G. A.A.mU.U.G*mU*mU*G* mC*mU*G. | 77% |
| 14397 | 1787 | 1165 | A.G.mU.G.G.A.mU.C. mC.A.mC.G.A.Chl | 1166 | P.mU.fC.G.fU.G.G.A.fU. fC.fC.A.mC.mU*mU*mC* mC*A*G*C. | n/a |
| 14398 | 1867 | 1167 | mU.A.mC.A.G.mC.A.A. G.G.mU.mC.mC.Chl | 1168 | P.mG.G.A.fC.fC.fU.fU. G.fC.fU.G.mU.A*mC*mU* G*mC*G*U. | 82% |
| 14399 | 2002 | 1169 | A.A.mC.A.mU.G.A.mU. mC.G.mU.G.mC.Chl | 1170 | P.mG.fC.A.fC.G.A.fU. fC.A.fU.G.mU.mU*G*G* A*mC*A*G. | n/a |
| 14400 | 2003 | 1171 | A.mC.A.mU.G.A.mU. mC.G.mU.G.mC.G.Chl | 1172 | P.mC.G.fC.A.fC.G.A.fU. fC.A.mU.G.mU*mU*G*G* A*mC*A. | n/a |
| 14401 | 1869 | 1173 | mC.A.G.mC.A.A.G.G. mU.mC.mC.mU.G.Chl | 1174 | P.mC.A.G.G.A.fC.fC.fU. fU.G.mC.mU.G*mU*A*mC* mU*G*C. | 82% |
| 14402 | 2000 | 1175 | mC.mC.A.A.mC.A.mU. G.A.mU.mC.G.mU.Chl | 1176 | P.mA.fC.G.A.fU.fC.A. fU.G.fU.mU.G.G*A*mC* A*G*mC*U. | 66% |
| 14403 | 986 | 1177 | A.G.mC.G.G.A.A.G. mC.G.mC.A.mU.Chl | 1178 | P.mA.fU.G.fC.G.fC.fU. fU.fC.fC.G.mC.mU*mU* mC*A*mC*mC*A. | 78% |
| 14404 | 995 | 1179 | G.mC.A.mU.mC.G.A.G. G.mC.mC.A.mU.Chl | 1180 | P.mA.fU.G.G.fC.fC.fU. fC.G.A.mU.G.mC*G*mC* mU*mU*mC*C. | 79% |
| 14405 | 963 | 1181 | G.A.mC.mU.A.mU.mC. G.A.mC.A.mU.G.Chl | 1182 | P.mC.A.fU.G.fU.fC.G.A. fU.A.G.mU.mC*mU*mU*G* mC*A*G. | 80% |
| 14406 | 955 | 1183 | A.mC.mC.mU.G.mC.A. A.G.A.mC.mU.A.Chl | 1184 | P.mU.A.G.fU.fC.fU.fU. G.fC.A.G.G.mU*G*G*A* mU*A*G. | 88% |
| 14407 | 1721 | 1185 | G.mC.mU.mC.mC.A.mC. G.G.A.G.A.A.Chl | 1186 | P.mU.fU.fC.fU.fC.fC. G.fU.G.G.A.G.mC*mU*G* A*A*G*C. | n/a |
| 18454 | 1246 | 1187 | mC.A.mC.A.G.mC.A. mU.A.mU.A.mU.A.Chl | 1188 | P.mU.A.fU.A.fU.A.fU. G.fC.fU.G.fU.G*fU*G* fU*A*fC*U. | 58% |
| 18455 | 1248 | 1189 | mC.A.G.mC.A.mU.A. mU.A.mU.A.mU.A.Chl | 1190 | P.mU.A.fU.A.fU.A.fU. A.fU.G.fC.fU.G*fU*G* fU*G*fU*A. | 87% |
| 18456 | 1755 | 1191 | G.mU.A.mC.A.mU.mU. G.A.mC.mU.mU.A.Chl | 1192 | P.mU.A.A.G.fU.fC.A.A. fU.G.fU.A.fC*A*G*fC* fU*G*C. | 107% |
| 18457 | 1755 | 1193 | mU.G.mU.A.mC.A.mU. mU.G.A.mC.mU.mU.A. Chl | 1194 | P.mU.A.A.G.fU.fC.A.A. fU.G.fU.A.fC*A*G*fC* fU*G*C. | 77% |
| 18458 | 1708 | 1195 | A.A.mC.mU.A.mU.mU. G.mC.mU.mU.mC.A.Chl | 1196 | P.mU.G.A.A.G.fC.A.A. fU.A.G.fU.fU*G*G*fU* G*fU*C. | 75% |
| 18459 | 1708 | 1197 | mC.A.A.mC.mU.A.mU. mU.G.mC.mU.mU.mC.A. Chl | 1198 | P.mU.G.A.A.G.fC.A.A. fU.A.G.fU.fU*G*G*fU* G*fU*C. | 73% |

TABLE 7-continued

TGFβ1 (Accession Number: NM_000660.3)

| Oligo Number | Start Site | SEQ ID NO | Sense sequence | SEQ ID NO | Antisense sequence | % remaining expression (1 uM A549) |
|---|---|---|---|---|---|---|
| 18460 | 1250 | 1199 | G.mC.A.mU.A.mU.A. mU.A.mU.G.mU.A.Chl | 1200 | P.mU.A.fC.A.fU.A.fU. A.fU.A.fU.G.fC*fU*G* fU*G*fU*G. | n/a |
| 18461 | 1754 | 1201 | mU.G.mU.A.mC.A.mU. mU.G.A.mC.mU.A.Chl | 1202 | P.mU.A.G.fU.fC.A.A.fU. G.fU.A.fC.A*G*fC*fU* G*fC*C. | 91% |
| 18462 | 1754 | 1203 | mC.mU.G.mU.A.mC.A. mU.mU.G.A.mC.mU.A. Chl | 1204 | P.mU.A.G.fU.fC.A.A.fU. G.fU.A.fC.A*G*fC*fU* G*fC*C. | 92% |
| 18463 | 1249 | 1205 | A.G.mC.A.mU.A.mU.A. mU.A.mU.G.A.Chl | 1206 | P.mU.fC.A.fU.A.fU.A. fU.A.fU.G.fC.fU*G*fU* G*fU*G*U. | n/a |
| 18464 | 1383 | 1207 | mC.A.G.mC.A.A.mC.A. A.mU.mU.mC.A.Chl | 1208 | P.mU.G.A.A.fU.fU.G. fU.fU.G.fC.fU.G*fU*A* fU*fU*fU*C. | 77% |
| 18465 | 1251 | 1209 | mC.A.mU.A.mU.A.mU. A.mU.G.mU.mU.A.Chl | 1210 | P.mU.A.A.fC.A.fU.A. DU.A.fU.A.fU.G*fC*fU* G*fU*G*U. | 84% |
| 18466 | 1713 | 1211 | mU.mU.G.mC.mU.mU. mC.A.G.mC.mU.mC.A. Chl | 1212 | P.mU.G.A.G.fC.fU.G.A. A.G.fC.A.A*fU*A*G*fU* fU*G. | n/a |
| 18467 | 1713 | 1213 | A.mU.mU.G.mC.mU.mU. mC.A.G.mC.mU.mC.A. Chl | 1214 | P.mU.G.A.G.fC.fU.G.A. A.G.fC.A.A*fU*A*G*fU* fU*G. | 83% |
| 18468 | 1247 | 1215 | A.mC.A.G.mC.A.mU.A. mU.A.mU.A.A.Chl | 1216 | P.mU.fU.A.fU.A.fU.A. fU.G.fC.fU.G.fU*G*fU* G*fU*A*C. | 96% |
| 18469 | 1712 | 1217 | A.mU.mU.G.mC.mU.mU. mC.A.G.mC.mU.A.Chl | 1218 | P.mU.A.G.fC.fU.G.A.A. G.fC.A.A.fU*A*G*fU* fU*G*G. | 90% |
| 18470 | 1712 | 1219 | mU.A.mU.mU.G.mC.mU. mU.mC.A.G.mC.mU.A. Chl | 1220 | P.mU.A.G.fC.fU.G.A.A. G.fC.A.A.fU*A*G*fU* fU*G*G. | 98% |
| 18471 | 1212 | 1221 | mC.A.A.G.mU.mU.mC. A.A.G.mC.A.A.Chl | 1222 | P.mU.fU.G.fC.fU.fU.G. A.A.fC.fU.fU.G*fU*fC* A*fU*A*G. | n/a |
| 18472 | 1222 | 1223 | mC.A.G.A.G.mU.A.mC. A.mC.A.mC.A.Chl | 1224 | P.mU.G.fU.G.fU.G.fU. A.fC.fU.fC.fU.G*C*fU* fU*G*A*A. | 45% |
| 18473 | 1228 | 1225 | A.mC.A.mC.A.mC.A.G. mC.A.mU.A.A.Chl | 1226 | P.mU.fU.A.fU.G.fC.fU. G.fU.G.fU.G.fU*A*fC* fU*fC*fU*G. | 36% |
| 18474 | 1233 | 1227 | mC.A.G.mC.A.mU.A. mU.A.mU.A.mU.A.Chl | 1228 | P.mU.A.fU.A.fU.A.fU. A.fU.G.fC.fU.G*fU*G* fU*G*fU*A. | 68% |
| 18475 | 1218 | 1229 | mU.mC.A.A.G.mC.A.G. A.G.mU.A.A.Chl | 1230 | P.mU.fU.A.fC.fU.fC.fU. G.fC.fU.fU.G.A*A*fC* fU*fU*G*U. | 64% |
| 18476 | 1235 | 1231 | A.G.mC.A.mU.A.mU.A. mU.A.mU.G.A.Chl | 1232 | P.mU.fC.A.fU.A.fU.A. fU.A.fU.G.fC.fU*G*fU* G*fU*G*U. | 78% |
| 18477 | 1225 | 1233 | A.G.A.G.mU.A.mC.A. mC.A.mC.A.A.Chl | 1234 | P.mU.fU.G.fU.F.fU.G. fU.A.fC.fU.fC.fU*G* fC*fU*fU*G*A. | 92% |

TABLE 7-continued

TGFβ1 (Accession Number: NM_000660.3)

| Oligo Number | Start Site | SEQ ID NO | Sense sequence | SEQ ID NO | Antisense sequence | % remaining expression (1 uM A549) |
|---|---|---|---|---|---|---|
| 18478 | 1221 | 1235 | A.A.G.mC.A.G.A.G. mU.A.mC.A.A.Chl | 1236 | P.mU.fU.G.fU.A.fC. fC.fU.G.fC.fU.fU*G*A* A*fC*fU*U. | 103% |
| 18479 | 1244 | 1237 | mU.mU.mC.A.A.mC.A. mC.A.mU.mC.A.A.Chl | 1238 | P.mU.fU.G.fU.G.fU. G.fU.fU.G.A.A*G*A*A* fC*A*U. | 84% |
| 18480 | 1224 | 1239 | A.G.mC.A.G.A.G.mU. A.mC.A.mC.A.Chl | 1240 | P.mU.G.fU.G.fU.A.fC. fU.fC.fU.G.fC.fU*fU* G*A*A*fC*U. | 37% |
| 18481 | 1242 | 1241 | A.mU.A.mU.A.mU.G. mU.mU.mC.mU.mU.A. Chl | 1242 | P.mU.A.A.G.A.A.fC.A. fU.A.fU.A.fU*A*fU*G* fC*fU*G. | 62% |
| 18482 | 1213 | 1243 | G.A.mC.A.A.G.mU.mU. mC.A.A.G.A.Chl | 1244 | P.mU.fC.fU.fU.G.A.A. fC.fU.fU.G.fU.fC*A* fU*A*G*A*U. | 47% |
| 18483 | 1760 | 1245 | mU.mU.A.A.A.G.A.mU. G.G.A.G.A.Chl | 1246 | P.mU.fC.fU.fC.fC.A.fU. fC.fU.fU.fU.A.A*fU*G* G*G*G*C. | 69% |
| 18484 | 1211 | 1247 | mC.mU.A.mU.G.A.mC. A.A.G.mU.mU.A.Chl | 1248 | P.mU.A.A.fC.fU.fU.G. fU.fC.A.fU.A.G*A*fU* fU*fU*fC*G. | n/a |
| 19411 | 1212 | 1249 | mC.A.A.mC.G.A.A.A. mU.mC.mU.A.A.Chl | 1250 | P.mU.fU.A.G.A.fU.fU. fU.fC.G.fU.fU.G*fU*G* G*G*fU*fU. | 52% |
| 19413 | 1228 | 1253 | A.A.G.mU.mU.mC.A.A. G.mC.A.G.A.Chl | 1254 | P.mU.fC.fU.G.fC.fU.fU. G.A.A.fC.fU.fU*G*fU* fC*A*fU*A. | n/a |
| 19414 | 1233 | 1255 | mC.A.A.G.mC.A.G.A. G.mU.A.mC.A.Chl | 1256 | P.mU.G.fU.A.fC.fU.fC. fU.G.fC.fU.fU.G*A*A* fC*fU*fU*G. | 41% |
| 19415 | 1218 | 1257 | A.A.mU.mC.mU.A.mU. G.A.mC.A.A.A.Chl | 1258 | P.mU.fU.fU.G.fU.fC.A. fU.A.G.A.fU.fU*fU*fC* G*fU*fU*G. | 104% |
| 19416 | 1244 | 1259 | mC.A.mC.A.mC.A.G. mC.A.mU.A.mU.A.Chl | 1260 | P.mU.A.fU.A.fU.G.fC. fU.G.fU.G.fU.G*fU*A* fC*fU*fC*fU. | 31% |
| 19417 | 655 | 1261 | G.A.A.A.mU.A.mU.A. G.mC.A.A.A.Chl | 1262 | P.mU.fU.fU.G.fC.fU.A. fU.A.fU.fU.fU.fC*fU* G*G*fU*A*G. | n/a |
| 19418 | 644 | 1263 | G.A.A.mC.A.mU.mC.mU. A.mC.mC.A.G.A.Chl | 1264 | P.mU.fC.fU.G.G.fU.A.G. A.G.fU.fU.fC*fU*A*fC* G*fU*G. | n/a |
| 19419 | 819 | 1265 | G.mC.A.A.A.G.A.mU. A.A.mU.G.A.Chl | 1266 | P.mU.fC.A.fU.fU.A.fU. fC.fU.fU.fU.G.fC*fU* G*fU*fC*A*C. | n/a |
| 19420 | 645 | 1267 | A.A.mC.mU.mC.mU.A. mC.mC.A.G.A.A.Chl | 1268 | P.mU.fU.fC.fU.G.G.fU. A.G.A.G.fU.fU*fU*fU* A*fC*G*U. | n/a |
| 19421 | 646 | 1269 | A.mC.mU.mC.mU.A.mC. mC.A.G.A.A.A.Chl | 1270 | P.mU.fU.fU.fC.fU.G.G. fU.A.G.A.G.fU*fU*fC* fU*A*fC*G. | n/a |
| 19422 | 816 | 1271 | A.mC.A.G.mC.A.A.A. G.A.mU.A.A.Chl | 1272 | P.mU.fU.fU.A.fU.fC.fU. fU.G.fC.fU.G.fU*fC*A* fC*A*A*G. | n/a |

TABLE 7-continued

TGFβ1 (Accession Number: NM_000660.3)

| Oligo Number | Start Site | SEQ ID NO | Sense sequence | SEQ ID NO | Antisense sequence | % remaining expression (1 uM A549) |
|---|---|---|---|---|---|---|
| 19423 | 495 | 1273 | mC.A.A.mU.mC.mU.A. mU.G.A.mC.A.A.Chl | 1274 | P.mU.fU.G.fU.fC.A.fU. A.G.A.fU.fU.G*fC*G* fU*fU*G*U. | n/a |
| 19424 | 614 | 1275 | A.A.A.mU.mU.mC.A.A. G.mU.mC.A.A.Chl | 1276 | P.mU.fU.fU.fC.fU.fU. G.A.A.fU.fC.fU*fC*fU* G*fC*A*G. | n/a |
| 19425 | 627 | 1277 | mC.mU.G.mU.G.A.G. mC.A.A.mC.A.Chl | 1278 | P.mU.G.fU.fU.G.fC.fU. fC.fC.A.fC.A.G*fU*fU* G*A*fC*U. | n/a |
| 19426 | 814 | 1279 | mU.G.A.mC.A.G.mC.A. A.A.G.A.A.Chl | 1280 | P.mU.fU.fC.fU.fU.fU. G.fC.fU.fU.G.fU.fC.A*fC* A*A*G*A*G. | n/a |
| 19427 | 501 | 1281 | A.mU.G.A.mC.A.A.A. A.mC.mC.A.A.Chl | 1282 | P.mU.fU.G.G.fU.fU. fU.G.fU.fU.fU.fC.A.fU*A*G* A*fU*fU*G. | n/a |
| 19428 | 613 | 1283 | G.A.G.A.mU.mU.mC.A. A.G.mU.mC.A.Chl | 1284 | P.mU.G.A.fC.fU.fU.G. A.A.fU.fC.fU.fC*fU*G* fC*A*G*G. | n/a |
| 21240 | 1244 | 1285 | mC.A.mC.A.mC.A.G. mC.A.mU.A.mU.A.Chl | 1286 | P.mU.A.fU.A.fU.G.fC. fU.G.fU.G.fU.G*mU*A* mC*mU*mC*U. | 0.875 |
| 21241 | 1244 | 1287 | mC.A.mC.A.mC.A.G. mC.A.mU.A.mU.A.Chl | 1288 | P.mU.A.fU.A.fU.G.fC. fU.G.fU.G.fU.G*mU*mA* mU*mU*mC*U. | 0.88 |
| 21242 | 1244 | 1289 | mC.A.mC.A.mC.A.G. mC.A.mU.A.mU.A.Chl | 1290 | P.mU.A.fU.A.fU.G.fC. fU.G.fU.G.fU.mG*mU* mA*mC*mU*mC*U. | 0.635 |
| 21243 | 1244 | 1291 | mC.A.mC.A.mC.A.G. mC.A.mU.A.mU.A.Chl | 1292 | P.mU.A.fU.A.fU.G.fC. fU.G.fU.G.fU.mG*fU*mA* fC*mU*fC*U. | 0.32 |
| 21244 | 1244 | 1293 | mC.A.mC.A.mC.A.G. mC.A.mU.A.mU.A.Chl | 1294 | P.mU.A.fU.A.fU.G.fC. fU.G.fU.G.fU.G*fU*A* fC*mU*mC*U. | 0.36 |
| 21245 | 1244 | 1295 | mC.A.mC.A.mC.A.G. mC.A.mU.A*mU*mA. TEG-Chl | 1296 | P.mU.A.fU.A.fU.G.fC. fU.G.fU.G.fU.G*fU*A* fC*fU*fC*fU. | 0.265 |
| 21246 | 1244 | 1297 | mC*mA*mC.A.mC.A.G. mC.A.mU.A*mU*mA. TEG-Chl | 1298 | P.mU.A.fU.A.fU.G.fC. fU.G.fU.G.fU.G*fU*A* fC*fU*fC*fU. | 0.334 |
| 21247 | 1244 | 1299 | mC*mA*mC.mA.mC.mA. mG.mC.mA.mU.mA*mU* mA.TEG-Chl | 1300 | P.mU.A.fU.A.fU.G.fC. fU.G.fU.G.fU.G*fU*A* fC*fU*fC*fU. | 0.29 |
| 21248 | 614 | 1301 | mA.G.A.mU.mU.mC.A. A.G.mU.mC*mA*mA. TEG-Chl | 1302 | P.mU.fU.G.A.fC.fU.fU. G.A.A.fU.fC.fU*fC*fU* G*fC*fU*U. | n/a |
| 20608 | 1244 | 1305 | mC.A.mC.A.mC.A.G. mC.A.mU.A.mU.A.Chl | 1306 | P.mU.A.fU.A.fU.G.fC. fU.G.fU.G.mU.G*mU*A* mC*mU*mC*U. | 79% |
| 20609 | 1244 | 1307 | mC.A.mC.A.mC.A.G. mC.A.mU.A.mU.A.Chl | 1308 | P.mU.A.fU.A.fU.G.fC. fU.G.fU.G.mU.G*fU*A* mC*fU*mC*U. | 60% |
| 20610 | 1244 | 1309 | mC.A.mC.A.mC.A.G. mC.A.mU.A.mU.A.Chl | 1310 | P.mU.A.U.A.U.G.C.U.G. U.G.mU.G*mU*A*mC*mU* mC*U. | 93% |

TABLE 7-continued

TGFβ1 (Accession Number: NM_000660.3)

| Oligo Number | Start Site | SEQ ID NO | Sense sequence | SEQ ID NO | Antisense sequence | % remaining expression (1 uM A549) |
|---|---|---|---|---|---|---|
| 20611 | 1244 | 1311 | mC.A.mC.A.mC.A.G. mC.A.mU.A.mU.A.Chl | 1312 | P.mU.A.fU.A.fU.G.fC. fU.G.fU.G.mU.mG*mU* mA*mC*mU*mC*U. | n/a |
| 21374 | 614 | 1313 | mC*mA*mC.mA.mC.mA. mG.mC.mA.mU.mA*mU* mA.TEG-Chl | 1314 | P.mU.A.fU.A.fU.G.fC. fU.G.fU.G.fU.mG*fU* mA*fC.mU*fC*U. | 24% |

Chl = cholesterol with hydroxyprolinol linker
TEG-chl = cholesterol with TEG linker
m = 2'Ome
f = 2'fluoro
\* = phosphorothioate linkage
. = phosphodiester linkage

TABLE 8

Examples of VEGF (Accession No. NM_001171623.1) sd-rxRNA® sequences

| Oligo ID | Gene Region | Ref Pos | SEQ ID | Sense sequence | SEQ ID | Antisense sequence | % remaining mRNA expression (qPCR, 1 uM sd-rxRNA®, Hek293) |
|---|---|---|---|---|---|---|---|
| 19850 | CDS | 1389 | 1315 | GAUGAGCUUCCUA | 1316 | UAGGAAGCUCAUCUCUCCU | 161% |
| 19851 | 3'UTR | 1853 | 1317 | AGAACAGUCCUUA | 1318 | UAAGGACUGUUCUGUCGAU | 38% |
| 19852 | 3'UTR | 1854 | 1319 | GAACAGUCCUUAA | 1320 | UUAAGGACUGUUCUGUCGA | 124% |
| 19853 | 3'UTR | 1857 | 1321 | CAGUCCUUAAUCA | 1322 | UGAUUAAGGACUGUUCUGU | 124% |
| 19854 | 3'UTR | 1859 | 1323 | GUCCUUAAUCCAA | 1324 | UUGGAUUAAGGACUGUUCU | n/a |
| 19855 | 3'UTR | 1863 | 1325 | UUAAUCCAGAAAA | 1326 | UUUUCUGGAUUAAGGACUG | 120% |
| 19856 | 3'UTR | 2183 | 1327 | UGUUAUUGGUGUA | 1328 | UACACCAAUAACAUUAGCA | 114% |
| 19857 | 3'UTR | 2790 | 1329 | UUGAAACCACUAA | 1330 | UUAGUGGUUUCAAUGGUGU | 136% |
| 19858 | 3'UTR | 2931 | 1331 | GAGAAAGAGAAA | 1332 | UUUCUCUUUUCUCUGCCUC | 103% |
| 19859 | 3'UTR | 2932 | 1333 | AGAAAGAGAAAA | 1334 | UUUUCUCUUUUCUCUGCCU | 106% |
| 19860 | 3'UTR | 2933 | 1335 | GAAAAGAGAAAGA | 1336 | UCUUUCUCUUUUCUCUGCC | 115% |
| 19861 | 3'UTR | 3199 | 1337 | ACACUCAGCUCUA | 1338 | UAGAGCUGAGUGUUAGCAA | 123% |
| 19862 | 3'UTR | 3252 | 1339 | AAAUAAGGUUUCA | 1340 | UGAAACCUUAUUUCAAAGG | 131% |
| 19863 | 3'UTR | 3427 | 1341 | AAUCUCUCUCCUA | 1342 | UAGGAGAGAGAUUUAGUAU | 103% |
| 19864 | 3'UTR | 3429 | 1343 | UCUCUCUCCUUUA | 1344 | UAAAGGAGAGAGAUUUAGU | 136% |
| 19865 | 3'UTR | 3430 | 1345 | CUCUCUCCUUUUA | 1346 | UAAAAGGAGAGAGAUUUAG | 130% |
| 19866 | 3'UTR | 3471 | 1347 | AUUGGUGCUACUA | 1348 | UAGUAGCACCAAUAAAUAA | 125% |
| 19867 | 3'UTR | 3476 | 1349 | UGCUACUGUUUAA | 1350 | UUAAACAGUAGCACCAAUA | 93% |
| 19868 | 3'UTR | 1852 | 1351 | CAGAACAGUCCUA | 1352 | UAGGACUGUUCUGUCGAUG | 83% |
| 19869 | CDS | 1343 | 1353 | UGCAGAUUAUGCA | 1354 | UGCAUAAUCUGCAUGGUGA | n/a |
| 19870 | CDS | 1346 | 1355 | GAUUAUGCGGAUA | 1356 | UAUCCGCAUAAUCUGCAUG | n/a |
| 19871 | CDS | 1352 | 1357 | UGCGGAUCAAACA | 1358 | UGUUUGAUCCGCAUAAUCU | 74% |
| 19872 | 3'UTR | 1985 | 1359 | GGAUUCGCCAUUA | 1360 | UAAUGGCGAAUCCAAUUCC | n/a |

TABLE 8-continued

Examples of VEGF (Accession No. NM_001171623.1) sd-rxRNA ® sequences

| Oligo ID | Gene Region | Ref Pos | SEQ ID | Sense sequence | SEQ ID | Antisense sequence | % remaining mRNA expression (qPCR, 1 uM sd-rxRNA ®, Hek293) |
|---|---|---|---|---|---|---|---|
| 19873 | 3'UTR | 2210 | 1361 | UUGACUGCUGUGA | 1362 | UCACAGCAGUCAAAUACAU | n/a |
| 19874 | 3'UTR | 2447 | 1363 | CAGAAAGACAGAA | 1364 | UUCUGUCUUUCUGUCCGUC | n/a |
| 19875 | 3'UTR | 2792 | 1365 | GAAACCACUAGUA | 1366 | UACUAGUGGUUUCAAUGGU | n/a |
| 19876 | 3'UTR | 2794 | 1367 | AACCACUAGUUCA | 1368 | UGAACUAGUGGUUUCAAUG | n/a |
| 19877 | 3'UTR | 3072 | 1369 | UAUCUUUUGCUCA | 1370 | UGAGCAAAAGAUACAUCUC | n/a |
| 19878 | 3'UTR | 3073 | 1371 | AUCUUUUGCUCUA | 1372 | UAGAGCAAAAGAUACAUCU | n/a |
| 19879 | 3'UTR | 3162 | 1373 | UCACUAGCUUAUA | 1374 | UAUAAGCUAGUGACUGUCA | n/a |
| 19880 | 3'UTR | 3163 | 1375 | CACUAGCUUAUCA | 1376 | UGAUAAGCUAGUGACUGUC | n/a |

TABLE 9

Examples of selected VEGF rxRNAori Sequences

| Oligo ID | Start Site | 25 mer Sense Sequence | 25mer Anti-sense sequence |
|---|---|---|---|
| 18760 | 1853 | 5'-AUCACCAUCGACAGAACAGUCCUUA (SEQ ID NO: 13) | 5'-UAAGGACUGUUCUGUCGAUGGUGAU (SEQ ID NO: 1377) |
| 18886 | 1352 | 5'-CCAUGCAGAUUAUGCGGAUCAAACA (SEQ ID NO: 28) | 5'-UGUUUGAUCCGCAUAAUCUGCAUGG (SEQ ID NO: 1378) |

TABLE 10

Optimized VEGf sd-rxRNA ® Sequences With Increased Stability

| Duplex | Oligo ID | SEQ ID NO | |
|---|---|---|---|
| 19851 | 19790 | 1379 | A.G.A.A.mC.A.G.mU.mC.mC.mU.mU.A.Chl |
|  | 19791 | 1380 | P.mU.A.A.G.G.A.fC.fU.G.fU.fU.fC.fU*G*fU*fC*G*A*U |
|  | Description | | |
| SS | 3' Ome block | 1381 | A.G.A.A.mC.A.G.mU.mC.mC.mU*mU*mA-TEG-Chl |
|  | Complete Ome | 1382 | mA.mG.mA.mA.mC.mA.mG.mU.mC.mC*mU*mA-TEG-Chl |
|  | 3' and 5' Ome block | 1383 | mA.mG.A.A.mC.A.G.mU.mC.mC*mU*mA-TEG-Chl |
| AS - no > 3 2'OH | Pos 5 2'Ome G | 1384 | P.mU.A.A.G.mG.A.fC.fU.G.fU.fU.fC.fU*G*fU*fC*G*A*U |
|  | Pos 4 2'Ome G | 1385 | P.mU.A.A.mG.G.A.fC.fU.G.fU.fU.fC.fU*G*fU*fC*G*A*U |
|  | Pos 3 2'Ome A | 1386 | P.mU.A.mA.G.G.A.fC.fU.G.fU.fU.fC.fU*G*fU*fC*G*A*U |
|  | Pos 4 2'F G | 1387 | P.mU.A.A.fG.G.A.fC.fU.G.fU.fU.fC.fU*G*fU*fC*G*A*U |
| Stabilizing 3' end (no 2'OH | No 2'OH 3' tail | 1388 | P.mU.A.A.mG.G.A.fC.fU.G.fU.fU.fC.fU*mG*fU*fC*mG*mA*U |
|  | (1) 2'OH 3' tail | 1389 | P.mU.A.A.mG.G.A.fC.fU.G.fU.fU.fC.fU*G*fU*fC*mG*mA*U |
|  | No 2'OH 3' tail | 1390 | P.mU.A.A.fG.G.A.fC.fU.G.fU.fU.fC.fU*mG*fU*fC*mG*mA*U |
|  | (1) 2'OH 3' tail | 1391 | P.mU.A.A.fG.G.A.fC.fU.G.fU.fU.fC.fU*G*fU*fC*mG*mA*U |
|  | No 2'OH 3' tail | 1392 | P.mU.A.A.fG.G.A.fC.fU.G.fU.fU.fC.fU*fG*fU*fC*mG*mA*U |
| 5 methyl C and U | | 1393 | P.mY.A.A.fG.G.A.fX.fY.G.fY.fY.fX.fU*G*fY*fX*mG*mA*U |
|  | | 1394 | P.mY.A.A.fG.G.A.fX.fY.G.fY.fY.fX.fU*mG*fY*fX*mG*mA*U |

TABLE 10-continued

Optimized VEGf sd-rxRNA ® Sequences With Increased Stability

| Duplex | Oligo ID | SEQ ID NO | |
|---|---|---|---|
| | | 1395 | P.mY.A.A.mG.G.A.fX.fY.G.fY.fY.fX.fU*G*fY*fX*mG*mA*U |
| | | 1396 | P.mY.A.A.mG.G.A.fX.fY.G.fY.fY.fX.fU*mG*fY*fX*mG*mA*U |
| 19871 | 19830 | 1397 | mU.G.mC.G.G.A.mU.mC.A.A.A.mC.A.Chl |
| | 19831 | 1398 | P.mU.G.fU.fU.fU.G.A.fU.fC.fC.G.fC.A*fU*A*A*fU*fC*U |

Key
Chl = cholesterol with hydroxyprolinol linker
TEG-chl = cholesterol with TEG linker
m = 2'Ome
f = 2'fluoro
* = phosphorothioate linkage
. = phosphodiester linkage

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety. This application incorporates by reference the entire contents, including all the drawings and all parts of the specification (including sequence listing or amino acid/polynucleotide sequences) of PCT Publication No. WO2010/033247 (Application No. PCT/US2009/005247), filed on Sep. 22, 2009, and entitled "REDUCED SIZE SELF-DELIVERING RNAI COMPOUNDS" and PCT Publication No. WO2009/102427 (Application No. PCT/US2009/000852), filed on Feb. 11, 2009, and entitled, "MODIFIED RNAI POLYNUCLEOTIDES AND USES THEREOF."

The invention claimed is:

1. A method for delivering a nucleic acid to an eye of a subject in need thereof, comprising
   administering to the eye of the subject an sd-rxRNA®, in an effective amount to promote RNA interference by the sd-rxRNA® in the eye,
   wherein the sd-rxRNA® comprises a guide strand and a passenger strand, wherein the sd-rxRNA® includes a double stranded region and a single stranded region, wherein the double stranded region is 8-15 nucleotides long, wherein the single stranded region is at the 3' end of the guide strand and is 4-12 nucleotides long, wherein the single stranded region contains 3, 4, 5, 6, 7, 8, 9, 10, 11, or 12 phosphorothioate modifications, wherein at least 40% of the nucleotides of the sd-rxRNA® are modified,
   wherein the sd-rxRNA® is directed against a gene encoding TGFβ1 or TGFβ2, and wherein the sd-rxRNA comprises at least 12 contiguous nucleotides of a sequence selected from the group consisting of SEQ ID NOs: 1027-1314.

2. The method of claim 1, wherein the administration of the sd-rxRNA® is intravitreal.

3. The method of claim 1, wherein the method is a method for treating an ocular disorder, optionally wherein the ocular disorder is selected from the group consisting of: vascular leakage, neovascularization, age-related macular degeneration (AMD), choroidal neovascularization (wet AMD), geographic atrophy (advanced dry AMD), early-to-intermediate dry AMD, post surgical cystoid macular edema (CME), nonproliferative diabetic retinopathy (NPDR), diabetic macular edema (DME), macular edema secondary to retinal vein occlusion (RVO), proliferative diabetic retinopathy (PDR), glaucoma, neovascular glaucoma (NVG), retinopathy of prematurity (ROP), fibroproliferative retinal disease, proliferative vitreoretinopathy (PVR), epiretinal membranes/vitreomacular adhesions, retinal degenerative disease, retinitis pigmentosa, retinal vascular occlusive disorders, retinal vein occlusion, retinal artery occlusion, retinoblastoma, trabeculectomy failure due to scarring, and uveitis.

4. The method of claim 3, wherein the ocular disorder is proliferative vitreoretinopathy (PVR).

5. The method of claim 1, wherein two or more different sd-rxRNA® molecules that are directed against genes encoding for two or more different proteins are both administered to the eye of the subject.

6. The method of claim 5, wherein the sd-rxRNA® molecules comprise sd-rxRNA® molecules directed against VEGF and TGFβ1 and/or TGFβ2.

7. The method of claim 6, wherein the sd-rxRNA® that is directed against VEGF is directed against a sequence comprising at least 12 contiguous nucleotides of a sequence selected from the group consisting of SEQ ID NOS: 1-182, 1315-1376, and 1379-1398.

8. The method of claim 1, wherein the sense strand of the sd-rxRNA® comprises at least 12 contiguous nucleotides of the group consisting of SEQ ID NOs: 1155 (mU*mC*mA.mU.mC.mA.mG.mU.mG.mU.mU*mA*mA.TEG-Chl), 1157 (mU*mC*mA.mU.mC.mA.mG.mU.mG.mU.mU*mA*mA.TEG-Chl), and 1313 (mC*mA*mC.mA.mC.mA.mG.mC.mA.mU.mA*mU*mA.TEG-Chl).

9. The method of claim 1, wherein the antisense strand of the sd-rxRNA® comprises at least 12 contiguous nucleotides of the group consisting of SEQ ID NOs: 1156 (P.mU.fU. A. A.fC. A.fC.fU. G. A.fU. G. A* A*fC*fC*mA*mA* G.), 1158 (P.mU.fU. A. A.fC. A.fC.fU. G. A.fU. G.mA*mA*fC*fC*mA*mA* G.), and 1314 (P.mU. A.fU. A.fU. G.fC.fU. G.fU. G.fU.mG*fU*mA*fC*mU*fC* U.).

10. The method of claim 1, wherein the sense strand of the sd-rxRNA® comprises SEQ ID NO: 1313 (mC*mA*mC.mA.mC.mA.mG.mC.mA.mU.mA*mU*mA.TEG-Chl) and the antisense strand of the sd-rxRNA® comprises SEQ ID NO: 1314 (P.mU. A.fU. A.fU. G.fC.fU. G.fU. G.fU.mG*fU*mA*fC*mU*fC* U.).

11. The method of claim 1, wherein the sense strand of the sd-rxRNA® comprises SEQ ID NO: 1155 (mU*mC*mA.mU.mC.mA.mG.mU.mG.mU.mU*mA*mA.TEG-Chl) and the antisense strand of the sd-rxRNA® comprises SEQ ID NO: 1156 (P.mU.fU. A. A.fC. A.fC.fU. G. A.fU. G. A* A*fC*fC*mA*mA* G.).

12. The method of claim 1, wherein the sense strand of the sd-rxRNA® comprises SEQ ID NO: 1157 (mU*mC*mA.mU.mC.mA.mG.mU.mG.mU.mU*mA*mA.TEG-Chl) and the antisense strand of the sd-rxRNA® comprises SEQ ID NO: 1158 (P.mU.fU. A. A.fC. A.fC.fU. G. A.fU. G.mA*mA*fC*fC*mA*mA* G.).

13. The method of claim 1, wherein the sd-rxRNA® is hydrophobically modified, optionally wherein the sd-rxRNA® is linked to one or more hydrophobic conjugates, and/or the sd-rxRNA® includes at least one 5-methyl C or U modification.

14. The method of claim 7, wherein the sense strand of the sd-rxRNA® that is directed against VEGF comprises at least 12 contiguous nucleotides of a sequence selected from the group consisting of: SEQ ID NOs: 1317 (AGAACAGUCCUUA), 1357 (UGCGGAUCAAACA), 1379 (A. G. A. A.mC. A. G.mU.mC.mC.mU.mU. A.Chl), and 1397 (mU. G.mC. G. G. A.mU.mC. A. A. A.mC. A.Chl), and wherein the antisense strand of the sd-rxRNA® that is directed against VEGF comprises at least 12 contiguous nucleotides of a sequence selected from the group consisting of: SEQ ID NOs: 1318 (UAAGGACUGUUCUGUCGAU), 1358 (UGUUUGAUCCGCAUAAUCU), 1380 (P.mU. A. A. G. G. A.fC.fU. G.fU.fU.fC.fU* G*fU*fC* G* A* U), and 1398 (P.mU. G.fU.fU.fU. G. A.fU.fC.fC. G.fC. A*fU* A* A*fU*fC* U).

15. The method of claim 14, wherein the sense strand of the sd-rxRNA® comprises SEQ ID NO: 1317 (AGAACAGUCCUUA) and the antisense strand of the sd-rxRNA® comprises SEQ ID NO: 1318 (UAAGGACUGUUCUGUCGAU).

16. The method of claim 14, wherein the sense strand of the sd-rxRNA® comprises SEQ ID NO: 1357 (UGCGGAUCAAACA) and the antisense strand of the sd-rxRNA® comprises SEQ ID NO: 1358 (UGUUUGAUCCGCAUAAUCU).

17. The method of claim 14, wherein the sense strand of the sd-rxRNA® comprises SEQ ID NO: 1379 (A. G. A. A.mC. A. G.mU.mC.mC.mU.mU. A.Chl) and the antisense strand of the sd-rxRNA® comprises SEQ ID NO: 1380 (P.mU. A. A. G. G. A.fC.fU. G.fU.fU.fC.fU* G*fU*fC* G* A* U).

18. The method of claim 14, wherein the sense strand of the sd-rxRNA® comprises SEQ ID NO: 1397 (mU. G.mC. G. G. A.mU.mC. A. A. A.mC. A.Chl) and the antisense strand of the sd-rxRNA® comprises SEQ ID NO: 1398 (P.mU. G.fU.fU.fU. G. A.fU.fC.fC. G.fC. A*fU* A* A*fU*fC* U).

19. The method of claim 7, wherein the sd-rxRNA® is hydrophobically modified, optionally wherein the sd-rxRNA® is linked to one or more hydrophobic conjugates, and/or the sd-rxRNA® includes at least one 5-methyl C or U modification.

\* \* \* \* \*

SEQUENCE LISTING

```
<160> NUMBER OF SEQ ID NOS: 1425

<210> SEQ ID NO 1
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 1
uaucauuuau uuauuggugc uacua                                        25

<210> SEQ ID NO 2
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 2
uuaauuuugc uaacacucag cucua                                        25

<210> SEQ ID NO 3
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 3
ccucacacca uugaaaccac uagua                                        25
```

-continued

```
<210> SEQ ID NO 4
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 4
cuacauacua aaucucucuc cuuua                                              25

<210> SEQ ID NO 5
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 5
ccaacaucac caugcagauu augca                                              25

<210> SEQ ID NO 6
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 6
gcacauagga gagaugagcu uccua                                              25

<210> SEQ ID NO 7
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 7
aucggugaca gucacuagcu uauca                                              25

<210> SEQ ID NO 8
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 8
uuuaugagau guaucuuuug cucua                                              25

<210> SEQ ID NO 9
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 9
uacauacuaa aucucucucc uuuua                                              25

<210> SEQ ID NO 10
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 10
uaacagugcu aauguuauug gugua                                          25

<210> SEQ ID NO 11
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 11
uuguggaggc agagaaaaga gaaaa                                          25

<210> SEQ ID NO 12
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 12
cacuggaugu auuugacugc uguga                                          25

<210> SEQ ID NO 13
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 13
aucaccaucg acagaacagu ccuua                                          25

<210> SEQ ID NO 14
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 14
aucgacagaa caguccuuaa uccaa                                          25

<210> SEQ ID NO 15
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 15
auuuaugaga uguaucuuuu gcuca                                          25

<210> SEQ ID NO 16
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 16
ucacaccauu gaaaccacua guuca                                          25

<210> SEQ ID NO 17
<211> LENGTH: 25
```

```
<212> TYPE: RNA
<213> ORGANISM: Artificial Sequence
<220> FEATURE:
<223> OTHER INFORMATION: Synthetic Polynucleotide

<400> SEQUENCE: 17
uuuauuuauu ggugcuacug uuuaa                                              25

<210> SEQ ID NO 18
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 18
uucuacauac uaaaucucuc uccua                                              25

<210> SEQ ID NO 19
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 19
ucaccaucga cagaacaguc cuuaa                                              25

<210> SEQ ID NO 20
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 20
ccucuuggaa uuggauucgc cauua                                              25

<210> SEQ ID NO 21
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 21
ccaucgacag aacaguccuu aauca                                              25

<210> SEQ ID NO 22
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 22
caucaccaug cagauuaugc ggaua                                              25

<210> SEQ ID NO 23
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 23
```
guccucacac cauugaaacc acuaa                                      25

<210> SEQ ID NO 24
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 24
gaucggugac agucacuagc uuaua                                      25

<210> SEQ ID NO 25
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 25
uguggaggca gagaaaagag aaaga                                      25

<210> SEQ ID NO 26
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 26
aggucagacg gacagaaaga cagaa                                      25

<210> SEQ ID NO 27
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 27
auuguggagg cagagaaaag agaaa                                      25

<210> SEQ ID NO 28
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 28
ccaugcagau uaugcggauc aaaca                                      25

<210> SEQ ID NO 29
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 29
acagaacagu ccuuaaucca gaaaa                                      25

<210> SEQ ID NO 30
<211> LENGTH: 25
<212> TYPE: RNA
<213> ORGANISM: Artificial Sequence

```
<220> FEATURE:
<223> OTHER INFORMATION: Synthetic Polynucleotide

<400> SEQUENCE: 30
cacauuccuu ugaaauaagg uuuca                                              25

<210> SEQ ID NO 31
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 31
caucaccauc gacagaacag uccua                                              25

<210> SEQ ID NO 32
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 32
uccaacauca ccaugcagau uauga                                              25

<210> SEQ ID NO 33
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 33
ugcccauugu ggaggcagag aaaaa                                              25

<210> SEQ ID NO 34
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 34
gcagauuaug cggaucaaac cucaa                                              25

<210> SEQ ID NO 35
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 35
acuggaugua uuugacugcu gugga                                              25

<210> SEQ ID NO 36
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 36
caccaucgac agaacagucc uuaaa                                              25
```

```
<210> SEQ ID NO 37
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 37
uuaacagugc uaauguuauu gguga                                              25

<210> SEQ ID NO 38
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 38
caugcagauu augcggauca aacca                                              25

<210> SEQ ID NO 39
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 39
ggaaaagaua uuaacaucac gucua                                              25

<210> SEQ ID NO 40
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 40
aguccaacau caccaugcag auuaa                                              25

<210> SEQ ID NO 41
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 41
ccagcacaca uuccuuugaa auaaa                                              25

<210> SEQ ID NO 42
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 42
auuuaauuuu gcuaacacuc agcua                                              25

<210> SEQ ID NO 43
<211> LENGTH: 25
<212> TYPE: RNA
<213> ORGANISM: Artificial Sequence
<220> FEATURE:
<223> OTHER INFORMATION: Synthetic Polynucleotide
```

<400> SEQUENCE: 43
agagaaagug uuuuauauac gguaa                                    25

<210> SEQ ID NO 44
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 44
ggagagauga gcuuccuaca gcaca                                    25

<210> SEQ ID NO 45
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 45
uggaggcaga gaaaagagaa aguga                                    25

<210> SEQ ID NO 46
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 46
ugauaaaaua gacauugcua uucua                                    25

<210> SEQ ID NO 47
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 47
gugacaguca cuagcuuauc uugaa                                    25

<210> SEQ ID NO 48
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 48
uauuuauugg ugcuacuguu uauca                                    25

<210> SEQ ID NO 49
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 49
cuaauguuau uggugucuuc acuga                                    25

<210> SEQ ID NO 50

```
-continued

<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 50
aggaguccaa caucaccaug cagaa                                          25

<210> SEQ ID NO 51
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 51
augcagauua ugcggaucaa accua                                          25

<210> SEQ ID NO 52
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 52
guccaacauc accaugcaga uuaua                                          25

<210> SEQ ID NO 53
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 53
cauuguggag gcagagaaaa gagaa                                          25

<210> SEQ ID NO 54
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 54
aaaccugaaa ugaaggaaga ggaga                                          25

<210> SEQ ID NO 55
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 55
auuaacagug cuaauguuau uggua                                          25

<210> SEQ ID NO 56
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 56
```
acagugcuaa uguuauuggu gucua                                                25

<210> SEQ ID NO 57
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 57
ucucccugau cggugacagu cacua                                                25

<210> SEQ ID NO 58
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 58
ucuacauacu aaaucucucu ccuua                                                25

<210> SEQ ID NO 59
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 59
ucgacagaac aguccuuaau ccaga                                                25

<210> SEQ ID NO 60
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 60
uauuuaauuu ugcuaacacu cagca                                                25

<210> SEQ ID NO 61
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 61
acacauuccu uugaaauaag guuua                                                25

<210> SEQ ID NO 62
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 62
cccuggugga caucuuccag gagua                                                25

<210> SEQ ID NO 63
<211> LENGTH: 25
<212> TYPE: RNA

```
<213> ORGANISM: Artificial Sequence
<220> FEATURE:
<223> OTHER INFORMATION: Synthetic Polynucleotide

<400> SEQUENCE: 63
ucuuggaauu ggauucgcca uuuua                                     25

<210> SEQ ID NO 64
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 64
acaucaccau gcagauuaug cggaa                                     25

<210> SEQ ID NO 65
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 65
caccauugaa accacuaguu cugua                                     25

<210> SEQ ID NO 66
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 66
gccagcacau aggagagaug agcua                                     25

<210> SEQ ID NO 67
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 67
uaaaauagac auugcuauuc uguua                                     25

<210> SEQ ID NO 68
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 68
accaucgaca gaacaguccu uaaua                                     25

<210> SEQ ID NO 69
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 69
uaaacaacga caaagaaaua cagaa                                     25
```

<210> SEQ ID NO 70
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 70
uuauuuauug gugcuacugu uuaua                                    25

<210> SEQ ID NO 71
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 71
uuauuuuucu ugcugcuaaa ucaca                                    25

<210> SEQ ID NO 72
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 72
aaccugaaau gaaggaagag gagaa                                    25

<210> SEQ ID NO 73
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 73
uauuuuucuu gcugcuaaau cacca                                    25

<210> SEQ ID NO 74
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 74
caucgacaga acaguccuua aucca                                    25

<210> SEQ ID NO 75
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 75
ggaggcagag aaaagagaaa gugua                                    25

<210> SEQ ID NO 76
<211> LENGTH: 25
<212> TYPE: RNA
<213> ORGANISM: Artificial Sequence
<220> FEATURE:

```
<223> OTHER INFORMATION: Synthetic Polynucleotide

<400> SEQUENCE: 76
aaaagagaaa guguuuuaua uacga                                         25

<210> SEQ ID NO 77
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 77
auaaaauaga cauugcuauu cugua                                         25

<210> SEQ ID NO 78
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 78
aaaauagaca uugcuauucu guuua                                         25

<210> SEQ ID NO 79
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 79
caggaguacc cugaugagau cgaga                                         25

<210> SEQ ID NO 80
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 80
agugcuaaug uuauuggugu cuuca                                         25

<210> SEQ ID NO 81
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 81
aauuaacagu gcuaauguua uugga                                         25

<210> SEQ ID NO 82
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 82
aggaguaccc ugaugagauc gagua                                         25
```

```
<210> SEQ ID NO 83
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 83
agcacacauu ccuuugaaau aagga                                  25

<210> SEQ ID NO 84
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 84
auucauguuu ccaaucucuc ucuca                                  25

<210> SEQ ID NO 85
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 85
gagaaagugu uuuauauacg guaca                                  25

<210> SEQ ID NO 86
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 86
aacagugcua auguuauugg uguca                                  25

<210> SEQ ID NO 87
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 87
ucuagugcag uuuuucgaga uauua                                  25

<210> SEQ ID NO 88
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 88
uaggagagau gagcuuccua cagca                                  25

<210> SEQ ID NO 89
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 89
gugcuaaugu uauugguguc uucaa                                              25

<210> SEQ ID NO 90
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 90
auuuauuuau uggugcuacu guuua                                              25

<210> SEQ ID NO 91
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 91
ucucucuugc ucucuuauuu guaca                                              25

<210> SEQ ID NO 92
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 92
cacaccauug aaaccacuag uucua                                              25

<210> SEQ ID NO 93
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 93
gggaaaagau auuaacauca cguca                                              25

<210> SEQ ID NO 94
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 94
aucaccaugc agauuaugcg gauca                                              25

<210> SEQ ID NO 95
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 95
gugauucuga uaaaauagac auuga                                              25

<210> SEQ ID NO 96
<211> LENGTH: 25
```

```
<212> TYPE: RNA
<213> ORGANISM: Artificial Sequence
<220> FEATURE:
<223> OTHER INFORMATION: Synthetic Polynucleotide

<400> SEQUENCE: 96
cagcacacau uccuuugaaa uaaga                                            25

<210> SEQ ID NO 97
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 97
uaaaauucau guuccaauc ucuca                                             25

<210> SEQ ID NO 98
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 98
guacccugau gagaucgagu acaua                                            25

<210> SEQ ID NO 99
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 99
aaauucaugu uuccaaucuc ucuca                                            25

<210> SEQ ID NO 100
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 100
cuggauguau uugacugcug uggaa                                            25

<210> SEQ ID NO 101
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 101
auuaacauca cgucuuuguc ucuaa                                            25

<210> SEQ ID NO 102
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 102
```
uccucacacc auugaaacca cuaga                        25

<210> SEQ ID NO 103
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 103
ggccagcaca uaggagagau gagca                        25

<210> SEQ ID NO 104
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 104
gauaaaauag acauugcuau ucuga                        25

<210> SEQ ID NO 105
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 105
gauauuuaau uuugcuaaca cucaa                        25

<210> SEQ ID NO 106
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 106
accugaaaug aaggaagagg agaca                        25

<210> SEQ ID NO 107
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 107
aauucauguu uccaaucucu cucua                        25

<210> SEQ ID NO 108
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 108
ggggaaaaga uauuaacauc acgua                        25

<210> SEQ ID NO 109
<211> LENGTH: 25
<212> TYPE: RNA
<213> ORGANISM: Artificial Sequence

```
<220> FEATURE:
<223> OTHER INFORMATION: Synthetic Polynucleotide

<400> SEQUENCE: 109
cuacagcaca acaauguga augca                                              25

<210> SEQ ID NO 110
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 110
acacacccac ccacauacau acaua                                             25

<210> SEQ ID NO 111
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 111
aguuuuucga gauauuccgu aguaa                                             25

<210> SEQ ID NO 112
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 112
ggucccucuu ggaauuggau ucgca                                             25

<210> SEQ ID NO 113
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 113
gcaguuuuuc gagauauucc guaga                                             25

<210> SEQ ID NO 114
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 114
uuaaacaacg acaaagaaau acaga                                             25

<210> SEQ ID NO 115
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 115
auauuuaauu uugcuaacac ucaga                                             25
```

```
<210> SEQ ID NO 116
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 116
agaauucuac auacuaaauc ucuca                                    25

<210> SEQ ID NO 117
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 117
aaacaacgac aaagaaauac agaua                                    25

<210> SEQ ID NO 118
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 118
aacaucacca ugcagauuau gcgga                                    25

<210> SEQ ID NO 119
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 119
accauugaaa ccacuaguuc uguca                                    25

<210> SEQ ID NO 120
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 120
uccaggagua cccugaugag aucga                                    25

<210> SEQ ID NO 121
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 121
guuauuggug ucuucacugg augua                                    25

<210> SEQ ID NO 122
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 122
uggauguauu ugacugcugu ggaca                                      25

<210> SEQ ID NO 123
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 123
uguuauuggu gucuucacug gauga                                      25

<210> SEQ ID NO 124
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 124
gcuaauguua uuggugucuu cacua                                      25

<210> SEQ ID NO 125
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 125
aaaagauauu aacaucacgu cuuua                                      25

<210> SEQ ID NO 126
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 126
auauuaacau cacgucuuug ucuca                                      25

<210> SEQ ID NO 127
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 127
agauauuaac aucacgucuu uguca                                      25

<210> SEQ ID NO 128
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 128
aaauaagguu ucaauauaca ucuaa                                      25

<210> SEQ ID NO 129
```

```
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 129
gaguacccug augagaucga guaca                                              25

<210> SEQ ID NO 130
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 130
auuuauuggu gcuacuguuu aucca                                              25

<210> SEQ ID NO 131
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 131
auaaaauuca uguuuccaau cucua                                              25

<210> SEQ ID NO 132
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 132
ggaguccaac aucaccaugc agaua                                              25

<210> SEQ ID NO 133
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 133
cucuagugca guuuucgag auaua                                               25

<210> SEQ ID NO 134
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 134
uauuaacauc acgucuuugu cucua                                              25

<210> SEQ ID NO 135
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 135
```
gaguccaaca ucaccaugca gauua                                          25

<210> SEQ ID NO 136
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 136
gagaauucua cauacuaaau cucua                                          25

<210> SEQ ID NO 137
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 137
gacagaacag uccuuaaucc agaaa                                          25

<210> SEQ ID NO 138
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 138
ucccucuugg aauuggauuc gccaa                                          25

<210> SEQ ID NO 139
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 139
uuggugcuac uguuuauccg uaaua                                          25

<210> SEQ ID NO 140
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 140
uuuauuggug cuacuguuua uccga                                          25

<210> SEQ ID NO 141
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 141
cuagugcagu uuuucgagau auuca                                          25

<210> SEQ ID NO 142
<211> LENGTH: 25
<212> TYPE: RNA

```
<213> ORGANISM: Artificial Sequence
<220> FEATURE:
<223> OTHER INFORMATION: Synthetic Polynucleotide

<400> SEQUENCE: 142
guuuuucgag auauuccgua guaca                                    25

<210> SEQ ID NO 143
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 143
accaugcaga uuaugcggau caaaa                                    25

<210> SEQ ID NO 144
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 144 caguuuucg agauauuccg uagua                                     25

<210> SEQ ID NO 145
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 145
aagauauuaa caucacgucu uugua                                    25

<210> SEQ ID NO 146
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 146
cagcacauag gagagaugag cuuca                                    25

<210> SEQ ID NO 147
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 147
agugcaguuu uucgagauau uccga                                    25

<210> SEQ ID NO 148
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 148
auguuauugg ugucuucacu ggaua                                    25
```

<210> SEQ ID NO 149
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 149
uagugcaguu uuucgagaua uucca 25

<210> SEQ ID NO 150
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 150
gugcaguuuu ucgagauauu ccgua 25

<210> SEQ ID NO 151
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 151
acauaggaga gaugagcuuc cuaca 25

<210> SEQ ID NO 152
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 152
aaagauauua acaucacguc uuuga 25

<210> SEQ ID NO 153
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 153
gucucuagug caguuuucg agaua 25

<210> SEQ ID NO 154
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 154
cuauuuauga gauguaucuu uugca 25

<210> SEQ ID NO 155
<211> LENGTH: 25
<212> TYPE: RNA
<213> ORGANISM: Artificial Sequence
<220> FEATURE:

<223> OTHER INFORMATION: Synthetic Polynucleotide

<400> SEQUENCE: 155
ugcuaauguu auuguguucu ucaca  25

<210> SEQ ID NO 156
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 156
auauauauuu ggcaacuugu auuua  25

<210> SEQ ID NO 157
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 157
gauauuaaca ucacgucuuu gucua  25

<210> SEQ ID NO 158
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 158
gucccucuug gaauuggauu cgcca  25

<210> SEQ ID NO 159
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 159
aauucuacau acuaaaucuc ucuca  25

<210> SEQ ID NO 160
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 160
gcuccccagc acacauuccu uugaa  25

<210> SEQ ID NO 161
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 161
ccugaaauga aggaagagga gacua  25

```
<210> SEQ ID NO 162
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 162
uuaacaucac gcuuugucu cuaga                                           25

<210> SEQ ID NO 163
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 163
ggauguauuu gacugcugug gacua                                          25

<210> SEQ ID NO 164
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 164
gaauucuaca uacuaaaucu cucua                                          25

<210> SEQ ID NO 165
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 165
uauauauuug gcaacuugua uuuga                                          25

<210> SEQ ID NO 166
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 166
caaggccagc acauaggaga gauga                                          25

<210> SEQ ID NO 167
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 167
cggugacagu cacuagcuua ucuua                                          25

<210> SEQ ID NO 168
<211> LENGTH: 25
<212> TYPE: RNA
<213> ORGANISM: Artificial Sequence
<220> FEATURE:
<223> OTHER INFORMATION: Synthetic Polynucleotide
```

```
<400> SEQUENCE: 168
uuuaaacaac gacaaagaaa uacaa                                          25

<210> SEQ ID NO 169
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 169
ugaucgguga cagucacuag cuuaa                                          25

<210> SEQ ID NO 170
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 170
aguacccuga ugagaucgag uacaa                                          25

<210> SEQ ID NO 171
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 171
ugcaguuuuu cgagauauuc cguaa                                          25

<210> SEQ ID NO 172
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 172
uuuuucgaga uauuccguag uacaa                                          25

<210> SEQ ID NO 173
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 173
uuauuggugc uacuguuuau ccgua                                          25

<210> SEQ ID NO 174
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 174
cugaucggug acagucacua gcuua                                          25

<210> SEQ ID NO 175
<211> LENGTH: 25
```

```
<212> TYPE: RNA
<213> ORGANISM: Artificial Sequence
<220> FEATURE:
<223> OTHER INFORMATION: Synthetic Polynucleotide

<400> SEQUENCE: 175
uacuguuuau ccguaauaau uguga                                         25

<210> SEQ ID NO 176
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 176
uuuucgagau auccguagu acaua                                          25

<210> SEQ ID NO 177
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 177
auuggugcua cuguuuaucc guaaa                                         25

<210> SEQ ID NO 178
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 178
ucucuagugc aguuuucga gauaa                                          25

<210> SEQ ID NO 179
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 179
ggugacaguc acuagcuuau cuuga                                         25

<210> SEQ ID NO 180
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 180
auauauuugg caacuuguau uugua                                         25

<210> SEQ ID NO 181
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 181
```

```
uauuggugcu acuguuuauc cguaa                                             25

<210> SEQ ID NO 182
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 182
uuucgagaua uuccguagua cauaa                                             25

<210> SEQ ID NO 183
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 183
cucaugaauu aga                                                          13

<210> SEQ ID NO 184
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 184
ucuaauucau gagaaauac                                                    19

<210> SEQ ID NO 185
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 185
cugaggucaa uua                                                          13

<210> SEQ ID NO 186
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 186
uaauugaccu cagaagaug                                                    19

<210> SEQ ID NO 187
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 187
gaggucaauu aaa                                                          13

<210> SEQ ID NO 188
<211> LENGTH: 19
<212> TYPE: RNA
<213> ORGANISM: Artificial Sequence
```

```
<220> FEATURE:
<223> OTHER INFORMATION: Synthetic Polynucleotide

<400> SEQUENCE: 188
uuuaauugac cucagaaga                                                    19

<210> SEQ ID NO 189
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 189
ucugagguca auu                                                          13

<210> SEQ ID NO 190
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 190
aauugaccuc agaagaugc                                                    19

<210> SEQ ID NO 191
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 191
ugaggucaau uaa                                                          13

<210> SEQ ID NO 192
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 192
uuaauugacc ucagaagau                                                    19

<210> SEQ ID NO 193
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 193
uucugagguc aau                                                          13

<210> SEQ ID NO 194
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 194
auugaccuca gaagaugca                                                    19
```

<210> SEQ ID NO 195
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 195
gucagcugga uga                                                          13

<210> SEQ ID NO 196
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 196
ucauccagcu gacucguuu                                                    19

<210> SEQ ID NO 197
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 197
uucugaugaa ucu                                                          13

<210> SEQ ID NO 198
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 198
agauucauca gaaugguga                                                    19

<210> SEQ ID NO 199
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 199
uggacugagg uca                                                          13

<210> SEQ ID NO 200
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 200
ugaccucagu ccauaaacc                                                    19

<210> SEQ ID NO 201
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 201
gagucucacc auu                                      13

<210> SEQ ID NO 202
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 202
aauggugaga cucaucaga                                19

<210> SEQ ID NO 203
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 203
gacugagguc aaa                                      13

<210> SEQ ID NO 204
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 204
uuugaccuca guccauaaa                                19

<210> SEQ ID NO 205
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 205
ucacagccau gaa                                      13

<210> SEQ ID NO 206
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 206
uucauggcug ugaaauuca                                19

<210> SEQ ID NO 207
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 207
agucucacca uuc                                      13

<210> SEQ ID NO 208

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 208
gaauggugag acucaucag                                                    19

<210> SEQ ID NO 209
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 209
aagcggaaag cca                                                          13

<210> SEQ ID NO 210
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 210
uggcuuuccg cuuauauaa                                                    19

<210> SEQ ID NO 211
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 211
agcggaaagc caa                                                          13

<210> SEQ ID NO 212
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 212
uuggcuuucc gcuuauaua                                                    19

<210> SEQ ID NO 213
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 213
accacaugga uga                                                          13

<210> SEQ ID NO 214
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 214
```

```
ucauccaugu ggucauggc                                            19

<210> SEQ ID NO 215
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 215
gccaugacca cau                                                  13

<210> SEQ ID NO 216
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 216
auguggucau ggcuuucgu                                            19

<210> SEQ ID NO 217
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 217
aagccaugac cac                                                  13

<210> SEQ ID NO 218
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 218
guggucaugg cuuucguug                                            19

<210> SEQ ID NO 219
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 219
gcggaaagcc aau                                                  13

<210> SEQ ID NO 220
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 220
auuggcuuuc cgcuuauau                                            19

<210> SEQ ID NO 221
<211> LENGTH: 13
<212> TYPE: RNA
```

<213> ORGANISM: Artificial Sequence
<220> FEATURE:
<223> OTHER INFORMATION: Synthetic Polynucleotide

<400> SEQUENCE: 221
aaauuucgua uuu                                                          13

<210> SEQ ID NO 222
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 222
aaauacgaaa uuucaggug                                                    19

<210> SEQ ID NO 223
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 223
auuucguauu ucu                                                          13

<210> SEQ ID NO 224
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 224
agaaauacga aauuucagg                                                    19

<210> SEQ ID NO 225
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 225
aaagccauga cca                                                          13

<210> SEQ ID NO 226
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 226
uggucauggc uuucguugg                                                    19

<210> SEQ ID NO 227
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 227
acauggauga uau                                                          13

<210> SEQ ID NO 228
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 228
auaucaucca ugguggucau                                              19

<210> SEQ ID NO 229
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 229
gaaauuucgu auu                                                     13

<210> SEQ ID NO 230
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 230
aauacgaaau uucaggugu                                               19

<210> SEQ ID NO 231
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 231
gcgccuucug auu                                                     13

<210> SEQ ID NO 232
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 232
aaucagaagg cgcguucag                                               19

<210> SEQ ID NO 233
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 233
auuucucaug aau                                                     13

<210> SEQ ID NO 234
<211> LENGTH: 19
<212> TYPE: RNA
<213> ORGANISM: Artificial Sequence
<220> FEATURE:

<223> OTHER INFORMATION: Synthetic Polynucleotide

<400> SEQUENCE: 234
auucaugaga aauacgaaa                                                      19

<210> SEQ ID NO 235
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 235
cucucaugaa uag                                                            13

<210> SEQ ID NO 236
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 236
cuauucauga gagaauaac                                                      19

<210> SEQ ID NO 237
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 237
aaguccaacg aaa                                                            13

<210> SEQ ID NO 238
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 238
uuucguugga cuuacuugg                                                      19

<210> SEQ ID NO 239
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 239
augaugagag caa                                                            13

<210> SEQ ID NO 240
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 240
uugcucucau cauuggcuu                                                      19

<210> SEQ ID NO 241
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 241
gcgaggaguu gaa                                                          13

<210> SEQ ID NO 242
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 242
uucaacuccu cgcuuucca                                                    19

<210> SEQ ID NO 243
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 243
ugauugauag uca                                                          13

<210> SEQ ID NO 244
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 244
ugacuaucaa ucacaucgg                                                    19

<210> SEQ ID NO 245
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 245
agauagugca ucu                                                          13

<210> SEQ ID NO 246
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 246
agaugcacua ucuaauuca                                                    19

<210> SEQ ID NO 247
<211> LENGTH: 13
<212> TYPE: RNA
<213> ORGANISM: Artificial Sequence
<220> FEATURE:
<223> OTHER INFORMATION: Synthetic Polynucleotide

```
<400> SEQUENCE: 247
auguguaucu auu                                                          13

<210> SEQ ID NO 248
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 248
aauagauaca cauucaacc                                                    19

<210> SEQ ID NO 249
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 249
uucuauagaa gaa                                                          13

<210> SEQ ID NO 250
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 250
uucuucuaua gaaugaaca                                                    19

<210> SEQ ID NO 251
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 251
uuguccagca auu                                                          13

<210> SEQ ID NO 252
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 252
aauugcugga caaccgugg                                                    19

<210> SEQ ID NO 253
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 253
acauggaaag cga                                                          13

<210> SEQ ID NO 254
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 254
ucgcuuucca ugugugagg                                              19

<210> SEQ ID NO 255
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 255
gcaguccaga uua                                                    13

<210> SEQ ID NO 256
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 256
uaaucuggac ugcuugugg                                              19

<210> SEQ ID NO 257
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 257
ugguugaaug ugu                                                    13

<210> SEQ ID NO 258
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 258
acacauucaa ccaauaaac                                              19

<210> SEQ ID NO 259
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 259
uuaugaaacg agu                                                    13

<210> SEQ ID NO 260
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 260
```
acucguuuca uaacugucc    19

<210> SEQ ID NO 261
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 261
caguccagau uau    13

<210> SEQ ID NO 262
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 262
auaaucugga cugcuugug    19

<210> SEQ ID NO 263
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 263
auauaagcgg aaa    13

<210> SEQ ID NO 264
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 264
uuuccgcuua uauaaucug    19

<210> SEQ ID NO 265
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 265
uaccaguuaa aca    13

<210> SEQ ID NO 266
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 266
uguuuaacug guauggcac    19

<210> SEQ ID NO 267
<211> LENGTH: 13
<212> TYPE: RNA
<213> ORGANISM: Artificial Sequence

```
<220> FEATURE:
<223> OTHER INFORMATION: Synthetic Polynucleotide

<400> SEQUENCE: 267
uguucauucu aua                                                            13

<210> SEQ ID NO 268
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 268
uauagaauga acauagaca                                                      19

<210> SEQ ID NO 269
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 269
ccgaccaagg aaa                                                            13

<210> SEQ ID NO 270
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 270
uuuccuuggu cggcguuug                                                      19

<210> SEQ ID NO 271
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 271
gaauggugca uac                                                            13

<210> SEQ ID NO 272
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 272
guaugcacca uucaacucc                                                      19

<210> SEQ ID NO 273
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 273
auaugauggc cga                                                            13
```

```
<210> SEQ ID NO 274
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 274
ucggccauca uaugugucu                                                   19

<210> SEQ ID NO 275
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 275
agcaguccag auu                                                         13

<210> SEQ ID NO 276
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 276
aaucuggacu gcuuguggc                                                   19

<210> SEQ ID NO 277
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 277
gcauuuaguc aaa                                                         13

<210> SEQ ID NO 278
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 278
uuugacuaaa ugcaaagug                                                   19

<210> SEQ ID NO 279
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 279
agcauuccga ugu                                                         13

<210> SEQ ID NO 280
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 280
acaucggaau gcucauugc                                                    19

<210> SEQ ID NO 281
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 281
uagucaggaa cuu                                                          13

<210> SEQ ID NO 282
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 282 aaguccuga cuaucaauc                                                     19

<210> SEQ ID NO 283
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 283
ugcauuuagu caa                                                          13

<210> SEQ ID NO 284
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 284
uugacuaaau gcaaaguga                                                    19

<210> SEQ ID NO 285
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 285
gucugaugag ucu                                                          13

<210> SEQ ID NO 286
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 286
agacucauca gacugguga                                                    19

<210> SEQ ID NO 287
```

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 287
uagacacaua uga                                                            13

<210> SEQ ID NO 288
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 288
ucauaugugu cuacugugg                                                      19

<210> SEQ ID NO 289
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 289
cagacgagga cau                                                            13

<210> SEQ ID NO 290
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 290
auguccucgu cuguagcau                                                      19

<210> SEQ ID NO 291
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 291
cagccgugaa uuc                                                            13

<210> SEQ ID NO 292
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 292
gaauucacgg cugacuuug                                                      19

<210> SEQ ID NO 293
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 293
```
agucuggaaa uaa                                                      13

<210> SEQ ID NO 294
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 294 uuauuccag acucaaaua                                                 19

<210> SEQ ID NO 295
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 295
aguuuguggc uuc                                                      13

<210> SEQ ID NO 296
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 296
gaagccacaa acuaaacua                                                19

<210> SEQ ID NO 297
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 297
aguccaacga aag                                                      13

<210> SEQ ID NO 298
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 298
cuuucguugg acuuacuug                                                19

<210> SEQ ID NO 299
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 299
aaguuucgca gac                                                      13

<210> SEQ ID NO 300
<211> LENGTH: 19
<212> TYPE: RNA

<213> ORGANISM: Artificial Sequence
<220> FEATURE:
<223> OTHER INFORMATION: Synthetic Polynucleotide

<400> SEQUENCE: 300
gucugcgaaa cuucuuaga                                                19

<210> SEQ ID NO 301
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 301
agcaaugagc auu                                                      13

<210> SEQ ID NO 302
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 302
aaugcucauu gcucucauc                                                19

<210> SEQ ID NO 303
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 303
uuagauagug cau                                                      13

<210> SEQ ID NO 304
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 304
augcacuauc uaauucaug                                                19

<210> SEQ ID NO 305
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 305
uggugcauac aag                                                      13

<210> SEQ ID NO 306
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 306
cuuguaugca ccauucaac                                                19

<210> SEQ ID NO 307
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 307
augaaacgag uca                                                        13

<210> SEQ ID NO 308
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 308
ugacucguuu cauaacugu                                                  19

<210> SEQ ID NO 309
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 309
ccagagugcu gaa                                                        13

<210> SEQ ID NO 310
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 310
uucagcacuc uggucaucc                                                  19

<210> SEQ ID NO 311
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 311
cagccaugaa uuu                                                        13

<210> SEQ ID NO 312
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 312
aaauucaugg cuguggaau                                                  19

<210> SEQ ID NO 313
<211> LENGTH: 13
<212> TYPE: RNA
<213> ORGANISM: Artificial Sequence
<220> FEATURE:

```
<223> OTHER INFORMATION: Synthetic Polynucleotide

<400> SEQUENCE: 313
auugguugaa ugu                                                              13

<210> SEQ ID NO 314
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 314
acauucaacc aauaaacug                                                        19

<210> SEQ ID NO 315
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 315
gguugaaugu gua                                                              13

<210> SEQ ID NO 316
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 316
uacacauuca accaauaaa                                                        19

<210> SEQ ID NO 317
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 317
ggaaauaacu aau                                                              13

<210> SEQ ID NO 318
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 318
auuaguuauu uccagacuc                                                        19

<210> SEQ ID NO 319
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 319
ucaugaauag aaa                                                              13
```

```
<210> SEQ ID NO 320
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 320
uuucuauuca ugagagaau                                                    19

<210> SEQ ID NO 321
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 321
gccagcaacc gaa                                                          13

<210> SEQ ID NO 322
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 322
uucgguugcu ggcaggucc                                                    19

<210> SEQ ID NO 323
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 323
caccucacac aug                                                          13

<210> SEQ ID NO 324
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 324
caugugugag gugaugucc                                                    19

<210> SEQ ID NO 325
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 325
aguugaaugg ugc                                                          13

<210> SEQ ID NO 326
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 326
gcaccauuca acuccucgc                                               19

<210> SEQ ID NO 327
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 327
agucagcugg aug                                                     13

<210> SEQ ID NO 328
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 328
cauccagcug acucguuuc                                               19

<210> SEQ ID NO 329
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 329
uauaagcgga aag                                                     13

<210> SEQ ID NO 330
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 330
cuuuccgcuu auauaaucu                                               19

<210> SEQ ID NO 331
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 331
uuccgaugug auu                                                     13

<210> SEQ ID NO 332
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 332
aaucacaucg gaaugcuca                                               19

<210> SEQ ID NO 333
<211> LENGTH: 13
```

```
<212> TYPE: RNA
<213> ORGANISM: Artificial Sequence
<220> FEATURE:
<223> OTHER INFORMATION: Synthetic Polynucleotide

<400> SEQUENCE: 333
auaacuaaug ugu                                                              13

<210> SEQ ID NO 334
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 334
acacauuagu uauuccag                                                         19

<210> SEQ ID NO 335
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 335
ucauucuaua gaa                                                              13

<210> SEQ ID NO 336
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 336
uucuauagaa ugaacauag                                                        19

<210> SEQ ID NO 337
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 337
aacuaucacu gua                                                              13

<210> SEQ ID NO 338
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 338
uacagugaua guuugcauu                                                        19

<210> SEQ ID NO 339
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 339
```
gucaauugcu uau                                                       13

<210> SEQ ID NO 340
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 340
auaagcaauu gacaccacc                                                 19

<210> SEQ ID NO 341
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 341
agcaauuaau aaa                                                       13

<210> SEQ ID NO 342
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 342
uuuauuaauu gcuggacaa                                                 19

<210> SEQ ID NO 343
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 343
acgacucuga uga                                                       13

<210> SEQ ID NO 344
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 344
ucaucagagu cguucgagu                                                 19

<210> SEQ ID NO 345
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 345
uagugugguu uau                                                       13

<210> SEQ ID NO 346
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 346
auaaaccaca cuaucaccu                                              19

<210> SEQ ID NO 347
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 347
aagccaauga uga                                                    13

<210> SEQ ID NO 348
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 348
ucaucauugg cuuccgcu                                               19

<210> SEQ ID NO 349
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 349
auagucagga acu                                                    13

<210> SEQ ID NO 350
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 350
aguuccugac uaucaauca                                              19

<210> SEQ ID NO 351
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 351
agucagccgu gaa                                                    13

<210> SEQ ID NO 352
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 352
uucacggcug acuuuggaa                                              19
```

<210> SEQ ID NO 353
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 353
acuaccauga gaa                                                      13

<210> SEQ ID NO 354
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 354
uucucauggu agugaguuu                                                19

<210> SEQ ID NO 355
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 355
aaacaggcug auu                                                      13

<210> SEQ ID NO 356
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 356
aaucagccug uuuaacugg                                                19

<210> SEQ ID NO 357
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 357
gagugcugaa acc                                                      13

<210> SEQ ID NO 358
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 358
gguuucagca cucugguca                                                19

<210> SEQ ID NO 359
<211> LENGTH: 13
<212> TYPE: RNA
<213> ORGANISM: Artificial Sequence
<220> FEATURE:
<223> OTHER INFORMATION: Synthetic Polynucleotide

```
<400> SEQUENCE: 359
ugagcauucc gau                                                          13

<210> SEQ ID NO 360
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 360
aucggaaugc ucauugcuc                                                    19

<210> SEQ ID NO 361
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 361
aauuccacag cca                                                          13

<210> SEQ ID NO 362
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 362
uggcugugga auucacggc                                                    19

<210> SEQ ID NO 363
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 363
ugucaauugc uua                                                          13

<210> SEQ ID NO 364
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 364
uaagcaauug acaccacca                                                    19

<210> SEQ ID NO 365
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 365
accaugagaa uug                                                          13

<210> SEQ ID NO 366
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 366
caauucucau gguagugag                                                    19

<210> SEQ ID NO 367
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 367
ccaacgaaag cca                                                          13

<210> SEQ ID NO 368
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 368
uggcuuucgu uggacuuac                                                    19

<210> SEQ ID NO 369
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 369
cuggucacug auu                                                          13

<210> SEQ ID NO 370
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 370
aaucagugac caguucauc                                                    19

<210> SEQ ID NO 371
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 371
ugguuuaugg acu                                                          13

<210> SEQ ID NO 372
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 372
```
aguccauaaa ccacacuau                                                19

<210> SEQ ID NO 373
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 373
gaccagagug cug                                                      13

<210> SEQ ID NO 374
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 374
cagcacucug gucauccag                                                19

<210> SEQ ID NO 375
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 375
gaugugauug aua                                                      13

<210> SEQ ID NO 376
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 376
uaucaaucac aucggaaug                                                19

<210> SEQ ID NO 377
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 377
gucagccgug aau                                                      13

<210> SEQ ID NO 378
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 378
auucacggcu gacuuugga                                                19

<210> SEQ ID NO 379
<211> LENGTH: 13
<212> TYPE: RNA

```
<213> ORGANISM: Artificial Sequence
<220> FEATURE:
<223> OTHER INFORMATION: Synthetic Polynucleotide

<400> SEQUENCE: 379
aauguguauc uau                                                          13

<210> SEQ ID NO 380
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 380
auagauacac auucaacca                                                    19

<210> SEQ ID NO 381
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 381
uugagucugg aaa                                                          13

<210> SEQ ID NO 382
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 382
uuuccagacu caaauagau                                                    19

<210> SEQ ID NO 383
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 383
guccagcaau uaa                                                          13

<210> SEQ ID NO 384
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 384
uuaauugcug gacaaccgu                                                    19

<210> SEQ ID NO 385
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 385
ccagcaauua aua                                                          13
```

<210> SEQ ID NO 386
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 386
uauuaauugc uggacaacc                                              19

<210> SEQ ID NO 387
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 387
gacucgaacg acu                                                    13

<210> SEQ ID NO 388
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 388
agucguucga gucaaugga                                              19

<210> SEQ ID NO 389
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 389
accugccagc aac                                                    13

<210> SEQ ID NO 390
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 390
guugcuggca gguccgugg                                              19

<210> SEQ ID NO 391
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 391
gaugaaucug aua                                                    13

<210> SEQ ID NO 392
<211> LENGTH: 19
<212> TYPE: RNA
<213> ORGANISM: Artificial Sequence
<220> FEATURE:

<223> OTHER INFORMATION: Synthetic Polynucleotide

<400> SEQUENCE: 392
uaucagauuc aucagaaug                                                    19

<210> SEQ ID NO 393
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 393
ugaugaaucu gaua                                                         14

<210> SEQ ID NO 394
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 394
uaucagauuc aucagaaug                                                    19

<210> SEQ ID NO 395
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 395
auuugcuuuu gca                                                          13

<210> SEQ ID NO 396
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 396
ugcaaaagca aaucacugc                                                    19

<210> SEQ ID NO 397
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 397
gauuugcuuu ugca                                                         14

<210> SEQ ID NO 398
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 398
ugcaaaagca aaucacugc                                                    19

```
<210> SEQ ID NO 399
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 399
gugauuugcu uua                                                          13

<210> SEQ ID NO 400
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 400
uaaagcaaau cacugcaau                                                    19

<210> SEQ ID NO 401
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 401
agugauuugc uuua                                                         14

<210> SEQ ID NO 402
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 402
uaaagcaaau cacugcaau                                                    19

<210> SEQ ID NO 403
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 403
aauuucguau uua                                                          13

<210> SEQ ID NO 404
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 404
uaaauacgaa auuucaggu                                                    19

<210> SEQ ID NO 405
<211> LENGTH: 14
<212> TYPE: RNA
<213> ORGANISM: Artificial Sequence
<220> FEATURE:
<223> OTHER INFORMATION: Synthetic Polynucleotide
```

```
<400> SEQUENCE: 405
aaauuucgua uuua                                                    14

<210> SEQ ID NO 406
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 406
uaaauacgaa auuucaggu                                               19

<210> SEQ ID NO 407
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 407
cacagccaug aaa                                                     13

<210> SEQ ID NO 408
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 408
uuucauggcu gugaaauuc                                               19

<210> SEQ ID NO 409
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 409
ucacagccau gaaa                                                    14

<210> SEQ ID NO 410
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 410
uuucauggcu gugaaauuc                                               19

<210> SEQ ID NO 411
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 411
gauuugcuuu uga                                                     13

<210> SEQ ID NO 412
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 412
ucaaaagcaa aucacugca                                                    19

<210> SEQ ID NO 413
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 413
ugauuugcuu uuga                                                         14

<210> SEQ ID NO 414
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 414
ucaaaagcaa aucacugca                                                    19

<210> SEQ ID NO 415
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 415
uugcuuuugc cua                                                          13

<210> SEQ ID NO 416
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 416
uaggcaaaag caaaucacu                                                    19

<210> SEQ ID NO 417
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 417
uuugcuuuug ccua                                                         14

<210> SEQ ID NO 418
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 418
```
uaggcaaaag caaaucacu                               19

<210> SEQ ID NO 419
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 419
uuucucaguu uaa                                     13

<210> SEQ ID NO 420
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 420
uuaaacugag aagaagca                                19

<210> SEQ ID NO 421
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 421
uugcauuuag uca                                     13

<210> SEQ ID NO 422
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 422
ugacuaaaug caaagugag                               19

<210> SEQ ID NO 423
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 423
acuuugcauu uaa                                     13

<210> SEQ ID NO 424
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 424
uuaaaugcaa agugagaaa                               19

<210> SEQ ID NO 425
<211> LENGTH: 13
<212> TYPE: RNA
<213> ORGANISM: Artificial Sequence

```
<220> FEATURE:
<223> OTHER INFORMATION: Synthetic Polynucleotide

<400> SEQUENCE: 425
auuuagucaa aaa                                                          13

<210> SEQ ID NO 426
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 426
uuuuugacua aaugcaaag                                                    19

<210> SEQ ID NO 427
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 427
uucuuucuca gua                                                          13

<210> SEQ ID NO 428
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 428
uacugagaaa gaagcauuu                                                    19

<210> SEQ ID NO 429
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 429
ucuuucucag uua                                                          13

<210> SEQ ID NO 430
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 430
uaacugagaa agaagcauu                                                    19

<210> SEQ ID NO 431
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 431
gaaagagaac aua                                                          13
```

<210> SEQ ID NO 432
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 432
uauguucucu uucauuuug                                                  19

<210> SEQ ID NO 433
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 433
cuuugcauuu aga                                                        13

<210> SEQ ID NO 434
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 434
ucuaaaugca aagugagaa                                                  19

<210> SEQ ID NO 435
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 435
uuugcauuua gua                                                        13

<210> SEQ ID NO 436
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 436
uacuaaaugc aaagugaga                                                  19

<210> SEQ ID NO 437
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 437
cucacuuugc aua                                                        13

<210> SEQ ID NO 438
<211> LENGTH: 19
<212> TYPE: RNA
<213> ORGANISM: Artificial Sequence
<220> FEATURE:
<223> OTHER INFORMATION: Synthetic Polynucleotide -continued

<400> SEQUENCE: 438
uaugcaaagu gagaaauug                                                     19

<210> SEQ ID NO 439
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 439
uucucacuuu gca                                                           13

<210> SEQ ID NO 440
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 440
ugcaaaguga gaaauugua                                                     19

<210> SEQ ID NO 441
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 441
cacuccaguu gua                                                           13

<210> SEQ ID NO 442
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 442
uacaacugga gugaaaacu                                                     19

<210> SEQ ID NO 443
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 443
aaugaaagag aaa                                                           13

<210> SEQ ID NO 444
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 444
uuucucuuuc auuuugcua                                                     19

<210> SEQ ID NO 445

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 445
ugcagugauu uga                                                         13

<210> SEQ ID NO 446
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 446
ucaaaucacu gcaauucuc                                                   19

<210> SEQ ID NO 447
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 447
ugaaagagaa caa                                                         13

<210> SEQ ID NO 448
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 448
uuguucucuu ucauuuugc                                                   19

<210> SEQ ID NO 449
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 449
accugaaauu uca                                                         13

<210> SEQ ID NO 450
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 450
ugaaauuuca gguguuuau                                                   19

<210> SEQ ID NO 451
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 451
```

```
gaauugcagu gaa                                                      13

<210> SEQ ID NO 452
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 452
uucacugcaa uucucaugg                                                19

<210> SEQ ID NO 453
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 453
ggcugauucu gga                                                      13

<210> SEQ ID NO 454
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 454
uccagaauca gccuguuua                                                19

<210> SEQ ID NO 455
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 455
agugauuugc uuua                                                     14

<210> SEQ ID NO 456
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 456
uaaagcaaau cacugcaau                                                19

<210> SEQ ID NO 457
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 457
agugauuugc uuua                                                     14

<210> SEQ ID NO 458
<211> LENGTH: 19
<212> TYPE: RNA
```

```
<213> ORGANISM: Artificial Sequence
<220> FEATURE:
<223> OTHER INFORMATION: Synthetic Polynucleotide

<400> SEQUENCE: 458
uaaagcaaau cacugcaau                                                    19

<210> SEQ ID NO 459
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 459
agugauuugc uuua                                                         14

<210> SEQ ID NO 460
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 460
uaaagcaaau cacugcaau                                                    19

<210> SEQ ID NO 461
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 461
agugauuugc uuua                                                         14

<210> SEQ ID NO 462
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 462
uaaagcaaau cacugcaau                                                    19

<210> SEQ ID NO 463
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 463
cacauuugau uga                                                          13

<210> SEQ ID NO 464
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 464
ucaaucaaau gugaucugg                                                    19
```

<210> SEQ ID NO 465
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 465
cacugccuca auu                                                          13

<210> SEQ ID NO 466
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 466
aauugaggca guguugaug                                                    19

<210> SEQ ID NO 467
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 467
aaauaccagu cuu                                                          13

<210> SEQ ID NO 468
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 468
aagacuggua uuucaucug                                                    19

<210> SEQ ID NO 469
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 469
cauuugauug aca                                                          13

<210> SEQ ID NO 470
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 470
ugucaaucaa augugaucu                                                    19

<210> SEQ ID NO 471
<211> LENGTH: 13
<212> TYPE: RNA
<213> ORGANISM: Artificial Sequence
<220> FEATURE:

-continued

<223> OTHER INFORMATION: Synthetic Polynucleotide

<400> SEQUENCE: 471
gaaaacugcu caa                                                            13

<210> SEQ ID NO 472
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 472
uugagcaguu uucuccaua                                                      19

<210> SEQ ID NO 473
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 473
accucuccua uua                                                            13

<210> SEQ ID NO 474
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 474
uaauaggaga gguuagaga                                                      19

<210> SEQ ID NO 475
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 475
uccaccaacu uaa                                                            13

<210> SEQ ID NO 476
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 476
uuaaguuggu ggacuguca                                                      19

<210> SEQ ID NO 477
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 477
guccaccaac uuaa                                                           14

```
<210> SEQ ID NO 478
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 478
uuaaguuggu ggacuguca                                           19

<210> SEQ ID NO 479
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 479
cuccuauuau aca                                                 13

<210> SEQ ID NO 480
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 480
uguauaauag gagagguua                                           19

<210> SEQ ID NO 481
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 481
gaucacauuu gaa                                                 13

<210> SEQ ID NO 482
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 482
uucaaaugug aucuggaug                                           19

<210> SEQ ID NO 483
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 483
agaucacauu ugaa                                                14

<210> SEQ ID NO 484
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 484
uucaaaugug aucuggaug                                                    19

<210> SEQ ID NO 485
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 485
aaccucuccu aua                                                          13

<210> SEQ ID NO 486
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 486
uauaggagag guuagagaa                                                    19

<210> SEQ ID NO 487
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 487
guugacaucc aga                                                          13

<210> SEQ ID NO 488
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 488
ucuggauguc aacacauaa                                                    19

<210> SEQ ID NO 489
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 489
ccuuccuucg aaa                                                          13

<210> SEQ ID NO 490
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 490
uuucgaagga agggaaugu                                                    19

<210> SEQ ID NO 491
<211> LENGTH: 13
```

```
<212> TYPE: RNA
<213> ORGANISM: Artificial Sequence
<220> FEATURE:
<223> OTHER INFORMATION: Synthetic Polynucleotide

<400> SEQUENCE: 491
acuccaaaca caa                                                          13

<210> SEQ ID NO 492
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 492
uuguguuugg aguggguuu                                                    19

<210> SEQ ID NO 493
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 493
cacuccaaac aaa                                                          13

<210> SEQ ID NO 494
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 494
uuguguuugg agugguuu                                                     19

<210> SEQ ID NO 495
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 495
cacuccaaac aca                                                          13

<210> SEQ ID NO 496
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 496
uguguuugga guggguuuc                                                    19

<210> SEQ ID NO 497
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 497
```
ccaccaacuu aca                                                          13

<210> SEQ ID NO 498
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 498
uguaaguugg uggacuguc                                                    19

<210> SEQ ID NO 499
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 499
uccaccaacu uaca                                                         14

<210> SEQ ID NO 500
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 500
uguaaguugg uggacuguc                                                    19

<210> SEQ ID NO 501
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 501
aauaccaguc uua                                                          13

<210> SEQ ID NO 502
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 502
uaagacuggu auuucaucu                                                    19

<210> SEQ ID NO 503
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 503
gaccaguaua aga                                                          13

<210> SEQ ID NO 504
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 504
ucuuauacug gucaaaucc                                                    19

<210> SEQ ID NO 505
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 505
gucuuuuaau gaa                                                          13

<210> SEQ ID NO 506
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 506
uucauuaaaa gacugguau                                                    19

<210> SEQ ID NO 507
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 507
aauuucaugu cua                                                          13

<210> SEQ ID NO 508
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 508
uagacaugaa auuacuggu                                                    19

<210> SEQ ID NO 509
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 509
aucacauuug aua                                                          13

<210> SEQ ID NO 510
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 510
uaucaaaugu gaucuggau                                                    19
```

```
<210> SEQ ID NO 511
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 511
gaucacauuu gaua                                                           14

<210> SEQ ID NO 512
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 512
uaucaaaugu gaucuggau                                                      19

<210> SEQ ID NO 513
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 513
uccagaucac aua                                                            13

<210> SEQ ID NO 514
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 514
uaugugaucu ggaugucaa                                                      19

<210> SEQ ID NO 515
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 515
uacugauagg aga                                                            13

<210> SEQ ID NO 516
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 516
ucuccuauca guauuagcc                                                      19

<210> SEQ ID NO 517
<211> LENGTH: 13
<212> TYPE: RNA
<213> ORGANISM: Artificial Sequence
<220> FEATURE:
<223> OTHER INFORMATION: Synthetic Polynucleotide
```

-continued

<400> SEQUENCE: 517
gugcaacacu uga                                                          13

<210> SEQ ID NO 518
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 518
ucaaguguug cacauaauc                                                    19

<210> SEQ ID NO 519
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 519
accaguauaa gua                                                          13

<210> SEQ ID NO 520
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 520
uacuuauacu ggucaaauc                                                    19

<210> SEQ ID NO 521
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 521
gaagucuaau gaa                                                          13

<210> SEQ ID NO 522
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 522
uucauuagac uucuacagu                                                    19

<210> SEQ ID NO 523
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 523
aagaagaaag uua                                                          13

<210> SEQ ID NO 524

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 524
uaacuuucuu cuuagaagc                                                19

<210> SEQ ID NO 525
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 525
ucacauuuga uua                                                      13

<210> SEQ ID NO 526
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 526
uaaucaaaug ugaucugga                                                19

<210> SEQ ID NO 527
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 527
aucacauuug auua                                                     14

<210> SEQ ID NO 528
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 528
uaaucaaaug ugaucugga                                                19

<210> SEQ ID NO 529
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 529
acauuugauu gaa                                                      13

<210> SEQ ID NO 530
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 530
```

-continued

```
uucaaucaaa ugugaucug                                               19

<210> SEQ ID NO 531
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 531
cacauuugau ugaa                                                    14

<210> SEQ ID NO 532
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 532
uucaaucaaa ugugaucug                                               19

<210> SEQ ID NO 533
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 533
auuugauuga caa                                                     13

<210> SEQ ID NO 534
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 534
uugucaauca aaugugauc                                               19

<210> SEQ ID NO 535
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 535 cauugauug acaa                                                     14

<210> SEQ ID NO 536
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 536
uugucaauca aaugugauc                                               19

<210> SEQ ID NO 537
<211> LENGTH: 13
<212> TYPE: RNA
```

```
<213> ORGANISM: Artificial Sequence
<220> FEATURE:
<223> OTHER INFORMATION: Synthetic Polynucleotide

<400> SEQUENCE: 537
caucugcaau aaa                                                      13

<210> SEQ ID NO 538
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 538
uuuauugcag augagagac                                                19

<210> SEQ ID NO 539
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 539
ucaucugcaa uaaa                                                     14

<210> SEQ ID NO 540
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 540
uuuauugcag augagagac                                                19

<210> SEQ ID NO 541
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 541
gaucacauuu gaa                                                      13

<210> SEQ ID NO 542
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 542
uucaaaugug aucggaug                                                 19

<210> SEQ ID NO 543
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 543
gaucacauuu gaa                                                      13
```

<210> SEQ ID NO 544
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 544
uucaaaugug aucuggaug                                                    19

<210> SEQ ID NO 545
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 545
gaucacauuu gaa                                                          13

<210> SEQ ID NO 546
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 546
uucaaaugug aucuggaug                                                    19

<210> SEQ ID NO 547
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 547
gaucacauuu gaa                                                          13

<210> SEQ ID NO 548
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 548
uucaaaugug aucuggaug                                                    19

<210> SEQ ID NO 549
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 549
gaucacauuu gaa                                                          13

<210> SEQ ID NO 550
<211> LENGTH: 19
<212> TYPE: RNA
<213> ORGANISM: Artificial Sequence
<220> FEATURE:

<223> OTHER INFORMATION: Synthetic Polynucleotide

<400> SEQUENCE: 550
uucaaaugug aucuggaug                                                    19

<210> SEQ ID NO 551
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 551
gaucacauuu gaua                                                         14

<210> SEQ ID NO 552
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 552
uaucaaaugu gaucuggaug                                                   20

<210> SEQ ID NO 553
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 553
gaucacauuu gaua                                                         14

<210> SEQ ID NO 554
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 554
uaucaaaugu gaucuggaug                                                   20

<210> SEQ ID NO 555
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 555
gaucacauuu gaua                                                         14

<210> SEQ ID NO 556
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 556
uaucaaaugu gaucuggaug                                                   20

```
<210> SEQ ID NO 557
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 557
gaucacauuu gaua                                                      14

<210> SEQ ID NO 558
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 558
uaucaaaugu gaucuggaug                                                20

<210> SEQ ID NO 559
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 559
gaucacauuu gaua                                                      14

<210> SEQ ID NO 560
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 560
uaucaaaugu gaucuggaug                                                20

<210> SEQ ID NO 561
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 561
gaucacauuu gaua                                                      14

<210> SEQ ID NO 562
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 562
uaucaaaugu gaucuggaug                                                20

<210> SEQ ID NO 563
<211> LENGTH: 14
<212> TYPE: RNA
<213> ORGANISM: Artificial Sequence
<220> FEATURE:
<223> OTHER INFORMATION: Synthetic Polynucleotide
```

```
<400> SEQUENCE: 563
gaucacauuu gaua                                                    14

<210> SEQ ID NO 564
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 564
uaucaaaugu gaucuggaug                                              20

<210> SEQ ID NO 565
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 565
gaucacauuu gaua                                                    14

<210> SEQ ID NO 566
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 566
uaucaaaugu gaucuggaug                                              20

<210> SEQ ID NO 567
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 567
gaucacauuu gaua                                                    14

<210> SEQ ID NO 568
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 568
uaucaaaugu gaucuggau                                               19

<210> SEQ ID NO 569
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 569
gaucacauuu gaua                                                    14

<210> SEQ ID NO 570
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 570
uaucaaaugu gaucuggau                                                    19

<210> SEQ ID NO 571
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 571
gaucacauuu gaua                                                         14

<210> SEQ ID NO 572
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 572
uaucaaaugu gaucuggau                                                    19

<210> SEQ ID NO 573
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 573
gaucacauuu gaua                                                         14

<210> SEQ ID NO 574
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 574
uaucaaaugu gaucuggau                                                    19

<210> SEQ ID NO 575
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 575
gaucacauuu gaua                                                         14

<210> SEQ ID NO 576
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 576
```

```
uaucaaaugu gaucuggau                                           19

<210> SEQ ID NO 577
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 577
gaucacauuu gaua                                                14

<210> SEQ ID NO 578
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 578
uaucaaaugu gaucuggau                                           19

<210> SEQ ID NO 579
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 579
gaucacauuu gaua                                                14

<210> SEQ ID NO 580
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 580
uaucaaaugu gaucuggau                                           19

<210> SEQ ID NO 581
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 581
gaucacauuu gaa                                                 13

<210> SEQ ID NO 582
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 582
uucaaaugug aucuggaug                                           19

<210> SEQ ID NO 583
<211> LENGTH: 13
<212> TYPE: RNA
<213> ORGANISM: Artificial Sequence
```

```
<220> FEATURE:
<223> OTHER INFORMATION: Synthetic Polynucleotide

<400> SEQUENCE: 583
gaucacauuu gaa                                                        13

<210> SEQ ID NO 584
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 584
uucaaaugug aucuggaug                                                  19

<210> SEQ ID NO 585
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 585
gaucacauuu gaa                                                        13

<210> SEQ ID NO 586
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 586
uucaaaugug aucuggaug                                                  19

<210> SEQ ID NO 587
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 587
gaucacauuu gaa                                                        13

<210> SEQ ID NO 588
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 588
uucaaaugug aucuggaug                                                  19

<210> SEQ ID NO 589
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 589
acaggaagau gua                                                        13
```

```
<210> SEQ ID NO 590
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 590
uacaucuucc uguaguaca                                                      19

<210> SEQ ID NO 591
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 591
gaguggagcg ccu                                                            13

<210> SEQ ID NO 592
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 592
aggcgcucca cucuguggu                                                      19

<210> SEQ ID NO 593
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 593
cgacuggaag aca                                                            13

<210> SEQ ID NO 594
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 594
ugucuuccag ucgguaagc                                                      19

<210> SEQ ID NO 595
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 595
ggagcgccug uuc                                                            13

<210> SEQ ID NO 596
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 596
gaacaggcgc uccacucug                                           19

<210> SEQ ID NO 597
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 597
gccauuacaa cug                                                 13

<210> SEQ ID NO 598
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 598
caguuguaau ggcaggcac                                           19

<210> SEQ ID NO 599
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 599
gagcuuucug gcu                                                 13

<210> SEQ ID NO 600
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 600
agccagaaag cucaaacuu                                           19

<210> SEQ ID NO 601
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 601
aguggagcgc cug                                                 13

<210> SEQ ID NO 602
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 602
caggcgcucc acucugugg                                           19

<210> SEQ ID NO 603
```

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 603
uggagcgccu guu                                                          13

<210> SEQ ID NO 604
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 604
aacaggcgcu ccacucugu                                                    19

<210> SEQ ID NO 605
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 605
guuugagcuu ucu                                                          13

<210> SEQ ID NO 606
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 606
agaaagcuca aacuugaua                                                    19

<210> SEQ ID NO 607
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 607
ugccauuaca acu                                                          13

<210> SEQ ID NO 608
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 608
aguuguaaug gcaggcaca                                                    19

<210> SEQ ID NO 609
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 609
```
acuggaagac acg                                                        13

<210> SEQ ID NO 610
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 610
cgugucuucc agucgguaa                                                  19

<210> SEQ ID NO 611
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 611
aacugccugg ucc                                                        13

<210> SEQ ID NO 612
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 612
ggaccaggca guuggcucu                                                  19

<210> SEQ ID NO 613
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 613
agaccugugc cug                                                        13

<210> SEQ ID NO 614
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 614
caggcacagg ucuugauga                                                  19

<210> SEQ ID NO 615
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 615
cagaguggag cgc                                                        13

<210> SEQ ID NO 616
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 616
gcgcuccacu cugggucu                                                    19

<210> SEQ ID NO 617
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 617
ccugguccag acc                                                         13

<210> SEQ ID NO 618
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 618
ggucuggacc aggcaguug                                                   19

<210> SEQ ID NO 619
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 619
ccauuacaac ugu                                                         13

<210> SEQ ID NO 620
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 620
acaguuguaa uggcaggca                                                   19

<210> SEQ ID NO 621
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 621
cugccauuac aac                                                         13

<210> SEQ ID NO 622
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 622
guuguaaugg caggcacag                                                   19
```

```
<210> SEQ ID NO 623
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 623
auuacaacug ucc                                                          13

<210> SEQ ID NO 624
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 624
ggacaguugu aauggcagg                                                    19

<210> SEQ ID NO 625
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 625
cauuacaacu guc                                                          13

<210> SEQ ID NO 626
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 626
gacaguugua auggcaggc                                                    19

<210> SEQ ID NO 627
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 627
agaguggagc gcc                                                          13

<210> SEQ ID NO 628
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 628
ggcgcuccac ucugugguc                                                    19

<210> SEQ ID NO 629
<211> LENGTH: 13
<212> TYPE: RNA
<213> ORGANISM: Artificial Sequence
<220> FEATURE:
```

<223> OTHER INFORMATION: Synthetic Polynucleotide

<400> SEQUENCE: 629
accgacugga aga                                                              13

<210> SEQ ID NO 630
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 630
ucuuccaguc gguaagccg                                                        19

<210> SEQ ID NO 631
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 631
auguacggag aca                                                              13

<210> SEQ ID NO 632
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 632
ugucuccgua caucuuccu                                                        19

<210> SEQ ID NO 633
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 633
gccuugcgaa gcu                                                              13

<210> SEQ ID NO 634
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 634
agcuucgcaa ggccugacc                                                        19

<210> SEQ ID NO 635
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 635
gcugcgagga gug                                                              13

```
<210> SEQ ID NO 636
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 636
cacuccucgc agcauuucc                                                    19

<210> SEQ ID NO 637
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 637
gccuaucaag uuu                                                          13

<210> SEQ ID NO 638
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 638
aaacuugaua ggcuuggag                                                    19

<210> SEQ ID NO 639
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 639
aauucugugg agu                                                          13

<210> SEQ ID NO 640
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 640
acuccacaga auuuagcuc                                                    19

<210> SEQ ID NO 641
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 641
uguacggaga cau                                                          13

<210> SEQ ID NO 642
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 642
augucuccgu acaucuucc                                              19

<210> SEQ ID NO 643
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 643
agccuaucaa guu                                                    13

<210> SEQ ID NO 644
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 644
aacuugauag gcuuggaga                                              19

<210> SEQ ID NO 645
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 645
caaguuugag cuu                                                    13

<210> SEQ ID NO 646
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 646
aagcucaaac uugauaggc                                              19

<210> SEQ ID NO 647
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 647
cuguggagua ugu                                                    13

<210> SEQ ID NO 648
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 648
acauacucca cagaauuua                                              19

<210> SEQ ID NO 649
<211> LENGTH: 13
```

```
<212> TYPE: RNA
<213> ORGANISM: Artificial Sequence
<220> FEATURE:
<223> OTHER INFORMATION: Synthetic Polynucleotide

<400> SEQUENCE: 649
aaauucugug gag                                                        13

<210> SEQ ID NO 650
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 650
cuccacagaa uuuagcucg                                                  19

<210> SEQ ID NO 651
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 651
uuucaguagc aca                                                        13

<210> SEQ ID NO 652
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 652
ugugcuacug aaacauuu                                                   19

<210> SEQ ID NO 653
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 653
caaugacauc uuu                                                        13

<210> SEQ ID NO 654
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 654
aaagauguca uugucuccg                                                  19

<210> SEQ ID NO 655
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 655
```

```
aguaccagug cac                                                    13

<210> SEQ ID NO 656
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 656
gugcacuggu acuugcagc                                              19

<210> SEQ ID NO 657
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 657
ggaagacacg uuu                                                    13

<210> SEQ ID NO 658
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 658
aaacgugucu uccagucgg                                              19

<210> SEQ ID NO 659
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 659
cuaucaaguu uga                                                    13

<210> SEQ ID NO 660
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 660
ucaaacuuga uaggcuugg                                              19

<210> SEQ ID NO 661
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 661
agcuaaauuc ugu                                                    13

<210> SEQ ID NO 662
<211> LENGTH: 19
<212> TYPE: RNA
<213> ORGANISM: Artificial Sequence
```

```
<220> FEATURE:
<223> OTHER INFORMATION: Synthetic Polynucleotide

<400> SEQUENCE: 662
acagaauuua gcucgguau                                              19

<210> SEQ ID NO 663
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 663
agguagaaug uaa                                                    13

<210> SEQ ID NO 664
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 664
uuacauucua ccuauggug                                              19

<210> SEQ ID NO 665
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 665
agcugaucag uuu                                                    13

<210> SEQ ID NO 666
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 666
aaacugauca gcuauauag                                              19

<210> SEQ ID NO 667
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 667
uucugcucag aua                                                    13

<210> SEQ ID NO 668
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 668
uaucugagca gaauuucca                                              19
```

```
<210> SEQ ID NO 669
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 669
uuaucuaagu uaa                                                          13

<210> SEQ ID NO 670
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 670
uuaacuuaga uaacuguac                                                    19

<210> SEQ ID NO 671
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 671
uauacgagua aua                                                          13

<210> SEQ ID NO 672
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 672
uauuacucgu auaagaugc                                                    19

<210> SEQ ID NO 673
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 673
gacuggacag cuu                                                          13

<210> SEQ ID NO 674
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 674
aagcugucca gucuaaucg                                                    19

<210> SEQ ID NO 675
<211> LENGTH: 13
<212> TYPE: RNA
<213> ORGANISM: Artificial Sequence
<220> FEATURE:
<223> OTHER INFORMATION: Synthetic Polynucleotide
```

-continued

<400> SEQUENCE: 675
auggccuuua uua                                                          13

<210> SEQ ID NO 676
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 676
uaauaaaggc cauuuguuc                                                    19

<210> SEQ ID NO 677
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 677
auaccgagcu aaa                                                          13

<210> SEQ ID NO 678
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 678
uuuagcucgg uaugucuuc                                                    19

<210> SEQ ID NO 679
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 679
uuguugagag ugu                                                          13

<210> SEQ ID NO 680
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 680
acacucucaa caaauaaac                                                    19

<210> SEQ ID NO 681
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 681
acauaccgag cua                                                          13

<210> SEQ ID NO 682

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 682
uagcucggua ugucuucau                                              19

<210> SEQ ID NO 683
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 683
agcagaaagg uua                                                    13

<210> SEQ ID NO 684
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 684
uaaccuuucu gcugguacc                                              19

<210> SEQ ID NO 685
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 685
aguuguuccu uaa                                                    13

<210> SEQ ID NO 686
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 686
uuaaggaaca acuugacuc                                              19

<210> SEQ ID NO 687
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 687
auuugaagug uaa                                                    13

<210> SEQ ID NO 688
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 688
```
uuacacuuca aauagcagg                                                19

<210> SEQ ID NO 689
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 689
aagcugaccu gga                                                      13

<210> SEQ ID NO 690
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 690
uccaggucag cuucgcaag                                                19

<210> SEQ ID NO 691
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 691
ggucaugaag aag                                                      13

<210> SEQ ID NO 692
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 692
cuucuucaug accucgccg                                                19

<210> SEQ ID NO 693
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 693
auggucaggc cuu                                                      13

<210> SEQ ID NO 694
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 694
aaggccugac caugcacag                                                19

<210> SEQ ID NO 695
<211> LENGTH: 13
<212> TYPE: RNA

<213> ORGANISM: Artificial Sequence
<220> FEATURE:
<223> OTHER INFORMATION: Synthetic Polynucleotide

<400> SEQUENCE: 695
gaagacacgu uug                                                          13

<210> SEQ ID NO 696
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 696
caaacguguc uuccagucg                                                    19

<210> SEQ ID NO 697
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 697
aggccuugcg aag                                                          13

<210> SEQ ID NO 698
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 698
cuucgcaagg ccugaccau                                                    19

<210> SEQ ID NO 699
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 699
uaccgacugg aag                                                          13

<210> SEQ ID NO 700
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 700
cuuccagucg guaagccgc                                                    19

<210> SEQ ID NO 701
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 701
accgcaagau cgg                                                          13

```
<210> SEQ ID NO 702
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 702
ccgaucuugc gguuggccg                                                  19

<210> SEQ ID NO 703
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 703
caggccuugc gaa                                                        13

<210> SEQ ID NO 704
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 704
uucgcaaggc cugaccaug                                                  19

<210> SEQ ID NO 705
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 705
cgagcuaaau ucu                                                        13

<210> SEQ ID NO 706
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 706
agaauuuagc ucgguaugu                                                  19

<210> SEQ ID NO 707
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 707
ucuguggagu aug                                                        13

<210> SEQ ID NO 708
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 708
cauacuccac agaauuuag					19

<210> SEQ ID NO 709
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 709
cggagacaug gca					13

<210> SEQ ID NO 710
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 710
ugccaugucu ccguacauc					19

<210> SEQ ID NO 711
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 711
augacaacgc cuc					13

<210> SEQ ID NO 712
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 712
gaggcguugu cauugguaa					19

<210> SEQ ID NO 713
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 713
gaggucauga aga					13

<210> SEQ ID NO 714
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 714
ucuucaugac cucgccguc					19

-continued

```
<210> SEQ ID NO 715
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 715
uaaauucugu gga                                                          13

<210> SEQ ID NO 716
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 716
uccacagaau uuagcucgg                                                    19

<210> SEQ ID NO 717
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 717
uggaagacac guu                                                          13

<210> SEQ ID NO 718
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 718
aacgugucuu ccagucggu                                                    19

<210> SEQ ID NO 719
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 719
aagauguacg gag                                                          13

<210> SEQ ID NO 720
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 720
cuccguacau cuuccugua                                                    19

<210> SEQ ID NO 721
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 721
aaugacaacg ccu                                                              13

<210> SEQ ID NO 722
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 722
aggcguuguc auugguaac                                                        19

<210> SEQ ID NO 723
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 723
ggcgagguca uga                                                              13

<210> SEQ ID NO 724
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 724
ucaugaccuc gccgucagg                                                        19

<210> SEQ ID NO 725
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 725
gacacguuug gcc                                                              13

<210> SEQ ID NO 726
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 726
ggccaaacgu gcuuccag                                                         19

<210> SEQ ID NO 727
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 727
acggagacau ggc                                                              13

<210> SEQ ID NO 728
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 728
gccaugucuc cguacaucu                                              19

<210> SEQ ID NO 729
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 729
ucaggccuug cga                                                    13

<210> SEQ ID NO 730
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 730
ucgcaaggcc ugaccaugc                                              19

<210> SEQ ID NO 731
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 731
gcgaagcuga ccu                                                    13

<210> SEQ ID NO 732
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 732
aggucagcuu cgcaaggcc                                              19

<210> SEQ ID NO 733
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 733
ggaagaugua cgg                                                    13

<210> SEQ ID NO 734
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 734
```

```
ccguacaucu uccuguagu                                                       19

<210> SEQ ID NO 735
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 735
gugacuucgg cuc                                                             13

<210> SEQ ID NO 736
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 736
gagccgaagu cacagaaga                                                       19

<210> SEQ ID NO 737
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 737
ugacuucggc ucc                                                             13

<210> SEQ ID NO 738
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 738
ggagccgaag ucacagaag                                                       19

<210> SEQ ID NO 739
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 739
uggucaggcc uug                                                             13

<210> SEQ ID NO 740
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 740
caaggccuga ccaugcaca                                                       19

<210> SEQ ID NO 741
<211> LENGTH: 13
<212> TYPE: RNA
<213> ORGANISM: Artificial Sequence
```

```
<220> FEATURE:
<223> OTHER INFORMATION: Synthetic Polynucleotide

<400> SEQUENCE: 741
ucaaguuuga gcu                                                          13

<210> SEQ ID NO 742
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 742
agcucaaacu ugauaggcu                                                    19

<210> SEQ ID NO 743
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 743
gccagaacug cag                                                          13

<210> SEQ ID NO 744
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 744
cugcaguucu ggccgacgg                                                    19

<210> SEQ ID NO 745
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 745
uggaguaugu acc                                                          13

<210> SEQ ID NO 746
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 746
gguacauacu ccacagaau                                                    19

<210> SEQ ID NO 747
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 747
gcuagagaag cag                                                          13
```

```
<210> SEQ ID NO 748
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 748
cugcuucucu agccugcag                                                19

<210> SEQ ID NO 749
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 749
ggucaggccu ugc                                                      13

<210> SEQ ID NO 750
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 750
gcaaggccug accaugcac                                                19

<210> SEQ ID NO 751
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 751
gagcuaaauu cug                                                      13

<210> SEQ ID NO 752
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 752
cagaauuuag cucgguaug                                                19

<210> SEQ ID NO 753
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 753
aagacacguu ugg                                                      13

<210> SEQ ID NO 754
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 754
ccaaacgugu cuuccaguc                                                    19

<210> SEQ ID NO 755
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 755
cgaggucaug aag                                                          13

<210> SEQ ID NO 756
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 756
cuucaugacc ucgccguca                                                    19

<210> SEQ ID NO 757
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 757
ggccuugcga agc                                                          13

<210> SEQ ID NO 758
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 758
gcuucgcaag gccugacca                                                    19

<210> SEQ ID NO 759
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 759
cuugcgaagc uga                                                          13

<210> SEQ ID NO 760
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 760
ucagcuucgc aaggccuga                                                    19

<210> SEQ ID NO 761
```

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 761
ccgacuggaa gac                                                          13

<210> SEQ ID NO 762
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 762
gucuuccagu cgguaagcc                                                    19

<210> SEQ ID NO 763
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 763
ccuaucaagu uug                                                          13

<210> SEQ ID NO 764
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 764
caaacuugau aggcuugga                                                    19

<210> SEQ ID NO 765
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 765
uguuccaaga ccu                                                          13

<210> SEQ ID NO 766
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 766
aggucuugga acaggcgcu                                                    19

<210> SEQ ID NO 767
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 767
```
cgaagcugac cug                                               13

<210> SEQ ID NO 768
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 768
caggucagcu ucgcaaggc                                         19

<210> SEQ ID NO 769
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 769
uugcgaagcu gac                                               13

<210> SEQ ID NO 770
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 770
gucagcuucg caaggccug                                         19

<210> SEQ ID NO 771
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 771
caaugacaac gcc                                               13

<210> SEQ ID NO 772
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 772
ggcguuguca uugguaacc                                         19

<210> SEQ ID NO 773
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 773
guaccagugc acg                                               13

<210> SEQ ID NO 774
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 774
cgugcacugg uacuugcag                                                    19

<210> SEQ ID NO 775
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 775
ccuguuccaa gac                                                          13

<210> SEQ ID NO 776
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 776
gucuuggaac aggcgcucc                                                    19

<210> SEQ ID NO 777
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 777
uacggagaca ugg                                                          13

<210> SEQ ID NO 778
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 778
ccaugucucc guacaucuu                                                    19

<210> SEQ ID NO 779
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 779
ugcgaagcug acc                                                          13

<210> SEQ ID NO 780
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 780
ggucagcuuc gcaaggccu                                                    19
```

<210> SEQ ID NO 781
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 781
ccuugcgaag cug                                                          13

<210> SEQ ID NO 782
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 782
cagcuucgca aggccugac                                                    19

<210> SEQ ID NO 783
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 783
cugugacuuc ggc                                                          13

<210> SEQ ID NO 784
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 784
gccgaaguca cagaagagg                                                    19

<210> SEQ ID NO 785
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 785
gcuaaauucu gug                                                          13

<210> SEQ ID NO 786
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 786
cacagaauuu agcucggua                                                    19

<210> SEQ ID NO 787
<211> LENGTH: 13
<212> TYPE: RNA
<213> ORGANISM: Artificial Sequence
<220> FEATURE:

<223> OTHER INFORMATION: Synthetic Polynucleotide

<400> SEQUENCE: 787
cuaaauucug ugg                                                          13

<210> SEQ ID NO 788
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 788
ccacagaauu uagcucggu                                                    19

<210> SEQ ID NO 789
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 789
agacacguuu ggc                                                          13

<210> SEQ ID NO 790
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 790
gccaaacgug ucuuccagu                                                    19

<210> SEQ ID NO 791
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 791
ccgcaagauc ggc                                                          13

<210> SEQ ID NO 792
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 792
gccgaucuug cgguuggcc                                                    19

<210> SEQ ID NO 793
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 793
uaucaaguuu gag                                                          13

```
<210> SEQ ID NO 794
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 794
cucaaacuug auaggcuug                                                    19

<210> SEQ ID NO 795
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 795
gaagcugacc ugg                                                          13

<210> SEQ ID NO 796
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 796
ccaggucagc uucgcaagg                                                    19

<210> SEQ ID NO 797
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 797
acauuaacuc aua                                                          13

<210> SEQ ID NO 798
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 798
uaugaguuaa ugucucuca                                                    19

<210> SEQ ID NO 799
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 799
gacauuaacu caua                                                         14

<210> SEQ ID NO 800
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 800
uaugaguuaa ugucucuca                                                  19

<210> SEQ ID NO 801
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 801
ugaagaaugu uaa                                                        13

<210> SEQ ID NO 802
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 802
uuaacauucu ucaaaccag                                                  19

<210> SEQ ID NO 803
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 803
uugaagaaug uuaa                                                       14

<210> SEQ ID NO 804
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 804
uuaacauucu ucaaaccag                                                  19

<210> SEQ ID NO 805
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 805
gauagcaucu uaa                                                        13

<210> SEQ ID NO 806
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 806
uuaagaugcu aucugauga                                                  19

<210> SEQ ID NO 807
<211> LENGTH: 14
```

```
<212> TYPE: RNA
<213> ORGANISM: Artificial Sequence
<220> FEATURE:
<223> OTHER INFORMATION: Synthetic Polynucleotide

<400> SEQUENCE: 807
agauagcauc uuaa                                                        14

<210> SEQ ID NO 808
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 808
uuaagaugcu aucugauga                                                   19

<210> SEQ ID NO 809
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 809
ugaaguguaa uua                                                         13

<210> SEQ ID NO 810
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 810
uaauuacacu ucaaauagc                                                   19

<210> SEQ ID NO 811
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 811
aauugagaag gaa                                                         13

<210> SEQ ID NO 812
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 812
uuccuucuca auuacacuu                                                   19

<210> SEQ ID NO 813
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 813
```
uugagaagga aaa                                         13

<210> SEQ ID NO 814
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 814
uuuuccuucu caauuacac                                   19

<210> SEQ ID NO 815
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 815
cauucugauu cga                                         13

<210> SEQ ID NO 816
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 816
ucgaaucaga augucagag                                   19

<210> SEQ ID NO 817
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 817
uucugauucg aaa                                         13

<210> SEQ ID NO 818
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 818
uuucgaauca gaaugucag                                   19

<210> SEQ ID NO 819
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 819
cugucgauua gaa                                         13

<210> SEQ ID NO 820
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 820
uucuaaucga caggauucc                                                19

<210> SEQ ID NO 821
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 821
uuugccugua aca                                                      13

<210> SEQ ID NO 822
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 822
uguuacaggc aaauucacu                                                19

<210> SEQ ID NO 823
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 823
auuugccugu aaca                                                     14

<210> SEQ ID NO 824
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 824
uguuacaggc aaauucacu                                                19

<210> SEQ ID NO 825
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 825
acaagccaga uua                                                      13

<210> SEQ ID NO 826
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 826
uaaucuggcu uguuacagg                                                19
```

<210> SEQ ID NO 827
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 827
aacaagccag auua                                                    14

<210> SEQ ID NO 828
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 828
uaaucuggcu uguuacagg                                               19

<210> SEQ ID NO 829
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 829
caguuuauuu gua                                                     13

<210> SEQ ID NO 830
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 830
uacaaauaaa cuguccgaa                                               19

<210> SEQ ID NO 831
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 831
uguugagagu gua                                                     13

<210> SEQ ID NO 832
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 832
uacacucuca acaaauaaa                                               19

<210> SEQ ID NO 833
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 833
uuguugagag ugua                                                14

<210> SEQ ID NO 834
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 834
uacacucuca acaaauaaa                                           19

<210> SEQ ID NO 835
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 835
ugcaccuuuc uaa                                                 13

<210> SEQ ID NO 836
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 836
uuagaaaggu gcaaacaug                                           19

<210> SEQ ID NO 837
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 837
uugcaccuuu cuaa                                                14

<210> SEQ ID NO 838
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 838
uuagaaaggu gcaaacaug                                           19

<210> SEQ ID NO 839
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 839
uugagcuuuc uga                                                 13

<210> SEQ ID NO 840

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 840
ucagaaagcu caaacuuga                                                      19

<210> SEQ ID NO 841
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 841
ugagagugug aca                                                            13

<210> SEQ ID NO 842
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 842
ugucacacuc ucaacaaau                                                      19

<210> SEQ ID NO 843
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 843
agugugacca aaa                                                            13

<210> SEQ ID NO 844
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 844
uuuuggucac acucucaac                                                      19

<210> SEQ ID NO 845
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 845
gagugugacc aaaa                                                           14

<210> SEQ ID NO 846
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 846
```

-continued

```
uuuuggucac acucucaac                                              19

<210> SEQ ID NO 847
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 847
gugugaccaa aaa                                                    13

<210> SEQ ID NO 848
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 848
uuuuugguca cacucucaa                                              19

<210> SEQ ID NO 849
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 849
ugugaccaaa aga                                                    13

<210> SEQ ID NO 850
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 850
ucuuuugguc acacucuca                                              19

<210> SEQ ID NO 851
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 851
gugugaccaa aaga                                                   14

<210> SEQ ID NO 852
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 852
ucuuuugguc acacucuca                                              19

<210> SEQ ID NO 853
<211> LENGTH: 13
<212> TYPE: RNA
```

```
<213> ORGANISM: Artificial Sequence
<220> FEATURE:
<223> OTHER INFORMATION: Synthetic Polynucleotide

<400> SEQUENCE: 853
gugaccaaaa gua                                                        13

<210> SEQ ID NO 854
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 854
uacuuuuggu cacacucuc                                                  19

<210> SEQ ID NO 855
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 855
gaccaaaagu uaa                                                        13

<210> SEQ ID NO 856
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 856
uuaacuuuug gucacacuc                                                  19

<210> SEQ ID NO 857
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 857
gcaccuuucu aga                                                        13

<210> SEQ ID NO 858
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 858
ucuagaaagg ugcaaacau                                                  19

<210> SEQ ID NO 859
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 859
ccuuucuagu uga                                                        13
```

```
<210> SEQ ID NO 860
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 860
ucaacuagaa aggugcaaa                                                    19

<210> SEQ ID NO 861
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 861
gcaccuuucu aga                                                          13

<210> SEQ ID NO 862
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 862
ucuagaaagg ugcaaacau                                                    19

<210> SEQ ID NO 863
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 863
gcaccuuucu aga                                                          13

<210> SEQ ID NO 864
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 864
ucuagaaagg ugcaaacau                                                    19

<210> SEQ ID NO 865
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 865
gcaccuuucu aga                                                          13

<210> SEQ ID NO 866
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 866
ucuagaaagg ugcaaacau                                                    19

<210> SEQ ID NO 867
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 867
gcaccuuucu aga                                                          13

<210> SEQ ID NO 868
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 868
ucuagaaagg ugcaaacau                                                    19

<210> SEQ ID NO 869
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 869
gcaccuuucu aga                                                          13

<210> SEQ ID NO 870
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 870
ucuagaaagg ugcaaacau                                                    19

<210> SEQ ID NO 871
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 871
gcaccuuucu aga                                                          13

<210> SEQ ID NO 872
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 872
ucuagaaagg ugcaaacau                                                    19

```
<210> SEQ ID NO 873
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 873
gcaccuuucu aga                                                       13

<210> SEQ ID NO 874
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 874
ucuagaaagg ugcaaacau                                                 19

<210> SEQ ID NO 875
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 875
gcaccuuucu aga                                                       13

<210> SEQ ID NO 876
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 876
ucuagaaagg ugcaaacau                                                 19

<210> SEQ ID NO 877
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 877
gcaccuuucu aga                                                       13

<210> SEQ ID NO 878
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 878
ucuagaaagg ugcaaacau                                                 19

<210> SEQ ID NO 879
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 879
gcaccuuucu aga                                                          13

<210> SEQ ID NO 880
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 880
ucuagaaagg ugcaaacau                                                    19

<210> SEQ ID NO 881
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 881
gcaccuuucu aga                                                          13

<210> SEQ ID NO 882
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 882
ucuagaaagg ugcaaacau                                                    19

<210> SEQ ID NO 883
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 883
gugaccaaaa gua                                                          13

<210> SEQ ID NO 884
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 884
uacuuuuggu cacacucuc                                                    19

<210> SEQ ID NO 885
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 885
gugaccaaaa gua                                                          13

<210> SEQ ID NO 886
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 886 uacuuuggu cacacucuc                                              19

<210> SEQ ID NO 887
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 887
gugaccaaaa gua                                                   13

<210> SEQ ID NO 888
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 888 uacuuuggu cacacucuc                                              19

<210> SEQ ID NO 889
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 889
uugcaccuuu cuaa                                                  14

<210> SEQ ID NO 890
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 890
uuagaaaggu gcaaacaagg                                            20

<210> SEQ ID NO 891
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 891
uugcaccuuu cuaa                                                  14

<210> SEQ ID NO 892
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 892
```

```
uuagaaaggu gcaaacaagg                                               20

<210> SEQ ID NO 893
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 893
uugcaccuuu cuaa                                                     14

<210> SEQ ID NO 894
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 894
uuagaaaggu gcaaacaagg                                               20

<210> SEQ ID NO 895
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 895
uugcaccuuu cuaa                                                     14

<210> SEQ ID NO 896
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 896
uuagaaaggu gcaaacaagg                                               20

<210> SEQ ID NO 897
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 897
uugcaccuuu cuaa                                                     14

<210> SEQ ID NO 898
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 898
uuagaaaggu gcaaacaagg                                               20

<210> SEQ ID NO 899
<211> LENGTH: 14
<212> TYPE: RNA
<213> ORGANISM: Artificial Sequence
```

```
<220> FEATURE:
<223> OTHER INFORMATION: Synthetic Polynucleotide

<400> SEQUENCE: 899
uugcaccuuu cuaa                                                              14

<210> SEQ ID NO 900
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 900
uuagaaaggu gcaaacaagg                                                        20

<210> SEQ ID NO 901
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 901
uugcaccuuu cuaa                                                              14

<210> SEQ ID NO 902
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 902
uuagaaaggu gcaaacaagg                                                        20

<210> SEQ ID NO 903
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 903
uugcaccuuu cuaa                                                              14

<210> SEQ ID NO 904
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 904
uuagaaaggu gcaaacaagg                                                        20

<210> SEQ ID NO 905
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 905
uugcaccuuu cuaa                                                              14
```

```
<210> SEQ ID NO 906
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 906
uuagaaaggu gcaaacaagg                                                    20

<210> SEQ ID NO 907
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 907
uugcaccuuu cuaa                                                          14

<210> SEQ ID NO 908
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 908
uuagaaaggu gcaaacaagg                                                    20

<210> SEQ ID NO 909
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 909
uugcaccuuu cuaa                                                          14

<210> SEQ ID NO 910
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 910
uuagaaaggu gcaaacaagg                                                    20

<210> SEQ ID NO 911
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 911
uugcaccuuu cuaa                                                          14

<210> SEQ ID NO 912
<211> LENGTH: 20
<212> TYPE: RNA
<213> ORGANISM: Artificial Sequence
<220> FEATURE:
<223> OTHER INFORMATION: Synthetic Polynucleotide
```

```
<400> SEQUENCE: 912
uuagaaaggu gcaaacaagg                                          20

<210> SEQ ID NO 913
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 913
uugcaccuuu cuaa                                                14

<210> SEQ ID NO 914
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 914
uuagaaaggu gcaaacaagg                                          20

<210> SEQ ID NO 915
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 915
uugcaccuuu cuaa                                                14

<210> SEQ ID NO 916
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 916
uuagaaaggu gcaaacaagg                                          20

<210> SEQ ID NO 917
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 917
uugcaccuuu cuaa                                                14

<210> SEQ ID NO 918
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 918
uuagaaaggu gcaaacaagg                                          20

<210> SEQ ID NO 919
```

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 919
ccuuucuagu uga                                                          13

<210> SEQ ID NO 920
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 920
ucaacuagaa aggugcaaa                                                    19

<210> SEQ ID NO 921
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 921
ccuuucuagu uga                                                          13

<210> SEQ ID NO 922
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 922
ucaacuagaa aggugcaaa                                                    19

<210> SEQ ID NO 923
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 923
ccuuucuagu uga                                                          13

<210> SEQ ID NO 924
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 924
ucaacuagaa aggugcaaa                                                    19

<210> SEQ ID NO 925
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 925
```
ccuuucuagu uga                                      13

<210> SEQ ID NO 926
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 926
ucaacuagaa aggugcaaa                                19

<210> SEQ ID NO 927
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 927
ccuuucuagu uga                                      13

<210> SEQ ID NO 928
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 928
ucaacuagaa aggugcaaa                                19

<210> SEQ ID NO 929
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 929
ccuuucuagu uga                                      13

<210> SEQ ID NO 930
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 930
ucaacuagaa aggugcaaa                                19

<210> SEQ ID NO 931
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 931
ccuuucuagu uga                                      13

<210> SEQ ID NO 932
<211> LENGTH: 19
<212> TYPE: RNA

<213> ORGANISM: Artificial Sequence
<220> FEATURE:
<223> OTHER INFORMATION: Synthetic Polynucleotide

<400> SEQUENCE: 932
ucaacuagaa aggugcaaa        19

<210> SEQ ID NO 933
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 933
ccuuucuagu uga        13

<210> SEQ ID NO 934
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 934
ucaacuagaa aggugcaaa        19

<210> SEQ ID NO 935
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 935
ccuuucuagu uga        13

<210> SEQ ID NO 936
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 936
ucaacuagaa aggugcaaa        19

<210> SEQ ID NO 937
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 937
ccuuucuagu uga        13

<210> SEQ ID NO 938
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 938
ucaacuagaa aggugcaaa        19

<210> SEQ ID NO 939
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 939
ccuuucuagu uga                                                        13

<210> SEQ ID NO 940
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 940
ucaacuagaa aggugcaaa                                                  19

<210> SEQ ID NO 941
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 941
ccuuucuagu uga                                                        13

<210> SEQ ID NO 942
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 942
ucaacuagaa aggugcaaa                                                  19

<210> SEQ ID NO 943
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 943
ccuuucuagu uga                                                        13

<210> SEQ ID NO 944
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 944
ucaacuagaa aggugcaaa                                                  19

<210> SEQ ID NO 945
<211> LENGTH: 13
<212> TYPE: RNA
<213> ORGANISM: Artificial Sequence
<220> FEATURE:

<223> OTHER INFORMATION: Synthetic Polynucleotide

<400> SEQUENCE: 945
gcaccuuucu aga                                                          13

<210> SEQ ID NO 946
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 946
ucuagaaagg ugcaaacau                                                    19

<210> SEQ ID NO 947
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 947
gcaccuuucu aga                                                          13

<210> SEQ ID NO 948
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 948
ucuagaaagg ugcaaacau                                                    19

<210> SEQ ID NO 949
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 949
gcaccuuucu aga                                                          13

<210> SEQ ID NO 950
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 950
ucuagaaagg ugcaaacau                                                    19

<210> SEQ ID NO 951
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 951
gcaccuuucu aga                                                          13

```
<210> SEQ ID NO 952
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 952
ucuagaaagg ugcaaacau                                              19

<210> SEQ ID NO 953
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 953
gcaccuuucu aga                                                    13

<210> SEQ ID NO 954
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 954
ucuagaaagg ugcaaacau                                              19

<210> SEQ ID NO 955
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 955
gcaccuuucu aga                                                    13

<210> SEQ ID NO 956
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 956
ucuagaaagg ugcaaacau                                              19

<210> SEQ ID NO 957
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 957
gcaccuuucu aga                                                    13

<210> SEQ ID NO 958
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 958
ucuagaaagg ugcaaacau                                                19

<210> SEQ ID NO 959
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 959
gcaccuuucu aga                                                      13

<210> SEQ ID NO 960
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 960
ucuagaaagg ugcaaacau                                                19

<210> SEQ ID NO 961
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 961
gcaccuuucu aga                                                      13

<210> SEQ ID NO 962
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 962
ucuagaaagg ugcaaacau                                                19

<210> SEQ ID NO 963
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 963
uugcaccuuu cuaa                                                     14

<210> SEQ ID NO 964
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 964
uuagaaaggu gcaaacaagg                                               20

<210> SEQ ID NO 965
<211> LENGTH: 14
```

```
<212> TYPE: RNA
<213> ORGANISM: Artificial Sequence
<220> FEATURE:
<223> OTHER INFORMATION: Synthetic Polynucleotide

<400> SEQUENCE: 965
uugcaccuuu cuaa                                                      14

<210> SEQ ID NO 966
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 966
uuagaaaggu gcaaacaagg                                                20

<210> SEQ ID NO 967
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 967
uugcaccuuu cuaa                                                      14

<210> SEQ ID NO 968
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 968
uuagaaaggu gcaaacaagg                                                20

<210> SEQ ID NO 969
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 969
uugcaccuuu cuaa                                                      14

<210> SEQ ID NO 970
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 970
uuagaaaggu gcaaacaagg                                                20

<210> SEQ ID NO 971
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 971
```
uugcaccuuu cuaa                                                                14

<210> SEQ ID NO 972
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 972
uuagaaaggu gcaaacaagg                                                          20

<210> SEQ ID NO 973
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 973
uugcaccuuu cuaa                                                                14

<210> SEQ ID NO 974
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 974
uuagaaaggu gcaaacaagg                                                          20

<210> SEQ ID NO 975
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 975
uugcaccuuu cuaa                                                                14

<210> SEQ ID NO 976
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 976
uuagaaaggu gcaaacaagg                                                          20

<210> SEQ ID NO 977
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 977
uugcaccuuu cuaa                                                                14

<210> SEQ ID NO 978
<211> LENGTH: 20
<212> TYPE: RNA
<213> ORGANISM: Artificial Sequence

```
<220> FEATURE:
<223> OTHER INFORMATION: Synthetic Polynucleotide

<400> SEQUENCE: 978
uuagaaaggu gcaaacaagg                                               20

<210> SEQ ID NO 979
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 979
uugcaccuuu cuaa                                                     14

<210> SEQ ID NO 980
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 980
uuagaaaggu gcaaacaagg                                               20

<210> SEQ ID NO 981
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 981
uugcaccuuu cuaa                                                     14

<210> SEQ ID NO 982
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 982
uuagaaaggu gcaaacaagg                                               20

<210> SEQ ID NO 983
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 983
uugcaccuuu cuaa                                                     14

<210> SEQ ID NO 984
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 984
uuagaaaggu gcaaacaagg                                               20
```

```
<210> SEQ ID NO 985
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 985
uugcaccuuu cuaa                                                         14

<210> SEQ ID NO 986
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 986
uuagaaaggu gcaaacaagg                                                   20

<210> SEQ ID NO 987
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 987
ccuuucuagu uga                                                          13

<210> SEQ ID NO 988
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 988
ucaacuagaa aggugcaaa                                                    19

<210> SEQ ID NO 989
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 989
ccuuucuagu uga                                                          13

<210> SEQ ID NO 990
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 990
ucaacuagaa aggugcaaa                                                    19

<210> SEQ ID NO 991
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 991
ccuuucuagu uga                                                          13

<210> SEQ ID NO 992
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 992
ucaacuagaa aggugcaaa                                                    19

<210> SEQ ID NO 993
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 993
gcaccuuucu aga                                                          13

<210> SEQ ID NO 994
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 994
ucuagaaagg ugcaaacau                                                    19

<210> SEQ ID NO 995
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 995
gcaccuuucu aga                                                          13

<210> SEQ ID NO 996
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 996
ucuagaaagg ugcaaacau                                                    19

<210> SEQ ID NO 997
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 997
gcaccuuucu aga                                                          13

<210> SEQ ID NO 998
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 998
ucuagaaagg ugcaaacau                                              19

<210> SEQ ID NO 999
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 999
gcaccuuucu aga                                                    13

<210> SEQ ID NO 1000
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1000
ucuagaaagg ugcaaacau                                              19

<210> SEQ ID NO 1001
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1001
gcaccuuucu aga                                                    13

<210> SEQ ID NO 1002
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1002
ucuagaaagg ugcaaacau                                              19

<210> SEQ ID NO 1003
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1003
gugaccaaaa gua                                                    13

<210> SEQ ID NO 1004
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1004
```
uacuuuuggu cacacucuc                                          19

<210> SEQ ID NO 1005
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1005
gugaccaaaa gua                                                13

<210> SEQ ID NO 1006
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1006
uacuuuuggu cacacucuc                                          19

<210> SEQ ID NO 1007
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1007
gugaccaaaa gua                                                13

<210> SEQ ID NO 1008
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1008
uacuuuuggu cacacucuc                                          19

<210> SEQ ID NO 1009
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1009
gugaccaaaa gua                                                13

<210> SEQ ID NO 1010
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1010
uacuuuuggu cacacucuc                                          19

<210> SEQ ID NO 1011
<211> LENGTH: 13
<212> TYPE: RNA

```
<213> ORGANISM: Artificial Sequence
<220> FEATURE:
<223> OTHER INFORMATION: Synthetic Polynucleotide

<400> SEQUENCE: 1011
gugaccaaaa gua                                                          13

<210> SEQ ID NO 1012
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1012 uacuuuggu cacacucuc                                                     19

<210> SEQ ID NO 1013
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1013
gugaccaaaa gua                                                          13

<210> SEQ ID NO 1014
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1014 uacuuuggu cacacucuc                                                     19

<210> SEQ ID NO 1015
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1015
gugaccaaaa gua                                                          13

<210> SEQ ID NO 1016
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1016 uacuuuggu cacacucuc                                                     19

<210> SEQ ID NO 1017
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1017
gugaccaaaa gua                                                          13
```

<210> SEQ ID NO 1018
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1018 uacuuuggu cacacucuc                                                  19

<210> SEQ ID NO 1019
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1019
gugaccaaaa gua                                                       13

<210> SEQ ID NO 1020
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1020 uacuuuggu cacacucuc                                                  19

<210> SEQ ID NO 1021
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1021
gcaccuuucu aga                                                       13

<210> SEQ ID NO 1022
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1022
ucuagaaagg ugcaaacau                                                 19

<210> SEQ ID NO 1023
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1023
gugaccaaaa gua                                                       13

<210> SEQ ID NO 1024
<211> LENGTH: 19
<212> TYPE: RNA
<213> ORGANISM: Artificial Sequence
<220> FEATURE:

<223> OTHER INFORMATION: Synthetic Polynucleotide

<400> SEQUENCE: 1024 uacuuuggu cacacucuc                                                19

<210> SEQ ID NO 1025
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1025
gugaccaaaa gua                                                     13

<210> SEQ ID NO 1026
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1026 uacuuuggu cacacucuc                                                19

<210> SEQ ID NO 1027
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1027
ggcucuccuu cga                                                     13

<210> SEQ ID NO 1028
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1028
ucgaaggaga gccauucgc                                               19

<210> SEQ ID NO 1029
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1029
gacaggaacc ugg                                                     13

<210> SEQ ID NO 1030
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1030
ccagguuccu gucuuuaug                                               19

```
<210> SEQ ID NO 1031
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1031
ccaaggaggu uua                                                          13

<210> SEQ ID NO 1032
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1032
uaaaccuccu uggcguagu                                                    19

<210> SEQ ID NO 1033
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1033
auuuccaucu aca                                                          13

<210> SEQ ID NO 1034
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1034
uguagaugga aaucaccuc                                                    19

<210> SEQ ID NO 1035
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1035
uccaucuaca aca                                                          13

<210> SEQ ID NO 1036
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1036
uguuguagau ggaaaucac                                                    19

<210> SEQ ID NO 1037
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 1037
uuuccaucua caa                                                        13

<210> SEQ ID NO 1038
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1038
uuguagaugg aaaucaccu                                                  19

<210> SEQ ID NO 1039
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1039
cgccaaggag guu                                                        13

<210> SEQ ID NO 1040
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1040
aaccuccuug gcguaguac                                                  19

<210> SEQ ID NO 1041
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1041
guggugauca gaa                                                        13

<210> SEQ ID NO 1042
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1042
uucugaucac cacuggu                                                    19

<210> SEQ ID NO 1043
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1043
cuccugcuaa ugu                                                        13

<210> SEQ ID NO 1044
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 1044
acauuagcag gagaugugg                                                19

<210> SEQ ID NO 1045
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1045
accuccacau aua                                                      13

<210> SEQ ID NO 1046
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1046
uauaugugga ggugccauc                                                19

<210> SEQ ID NO 1047
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1047
aaguccacua gga                                                      13

<210> SEQ ID NO 1048
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1048
uccuagugga cuuuauagu                                                19

<210> SEQ ID NO 1049
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1049
uggugaucag aaa                                                      13

<210> SEQ ID NO 1050
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1050
```

```
uuucugauca ccacuggua                                                      19

<210> SEQ ID NO 1051
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1051
aguccacuag gaa                                                            13

<210> SEQ ID NO 1052
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1052
uuccuagugg acuuuauag                                                      19

<210> SEQ ID NO 1053
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1053
acgccaagga ggu                                                            13

<210> SEQ ID NO 1054
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1054
accuccuugg cguaguacu                                                      19

<210> SEQ ID NO 1055
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1055
uauuuauugu gua                                                            13

<210> SEQ ID NO 1056
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1056
uacacaauaa auaacucac                                                      19

<210> SEQ ID NO 1057
<211> LENGTH: 14
<212> TYPE: RNA
<213> ORGANISM: Artificial Sequence
```

```
<220> FEATURE:
<223> OTHER INFORMATION: Synthetic Polynucleotide

<400> SEQUENCE: 1057
uuauuuauug ugua                                                         14

<210> SEQ ID NO 1058
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1058
uacacaauaa auaacucac                                                    19

<210> SEQ ID NO 1059
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1059
aucaguguua aaa                                                          13

<210> SEQ ID NO 1060
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1060
uuuuaacacu gaugaacca                                                    19

<210> SEQ ID NO 1061
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1061
caucaguguu aaaa                                                         14

<210> SEQ ID NO 1062
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1062
uuuuaacacu gaugaacca                                                    19

<210> SEQ ID NO 1063
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1063
auggcuuaag gaa                                                          13
```

<210> SEQ ID NO 1064
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1064
uuccuuaagc cauccauga                                                    19

<210> SEQ ID NO 1065
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1065
gauggcuuaa ggaa                                                         14

<210> SEQ ID NO 1066
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1066
uuccuuaagc cauccauga                                                    19

<210> SEQ ID NO 1067
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1067
uuguguucug uua                                                          13

<210> SEQ ID NO 1068
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1068
uaacagaaca caaacuucc                                                    19

<210> SEQ ID NO 1069
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1069
uuuguguucu guua                                                         14

<210> SEQ ID NO 1070
<211> LENGTH: 19
<212> TYPE: RNA
<213> ORGANISM: Artificial Sequence
<220> FEATURE:
<223> OTHER INFORMATION: Synthetic Polynucleotide

```
<400> SEQUENCE: 1070
uaacagaaca caaacuucc                                              19

<210> SEQ ID NO 1071
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1071
aaauacuuug cca                                                    13

<210> SEQ ID NO 1072
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1072
uggcaaagua uuuggucuc                                              19

<210> SEQ ID NO 1073
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1073
caaauacuuu gcca                                                   14

<210> SEQ ID NO 1074
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1074
uggcaaagua uuuggucuc                                              19

<210> SEQ ID NO 1075
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1075
cuugcacuac aaa                                                    13

<210> SEQ ID NO 1076
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1076
uuuguagugc aagucaaac                                              19

<210> SEQ ID NO 1077
```

```
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1077
acuugcacua caaa                                                         14

<210> SEQ ID NO 1078
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1078
uuuguagugc aagucaaac                                                    19

<210> SEQ ID NO 1079
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1079
gaauuuauua gua                                                          13

<210> SEQ ID NO 1080
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1080
uacuaauaaa uucuuccag                                                    19

<210> SEQ ID NO 1081
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1081
agaauuuauu agua                                                         14

<210> SEQ ID NO 1082
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1082
uacuaauaaa uucuuccag                                                    19

<210> SEQ ID NO 1083
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1083
```
uugcacuaca aaa                                          13

<210> SEQ ID NO 1084
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1084
uuuuguagug caagucaaa                                    19

<210> SEQ ID NO 1085
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1085
cuugcacuac aaaa                                         14

<210> SEQ ID NO 1086
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1086
uuuuguagug caagucaaa                                    19

<210> SEQ ID NO 1087
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1087
auaaaacagg uga                                          13

<210> SEQ ID NO 1088
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1088
ucaccuguuu uauuuccca                                    19

<210> SEQ ID NO 1089
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1089
aauaaaacag guga                                         14

<210> SEQ ID NO 1090
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 1090
ucaccuguuu uauuuucca                                                19

<210> SEQ ID NO 1091
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1091
gacaacaaca aca                                                      13

<210> SEQ ID NO 1092
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1092
uguuguuguu gucguuguu                                                19

<210> SEQ ID NO 1093
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1093
augcuuguaa caa                                                      13

<210> SEQ ID NO 1094
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1094
uuguuacaag caucaucgu                                                19

<210> SEQ ID NO 1095
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1095
cagaaacuca uga                                                      13

<210> SEQ ID NO 1096
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1096
ucaugaguuu cuggcaaag                                                19
```

<210> SEQ ID NO 1097
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1097
guauugcuau gca                                                       13

<210> SEQ ID NO 1098
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1098
ugcauagcaa uacagaaaa                                                 19

<210> SEQ ID NO 1099
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1099
ccagaaacuc aua                                                       13

<210> SEQ ID NO 1100
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1100
uaugaguuuc uggcaaagu                                                 19

<210> SEQ ID NO 1101
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1101
acucaaacga gca                                                       13

<210> SEQ ID NO 1102
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1102
ugcucguuug aguucaagu                                                 19

<210> SEQ ID NO 1103
<211> LENGTH: 13
<212> TYPE: RNA
<213> ORGANISM: Artificial Sequence
<220> FEATURE:

<223> OTHER INFORMATION: Synthetic Polynucleotide

<400> SEQUENCE: 1103
auaugaccga gaa                                                          13

<210> SEQ ID NO 1104
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1104
uucucgguca uauaauaac                                                    19

<210> SEQ ID NO 1105
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1105
cgacgacaac gaa                                                          13

<210> SEQ ID NO 1106
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1106
uucguugucg ucgucauca                                                    19

<210> SEQ ID NO 1107
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1107
guaaaccagu gaa                                                          13

<210> SEQ ID NO 1108
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1108
uucacugguu uacuaaacu                                                    19

<210> SEQ ID NO 1109
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1109
uugucaguuu aga                                                          13

```
<210> SEQ ID NO 1110
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1110
ucuaaacuga caaagaacc                                                19

<210> SEQ ID NO 1111
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1111
ucaucagugu uaa                                                      13

<210> SEQ ID NO 1112
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1112
uuaacacuga ugaaccaag                                                19

<210> SEQ ID NO 1113
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1113
aacucaaacg aga                                                      13

<210> SEQ ID NO 1114
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1114
ucucguuuga guucaaguu                                                19

<210> SEQ ID NO 1115
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1115
cgacaacaac aaa                                                      13

<210> SEQ ID NO 1116
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 1116
uuuguuguug ucguuguuc                                            19

<210> SEQ ID NO 1117
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1117
acgacaacga uga                                                  13

<210> SEQ ID NO 1118
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1118
ucaucguugu cgucgucau                                            19

<210> SEQ ID NO 1119
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1119
gcugccuaag gaa                                                  13

<210> SEQ ID NO 1120
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1120
uuccuuaggc agcugauac                                            19

<210> SEQ ID NO 1121
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1121
auucuacauu uca                                                  13

<210> SEQ ID NO 1122
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1122 ugaauguag aauaaggcc                                             19

<210> SEQ ID NO 1123
<211> LENGTH: 14
```

-continued

<212> TYPE: RNA
<213> ORGANISM: Artificial Sequence
<220> FEATURE:
<223> OTHER INFORMATION: Synthetic Polynucleotide

<400> SEQUENCE: 1123
caucaguguu aaaa                                                         14

<210> SEQ ID NO 1124
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1124
uuuuaacacu gaugaacca                                                    19

<210> SEQ ID NO 1125
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1125
caucaguguu aaaa                                                         14

<210> SEQ ID NO 1126
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1126
uuuuaacacu gaugaacca                                                    19

<210> SEQ ID NO 1127
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1127
caucaguguu aaaa                                                         14

<210> SEQ ID NO 1128
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1128
uuuuaacacu gaugaacca                                                    19

<210> SEQ ID NO 1129
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1129
caucagcguu aaaa                                                14

<210> SEQ ID NO 1130
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1130
uuuuaacacu gaugaacca                                           19

<210> SEQ ID NO 1131
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1131
ucaucagugu uaa                                                 13

<210> SEQ ID NO 1132
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1132
uuaacacuga ugaaccaag                                           19

<210> SEQ ID NO 1133
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1133
ucaucagugu uaa                                                 13

<210> SEQ ID NO 1134
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1134
uuaacacuga ugaaccaag                                           19

<210> SEQ ID NO 1135
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1135
ucaucagugu uaa                                                 13

<210> SEQ ID NO 1136
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 1136
uuaacacuga ugaaccaag                                              19

<210> SEQ ID NO 1137
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1137
ucaucagugu uaa                                                    13

<210> SEQ ID NO 1138
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1138
uuaacacuga ugaaccaag                                              19

<210> SEQ ID NO 1139
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1139
ucaucagugu uaa                                                    13

<210> SEQ ID NO 1140
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1140
uuaacacuga ugaaccaag                                              19

<210> SEQ ID NO 1141
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1141
ucaucagugu uaa                                                    13

<210> SEQ ID NO 1142
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1142
uuaacacuga ugaaccaag                                              19
```

-continued

<210> SEQ ID NO 1143
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1143
ucaucagugu uaa                                                     13

<210> SEQ ID NO 1144
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1144
uuaacacuga ugaaccaag                                               19

<210> SEQ ID NO 1145
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1145
ucaucagugu uaa                                                     13

<210> SEQ ID NO 1146
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1146
uuaacacuga ugaaccaag                                               19

<210> SEQ ID NO 1147
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1147
ucaucagugu uaa                                                     13

<210> SEQ ID NO 1148
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1148
uuaacacuga ugaaccaag                                               19

<210> SEQ ID NO 1149
<211> LENGTH: 13
<212> TYPE: RNA
<213> ORGANISM: Artificial Sequence
<220> FEATURE:
<223> OTHER INFORMATION: Synthetic Polynucleotide -continued

```
<400> SEQUENCE: 1149
ucaucagugu uaa                                                      13

<210> SEQ ID NO 1150
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1150
uuaacacuga ugaaccaag                                                19

<210> SEQ ID NO 1151
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1151
ucaucagugu uaa                                                      13

<210> SEQ ID NO 1152
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1152
uuaacacuga ugaaccaag                                                19

<210> SEQ ID NO 1153
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1153
ucaucagugu uaa                                                      13

<210> SEQ ID NO 1154
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1154
uuaacacuga ugaaccaag                                                19

<210> SEQ ID NO 1155
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1155
ucaucagugu uaa                                                      13

<210> SEQ ID NO 1156
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1156
uuaacacuga ugaaccaag                                                19

<210> SEQ ID NO 1157
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1157
ucaucagugu uaa                                                      13

<210> SEQ ID NO 1158
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1158
uuaacacuga ugaaccaag                                                19

<210> SEQ ID NO 1159
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1159
gcuaauggug gaa                                                      13

<210> SEQ ID NO 1160
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1160
uuccaccauu agcacgcgg                                                19

<210> SEQ ID NO 1161
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1161
ugaucgugcg cuc                                                      13

<210> SEQ ID NO 1162
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1162
```

```
gagcgcacga ucauguugg                                              19

<210> SEQ ID NO 1163
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1163
caauuccugg cga                                                    13

<210> SEQ ID NO 1164
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1164
ucgccaggaa uuguugcug                                              19

<210> SEQ ID NO 1165
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1165
aguggaucca cga                                                    13

<210> SEQ ID NO 1166
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1166
ucguggaucc acuuccagc                                              19

<210> SEQ ID NO 1167
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1167
uacagcaagg ucc                                                    13

<210> SEQ ID NO 1168
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1168
ggaccuugcu guacugcgu                                              19

<210> SEQ ID NO 1169
<211> LENGTH: 13
<212> TYPE: RNA
```

```
<213> ORGANISM: Artificial Sequence
<220> FEATURE:
<223> OTHER INFORMATION: Synthetic Polynucleotide

<400> SEQUENCE: 1169
aacaugaucg ugc                                                          13

<210> SEQ ID NO 1170
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1170
gcacgaucau guuggacag                                                    19

<210> SEQ ID NO 1171
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1171
acaugaucgu gcg                                                          13

<210> SEQ ID NO 1172
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1172
cgcacgauca uguuggaca                                                    19

<210> SEQ ID NO 1173
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1173
cagcaagguc cug                                                          13

<210> SEQ ID NO 1174
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1174
caggaccuug cuguacugc                                                    19

<210> SEQ ID NO 1175
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1175
ccaacaugau cgu                                                          13
```

<210> SEQ ID NO 1176
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1176
acgaucaugu uggacagcu                                                19

<210> SEQ ID NO 1177
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1177
agcggaagcg cau                                                      13

<210> SEQ ID NO 1178
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1178
augcgcuucc gcuucacca                                                19

<210> SEQ ID NO 1179
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1179
gcaucgaggc cau                                                      13

<210> SEQ ID NO 1180
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1180
auggccucga ugcgcuucc                                                19

<210> SEQ ID NO 1181
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1181
gacuaucgac aug                                                      13

<210> SEQ ID NO 1182
<211> LENGTH: 19
<212> TYPE: RNA
<213> ORGANISM: Artificial Sequence
<220> FEATURE:

```
<223> OTHER INFORMATION: Synthetic Polynucleotide

<400> SEQUENCE: 1182
caugucgaua gucuugcag                                                19

<210> SEQ ID NO 1183
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1183
accugcaaga cua                                                      13

<210> SEQ ID NO 1184
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1184
uagucuugca gguggauag                                                19

<210> SEQ ID NO 1185
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1185
gcuccacgga gaa                                                      13

<210> SEQ ID NO 1186
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1186
uucuccgugg agcugaagc                                                19

<210> SEQ ID NO 1187
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1187
cacagcauau aua                                                      13

<210> SEQ ID NO 1188
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1188
uauauaugcu guguguacu                                                19
```

```
<210> SEQ ID NO 1189
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1189
cagcauauau aua                                                          13

<210> SEQ ID NO 1190
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1190
uauauauaug cugugugua                                                    19

<210> SEQ ID NO 1191
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1191
guacauugac uua                                                          13

<210> SEQ ID NO 1192
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1192
uaagucaaug uacagcugc                                                    19

<210> SEQ ID NO 1193
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1193
uguacauuga cuua                                                         14

<210> SEQ ID NO 1194
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1194
uaagucaaug uacagcugc                                                    19

<210> SEQ ID NO 1195
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 1195
aacuauugcu uca                                                    13

<210> SEQ ID NO 1196
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1196
ugaagcaaua guugguguc                                              19

<210> SEQ ID NO 1197
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1197
caacuauugc uuca                                                   14

<210> SEQ ID NO 1198
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1198
ugaagcaaua guugguguc                                              19

<210> SEQ ID NO 1199
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1199
gcauauauau gua                                                    13

<210> SEQ ID NO 1200
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1200
uacauauaua ugcugugug                                              19

<210> SEQ ID NO 1201
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1201
uguacauuga cua                                                    13

<210> SEQ ID NO 1202
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 1202
uagucaaugu acagcugcc                                                19

<210> SEQ ID NO 1203
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1203
cuguacauug acua                                                     14

<210> SEQ ID NO 1204
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1204
uagucaaugu acagcugcc                                                19

<210> SEQ ID NO 1205
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1205
agcauauaua uga                                                      13

<210> SEQ ID NO 1206
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1206
ucauauauau gcugugugu                                                19

<210> SEQ ID NO 1207
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1207
cagcaacaau uca                                                      13

<210> SEQ ID NO 1208
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1208
```
ugaauuguug cuguauuuc				19

<210> SEQ ID NO 1209
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1209
cauauauaug uua				13

<210> SEQ ID NO 1210
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1210
uaacauauau augcugugu				19

<210> SEQ ID NO 1211
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1211
uugcuucagc uca				13

<210> SEQ ID NO 1212
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1212
ugagcugaag caauaguug				19

<210> SEQ ID NO 1213
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1213
auugcuucag cuca				14

<210> SEQ ID NO 1214
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1214
ugagcugaag caauaguug				19

<210> SEQ ID NO 1215
<211> LENGTH: 13
<212> TYPE: RNA
<213> ORGANISM: Artificial Sequence

```
<220> FEATURE:
<223> OTHER INFORMATION: Synthetic Polynucleotide

<400> SEQUENCE: 1215
acagcauaua uaa                                                        13

<210> SEQ ID NO 1216
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1216
uuauauaugc uguuguac                                                   19

<210> SEQ ID NO 1217
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1217
auugcuucag cua                                                        13

<210> SEQ ID NO 1218
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1218
uagcugaagc aauaguugg                                                  19

<210> SEQ ID NO 1219
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1219
uauugcuuca gcua                                                       14

<210> SEQ ID NO 1220
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1220
uagcugaagc aauaguugg                                                  19

<210> SEQ ID NO 1221
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1221
caaguucaag caa                                                        13
```

```
<210> SEQ ID NO 1222
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1222
uugcuugaac uugucauag                                                19

<210> SEQ ID NO 1223
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1223
cagaguacac aca                                                      13

<210> SEQ ID NO 1224
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1224
uguguguacu cugcuugaa                                                19

<210> SEQ ID NO 1225
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1225
acacacagca uaa                                                      13

<210> SEQ ID NO 1226
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1226
uuaugcugug uguacucug                                                19

<210> SEQ ID NO 1227
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1227
cagcauauau aua                                                      13

<210> SEQ ID NO 1228
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 1228
uauauauaug cugugugua                                            19

<210> SEQ ID NO 1229
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1229
ucaagcagag uaa                                                  13

<210> SEQ ID NO 1230
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1230
uuacucugcu ugaacuugu                                            19

<210> SEQ ID NO 1231
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1231
agcauauaua uga                                                  13

<210> SEQ ID NO 1232
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1232
ucauauauau gcugugugu                                            19

<210> SEQ ID NO 1233
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1233
agaguacaca caa                                                  13

<210> SEQ ID NO 1234
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1234
uuguguguac ucugcuuga                                            19

<210> SEQ ID NO 1235
```

```
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1235
aagcagagua caa                                                            13

<210> SEQ ID NO 1236
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1236
uuguacucug cuugaacuu                                                      19

<210> SEQ ID NO 1237
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1237
uucaacacau caa                                                            13

<210> SEQ ID NO 1238
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1238
uugauguguu gaagaacau                                                      19

<210> SEQ ID NO 1239
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1239
agcagaguac aca                                                            13

<210> SEQ ID NO 1240
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1240
uguguacucu gcuugaacu                                                      19

<210> SEQ ID NO 1241
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1241
```
auauauguuc uua                                                   13

<210> SEQ ID NO 1242
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1242
uaagaacaua uauaugcug                                             19

<210> SEQ ID NO 1243
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1243
gacaaguuca aga                                                   13

<210> SEQ ID NO 1244
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1244
ucuugaacuu gucauagau                                             19

<210> SEQ ID NO 1245
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1245
uuaaagaugg aga                                                   13

<210> SEQ ID NO 1246
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1246
ucuccaucuu uaaugggc                                              19

<210> SEQ ID NO 1247
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1247
cuaugacaag uua                                                   13

<210> SEQ ID NO 1248
<211> LENGTH: 19
<212> TYPE: RNA

```
<213> ORGANISM: Artificial Sequence
<220> FEATURE:
<223> OTHER INFORMATION: Synthetic Polynucleotide

<400> SEQUENCE: 1248
uaacuuguca uagauuucg                                                19

<210> SEQ ID NO 1249
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1249
caacgaaauc uaa                                                      13

<210> SEQ ID NO 1250
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1250
uuagauuucg uuguggguu                                                19

<210> SEQ ID NO 1251
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1251
uaugacaagu uca                                                      13

<210> SEQ ID NO 1252
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1252
ugaacuuguc auagauuuc                                                19

<210> SEQ ID NO 1253
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1253
aaguucaagc aga                                                      13

<210> SEQ ID NO 1254
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1254
ucugcuugaa cuugucaua                                                19
```

<210> SEQ ID NO 1255
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1255
caagcagagu aca                                                        13

<210> SEQ ID NO 1256
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1256
uguacucugc uugaacuug                                                  19

<210> SEQ ID NO 1257
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1257
aaucuaugac aaa                                                        13

<210> SEQ ID NO 1258
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1258
uuugucauag auuucguug                                                  19

<210> SEQ ID NO 1259
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1259
cacacagcau aua                                                        13

<210> SEQ ID NO 1260
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1260
uauaugcugu guguacucu                                                  19

<210> SEQ ID NO 1261
<211> LENGTH: 13
<212> TYPE: RNA
<213> ORGANISM: Artificial Sequence
<220> FEATURE:

<223> OTHER INFORMATION: Synthetic Polynucleotide

<400> SEQUENCE: 1261
gaaauauagc aaa                                                            13

<210> SEQ ID NO 1262
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1262
uuugcuauau uucugguag                                                      19

<210> SEQ ID NO 1263
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1263
gaacucuacc aga                                                            13

<210> SEQ ID NO 1264
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1264
ucugguagag uucuacgug                                                      19

<210> SEQ ID NO 1265
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1265
gcaaagauaa uga                                                            13

<210> SEQ ID NO 1266
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1266
ucauuaucuu ugcugucac                                                      19

<210> SEQ ID NO 1267
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1267
aacucuacca gaa                                                            13

```
<210> SEQ ID NO 1268
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1268
uucugguaga guucuacgu                                                     19

<210> SEQ ID NO 1269
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1269
acucuaccag aaa                                                           13

<210> SEQ ID NO 1270
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1270
uuucugguag aguucuacg                                                     19

<210> SEQ ID NO 1271
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1271
acagcaaaga uaa                                                           13

<210> SEQ ID NO 1272
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1272
uuaucuuugc ugucacaag                                                     19

<210> SEQ ID NO 1273
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1273
caaucuauga caa                                                           13

<210> SEQ ID NO 1274
<211> LENGTH: 19
<212> TYPE: RNA
<213> ORGANISM: Artificial Sequence
<220> FEATURE:
<223> OTHER INFORMATION: Synthetic Polynucleotide
```

```
<400> SEQUENCE: 1274
uugucauaga uugcguugu                                          19

<210> SEQ ID NO 1275
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1275
agauucaagu caa                                                13

<210> SEQ ID NO 1276
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1276
uugacuugaa ucucugcag                                          19

<210> SEQ ID NO 1277
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1277
cuguggagca aca                                                13

<210> SEQ ID NO 1278
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1278
uguugcucca caguugacu                                          19

<210> SEQ ID NO 1279
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1279
ugacagcaaa gaa                                                13

<210> SEQ ID NO 1280
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1280
uucuuugcug ucacaagag                                          19

<210> SEQ ID NO 1281
<211> LENGTH: 13
```

```
<212> TYPE: RNA
<213> ORGANISM: Artificial Sequence
<220> FEATURE:
<223> OTHER INFORMATION: Synthetic Polynucleotide

<400> SEQUENCE: 1281
augacaaaac caa                                                      13

<210> SEQ ID NO 1282
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1282
uugguuuugu cauagauug                                                19

<210> SEQ ID NO 1283
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1283
gagauucaag uca                                                      13

<210> SEQ ID NO 1284
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1284
ugacuugaau cucugcagg                                                19

<210> SEQ ID NO 1285
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1285
cacacagcau aua                                                      13

<210> SEQ ID NO 1286
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1286
uauaugcugu guguacucu                                                19

<210> SEQ ID NO 1287
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1287
```
cacacagcau aua                                                          13

<210> SEQ ID NO 1288
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1288
uauaugcugu guguacucu                                                    19

<210> SEQ ID NO 1289
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1289
cacacagcau aua                                                          13

<210> SEQ ID NO 1290
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1290
uauaugcugu guguacucu                                                    19

<210> SEQ ID NO 1291
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1291
cacacagcau aua                                                          13

<210> SEQ ID NO 1292
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1292
uauaugcugu guguacucu                                                    19

<210> SEQ ID NO 1293
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1293
cacacagcau aua                                                          13

<210> SEQ ID NO 1294
<211> LENGTH: 19
<212> TYPE: RNA
<213> ORGANISM: Artificial Sequence

```
<220> FEATURE:
<223> OTHER INFORMATION: Synthetic Polynucleotide

<400> SEQUENCE: 1294
uauaugcugu guguacucu                                                19

<210> SEQ ID NO 1295
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1295
cacacagcau aua                                                      13

<210> SEQ ID NO 1296
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1296
uauaugcugu guguacucu                                                19

<210> SEQ ID NO 1297
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1297
cacacagcau aua                                                      13

<210> SEQ ID NO 1298
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1298
uauaugcugu guguacucu                                                19

<210> SEQ ID NO 1299
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1299
cacacagcau aua                                                      13

<210> SEQ ID NO 1300
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1300
uauaugcugu guguacucu                                                19
```

```
<210> SEQ ID NO 1301
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1301
agauucaagu caa                                                          13

<210> SEQ ID NO 1302
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1302
uugacuugaa ucucugcuu                                                    19

<210> SEQ ID NO 1303
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1303
gugaccaaaa gua                                                          13

<210> SEQ ID NO 1304
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1304
cacacagcau aua                                                          13

<210> SEQ ID NO 1305
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1305
cacacagcau aua                                                          13

<210> SEQ ID NO 1306
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1306
uauaugcugu guguacucu                                                    19

<210> SEQ ID NO 1307
<211> LENGTH: 13
<212> TYPE: RNA
<213> ORGANISM: Artificial Sequence
<220> FEATURE:
<223> OTHER INFORMATION: Synthetic Polynucleotide
```

-continued

```
<400> SEQUENCE: 1307
cacacagcau aua                                                          13

<210> SEQ ID NO 1308
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1308
uauaugcugu guguacucu                                                    19

<210> SEQ ID NO 1309
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1309
cacacagcau aua                                                          13

<210> SEQ ID NO 1310
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1310
uauaugcugu guguacucu                                                    19

<210> SEQ ID NO 1311
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1311
cacacagcau aua                                                          13

<210> SEQ ID NO 1312
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1312
uauaugcugu guguacucu                                                    19

<210> SEQ ID NO 1313
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1313
cacacagcau aua                                                          13

<210> SEQ ID NO 1314
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1314
uauaugcugu guguacucu                                                      19

<210> SEQ ID NO 1315
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1315
gaugagcuuc cua                                                            13

<210> SEQ ID NO 1316
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1316
uaggaagcuc aucucuccu                                                      19

<210> SEQ ID NO 1317
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1317
agaacagucc uua                                                            13

<210> SEQ ID NO 1318
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1318
uaaggacugu ucugucgau                                                      19

<210> SEQ ID NO 1319
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1319
gaacagaccu uaa                                                            13

<210> SEQ ID NO 1320
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1320
```
uuaaggacug uucugucga	19

<210> SEQ ID NO 1321
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1321
caguccuuaa uca	13

<210> SEQ ID NO 1322
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1322
ugauuaagga cguucugu	19

<210> SEQ ID NO 1323
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1323
guccuuaauc caa	13

<210> SEQ ID NO 1324
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1324
uuggauuaag gacuguucu	19

<210> SEQ ID NO 1325
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1325
uuaauccaga aaa	13

<210> SEQ ID NO 1326
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1326
uuuucuggau uaaggacug	19

<210> SEQ ID NO 1327
<211> LENGTH: 13
<212> TYPE: RNA

```
<213> ORGANISM: Artificial Sequence
<220> FEATURE:
<223> OTHER INFORMATION: Synthetic Polynucleotide

<400> SEQUENCE: 1327
uguuauuggu gua                                                          13

<210> SEQ ID NO 1328
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1328
uacaccaaua acauuagca                                                    19

<210> SEQ ID NO 1329
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1329
uugaaaccac uaa                                                          13

<210> SEQ ID NO 1330
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1330
uuagugguuu caauggugu                                                    19

<210> SEQ ID NO 1331
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1331
gagaaaagag aaa                                                          13

<210> SEQ ID NO 1332
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1332
uuucucuuuu cucugccuc                                                    19

<210> SEQ ID NO 1333
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1333
agaaaagaga aaa                                                          13
```

```
<210> SEQ ID NO 1334
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1334
uuuucucuuu ucucugccu                                                  19

<210> SEQ ID NO 1335
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1335
gaaaagagaa aga                                                        13

<210> SEQ ID NO 1336
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1336
ucuuucucuu uucucugcc                                                  19

<210> SEQ ID NO 1337
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1337
acacucagcu cua                                                        13

<210> SEQ ID NO 1338
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1338
uagagcugag uguuagcaa                                                  19

<210> SEQ ID NO 1339
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1339
aaauaagguu uca                                                        13

<210> SEQ ID NO 1340
<211> LENGTH: 19
<212> TYPE: RNA
<213> ORGANISM: Artificial Sequence
<220> FEATURE:
```

<223> OTHER INFORMATION: Synthetic Polynucleotide

<400> SEQUENCE: 1340
ugaaaccuua uuucaaagg         19

<210> SEQ ID NO 1341
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1341
aaucucucuc cua         13

<210> SEQ ID NO 1342
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1342
uaggagagag auuuaguau         19

<210> SEQ ID NO 1343
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1343
ucucucuccu uua         13

<210> SEQ ID NO 1344
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1344
uaaaggagag agauuuagu         19

<210> SEQ ID NO 1345
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1345
cucucuccuu uua         13

<210> SEQ ID NO 1346
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1346
uaaaaggaga gagauuuag         19

-continued

```
<210> SEQ ID NO 1347
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1347
auuggugcua cua                                                        13

<210> SEQ ID NO 1348
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1348
uaguagcacc aauaaauaa                                                  19

<210> SEQ ID NO 1349
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1349
ugcuacuguu uaa                                                        13

<210> SEQ ID NO 1350
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1350
uuaaacagua gcaccaaua                                                  19

<210> SEQ ID NO 1351
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1351
cagaacaguc cua                                                        13

<210> SEQ ID NO 1352
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1352
uaggacuguu cugucgaug                                                  19

<210> SEQ ID NO 1353
<211> LENGTH: 13
<212> TYPE: RNA
<213> ORGANISM: Artificial Sequence
<220> FEATURE:
<223> OTHER INFORMATION: Synthetic Polynucleotide
```

```
<400> SEQUENCE: 1353
ugcagauuau gca                                                      13

<210> SEQ ID NO 1354
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1354
ugcauaaucu gcaugguga                                                19

<210> SEQ ID NO 1355
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1355
gauuaugcgg aua                                                      13

<210> SEQ ID NO 1356
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1356
uauccgcaua aucugcaug                                                19

<210> SEQ ID NO 1357
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1357
ugcggaucaa aca                                                      13

<210> SEQ ID NO 1358
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1358
uguuugaucc gcauaaucu                                                19

<210> SEQ ID NO 1359
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1359
ggauucgcca uua                                                      13

<210> SEQ ID NO 1360
<211> LENGTH: 19
```

```
<212> TYPE: RNA
<213> ORGANISM: Artificial Sequence
<220> FEATURE:
<223> OTHER INFORMATION: Synthetic Polynucleotide

<400> SEQUENCE: 1360
uaauggcgaa uccaauucc                                              19

<210> SEQ ID NO 1361
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1361
uugacugcug uga                                                    13

<210> SEQ ID NO 1362
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1362
ucacagcagu caaauacau                                              19

<210> SEQ ID NO 1363
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1363
cagaaagaca gaa                                                    13

<210> SEQ ID NO 1364
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1364
uucugucuuu cguccguc                                               19

<210> SEQ ID NO 1365
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1365
gaaaccacua gua                                                    13

<210> SEQ ID NO 1366
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1366
```
uacuaguggu uucaauggu                                    19

<210> SEQ ID NO 1367
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1367
aaccacuagu uca                                          13

<210> SEQ ID NO 1368
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1368
ugaacuagug guuucaaug                                    19

<210> SEQ ID NO 1369
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1369 uaucuuugc uca                                           13

<210> SEQ ID NO 1370
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1370
ugagcaaaag auacaucuc                                    19

<210> SEQ ID NO 1371
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1371 aucuuugcu cua                                           13

<210> SEQ ID NO 1372
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1372
uagagcaaaa gauacaucu                                    19

<210> SEQ ID NO 1373
<211> LENGTH: 13
<212> TYPE: RNA
<213> ORGANISM: Artificial Sequence

```
<220> FEATURE:
<223> OTHER INFORMATION: Synthetic Polynucleotide

<400> SEQUENCE: 1373
ucacuagcuu aua                                                          13

<210> SEQ ID NO 1374
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1374
uauaagcuag ugacuguca                                                    19

<210> SEQ ID NO 1375
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1375
cacuagcuua uca                                                          13

<210> SEQ ID NO 1376
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1376
ugauaagcua gugacuguc                                                    19

<210> SEQ ID NO 1377
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 1377
uaaggacugu ucugucgaug gugau                                             25

<210> SEQ ID NO 1378
<211> LENGTH: 25
<212> TYPE: RNA
<213> ORGANISM: Artificial Sequence
<220> FEATURE:
<223> OTHER INFORMATION: Synthetic Polynucleotide

<400> SEQUENCE: 1378
uguuugaucc gcauaaucug caugg                                             25

<210> SEQ ID NO 1379
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1379
agaacagucc uua                                                          13
```

-continued

<210> SEQ ID NO 1380
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1380
uaaggacugu ucugucgau                    19

<210> SEQ ID NO 1381
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1381
agaacagucc uua                    13

<210> SEQ ID NO 1382
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1382
agaacagucc uua                    13

<210> SEQ ID NO 1383
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1383
agaacagucc uua                    13

<210> SEQ ID NO 1384
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1384
uaaggacugu ucugucgau                    19

<210> SEQ ID NO 1385
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1385
uaaggacugu ucugucgau                    19

<210> SEQ ID NO 1386
<211> LENGTH: 19
<212> TYPE: RNA
<213> ORGANISM: Artificial Sequence
<220> FEATURE:
<223> OTHER INFORMATION: Synthetic Polynucleotide

```
<400> SEQUENCE: 1386
uaaggacugu ucugucgau                                          19

<210> SEQ ID NO 1387
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1387
uaaggacugu ucugucgau                                          19

<210> SEQ ID NO 1388
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1388
uaaggacugu ucugucgau                                          19

<210> SEQ ID NO 1389
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1389
uaaggacugu ucugucgau                                          19

<210> SEQ ID NO 1390
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1390
uaaggacugu ucugucgau                                          19

<210> SEQ ID NO 1391
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1391
uaaggacugu ucugucgau                                          19

<210> SEQ ID NO 1392
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1392
uaaggacugu ucugucgau                                          19

<210> SEQ ID NO 1393
```

```
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1393
uaaggacugu ucugucgau                                              19

<210> SEQ ID NO 1394
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1394
uaaggacugu ucugucgau                                              19

<210> SEQ ID NO 1395
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1395
uaaggacugu ucugucgau                                              19

<210> SEQ ID NO 1396
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1396
uaaggacugu ucugucgau                                              19

<210> SEQ ID NO 1397
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1397
ugcggaucaa aca                                                    13

<210> SEQ ID NO 1398
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1398
uguuugaucc gcauaaucu                                              19

<210> SEQ ID NO 1399
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1399
```

```
gaucacauuu gaa                                                      13

<210> SEQ ID NO 1400
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1400
uucaaaugug aucuggaug                                                19

<210> SEQ ID NO 1401
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1401
gaucacauuu gaa                                                      13

<210> SEQ ID NO 1402
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1402
uucaaaugug aucuggaug                                                19

<210> SEQ ID NO 1403
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1403
gaucacauuu gaa                                                      13

<210> SEQ ID NO 1404
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1404
uucaaaugug aucuggaug                                                19

<210> SEQ ID NO 1405
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1405
gaucacauuu gaua                                                     14

<210> SEQ ID NO 1406
<211> LENGTH: 20
<212> TYPE: RNA
```

```
<213> ORGANISM: Artificial Sequence
<220> FEATURE:
<223> OTHER INFORMATION: Synthetic Polynucleotide

<400> SEQUENCE: 1406
uaucaaaugu gaucuggaug                                               20

<210> SEQ ID NO 1407
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1407
gaucacauuu gaua                                                     14

<210> SEQ ID NO 1408
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 1408
uaucaaaugu gaucuggaug                                               20

<210> SEQ ID NO 1409
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1409
gaucacauuu gaua                                                     14

<210> SEQ ID NO 1410
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 1410
uaucaaaugu gaucuggaug                                               20

<210> SEQ ID NO 1411
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1411
gaucacauuu gaua                                                     14

<210> SEQ ID NO 1412
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 1412
uaucaaaugu gaucuggaug                                               20
```

<210> SEQ ID NO 1413
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1413
cacacaguau aua                                                          13

<210> SEQ ID NO 1414
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1414
uauauacugu gugugaugu                                                    19

<210> SEQ ID NO 1415
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1415
cggugacaau gaa                                                          13

<210> SEQ ID NO 1416
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1416
uucauuguca ccgugauuu                                                    19

<210> SEQ ID NO 1417
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1417
uauugcucug caa                                                          13

<210> SEQ ID NO 1418
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1418
uugcagagca auacagagg                                                    19

<210> SEQ ID NO 1419
<211> LENGTH: 14
<212> TYPE: RNA
<213> ORGANISM: Artificial Sequence
<220> FEATURE:

<223> OTHER INFORMATION: Synthetic Polynucleotide

<400> SEQUENCE: 1419
aaauuccauc gugu                                                        14

<210> SEQ ID NO 1420
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 1420
acacgaugga auuugcuguu                                                  20

<210> SEQ ID NO 1421
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1421
cuguggaagu cua                                                         13

<210> SEQ ID NO 1422
<211> LENGTH: 13
<212> TYPE: RNA
<213> ORGANISM: Artificial Sequence
<220> FEATURE:
<223> OTHER INFORMATION: Synthetic Polynucleotide

<400> SEQUENCE: 1422
gcaccuuucu aga                                                         13

<210> SEQ ID NO 1423
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 1423
ucuagaaagg ugcaaacau                                                   19

<210> SEQ ID NO 1424
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 1424
uugcaccuuu cuaa                                                        14

<210> SEQ ID NO 1425
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 1425
uuagaaaggu gcaaacaagg                                                  20